United States Patent
Krieg et al.

(10) Patent No.: US 10,174,328 B2
(45) Date of Patent: Jan. 8, 2019

(54) COMPOSITIONS AND METHODS FOR TREATING AMYOTROPHIC LATERAL SCLEROSIS

(71) Applicant: Translate Bio MA, Inc., Lexington, MA (US)

(72) Inventors: Arthur M. Krieg, Cambridge, MA (US); James Barsoum, Lexington, MA (US)

(73) Assignee: Translate Bio MA, Inc., Lexington, MA (US)

( * ) Notice: Subject to any disclaimer, the term of this patent is extended or adjusted under 35 U.S.C. 154(b) by 0 days.

(21) Appl. No.: 15/026,774

(22) PCT Filed: Oct. 3, 2014

(86) PCT No.: PCT/US2014/059111
§ 371 (c)(1),
(2) Date: Apr. 1, 2016

(87) PCT Pub. No.: WO2015/051283
PCT Pub. Date: Apr. 9, 2015

(65) Prior Publication Data
US 2016/0222391 A1    Aug. 4, 2016

Related U.S. Application Data

(60) Provisional application No. 61/887,019, filed on Oct. 4, 2013.

(51) Int. Cl.
| | |
|---|---|
| *C12N 15/11* | (2006.01) |
| *C12N 15/113* | (2010.01) |
| *A61K 31/7088* | (2006.01) |
| *A61K 31/711* | (2006.01) |
| *A61K 31/7105* | (2006.01) |
| *A61K 31/712* | (2006.01) |
| *A61K 31/713* | (2006.01) |
| *C12N 15/63* | (2006.01) |
| *A61K 48/00* | (2006.01) |
| *A61K 9/00* | (2006.01) |
| *C12N 15/67* | (2006.01) |

(52) U.S. Cl.
CPC ............ *C12N 15/63* (2013.01); *A61K 9/0019* (2013.01); *A61K 31/7088* (2013.01); *A61K 48/00* (2013.01); *C12N 15/113* (2013.01); *C12N 15/67* (2013.01); *C12N 2310/11* (2013.01); *C12N 2310/3231* (2013.01); *C12N 2310/343* (2013.01); *C12N 2320/31* (2013.01); *C12N 2320/33* (2013.01); *C12N 2510/00* (2013.01)

(58) Field of Classification Search
None
See application file for complete search history.

(56) References Cited

U.S. PATENT DOCUMENTS

| | | |
|---|---|---|
| 5,976,879 A | 11/1999 | Kole et al. |
| 6,040,142 A | 3/2000 | Melki et al. |
| 6,080,577 A | 6/2000 | Melki et al. |
| 6,187,545 B1 | 2/2001 | McKay et al. |
| 6,346,614 B1 | 2/2002 | Metelev et al. |
| 6,531,584 B1 | 3/2003 | Cook et al. |
| 6,831,166 B2 | 12/2004 | Manoharan et al. |
| 7,033,752 B1 | 4/2006 | Melki et al. |
| 7,041,816 B2 | 5/2006 | Ravikumar et al. |
| 7,838,657 B2 | 11/2010 | Singh et al. |
| 7,960,541 B2 | 6/2011 | Wilton et al. |
| 8,067,569 B2 | 11/2011 | Iversen et al. |
| 8,110,560 B2* | 2/2012 | Singh .................. C12N 15/113 514/44 R |
| 8,153,365 B2 | 4/2012 | Wengel et al. |
| 8,153,602 B1 | 4/2012 | Bennett et al. |
| 8,222,221 B2 | 7/2012 | Corey et al. |
| 8,232,384 B2 | 7/2012 | Wilton et al. |
| 8,361,977 B2 | 1/2013 | Baker et al. |
| 2004/0038274 A1 | 2/2004 | Cook et al. |
| 2004/0063751 A1* | 4/2004 | Isakson ................ A61K 31/505 514/311 |
| 2005/0100923 A1 | 5/2005 | Dreyfuss et al. |
| 2005/0130924 A1 | 6/2005 | Monia et al. |
| 2005/0226848 A1 | 10/2005 | Kuwabara et al. |
| 2005/0233455 A1 | 10/2005 | Damha et al. |
| 2006/0089490 A1 | 4/2006 | Melki et al. |
| 2006/0128646 A1 | 6/2006 | Christensen et al. |
| 2007/0166737 A1 | 7/2007 | Melki et al. |
| 2007/0269815 A1 | 11/2007 | Rivory et al. |
| 2007/0292408 A1 | 12/2007 | Singh et al. |

(Continued)

FOREIGN PATENT DOCUMENTS

| | | |
|---|---|---|
| CA | 2805791 A1 | 1/2012 |
| EP | 0 999 270 A1 | 5/2000 |

(Continued)

OTHER PUBLICATIONS

Taylor et al. Drug Discovery Today 1999, vol. 4, pp. 562-567.*
Genbank Submission; NCBI, Accession No. AM773775. Radha et al., Jul. 13, 2007.
Genbank Submission; NCBI, Accession No. NG_008691.1 Mar. 2011. 11 pages.
Anderson et al., Post-transcriptional regulons coordinate the initiation and resolution of inflammation. Nat Rev Immunol. Jan. 2010;10(1):24-35. doi: 10.1038/nri2685.
Blauw et al., SMN1 gene duplications are associated with sporadic ALS. Neurology. Mar. 13, 2012;78(11):776-80. doi: 10.1212/WNL. 0b013e318249f697. Epub Feb. 8, 2012.

(Continued)

*Primary Examiner* — Tracy Vivlemore
(74) *Attorney, Agent, or Firm* — Wolf, Greenfield & Sacks, P.C.

(57) ABSTRACT

Methods for modulating expression of SMN1 and/or SMN2 in cells obtained from subjects having ALS or in subjects having ALS using single stranded oligonucleotides are provided. Methods for treating ALS using single stranded oligonucleotides are also provided.

45 Claims, 25 Drawing Sheets

Specification includes a Sequence Listing.

(56) References Cited

U.S. PATENT DOCUMENTS

| | | | |
|---|---|---|---|
| 2008/0242629 A1 | 10/2008 | Crooke et al. | |
| 2009/0099109 A1 | 4/2009 | Shames et al. | |
| 2009/0143326 A1 | 6/2009 | Obad et al. | |
| 2009/0324549 A1 | 12/2009 | Battaglia et al. | |
| 2010/0021914 A1 | 1/2010 | Moeller et al. | |
| 2010/0087511 A1 | 4/2010 | Singh et al. | |
| 2010/0216238 A1* | 8/2010 | Baker .................. | C12N 15/111 435/375 |
| 2010/0256223 A1 | 10/2010 | Moeller et al. | |
| 2011/0077286 A1 | 3/2011 | Damha et al. | |
| 2011/0086833 A1 | 4/2011 | Paushkin et al. | |
| 2011/0159587 A1 | 6/2011 | Krainer et al. | |
| 2011/0319317 A1 | 12/2011 | Collard et al. | |
| 2012/0149756 A1 | 6/2012 | Schumperli et al. | |
| 2012/0220761 A1* | 8/2012 | Zlatev .................. | C07H 21/00 536/25.31 |
| 2012/0289583 A1 | 11/2012 | Collard et al. | |
| 2012/0295953 A1 | 11/2012 | Collard et al. | |
| 2012/0295959 A1 | 11/2012 | Collard et al. | |
| 2012/0322853 A1 | 12/2012 | Collard et al. | |
| 2013/0116300 A1 | 5/2013 | Collard et al. | |
| 2013/0137751 A1 | 5/2013 | Collard et al. | |
| 2013/0143946 A1 | 6/2013 | Collard et al. | |
| 2013/0210893 A1 | 8/2013 | Collard et al. | |
| 2013/0245095 A1 | 9/2013 | Collard et al. | |
| 2013/0253036 A1 | 9/2013 | Collard et al. | |
| 2013/0289092 A1* | 10/2013 | Rigo .................. | C12N 15/111 514/44 A |
| 2014/0120562 A1* | 5/2014 | Julien .................. | C12Q 1/6883 435/7.92 |
| 2015/0252364 A1 | 9/2015 | Krieg et al. | |

FOREIGN PATENT DOCUMENTS

| | | |
|---|---|---|
| EP | 14851110.8 | 2/2017 |
| JP | 3420984 B2 | 6/2003 |
| WO | WO 92/00386 A1 | 1/1992 |
| WO | WO 94/02499 A1 | 2/1994 |
| WO | WO 95/33852 A1 | 12/1995 |
| WO | WO 2001/066129 A1 | 9/2001 |
| WO | WO 2001/072765 A1 | 10/2001 |
| WO | WO 2002/038738 A2 | 5/2002 |
| WO | WO 2007/002390 A2 | 1/2007 |
| WO | WO 2008/029619 A1 | 3/2008 |
| WO | WO 2008/113832 A2 | 9/2008 |
| WO | WO 2009/064920 A2 | 5/2009 |
| WO | WO 2009/124341 A1 | 10/2009 |
| WO | WO 2009/151546 A2 | 12/2009 |
| WO | WO 2010/093860 A2 | 8/2010 |
| WO | WO 2010/124231 A2 | 10/2010 |
| WO | WO 2011/009624 A1 | 1/2011 |
| WO | WO 2011/032109 A1 | 3/2011 |
| WO | WO 2011/048125 A1 | 4/2011 |
| WO | WO 2011/146675 A2 | 11/2011 |
| WO | WO 2012/024478 A2 | 2/2012 |
| WO | WO 2012/027033 A1 | 3/2012 |
| WO | WO 2012/064806 A2 | 5/2012 |
| WO | WO 2012/144220 A2 | 10/2012 |
| WO | WO 2012/174610 A1 | 12/2012 |
| WO | WO 2013/006619 A1 | 1/2013 |
| WO | WO 2013/173598 A1 | 11/2013 |
| WO | WO 2013/173637 A1 | 11/2013 |
| WO | WO 2013/173638 A1 | 11/2013 |
| WO | WO 2013/173645 A1 | 11/2013 |
| WO | WO 2013/173652 A1 | 11/2013 |
| WO | WO 2014/172698 A1 | 10/2014 |
| WO | WO 2014/203518 A1 | 12/2014 |

OTHER PUBLICATIONS

Boyer et al., Polycomb complexes repress developmental regulators in murine embryonic stem cells. Nature. May 18, 2006;441(7091):349-53. Epub Apr. 19, 2006.

Burghes et al., Antisense oligonucleotides and spinal muscular atrophy: skipping along. Genes Dev. Aug. 1, 2010;24(15):1574-9. doi:10.1101/gad.1961710.

Burglen et al., Structure and organization of the human survival motor neurone (SMN) gene. Genomics. Mar. 15, 1996;32(3):479-82.

Chow et al., Inducible XIST-dependent X-chromosome inactivation in human somatic cells is reversible. Proc Natl Acad Sci U S A. Jun. 12, 2007;104(24):10104-9. Epub May 30, 2007.

Corcia et al., Homozygous SMN2 deletion is a protective factor in the Swedish ALS population. Eur J Hum Genet. May 2012;20(5):588-91. doi: 10.1038/ejhg.2011.255. Epub Jan. 25, 2012.

Corcia et al., The importance of the SMN genes in the genetics of sporadic ALS. Amyotroph Lateral Scler. Oct.-Dec. 2009;10(5-6):436-40. doi: 10.3109/17482960902759162.

Core et al., Nascent RNA sequencing reveals widespread pausing and divergent initiation at human promoters. Science. Dec. 19, 2008;322(5909):1845-8. doi: 10.1126/science.1162228. Epub Dec. 4, 2008.

Daughters et al., RNA gain-of-function in spinocerebellar ataxia type 8. PLoS Genet. Aug. 2009;5(8):e1000600. doi: 10.1371/journal.pgen.1000600. Epub Aug. 14, 2009.

Dominski et al., Identification and characterization by antisense oligonucleotides of exon and intron sequences required for splicing. Mol Cell Biol. Nov. 1994; 14(11): 7445-7454.

Dominski et al., Restoration of correct splicing in thalassemic pre-mRNA by antisense oligonucleotides. Proc Natl Acad Sci U S A. Sep. 15, 1993;90(18):8673-7.

Du et al., Progress toward therapy with antisense-mediated splicing modulation. Curr Opin Mol Ther. Apr. 2009;11(2):116-23.

Feldkotter et al., Quantitative analyses of SMN1 and SMN2 based on real-time lightCycler PCR: fast and highly reliable carrier testing and prediction of severity of spinal muscular atrophy. Am J Hum Genet. Feb. 2002;70(2):358-68. Epub Dec. 21, 2001.

Gerbino et al., Mislocalised FUS mutants stall spliceosomal snRNPs in the cytoplasm. Neurobiol Dis. Jul. 2013;55:120-8. doi:10.1016/j.nbd.2013.03.003. Epub Mar. 21, 2013.

Groen et al., ALS-associated mutations in FUS disrupt the axonal distribution and function of SMN. Hum Mol Genet. Sep. 15, 2013;22(18):3690-704. doi: 10.1093/hmg/ddt222. Epub May 15, 2013.

Houseley et al., RNA-quality control by the exosome. Nat Rev Mol Cell Biol. Jul. 2006;7(7):529-39.

Hua et al., Antisense correction of SMN2 splicing in the CNS rescues necrosis in a type III SMA mouse model. Genes Dev. Aug. 1, 2010;24(15):1634-44. doi: 10.1101/gad.1941310. Epub Jul. 12, 2010.

Hua et al., Antisense Masking of an hnRNP A1/A2 Intronic Splicing Silencer Corrects SMN2 Splicing in Transgenic Mice. Am J Hum Genet. Apr. 11, 2008; 82(4):834-48. Published online Apr. 4, 2008. doi: 10.1016/j.ajhg.2008.01.014.

Hua et al., Enhancement of SMN2 Exon 7 Inclusion by Antisense Oligonucleotides Targeting the Exon. PLoS Biol. Apr. 2007;5(4):e73. Published online Mar. 13, 2007. doi: 10.1371/journal.pbio.0050073.

Hua et al., Peripheral SMN restoration is essential for long-term rescue of a severe spinal muscular atrophy mouse model. Nature. Oct. 5, 2011;478(7367):123-6. doi: 10.1038/nature10485.

Jepsen et al., Locked nucleic acid: a potent nucleic acid analog in therapeutics and biotechnology. Oligonucleotides. 2004;14(2):130-46. Review.

Kariya et al., Mutant superoxide dismutase 1 (SOD1), a cause of amyotrophic lateral sclerosis, disrupts the recruitment of SMN, the spinal muscular atrophy protein to nuclear Cajal bodies. Hum Mol Genet. Aug. 1, 2012;21(15):3421-34. doi: 10.1093/hmg/dds174. Epub May 11, 2012.

Keil et al., A short antisense oligonucleotide ameliorates symptoms of severe mouse models of spinal muscular atrophy. Mol Ther Nucleic Acids. Jul. 8, 2014;3:e174. doi: 10.1038/mtba.2014.23.

Kim et al., Identification of clustered YY1 binding sites in imprinting control regions. Genome Res. Jul. 2006;16(7):901-11. Epub Jun. 7, 2006.

(56) References Cited

OTHER PUBLICATIONS

Lee et al., Homozygous SMN2 Deletion is a Major Risk Factor among Twenty-Five Korean Sporadic Amyotrophic Lateral Sclerosis Patients. Yonsei Med J. Jan. 2012;53(1):53-57.

Lee, Lessons from X-chromosome inactivation: long ncRNA as guides and tethers to the epigenome. Genes Dev. Aug. 15, 2009;23(16):1831-42. doi: 10.1101/gad.1811209.

Lim et al., Modulation of survival motor neuron pre-mRNA splicing by inhibition of alternative 3' splice site pairing. J Biol Chem. Nov. 30, 2001;276(48):45476-83. Epub Oct. 2, 2001.

Mercer et al., Long non-coding RNAs: insights into functions. Nat Rev Genet. Mar. 2009;10(3):155-9. Review.

Merienne et al., SCA8 CAG/CTG expansions, a tale of two TOXICities: a unique or common case? PLoS Genet. Aug. 2009;5(8):e1000593. doi: 10.1371/journal.pgen.1000593. Epub Aug. 14, 2009.

Miller et al., A TALE nuclease architecture for efficient genome editing. Nat Biotechnol. Feb. 2011;29(2):143-8. doi: 10.1038/nbt. 1755. Epub Dec. 22, 2010.

Miyajima et al., Identification of a cis-acting element for the regulation of SMN exon 7 splicing. J Biol Chem. Jun. 28, 2002;277(26):23271-7. Epub Apr. 15, 2002.

Modarresi et al., Inhibition of natural antisense transcripts in vivo results in gene-specific transcriptional upregulation. Nat Biotechnol. Mar. 25, 2012;30(5):453-9. doi: 10.1038/nbt.2158. Supplementary Information.

Munroe, Antisense RNA inhibits splicing of pre-mRNA in vitro. EMBO J. Aug. 1988; 7(8): 2523-32.

Numata et al., Comparative analysis of cis-encoded antisense RNAs in eukaryotes. Gene. May 1, 2007;392(1-2):134-41.

Pandey et al., Kcnq1ot1 antisense noncoding RNA mediates lineage-specific transcriptional silencing through chromatin-level regulation. Mol Cell. Oct. 24, 2008;32(2):232-46. doi: 10.1016/j.molcel. 2008.08.022.

Petersen et al., LNA: a versatile tool for therapeutics and genomics. TRENDS Biotech. Feb. 2003;21(2):74-81. Review.

Reyon et al., Flash assembly of TALENs for high-throughput genome editing. Nat Biotechnol. May 2012;30(5):460-5. doi: 10.1038/nbt.2170.

Shiraki et al., Cap analysis gene expression for high-throughput analysis of transcriptional starting point and identification of promoter usage. Proc Natl Acad Sci U S A. Dec. 23, 2003;100(26):15776-81. Epub Dec. 8, 2003.

Shore et al., Pregnancy-induced noncoding RNA (PINC) associates with polycomb repressive complex 2 and regulates mammary epithelial differentiation. PLoS Genet. 2012;8(7):e1002840. doi: 10.1371/journal.pgen.1002840. Epub Jul. 26, 2012.

Singh et al., A short antisense oligonucleotide masking a unique intronic motif prevents skipping of a critical exon in spinal muscular atrophy. RNA Biol. Jul.-Aug. 2009;6(3):341-50. Epub Jul. 14, 2009.

Singh et al., Splicing of a Critical Exon of Human Survival Motor Neuron Is Regulated by a Unique Silencer Element Located in the Last Intron. Mol Cell Biol. Feb. 2006;26(4):1333-46. doi: 10.1128/MCB.26.4.1333-1346.2006.

Skordis et al., Bifunctional antisense oligonucleotides provide a trans-acting splicing enhancer that stimulates SMN2 gene expression in patient fibroblasts. Proc Natl Acad Sci U S A. Apr. 1, 2003;100(7):4114-9. Epub Mar. 17, 2003.

Tsuiji et al., Spliceosome integrity is defective in the motor neuron diseases ALS and SMA. EMBO Mol Med. Feb. 2013;5(2):221-34. doi: 10.1002/emmm.201202303. Epub Jan. 25, 2013.

Turner et al., Survival motor neuron deficiency enhances progression in an amyotrophic lateral sclerosis mouse model. Neurobiol Dis. Jun. 2009;34(3):511-7. doi: 10.1016/j.nbd.2009.03.005. Epub Mar. 28, 2009.

Valen et al., Genome-wide detection and analysis of hippocampus core promoters using DeepCAGE. Genome Res. Feb. 2009;19(2):255-65. doi: 10.1101/gr.084541.108. Epub Dec. 11, 2008.

Veldink et al., SMN genotypes producing less SMN protein increase susceptibility to and severity of sporadic ALS. Neurology. Sep. 27, 2005;65(6):820-5. Epub Aug. 10, 2005.

Wang et al., Molecular mechanisms of long noncoding RNAs. Cell Press. Sep. 16, 2011; 43(6):904-14.

Yamazaki et al., FUS-SMN protein interactions link the motor neuron diseases ALS and SMA. Cell Rep. Oct. 25, 2012;2(4):799-806. doi:10.1016/j.celrep.2012.08.025. Epub Sep. 27, 2012.

Yap et al., Molecular interplay of the noncoding RNA ANRIL and methylated histone H3 lysine 27 by polycomb CBX7 in transcriptional silencing of INK4a. Mol Cell. Jun. 11, 2010;38(5):662-74. doi: 10.1016/j.molcel.2010.03.021. Epub Jun. 11, 2011. 23 pages.

Kanhere et al., Short RNAs are transcribed from repressed polycomb target genes and interact with polycomb repressive complex-2. Mol Cell. Jun. 11, 2010;38(5):675-88. doi: 10.1016/j.molcel.2010.03. 019.

Williams et al., Oligonucleotide-mediated survival of motor neuron protein expression in CNS improves phenotype in a mouse model of spinal muscular atrophy. J Neurosci. Jun. 17, 2009;29(24):7633-8. doi: 10.1523/JNEUROSCI.0950-09.2009.

Woo et al., Gene activation of SMN by selective disruption of lncRNA-mediated recruitment of PRC2 for the treatment of spinal muscular atrophy. Proc Natl Acad Sci U S A. Feb. 21, 2017;114(8):E1509-E1518. doi:10.1073/pnas.1616521114. Epub Feb. 13, 2017.

Aartsma-Rus et al., Antisense-induced multiexon skipping for Duchenne muscular dystrophy makes more sense. Am J Hum Genet. Jan. 2004;74(1):83-92.

Wu et al., Binding interactions between long noncoding RNA HOTAIR and PRC2 proteins. Biochemistry. Dec. 31, 2013;52(52):9519-27. doi: 10.1021/bi401085h.

Zhou et al., Targeting RNA-splicing for SMA treatment. Mol Cells. Mar. 2012;33(3):223-8. doi: 10.1007/s10059-012-0005-6.

PCT/US2014/059111, Jan. 13, 2015, International Search Report and Written Opinion.

PCT/US2014/059111, Apr. 14, 2016, International Preliminary Report on Patentability.

* cited by examiner

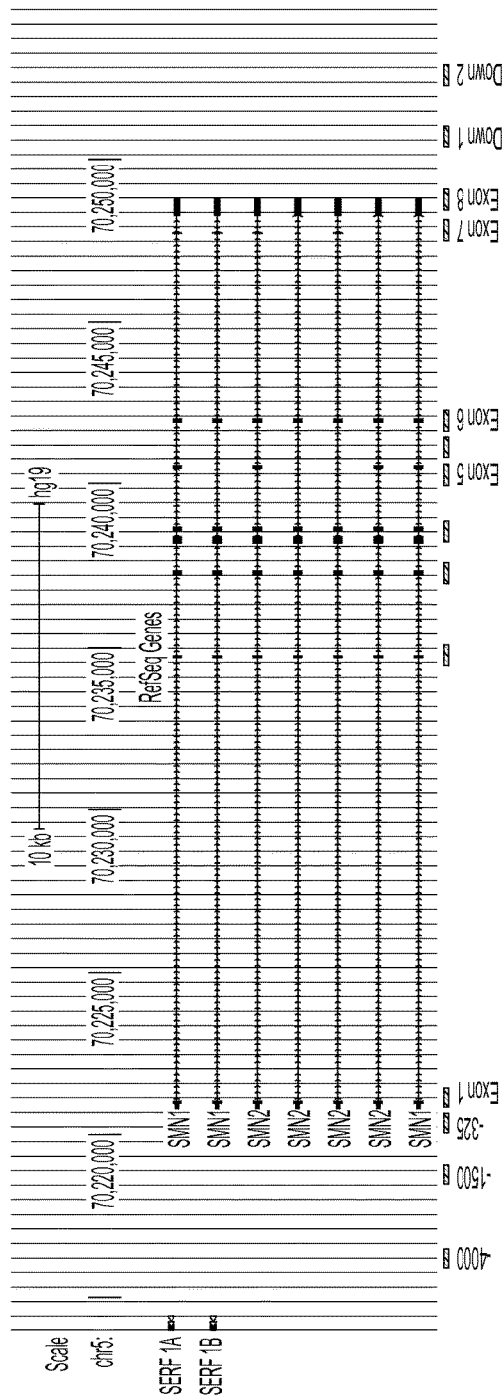
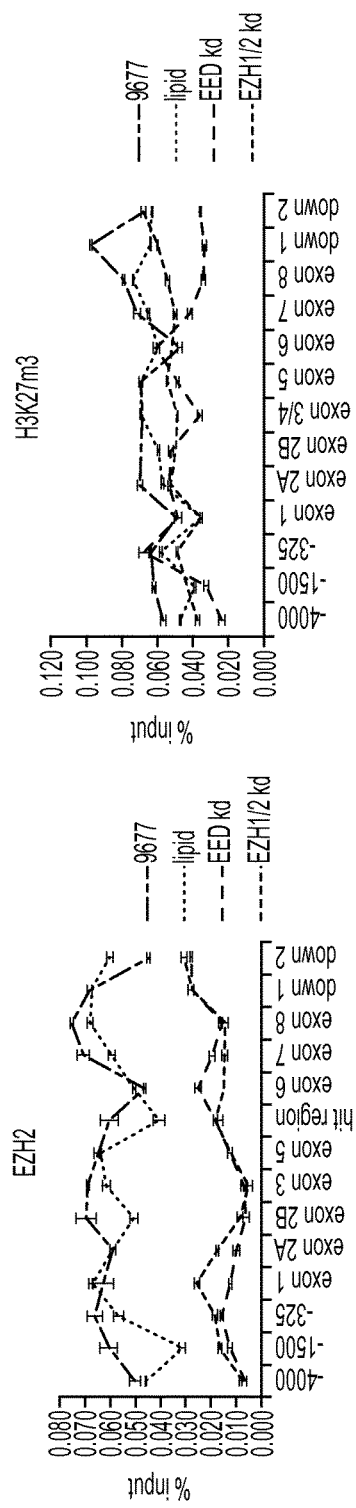
Fig. 11A
Fig. 11B
Fig. 11C

COMPOSITIONS AND METHODS FOR TREATING AMYOTROPHIC LATERAL SCLEROSIS

CROSS-REFERENCE TO RELATED APPLICATIONS

This application is a national stage filing under U.S.C. § 371 of PCT International Application PCT/US2014/059111, with an international filing date of Oct. 3, 2014, which claims the benefit under 35 U.S.C. § 119(e) of U.S. Provisional Application No. 61/887,019, entitled "COMPOSITIONS AND METHODS FOR TREATING AMYOTROPHIC LATERAL SCLEROSIS", filed Oct. 4, 2013, the contents of each of which are incorporated herein by reference in its entirety.

FIELD OF THE INVENTION

The invention relates to oligonucleotide based compositions, as well as methods of using oligonucleotide based compositions for treating disease.

BACKGROUND OF THE INVENTION

Amyotrophic Lateral Sclerosis (ALS) is a progressive neurodegenerative disease that affects motor neurons and eventually results in death. A number of genes have been associated with ALS, including superoxide dismutase 1 (SOD1), fused in sarcoma/translocated in liposarcoma (FUS/TLS), and to the loss of normal TAR DNA-binding protein 43 (TDP-43), survival of motor neuron (SMN) and others. There is currently no cure for ALS.

Survival of motor neuron (SMN) is a protein involved in transcriptional splicing through its involvement in assembly of small nuclear ribonucleoproteins (snRNPs). snRNPs are protein-RNA complexes that bind with pre-mRNA to form a spliceosome, which then splices the pre-mRNA, most often resulting in removal of introns. Three genes encode SMN or a variant of SMN, including SMN1 (survival of motor neuron 1, telomeric), SMN2 (survival of motor neuron 2, centromeric), and SMNP (survival of motor neuron 1, telomeric pseudogene). SMN1 and SMN2 are a result of a gene duplication at 5q13 in humans. A lack of SMN activity results in widespread splicing defects, especially in spinal motor neurons, and degeneration of the spinal cord lower motor neurons.

SUMMARY OF THE INVENTION

Aspects of the invention relate to methods and compositions for treating motor neuron diseases, such as, Amyotrophic Lateral Sclerosis (ALS), Primary Lateral Sclerosis, Progressive Muscular Atrophy, Progressive Bulbar Palsy or Pseudobulbar Palsy. In some embodiments, methods are provided for treating ALS that involve administering to a subject having ALS one or more single stranded oligonucleotides that cause upregulation of SMN in cells (e.g., motor neurons). In some embodiments, single stranded oligonucleotides are provided that target a PRC2-associated region of a SMN gene (e.g., human SMN1, human SMN2) and thereby cause upregulation of the gene. For example, according to some aspects of the invention methods are provided for increasing expression of full-length SMN protein in a cell for purposes of treating ALS. In other aspects, methods and compositions are provided herein for promoting Gem formation in cells (e.g., motor neurons) of patients having a motor neuron disease (e.g., ALS, Primary Lateral Sclerosis, Progressive Muscular Atrophy, Progressive Bulbar Palsy, Pseudobulbar Palsy, or SMA). Accordingly, in some embodiments, methods and compositions are provided for improving, at least partially, spliceosome integrity in neurons.

Accordingly, aspects of the invention disclosed herein provide methods and compositions that are useful for upregulating SMN (SMN1, SMN2) in cells. In some embodiments, single stranded oligonucleotides are provided that target a PRC2-associated region of the gene encoding SMN1 or SMN2. In some embodiments, these single stranded oligonucleotides activate or enhance expression of SMN1 or SMN2 by relieving or preventing PRC2 mediated repression of SMN1 or SMN2. In some embodiments, the cells comprise an SMN1 gene that does not have a mutation associated with Spinal Muscular Atrophy (SMA).

In some embodiments, methods provided herein comprise delivering to a cell a first single stranded oligonucleotide complementary with a PRC2-associated region of an SMN gene, e.g., a PRC2-associated region of SMN1 or SMN2, and a second single stranded oligonucleotide complementary with a splice control sequence of a precursor mRNA of an SMN gene, e.g., a precursor mRNA of SMN1 or SMN2, in amounts sufficient to increase expression of a mature mRNA of SMN1 or SMN2 that comprises (or includes) exon 7 in the cell. In some embodiments, the cell comprises an SMN1 gene that does not have a mutation associated with Spinal Muscular Atrophy (SMA).

According to some aspects of the invention single stranded oligonucleotides are provided that have a region of complementarity that is complementarty with (e.g., at least 8 consecutive nucleotides of) a PRC2-associated region of an SMN gene, e.g., a PRC2-associated region of the nucleotide sequence set forth as SEQ ID NO: 1, 2, 4, or 5. In some embodiments, the oligonucleotide has at least one of the following features: a) a sequence that is 5'X-Y-Z, in which X is any nucleotide and in which X is at the 5' end of the oligonucleotide, Y is a nucleotide sequence of 6 nucleotides in length that is not a human seed sequence of a microRNA, and Z is a nucleotide sequence of 1 to 23 nucleotides in length; b) a sequence that does not comprise three or more consecutive guanosine nucleotides; c) a sequence that has less than a threshold level of sequence identity with every sequence of nucleotides, of equivalent length to the second nucleotide sequence, that are between 50 kilobases upstream of a 5'-end of an off-target gene and 50 kilobases downstream of a 3'-end of the off-target gene; d) a sequence that is complementary to a PRC2-associated region that encodes an RNA that forms a secondary structure comprising at least two single stranded loops; and e) a sequence that has greater than 60% G-C content. In some embodiments, the single stranded oligonucleotide has at least two of features a), b), c), d), and e), each independently selected. In some embodiments, the single stranded oligonucleotide has at least three of features a), b), c), d), and e), each independently selected. In some embodiments, the single stranded oligonucleotide has at least four of features a), b), c), d), and e), each independently selected. In some embodiments, the single stranded oligonucleotide has each of features a), b), c), d), and e). In certain embodiments, the oligonucleotide has the sequence 5'X-Y-Z, in which the oligonucleotide is 8-50 nucleotides in length.

According to some aspects of the invention, single stranded oligonucleotides are provided that have a sequence X-Y-Z, in which X is any nucleotide, Y is a nucleotide sequence of 6 nucleotides in length that is not a seed sequence of a human microRNA, and Z is a nucleotide sequence of 1 to 23 nucleotides in length, in which the single stranded oligonucleotide is complementary with a PRC2-associated region of an SMN gene, e.g., a PRC2-associated region of the nucleotide sequence set forth as SEQ ID NO: 1, 2, 4, or 5. In some aspects of the invention, single stranded oligonucleotides are provided that have a sequence 5'-X-Y-Z, in which X is any nucleotide, Y is a nucleotide sequence of 6 nucleotides in length that is not a seed sequence of a human microRNA, and Z is a nucleotide sequence of 1 to 23 nucleotides in length, in which the single stranded oligonucleotide is complementary with at least 8 consecutive nucleotides of a PRC2-associated region of an SMN gene, e.g., a PRC2-associated region of the nucleotide sequence set forth as SEQ ID NO: 1, 2, 4, or 5. In some embodiments, Y is a sequence selected from Table 1. In some embodiments, the PRC2-associated region is a sequence listed in any one of SEQ ID NOS: 9 to 18.

In some embodiments, the single stranded oligonucleotide comprises a nucleotide sequence as set forth in any one of SEQ ID NOS: 30 to 13087 or 13108 to 13116, or a fragment thereof that is at least 8 nucleotides. In some embodiments, the single stranded oligonucleotide comprises a nucleotide sequence as set forth in any one of SEQ ID NOS: 30 to 13087 or 13108 to 13116, in which the 5' end of the nucleotide sequence provided is the 5' end of the oligonucleotide. In some embodiments, the region of complementarity (e.g., the at least 8 consecutive nucleotides) is also present within the nucleotide sequence set forth as SEQ ID NO: 7 or 8.

In some embodiments, a PRC2-associated region is a sequence listed in any one of SEQ ID NOS: 9 to 14. In some embodiments, the single stranded oligonucleotide comprises a nucleotide sequence as set forth in any one of SEQ ID NOS: 30 to 8329 and 13093 to 13094 or a fragment thereof that is at least 8 nucleotides. In some embodiments, the single stranded oligonucleotide comprises a nucleotide sequence as set forth in any one of SEQ ID NOS: 30 to 8329 and 13093 to 13094, wherein the 5' end of the nucleotide sequence provided is the 5' end of the oligonucleotide. In some embodiments, the at least 8 consecutive nucleotides are also present within the nucleotide sequence set forth as SEQ ID NO: 7.

In some embodiments, a PRC2-associated region is a sequence listed in any one of SEQ ID NOS: 15 to 18. In some embodiments, the single stranded oligonucleotide comprises a nucleotide sequence as set forth in any one of SEQ ID NOS: 1158-1159, 1171, 1482-1483, 1485-1486, 2465-2471, 2488-2490, 2542-2546, 2656-2657, 2833-2835, 3439-3440, 3916-3918, 4469-4472, 4821, 5429, 5537, 6061, 7327, 8330-13061, 13062-13087 and 13108-13116 or a fragment thereof that is at least 8 nucleotides. In some embodiments, the at least 8 consecutive nucleotides are present within the nucleotide sequence set forth as SEQ ID NO: 8.

In some embodiments, the single stranded oligonucleotide comprises a nucleotide sequence as set forth in any one of SEQ ID NOS: 30 to 13087 or 13108 to 13116. In some embodiments, the oligonucleotide is up to 50 nucleotides in length. In some embodiments, the single stranded oligonucleotide comprises a fragment of at least 8 nucleotides of a nucleotide sequence as set forth in any one of SEQ ID NOS: 30 to 13087 or 13108 to 13116.

In some embodiments, a single stranded oligonucleotide comprises a nucleotide sequence as set forth in Table 4. In some embodiments, the single stranded oligonucleotide comprises a fragment of at least 8 nucleotides of a nucleotide sequence as set forth in Table 4 or Table 6. In some embodiments, a single stranded oligonucleotide consists of a nucleotide sequence as set forth in Table 4 or Table 6.

According to some aspects of the invention, compounds are provided that comprise the general formula A-B-C, wherein A is a single stranded oligonucleotide complementary with at least 8 consecutive nucleotides of a PRC2-associated region of a gene, B is a linker, and C is a single stranded oligonucleotide complementary to a splice control sequence of a precursor mRNA of the gene. In some embodiments, B comprises an oligonucleotide, peptide, low pH labile bond, or disulfide bond. In some embodiments, the splice control sequence resides in an exon of the gene. In some embodiments, the splice control sequence traverses an intron-exon junction of the gene. In some embodiments, the splice control sequence resides in an intron of the gene. In some embodiments, the splice control sequence comprises at least one hnRNAP binding sequence. In some embodiments, hybridization of an oligonucleotide having the sequence of C with the splice control sequence of the precursor mRNA in a cell results in inclusion of a particular exon in a mature mRNA that arises from processing of the precursor mRNA in the cell. In some embodiments, hybridization of an oligonucleotide having the sequence of C with the splice control sequence of the precursor mRNA in a cell results in exclusion of a particular intron or exon in a mature mRNA that arises from processing of the precursor mRNA in the cell.

In some embodiments, the gene is SMN1 or SMN2. In some embodiments, the splice control sequence resides in intron 6, intron 7, exon 7, exon 8 or at the junction of intron 7 and exon 8 of SMN1 or SMN2. In some embodiments, the splice control sequence comprises the sequence: CAG-CAUUAUGAAAG (SEQ ID NO: 13100). In some embodiments, B comprises a sequence selected from: TCACTTTCATAATGCTGG (SEQ ID NO: 13088); TCACTTTCATAATGC (SEQ ID NO: 13089); CACTTTCATAATGCT (SEQ ID NO: 13090); ACTTTCATAATGCTG (SEQ ID NO: 13090); and CTTTCATAATGCTGG (SEQ ID NO: 13092).

In some embodiments, A has a sequence 5'-X-Y-Z, wherein X is any nucleotide, Y is a nucleotide sequence of 6 nucleotides in length that is not a seed sequence of a human microRNA, and Z is a nucleotide sequence of 1-23 nucleotides in length. In some embodiments, the PRC2-associated region of an SMN2 gene is a PRC2-associated region within SEQ ID NO: 1, 2, 4 or 5. In some embodiments, Y is a sequence selected from Table 1. In some embodiments, the PRC2-associated region is a sequence set forth in any one of SEQ ID NOS: 9 to 23. In some embodiments, A comprises a nucleotide sequence as set forth in any one of SEQ ID NOS: 30 to 8329 and 13088 to 13094 or a fragment thereof that is at least 8 nucleotides. In some embodiments, A comprises a nucleotide sequence as set forth in any one of SEQ ID NOS: 30 to 8329 and 13088 to 13094, wherein the 5' end of the nucleotide sequence provided is the 5' end of A. In some embodiments, the at least 8 consecutive nucleotides are also present within the nucleotide sequence set forth as SEQ ID NO: 7. In some embodiments, the PRC2-associated region is a sequence set forth in any one of SEQ ID NOS: 24 to 29.

In some embodiments, A comprises a nucleotide sequence as set forth in any one of SEQ ID NOS: 1158-1159, 1171, 1482-1483, 1485-1486, 2465-2471, 2488-2490, 2542-2546, 2656-2657, 2833-2835, 3439-3440, 3916-3918, 4469-4472, 4821, 5429, 5537, 6061, 7327, 8330-13061, 13062-13087, and 13108-13116 or a fragment thereof that is at least 8 nucleotides. In some embodiments, the at least 8 consecutive nucleotides are present within the nucleotide sequence set forth as SEQ ID NO: 8. In some embodiments, A does not comprise three or more consecutive guanosine nucleotides. In some embodiments, A does not comprise four or more consecutive guanosine nucleotides. In some embodiments, A or C is 8 to 30 nucleotides in length. In some embodiments, A is 8 to 10 nucleotides in length and all but 1, 2, or 3 of the nucleotides of the complementary sequence of the PRC2-associated region are cytosine or guanosine nucleotides. In some embodiments, B is an oligonucleotide comprising 1 to 10 thymidines or uridines. In some embodiments, B is more susceptible to cleavage in a mammalian extract than A and C.

In some embodiments, A comprises a nucleotide sequence selected from GCTUTGGGAAGUAUG (SEQ ID NO: 11394), CUTUGGGAAGTATG (SEQ ID NO: 11395) and GGTACATGAGTGGCT (SEQ ID NO: 11419); B comprises the nucleotide sequence TTTT or UUUU; and C comprises the nucleotide sequence TCACTTTCATAATGCTGG (SEQ ID NO: 13088); TCACTTTCATAATGC (SEQ ID NO: 13089); CACTTTCATAATGCT (SEQ ID NO: 13090); ACTTTCATAATGCTG (SEQ ID NO: 13091); or CTTTCATAATGCTGG (SEQ ID NO: 13092), and wherein the 3' end of A is linked to the 5' end of B, and the 3' end of B is linked to 5' end of C.

In some embodiments, the single stranded oligonucleotide does not comprise three or more consecutive guanosine nucleotides. In some embodiments, the single stranded oligonucleotide does not comprise four or more consecutive guanosine nucleotides.

In some embodiments, the single stranded oligonucleotide is 8 to 30 nucleotides in length. In some embodiments, the single stranded oligonucleotide is up to 50 nucleotides in length. In some embodiments, the single stranded oligonucleotide is 8 to 10 nucleotides in length and all but 1, 2, or 3 of the nucleotides of the complementary sequence of the PRC2-associated region are cytosine or guanosine nucleotides.

In some embodiments, the single stranded oligonucleotide is complementary with at least 8 consecutive nucleotides of a PRC2-associated region of an SMN gene, e.g., a PRC2-associated region of a nucleotide sequence set forth as SEQ ID NO: 1, 2, 4, or 5, in which the nucleotide sequence of the single stranded oligonucleotide comprises one or more of a nucleotide sequence selected from the group consisting of (a) (X)Xxxxxx, (X)xXxxxx, (X)xxXxxx, (X)xxxXxx, (X)xxxxXx and (X)xxxxxX, (b) (X)XXxxxx, (X)XxXxxx, (X)XxxXxx, (X)XxxxXx, (X)XxxxxX, (X)xXXxxx, (X)xXxXxx, (X)xXxxXx, (X)xXxxxX, (X)xxXXxx, (X)xxXxXx, (X)xxXxxX, (X)xxxXXx, (X)xxxXxX and (X)xxxxXX, (c) (X)XXXxxx, (X)xXXXxx, (X)xxXXXx, (X)xxxXXX, (X)XXxXxx, (X)XXxxXx, (X)XXxxxX, (X)xXXxXx, (X)xXXxxX, (X)xxXXxX, (X)XxXXxx, (X)XxxXXx, (X)XxxxXX, (X)xXxXXx, (X)xXxxXX, (X)xxXxXx, (X)xXxXxX and (X)XxXxXx, (d) (X)xxXXX, (X)xXxXXX, (X)xXXxXX, (X)xXXXxX, (X)xXXXXx, (X)XxxXXX, (X)XxXxXX, (X)XxXXxX, (X)XxXXXx, (X)XXxxXX, (X)XXxXxX, (X)XXxXXx, (X)XXXxxX, (X)XXXxXx, (X)XXXXxx, and (X)XXXXxx, (e) (X)xXXXXX, (X)XxXXXX, (X)XXxXXX, (X)XXXxXX, (X)XXXXxX and (X)XXXXXx, and (f) XXXXXX, XxXXXXX, XXxXXXX, XXXxXXX, XXXXxXX, XXXXXxX and XXXXXXx, wherein "X" denotes a nucleotide analogue, (X) denotes an optional nucleotide analogue, and "x" denotes a DNA or RNA nucleotide unit.

In some embodiments, at least one nucleotide of the oligonucleotide is a nucleotide analogue. In some embodiments, the at least one nucleotide analogue results in an increase in Tm of the oligonucleotide in a range of 1 to 5° C. compared with an oligonucleotide that does not have the at least one nucleotide analogue.

In some embodiments, at least one nucleotide of the oligonucleotide comprises a 2' O-methyl. In some embodiments, each nucleotide of the oligonucleotide comprises a 2' O-methyl. In some embodiments, the oligonucleotide comprises at least one ribonucleotide, at least one deoxyribonucleotide, or at least one bridged nucleotide. In some embodiments, the bridged nucleotide is a LNA nucleotide, a cEt nucleotide or a ENA modified nucleotide. In some embodiments, each nucleotide of the oligonucleotide is a LNA nucleotide.

In some embodiments, the nucleotides of the oligonucleotide comprise alternating deoxyribonucleotides and 2'-fluoro-deoxyribonucleotides. In some embodiments, the nucleotides of the oligonucleotide comprise alternating deoxyribonucleotides and 2'-O-methyl nucleotides. In some embodiments, the nucleotides of the oligonucleotide comprise alternating deoxyribonucleotides and ENA nucleotide analogues. In some embodiments, the nucleotides of the oligonucleotide comprise alternating deoxyribonucleotides and LNA nucleotides. In some embodiments, the 5' nucleotide of the oligonucleotide is a deoxyribonucleotide. In some embodiments, the nucleotides of the oligonucleotide comprise alternating LNA nucleotides and 2'-O-methyl nucleotides. In some embodiments, the 5' nucleotide of the oligonucleotide is a LNA nucleotide. In some embodiments, the nucleotides of the oligonucleotide comprise deoxyribonucleotides flanked by at least one LNA nucleotide on each of the 5' and 3' ends of the deoxyribonucleotides.

In some embodiments, the single stranded oligonucleotide comprises modified internucleotide linkages (e.g., phosphorothioate internucleotide linkages or other linkages) between at least two, at least three, at least four, at least five or more nucleotides. In some embodiments, the single stranded oligonucleotide comprises modified internucleotide linkages (e.g., phosphorothioate internucleotide linkages or other linkages) between between all nucleotides.

In some embodiments, the nucleotide at the 3' position of the oligonucleotide has a 3' hydroxyl group. In some embodiments, the nucleotide at the 3' position of the oligonucleotide has a 3' thiophosphate. In some embodiments, the single stranded oligonucleotide has a biotin moiety or other moiety conjugated to its 5' or 3' nucleotide. In some embodiments, the single stranded oligonucleotide has cholesterol, Vitamin A, folate, sigma receptor ligands, aptamers, peptides, such as CPP, hydrophobic molecules, such as lipids, ASGPR or dynamic polyconjugates and variants thereof at its 5' or 3' end.

According to some aspects of the invention compositions are provided that comprise any of the oligonucleotides disclosed herein, and a carrier. In some embodiments, compositions are provided that comprise any of the oligonucleotides in a buffered solution. In some embodiments, the oligonucleotide is conjugated to the carrier. In some embodiments, the carrier is a peptide. In some embodiments, the carrier is a steroid. According to some aspects of the invention pharmaceutical compositions are provided that comprise any of the oligonucleotides disclosed herein, and a pharmaceutically acceptable carrier.

According to other aspects of the invention, kits are provided that comprise a container housing any of the compositions disclosed herein.

According to some aspects of the invention, methods of increasing expression of SMN1 or SMN2 in a cell are provided. In some embodiments, the cell comprises a SMN1 gene that does not have a mutation associated with Spinal Muscular Atrophy (SMA). In some embodiments, the cell has a wild-type SMN1 gene. In some embodiments, the methods involve delivering any one or more of the single stranded oligonucleotides disclosed herein into the cell. In some embodiments, delivery of the single stranded oligonucleotide into the cell results in a level of expression of SMN1 or SMN2 that is greater (e.g., at least 50% greater) than a level of expression of SMN1 or SMN2 in a control cell that does not comprise the single stranded oligonucleotide.

According to some aspects of the invention, methods of increasing levels of SMN1 or SMN2 in a subject are provided. According to some aspects of the invention, methods of treating a condition (e.g., ALS, Primary Lateral Sclerosis, Progressive Muscular Atrophy, Progressive Bulbar Palsy, or Pseudobulbar Palsy) associated with decreased levels of SMN1 or SMN2 in a subject are provided. In some embodiments, the methods involve administering any one or more of the single stranded oligonucleotides disclosed herein to the subject.

Aspects of the invention relate to methods of increasing expression of SMN protein in a cell. In some embodiments, the cell comprises an SMN1 gene that does not have a mutation associated with Spinal Muscular Atrophy (SMA). In some embodiments, the method comprise delivering to the cell a first single stranded oligonucleotide complementary with at least 8 consecutive nucleotides of a PRC2-associated region of SMN2 and a second single stranded oligonucleotide complementary with a splice control sequence of a precursor mRNA of SMN2, in amounts sufficient to increase expression of a mature mRNA of SMN2 that comprises exon 7 in the cell. In some embodiments, the region of complementarity with at least 8 consecutive nucleotides of a PRC2-associated region of SMN 2 has at least 1, at least 2, at least 3, at least 4, at least 5, at least 6, at least 7, at least 8, or more mismatches with a corresponding region of SMN1. As used herein the term, "splice control sequence" refers to a nucleotide sequence that when present in a precursor mRNA influences splicing of that precursor mRNA in a cell. In some embodiments, a splice control sequence includes one or more binding sites for a molecule that regulates mRNA splicing, such as a hnRNAP protein. In some embodiments, a splice control sequence comprises the sequence CAG or AAAG. In some embodiments, a splice control sequence resides in an exon (e.g., an exon of SMN1 or SMN2, such as exon 7 or exon 8). In some embodiments, a splice control sequence traverses an intron-exon junction (e.g., an intron-exon junction of SMN1 or SMN2, such as the intron 6/exon 7 junction or the intron 7/exon 8 junction). In some embodiments, a splice control sequence resides in an intron (e.g., an intron of SMN1 or SMN2, such as intron 6 or intron 7). In some embodiments, a splice control sequence comprises the sequence: CAG-CAUUAUGAAAG (SEQ ID NO: 13100) or a portion thereof.

In some embodiments, the second single stranded oligonucleotide is splice switching oligonucleotide that comprises a sequence selected from: TCACTTTCATAAT-GCTGG (SEQ ID NO: 13088); TCACTTTCATAATGC (SEQ ID NO: 13089); CACTTTCATAATGCT (SEQ ID NO: 13090); ACTTTCATAATGCTG (SEQ ID NO: 13091); and CTTTCATAATGCTGG (SEQ ID NO: 13092). In some embodiments, the second single stranded oligonucleotide is 8 to 30 nucleotides in length.

In some embodiments, the first single stranded oligonucleotide has a sequence 5'-X-Y-Z, wherein X is any nucleotide, Y is a nucleotide sequence of 6 nucleotides in length that is not a seed sequence of a human microRNA, and Z is a nucleotide sequence of 1-23 nucleotides in length. In some embodiments, the PRC2-associated region of an SMN2 gene is a PRC2-associated region within SEQ ID NO: 1, 2, 4 or 5. In some embodiments, Y is a sequence selected from Table 1. In some embodiments, the PRC2-associated region is a sequence set forth in any one of SEQ ID NOS: 9 to 23. In some embodiments, the first single stranded oligonucleotide comprises a nucleotide sequence as set forth in any one of SEQ ID NOS: 30 to 8329 and 13088 to 13094 or a fragment thereof that is at least 8 nucleotides. In some embodiments, the first single stranded oligonucleotide comprises a nucleotide sequence as set forth in any one of SEQ ID NOS: 30 to 8329 and 13088 to 13094, wherein the 5' end of the nucleotide sequence provided is the 5' end of the first single stranded oligonucleotide. In some embodiments, the at least 8 consecutive nucleotides are also present within the nucleotide sequence set forth as SEQ ID NO: 7.

In some embodiments, the PRC2-associated region is a sequence set forth in any one of SEQ ID NOS: 24 to 29. In some embodiments, the first single stranded oligonucleotide comprises a nucleotide sequence as set forth in any one of SEQ ID NOS: 1158-1159, 1171, 1482-1483, 1485-1486, 2465-2471, 2488-2490, 2542-2546, 2656-2657, 2833-2835, 3439-3440, 3916-3918, 4469-4472, 4821, 5429, 5537, 6061, 7327, 8330-13061, 13062-13087, and 13108-13116 or a fragment thereof that is at least 8 nucleotides. In some embodiments, the at least 8 consecutive nucleotides are present within the nucleotide sequence set forth as SEQ ID NO: 8. In some embodiments, the first single stranded oligonucleotide does not comprise three or more consecutive guanosine nucleotides. In some embodiments, the first single stranded oligonucleotide does not comprise four or more consecutive guanosine nucleotides. In some embodiments, the first single stranded oligonucleotide is 8 to 30 nucleotides in length. In some embodiments, the first single stranded oligonucleotide is 8 to 10 nucleotides in length and all but 1, 2, or 3 of the nucleotides of the complementary sequence of the PRC2-associated region are cytosine or guanosine nucleotides.

In some embodiments, the first single stranded oligonucleotide and the second single stranded oligonucleotide are delivered to the cell simultaneously. In some embodiments, the cell is in a subject and the step of delivering to the cell comprises administering the first single stranded oligonucleotide and the second single stranded oligonucleotide to the subject as a co-formulation. In some embodiments, the first single stranded oligonucleotide is covalently linked to the second single stranded oligonucleotide through a linker. In some embodiments, the linker comprises an oligonucleotide, a peptide, a low pH-labile bond, or a disulfide bond. In some embodiments, the linker comprises an oligonucleotide, optionally wherein the oligonucleotide comprises 1 to 10 thymidines or uridines. In some embodiments, the linker is more susceptible to cleavage in a mammalian extract than the first and second single stranded oligonucleotides. In some embodiments, the first single stranded oligonucleotide is not covalently linked to the second single stranded oligonucleotide. In some embodiments, the first single stranded oligonucleotide and the second single stranded oligonucleotide are delivered to the cell separately.

According to some aspects of the invention, methods are provided for treating ALS in a subject. The methods, in some embodiments, comprise administering to the subject a first single stranded oligonucleotide complementary with at least 8 consecutive nucleotides of a PRC2-associated region of SMN2 and a second single stranded oligonucleotide complementary with a splice control sequence of a precursor mRNA of SMN2, in amounts sufficient to increase expression of SMN protein in the subject.

According to some aspects of the invention methods are provided for treating ALS in a subject that involve administering to the subject a first single stranded oligonucleotide complementary with a PRC2-associated region of SMN2 and a second single stranded oligonucleotide complementary with a splice control sequence of a precursor mRNA of SMN2, in amounts sufficient to increase expression of SMN protein in the subject. Related compositions are also provided. In some embodiments, compositions are provided that comprise a first single stranded oligonucleotide complementary with at least 8 consecutive nucleotides of a PRC2-associated region of SMN2, and a second single stranded oligonucleotide complementary to a splice control sequence of a precursor mRNA of SMN2. In some embodiments, compositions are provided that comprise a single stranded oligonucleotide complementary with at least 8 consecutive nucleotides of a PRC2-associated region of a gene, linked via a linker to a single stranded oligonucleotide complementary to a splice control sequence of a precursor mRNA of the gene. Related kits comprising single stranded oligonucleotides that regulate SMN1 or SMN2 expression are also provided.

According to some aspects of the invention compositions are provided that comprise any of the oligonucleotides or compounds disclosed herein, and a carrier. In some embodiments, compositions are provided that comprise any of the oligonucleotides or compounds in a buffered solution. In some embodiments, the oligonucleotide is conjugated to the carrier. In some embodiments, the carrier is a peptide. In some embodiments, the carrier is a steroid. According to some aspects of the invention pharmaceutical compositions are provided that comprise any of the oligonucleotides disclosed herein, and a pharmaceutically acceptable carrier.

According to some aspects of the invention, compositions are provided that comprise a first single stranded oligonucleotide complementary with at least 8 consecutive nucleotides of a PRC2-associated region of SMN2, and a second single stranded oligonucleotide complementary to a splice control sequence of a precursor mRNA of SMN2. In some embodiments, the splice control sequence resides in an exon of SMN2. In some embodiments, the exon is exon 7 or exon 8. In some embodiments, the splice control sequence traverses an intron-exon junction of SMN2. In some embodiments, the intron-exon junction is the intron 6/exon 7 junction or the intron 7/exon 8 junction. In some embodiments, the splice control sequence resides in an intron of SMN2. In some embodiments, the intron is intron 6 or intron 7 (SEQ ID NO: 13101). In some embodiments, the splice control sequence comprises the sequence: CAGCAUUAUGAAAG (SEQ ID NO: 13100) or a portion thereof. In some embodiments, the splice control sequence comprises at least one hnRNAP binding sequence. In some embodiments, the second single stranded oligonucleotide comprises a sequence selected from: TCACTTTCATAATGCTGG (SEQ ID NO: 13088); TCACTTTCATAATGC (SEQ ID NO: 13089); CACTTTCATAATGCT (SEQ ID NO: 13090); ACTTTCATAATGCTG (SEQ ID NO: 13091); and CTTTCATAATGCTGG (SEQ ID NO: 13092). In some embodiments, the first single stranded oligonucleotide has a sequence 5'-X-Y-Z, wherein X is any nucleotide, Y is a nucleotide sequence of 6 nucleotides in length that is not a seed sequence of a human microRNA, and Z is a nucleotide sequence of 1-23 nucleotides in length. In some embodiments, the PRC2-associated region of SMN2 is a PRC2-associated region within SEQ ID NO: 1, 2, 4 or 5. In some embodiments, Y is a sequence selected from Table 1. In some embodiments, the PRC2-associated region is a sequence set forth in any one of SEQ ID NOS: 9 to 23. In some embodiments, the first single stranded oligonucleotide comprises a nucleotide sequence as set forth in any one of SEQ ID NOS: 30 to 8329 and 13093 to 13094 or a fragment thereof that is at least 8 nucleotides. In some embodiments, the first single stranded oligonucleotide comprises a nucleotide sequence as set forth in any one of SEQ ID NOS: 30 to 8329 and 13093 to 13094, wherein the 5' end of the nucleotide sequence provided is the 5' end of the first single stranded oligonucleotide. In some embodiments, the at least 8 consecutive nucleotides are also present within the nucleotide sequence set forth as SEQ ID NO: 7. In some embodiments, the PRC2-associated region is a sequence set forth in any one of SEQ ID NOS: 24 to 29. In some embodiments, the first single stranded oligonucleotide comprises a nucleotide sequence as set forth in any one of SEQ ID NOS: 1158-1159, 1171, 1482-1483, 1485-1486, 2465-2471, 2488-2490, 2542-2546, 2656-2657, 2833-2835, 3439-3440, 3916-3918, 4469-4472, 4821, 5429, 5537, 6061, 7327, 8330-13061, 13062-13087, and 13108-13116 or a fragment thereof that is at least 8 nucleotides. In some embodiments, the at least 8 consecutive nucleotides are present within the nucleotide sequence set forth as SEQ ID NO: 8. In some embodiments, the first single stranded oligonucleotide does not comprise three or more consecutive guanosine nucleotides. In some embodiments, the first single stranded oligonucleotide does not comprise four or more consecutive guanosine nucleotides. In some embodiments, the first and/or second single stranded oligonucleotide is 8 to 30 nucleotides in length. In some embodiments, the first single stranded oligonucleotide is 8 to 10 nucleotides in length and all but 1, 2, or 3 of the nucleotides of the complementary sequence of the PRC2-associated region are cytosine or guanosine nucleotides. In some embodiments, the first single stranded oligonucleotide is covalently linked to the second single stranded oligonucleotide through a linker. In some embodiments, the linker comprises an oligonucleotide, a peptide, a low pH-labile bond, or a disulfide bond. In some embodiments, the linker comprises an oligonucleotide, optionally wherein the oligonucleotide comprises 1 to 10 thymidines or uridines. In some embodiments, the linker is more susceptible to cleavage in a mammalian extract than the first and second single stranded oligonucleotides. In some embodiments, the first single stranded oligonucleotide is not covalently linked to the second single stranded oligonucleotide. In some embodiments, the composition further comprises a carrier. In some embodiments, the carrier is a pharmaceutically acceptable carrier.

Further aspects of the invention provide methods for selecting oligonucleotides for activating or enhancing expression of SMN1 or SMN2. In some embodiments, methods are provided for selecting a set of oligonucleotides that is enriched in candidates (e.g., compared with a random selection of oligonucleotides) for activating or enhancing expression of SMN1 or SMN2. Accordingly, the methods may be used to establish sets of clinical candidates that are enriched in oligonucleotides that activate or enhance expression of SMN1 or SMN2. Such libraries may be utilized, for example, to identify lead oligonucleotides for developing therapeutics to treat SMN1 or SMN2. Furthermore, in some embodiments, oligonucleotide chemistries are provided that are useful for controlling the pharmacokinetics, biodistribution, bioavailability and/or efficacy of the single stranded oligonucleotides for activating expression of SMN1 or SMN2.

According to other aspects of the invention, kits are provided that comprise a container housing any of the compositions disclosed herein. According to other aspects of the invention, kits are provided that comprise a first container housing first single stranded oligonucleotide complementary with at least 8 consecutive nucleotides of a PRC2-associated region of a gene; and a second container housing a second single stranded oligonucleotide complementary to a splice control sequence of a precursor mRNA of the gene. In some embodiments, the splice control sequence resides in an exon of the gene. In some embodiments, the splice control sequence traverses an intron-exon junction of the gene. In some embodiments, the splice control sequence resides in an intron of the gene. In some embodiments, the splice control sequence comprises at least one hnRNAP binding sequence. In some embodiments, hybridization of an oligonucleotide having the sequence of C with the splice control sequence of the precursor mRNA in a cell results in inclusion of a particular exon in a mature mRNA that arises from processing of the precursor mRNA in the cell. In some embodiments, hybridization of an oligonucleotide having the sequence of C with the splice control sequence of the precursor mRNA in a cell results in exclusion of a particular intron or exon in a mature mRNA that arises from processing of the precursor mRNA in the cell. In some embodiments, the gene is SMN1 or SMN2. In some embodiments, the splice control sequence resides in intron 6, intron 7, exon 7, exon 8 or at the junction of intron 7 and exon 8. In some embodiments, the splice control sequence comprises the sequence: CAGCAUUAUGAAAG (SEQ ID NO: 13100). In some embodiments, the second single stranded oligonucleotide comprises a sequence selected from: TCACTTTCATAATGCTGG (SEQ ID NO: 13088); TCACTTTCATAATGC (SEQ ID NO: 13089); CACTTTCATAATGCT (SEQ ID NO: 13090); ACTTTCATAATGCTG (SEQ ID NO: XX); and CTTTCATAATGCTGG (SEQ ID NO: 13091). In some embodiments, the first single stranded oligonucleotide has a sequence 5'-X-Y-Z, wherein X is any nucleotide, Y is a nucleotide sequence of 6 nucleotides in length that is not a seed sequence of a human microRNA, and Z is a nucleotide sequence of 1-23 nucleotides in length. In some embodiments, the PRC2-associated region of an SMN2 gene is a PRC2-associated region within SEQ ID NO: 1, 2, 4 or 5. In some embodiments, Y is a sequence selected from Table 1. In some embodiments, the PRC2-associated region is a sequence set forth in any one of SEQ ID NOS: 9 to 23. In some embodiments, the first single stranded oligonucleotide comprises a nucleotide sequence as set forth in any one of SEQ ID NOS: 30 to 8329 and 13093 to 13094 or a fragment thereof that is at least 8 nucleotides. In some embodiments, the first single stranded oligonucleotide comprises a nucleotide sequence as set forth in any one of SEQ ID NOS: 30 to 8329 and 13093 to 13094, wherein the 5' end of the nucleotide sequence provided is the 5' end of the first single stranded oligonucleotide. In some embodiments, the at least 8 consecutive nucleotides are also present within the nucleotide sequence set forth as SEQ ID NO: 7. In some embodiments, the PRC2-associated region is a sequence set forth in any one of SEQ ID NOS: 24 to 29. In some embodiments, the first single stranded oligonucleotide comprises a nucleotide sequence as set forth in any one of SEQ ID NOS: 1158-1159, 1171, 1482-1483, 1485-1486, 2465-2471, 2488-2490, 2542-2546, 2656-2657, 2833-2835, 3439-3440, 3916-3918, 4469-4472, 4821, 5429, 5537, 6061, 7327, 8330-13061, 13062-13087, and 13108-13116 or a fragment thereof that is at least 8 nucleotides. In some embodiments, the at least 8 consecutive nucleotides are present within the nucleotide sequence set forth as SEQ ID NO: 8.

LNA/2'OMe alternating oligonucleotide (LM design) and DNA/LNA alternating oligonucleotides (DL design) were tested.

Figure 10A:
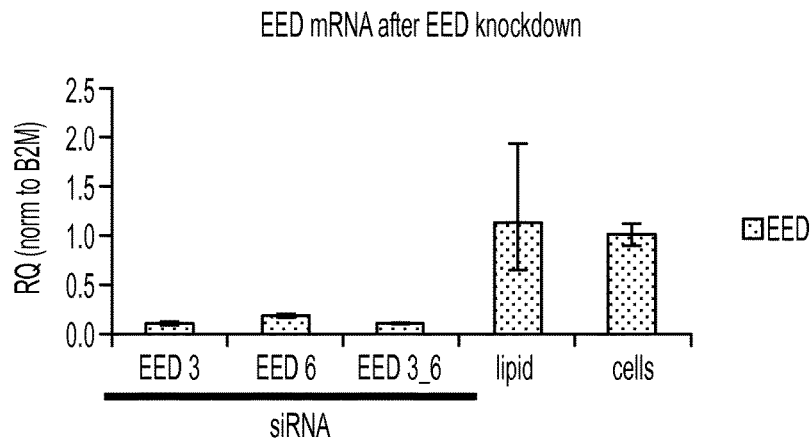

FIG. 10A provides a graph showing levels of EED (Embryonic ectoderm development) mRNA after EED knockdown.

Figure 10B:
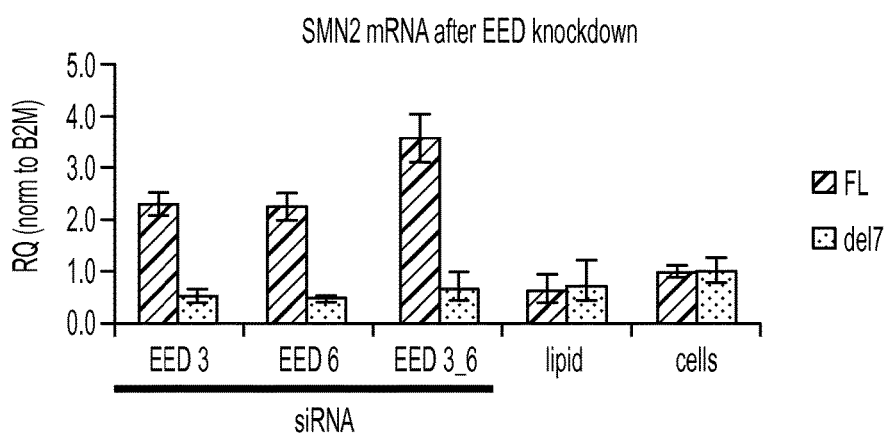

FIG. 10B provides a graph showing levels of SMN2 mRNA after EED knockdown. Levels of full-length (FL) and the exon 7 deleted (del7) SMN2 mRNA levels are shown.

Figure 10C:
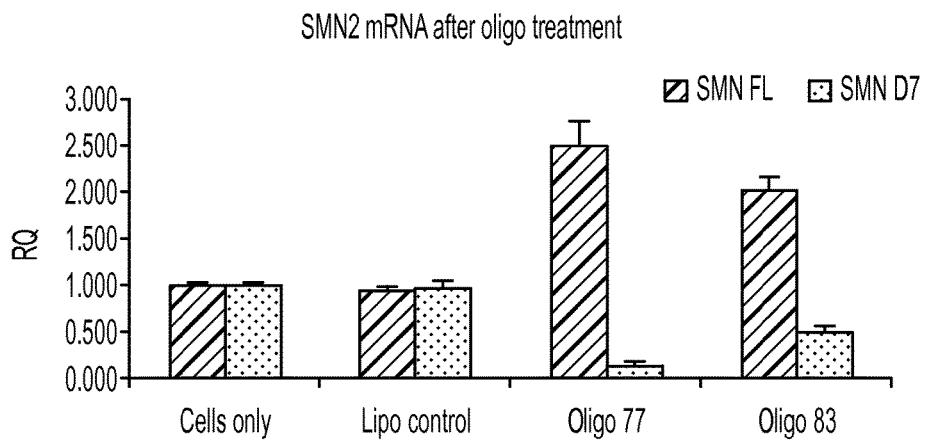

FIG. 10C provides a graph showing levels of SMN2 mRNA after treatment with SMN oligos 77 or 83 compared to controls (cells only or cell treated with lipofectamine only). Levels of full-length (FL) and the exon 7 deleted (del7) SMN2 mRNA levels are shown.

FIG. 11A provides a diagram showing the SMN2 locus and the locations of certain regions within the locus that are shown in FIGS. 11-14.

FIGS. 11B and 11C provide a series of graphs showing that knockdown of PRC2 components reduces the presence of EZH2 in the SMN chromatin. FIG. 11B shows EZH2 ChIP (chromatin immunoprecipitation) data and FIG. 11C shows H3K27m3 ChIP data.

Figure 11D:
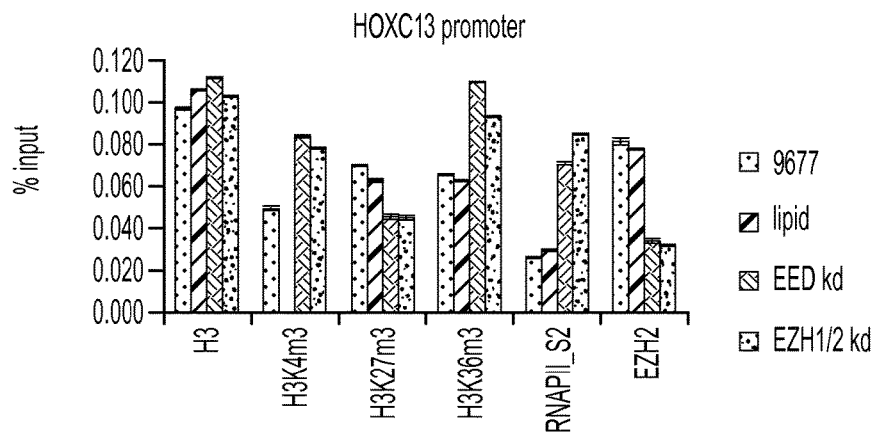

FIG. 11D provides a graph showing the presence of H3, H3K4m3, H3K27m3, H3K36m3, RNA polII_S2 and EZH2 at the HOXC13 promoter.

Figure 12A:
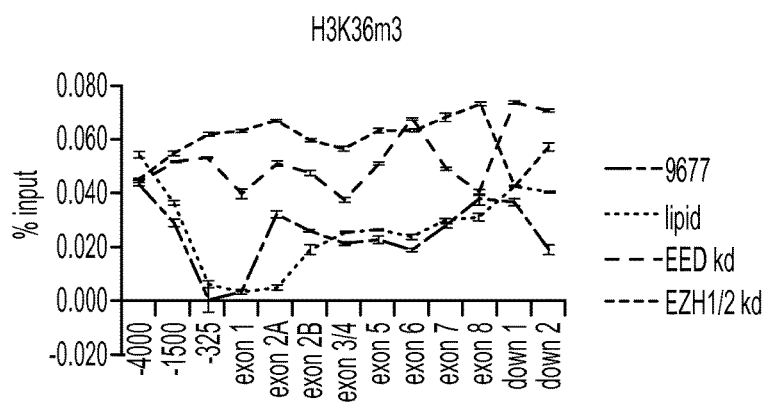
Figure 12B:
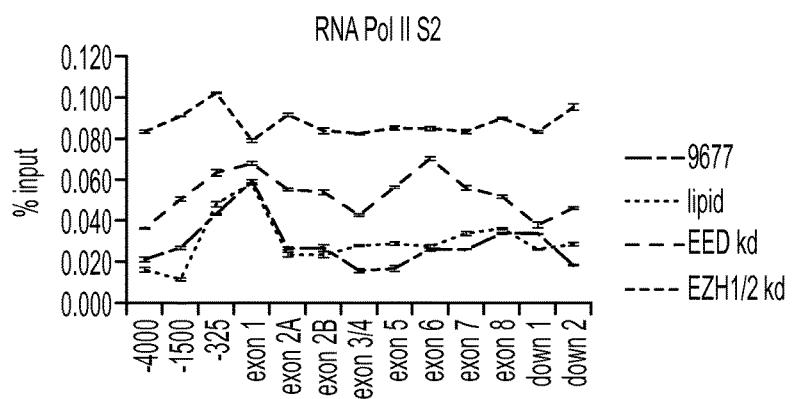
Figure 12C:
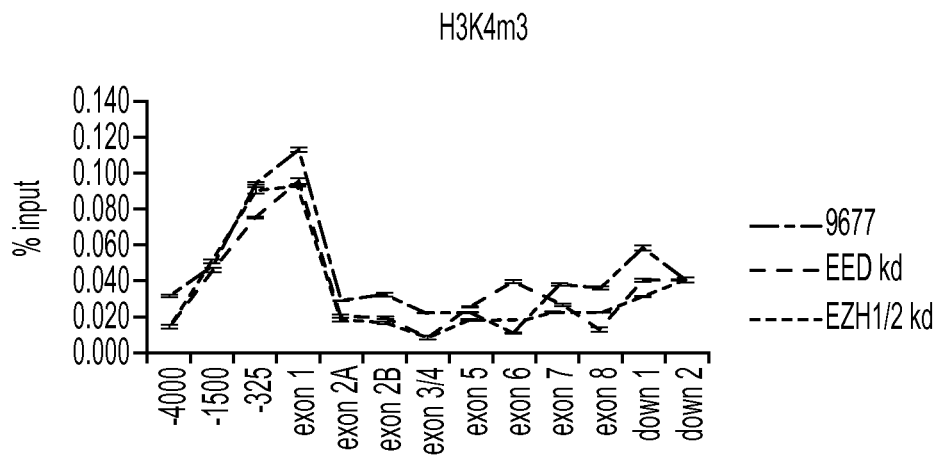
Figure 12D:
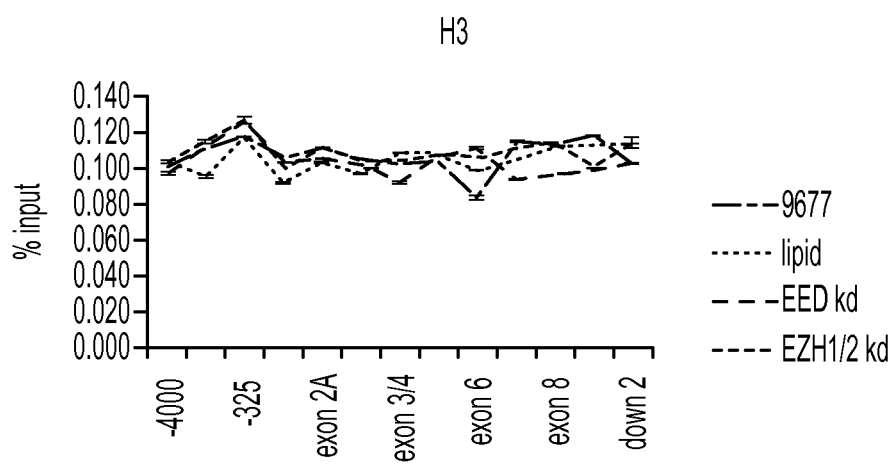

FIGS. 12A-D provide a series of graphs showing that knockdown of PRC2 components leads to an increase in marks of transcriptional activity. FIG. 12A shows H3K36m3 ChIP data, FIG. 12B shows RNA Pol II S2 ChIP data, FIG. 12. C shows H3K4m3 ChIP data, and FIG. 12D shows H3 ChIP data.

Figure 13A:
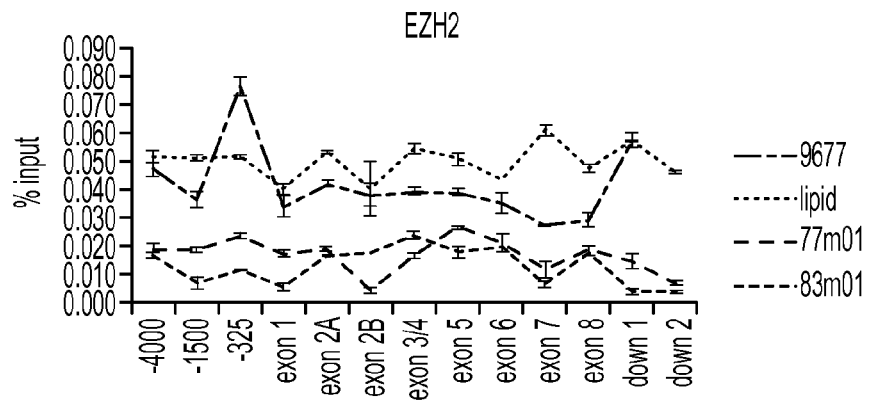

FIG. 13A provides a graph showing that SMN oligos 77 and 83 reduce EZH2 in SMN chromatin compared to controls (9677 cells only or lipid control). EZH2 ChIP data is shown.

Figure 13B:
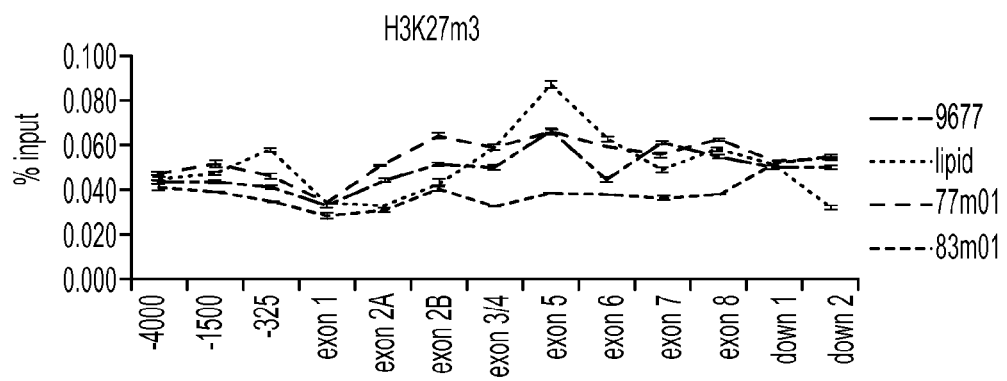

FIG. 13B provides a graph showing H3K27m3 in SMN chromatin after treatment with SMN oligos 77 or 83 compared to controls (9677 cells only or lipid control). H3K27m3 ChIP data is shown.

Figure 13C:
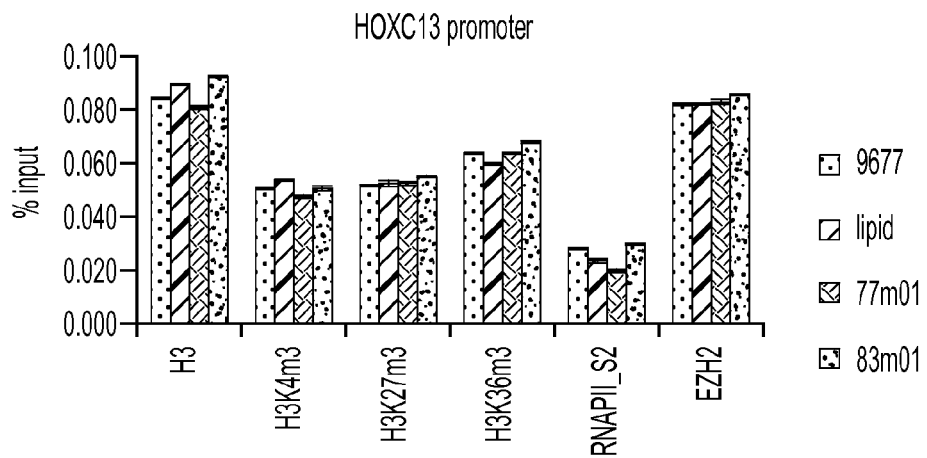

FIG. 13C provides a graph showing the presence of H3, H3K4m3, H3K27m3, H3K36m3, RNA polII_S2 and EZH2 at the HOXC13 promoter after treatment with SMN oligos compared to controls (9677 cells only or lipid control).

Figure 14A:
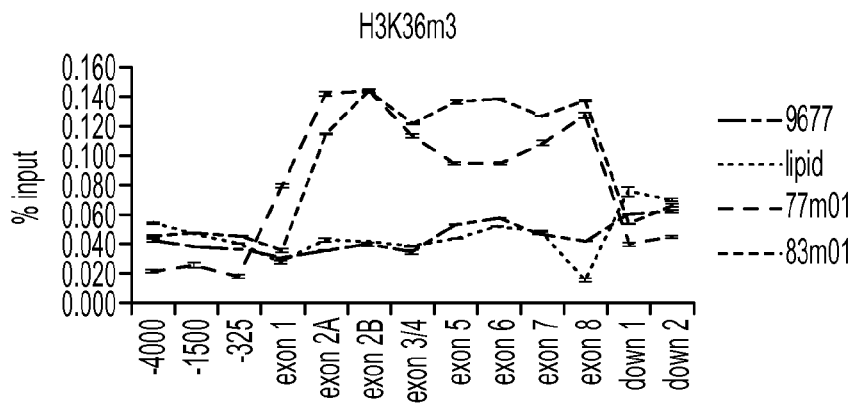

FIG. 14A provides a graph showing H3K36m3 in SMN chromatin after treatment with SMN oligos 77 or 83 compared to controls (9677 cells only or lipid control). H3K36m3 ChIP data is shown.

Figure 14B:
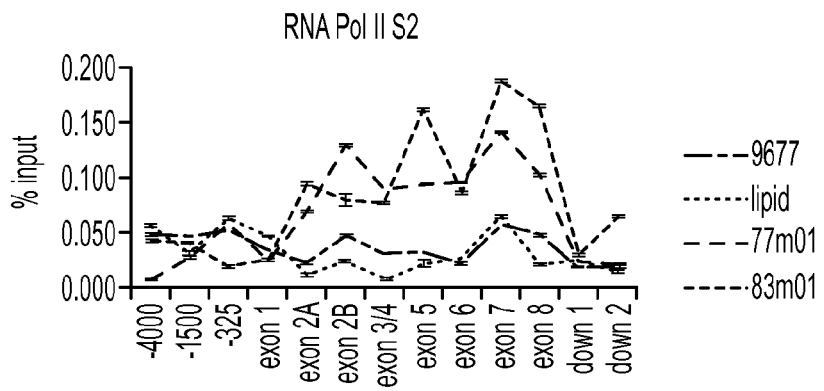

FIG. 14B provides a graph showing RNA PolII S2 in SMN chromatin after treatment with SMN oligos 77 or 83 compared to controls (9677 cells only or lipid control). RNA PolII S2 ChIP data is shown.

Figure 14C:
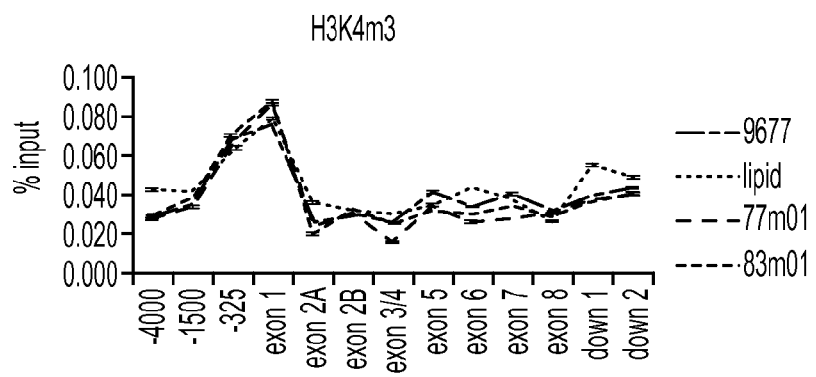

FIG. 14C provides a graph showing H3K4m3 in SMN chromatin after treatment with SMN oligos 77 or 83 compared to controls (9677 cells only or lipid control). H3K4m3 ChIP data is shown.

Figure 14D:
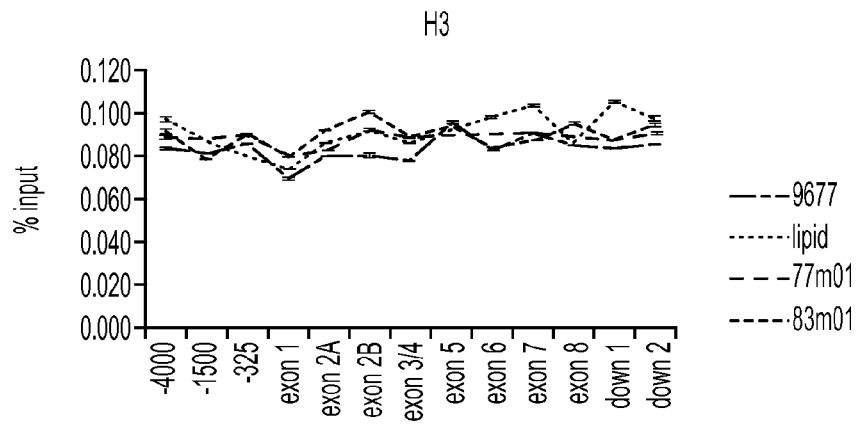

FIG. 14D provides a graph showing Histone 3 (H3) in SMN chromatin after treatment with SMN oligos 77 or 83 compared to controls (9677 cells only or lipid control). H3 ChIP data is shown.

Figure 15A:
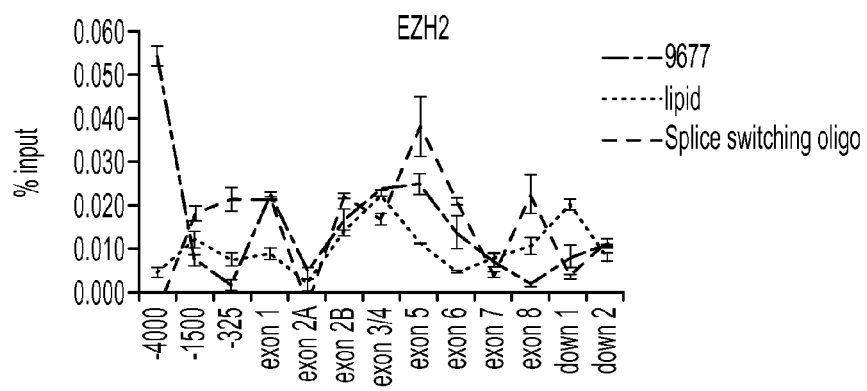

FIG. 15A provides a graph showing EZH2 in SMN chromatin after treatment with a splice switching oligo compared to controls (9677 cells only or lipid control). EZH2 ChIP data is shown.

Figure 15B:
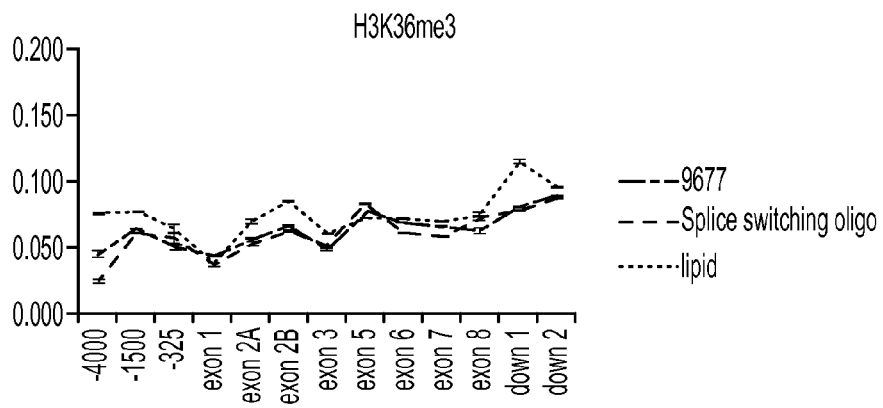

FIG. 15B provides a graph showing H3K36m3 in SMN chromatin after treatment with a splice switching oligo compared to controls (9677 cells only or lipid control). H3K36m3 ChIP data is shown.

Figure 15C:
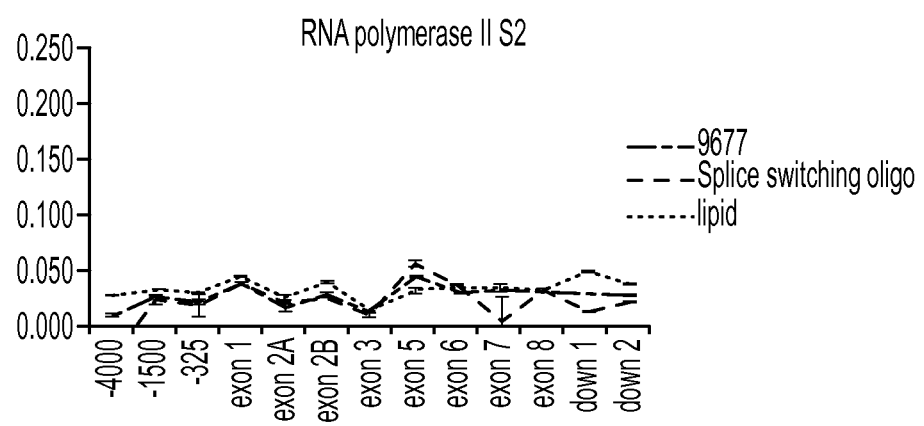

FIG. 15C provides a graph showing RNA PolII S2 in SMN chromatin after treatment with a splice switching oligo compared to controls (9677 cells only or lipid control). RNA PolII S2 ChIP data is shown.

Figure 16A:
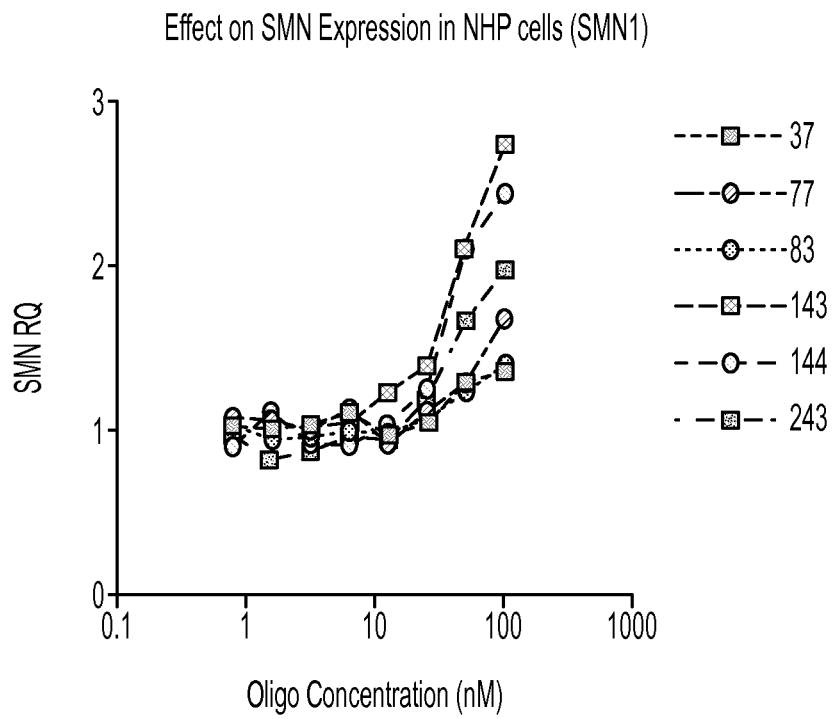

FIG. 16A provides a graph showing the level of SMN1 mRNA in non-human primate (NHP) cells treated with various SMN oligos (37, 77, 83, 143, 144, or 243).

Figure 16B:
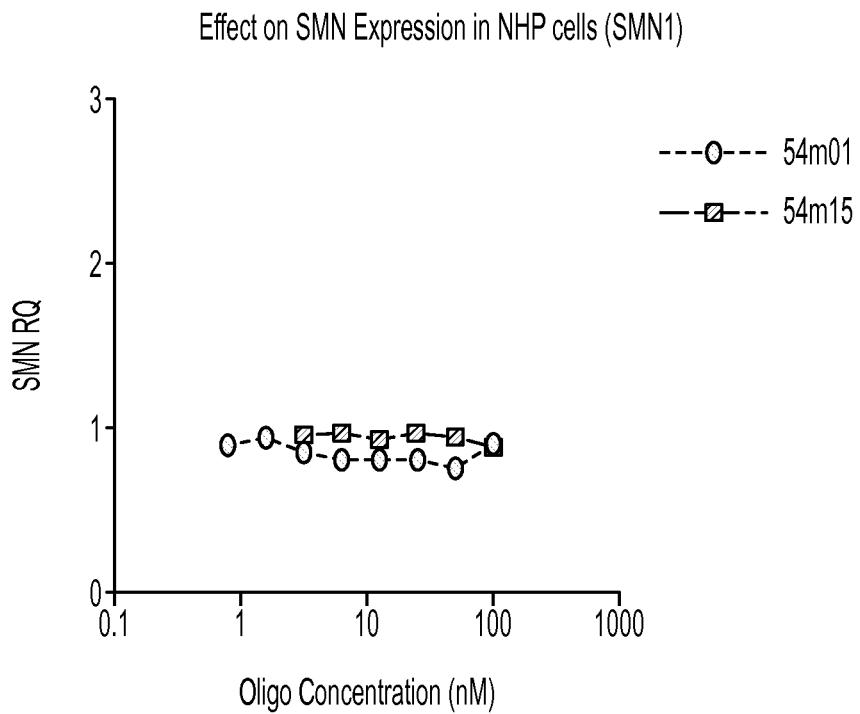

FIG. 16B provides a graph showing the level of SMN1 mRNA in non-human primate (NHP) cells treated with various splice-switching SMN oligos (54m01 or 54m15).

Figure 17A:
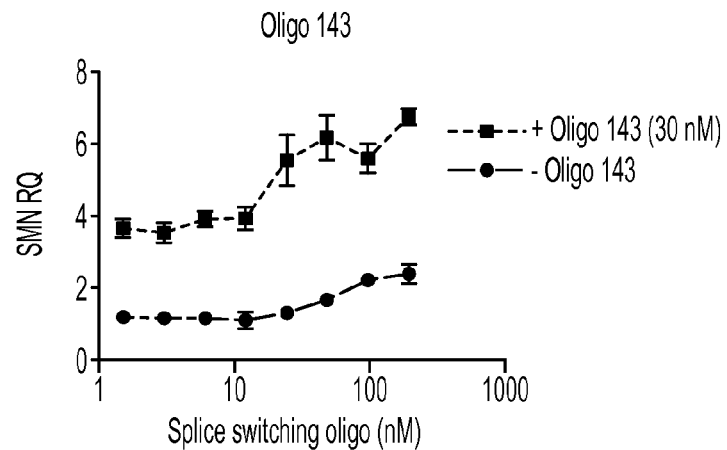
Figure 17B:
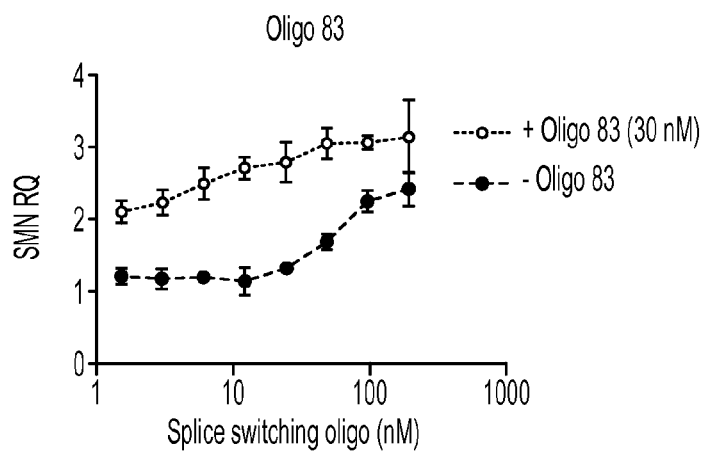
Figure 17C:
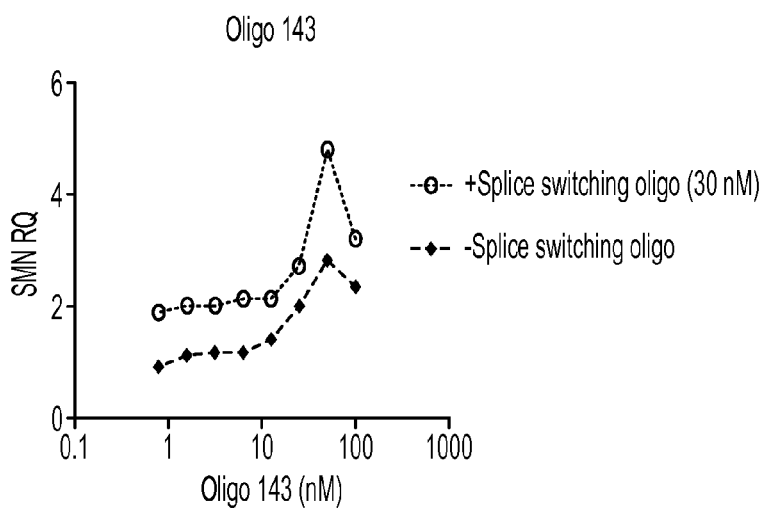
Figure 17D:
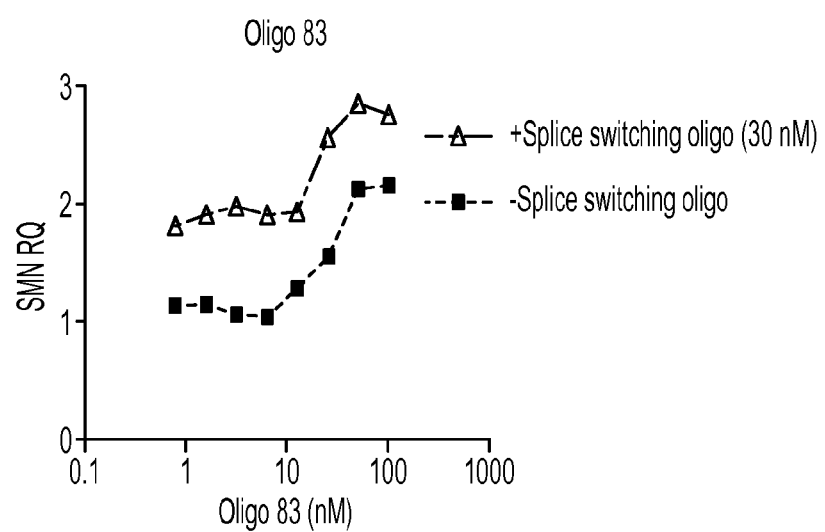

FIGS. 17A-D provides a series of graphs showing SMN2 mRNA levels in cells treated with an SMN oligo, a splice-switching oligo, or a combination thereof. FIG. 17A shows data for a splice switching oligo at various concentrations alone or in combination with SMN oligo 143. FIG. 17B shows data for a splice switching oligo at various concentrations alone or in combination with SMN oligo 83. FIG. 17C shows data for SMN oligo 143 at various concentrations alone or in combination with a splice switching oligo. FIG. 17D shows data for SMN oligo 83 at various concentrations alone or in combination with a splice switching oligo.

Figure 18:
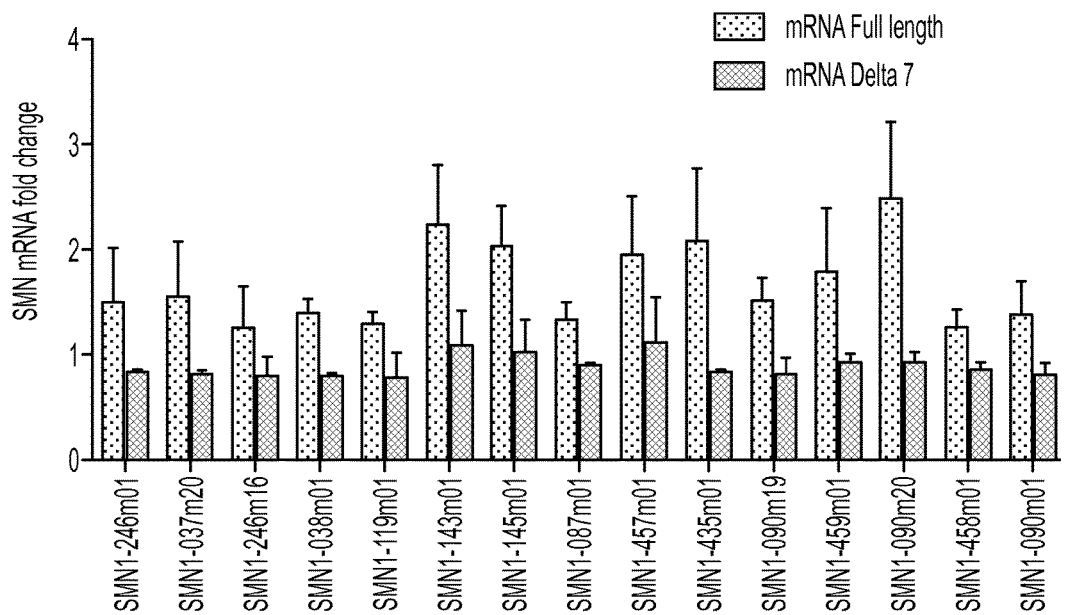

FIG. 18 is a graph showing SMN2 mRNA increase in SMA patient fibroblast cell line GM09677 treated with various SMN oligos. Both SMN full length and exon 7 deleted (delta 7) mRNA levels are shown.

Figure 19:
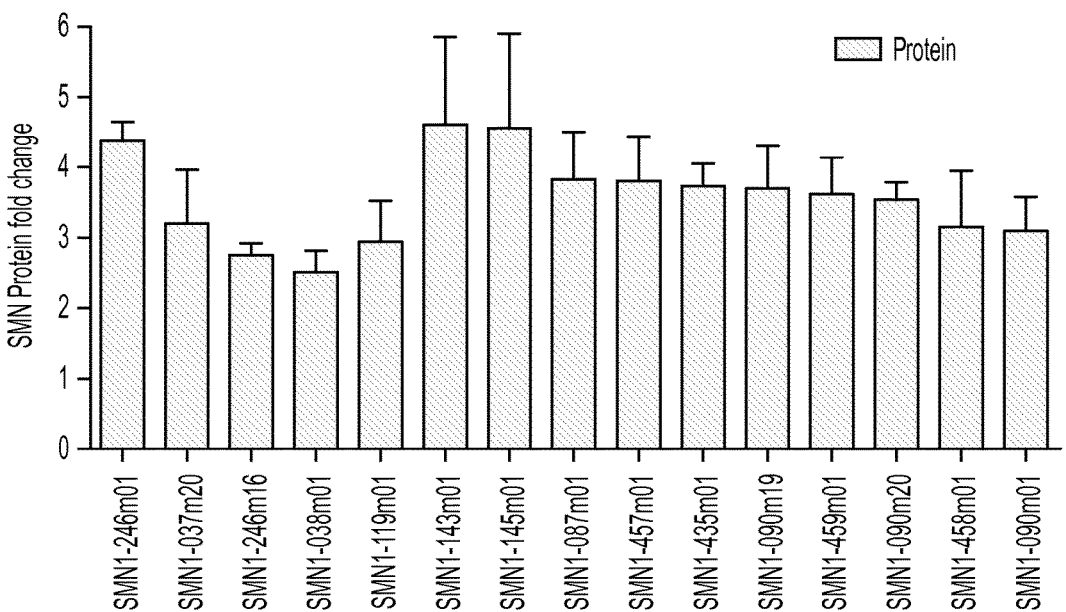

FIG. 19 is a graph showing SMN protein increase in SMA patient fibroblast cell line GM09677 treated with various SMN oligos.

Figure 20:
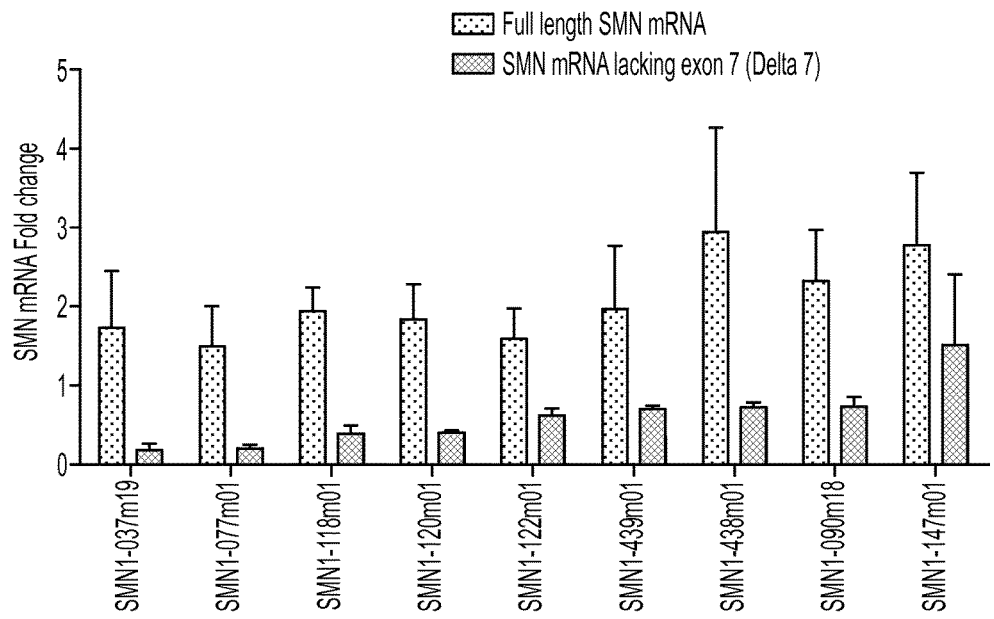

FIG. 20 is a graph showing SMN2 mRNA increase in SMA patient fibroblast cell line GM09677 treated with various splice-switching oligos.

Figure 21:
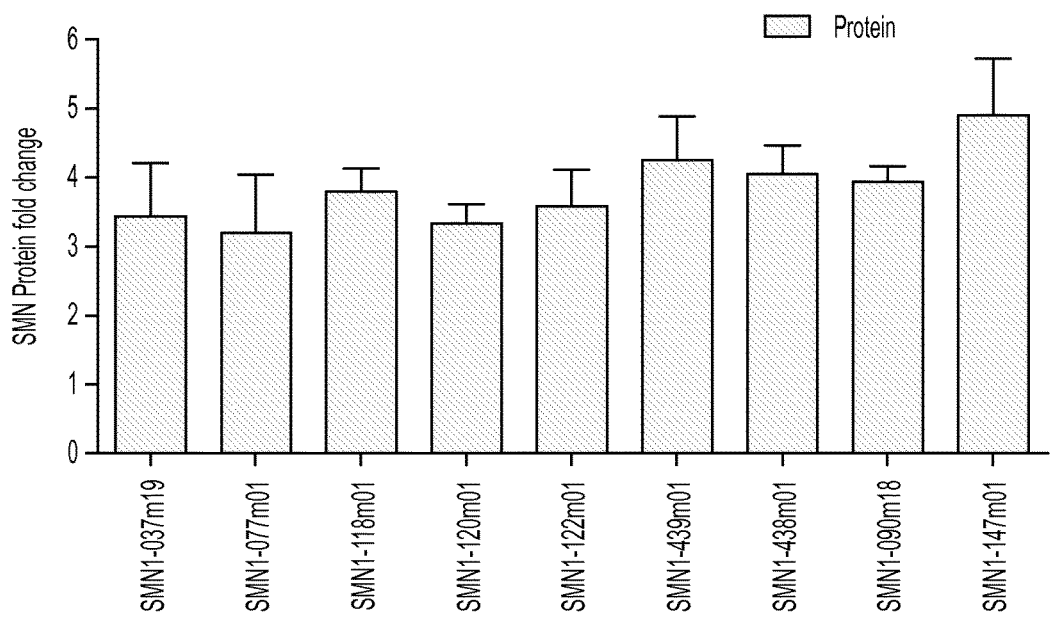

FIG. 21 is a graph showing SMN protein increase in SMA patient fibroblast cell line GM09677 treated with various splice-switching oligos.

BRIEF DESCRIPTION OF TABLES

Table 1: Hexamers that are not seed sequences of human miRNAs

Table 2: Oligonucleotide sequences made for testing in the lab. RQ (column 2) and RQ SE (column 3) shows the activity of the oligo relative to a control well (usually carrier alone) and the standard error or the triplicate replicates of the experiment. [oligo] is shown in nanomolar for in vitro experiments and in milligrams per kilogram of body weight for in vivo experiments.

Table 3: A listing of oligonucleotide modifications. The suffix "Sup" in Table 3 indicates that a 3' end nucleotide may, for synthesis purposes, be conjugated to a solid support. It should be appreciated that in general when conjugated to a solid support for synthesis, the synthesized oligonucleotide is released such that the solid support is not part of the final oligonucleotide product.

Table 4: Oligonucleotide sequences made for testing. The table shows the sequence of the modified nucleotides, where lnaX represents an LNA nucleotide with 3' phosphorothioate linkage, omeX is a 2'-O-methyl nucleotide, dX is a deoxy nucleotide. An s at the end of a nucleotide code indicates that the nucleotide had a 3' phosphorothioate linkage. The "-Sup" at the end of the sequence marks the fact that the 3' end lacks either a phosphate or thiophosphate on the 3' linkage. The Formatted Sequence column shows the sequence of the oligonucleotide, including modified nucleotides, for the oligonucleotides tested in Table 2, 7, 8 and 9.

Table 5: Cell lines

Appendix A from International (PCT) Patent Application No.: PCT/US2013/041440, published as PCT Publication No.: WO/2013/173638, is incorporated herein by reference; Appendix A contains Table 7, which shows RT-PCR data from testing of different oligonucleotides.

Appendix B from International (PCT) Patent Application No.: PCT/US2013/041440, published as PCT Publication No.: WO/2013/173638, is incorporated herein by reference; Appendix B contains Table 8, which shows RT-PCR data from testing of different combination treatments (e.g., two oligonucleotides, an oligonucleotide and a drug).

Appendix C from International (PCT) Patent Application No.: PCT/US2013/041440, published as PCT Publication No.: WO/2013/173638, is incorporated herein by reference; Appendix C contains Table 9, which shows ELISA data from testing of different oligonucleotides Note the following column information for Tables 7-9 in the above-referenced Appendices A-C, respectively. SEQID: sequence identifier of base sequence of oligonucleotide used; Oligo Name: name of oligonucleotide; Avg RQ: average relative quantification of RT-PCR based expression levels of target gene(s); Avg RQ SE: standard error of mean of relative quantification of RT-PCR based expression level; "% SMN over lipo only control" refers to the ratio of SMN protein levels (ng/mg total protein) when compared to Lipofectamine2000 (transfection reagent) treated cells converted into %; "% SMN CVV" refers to coefficient of variation; Exp #: Experiment reference number; Target: target gene; [oligo]: concentration of oligonucleotide used in nM unless otherwise indicated; Cell Line: cell line used; Assay Type: assay used; Time (hr): time of assay following treatment; $2^{nd}$ Drug: name of second oligonucleotide (identified by Oligo Name) or drug used in combination experiment; [$2^{nd}$]: concentration of second oligonucleotide or drug; Units: units of concentration; $3^{rd}$ Drug: name of third oligonucleotide (identified by Oligo Name) or drug used in combination experiment; [$3^{rd}$]: concentration of third oligonucleotide or drug; Notes: comments regarding experiment. Oligo Names correspond to those in Tables 2 and 4.

DETAILED DESCRIPTION OF CERTAIN EMBODIMENTS OF THE INVENTION

Amyotrophic Lateral Sclerosis (ALS), also referred to as Lou Gehrig's disease and Charcot's disease, is a motor neuron disease characterized by rapidly progressive weakness, muscle atrophy and fasciculations, muscle spasticity, difficulty speaking (dysarthria), difficulty swallowing (dysphagia), and difficulty breathing (dyspnea), resulting in eventual death of the patient. These hallmarks of ALS are caused by damage to the neurons that control voluntary muscle movement.

Loss of Gems has been described in both ALS patient-derived cells and in animal models. It has been recognized that loss of Gems also occurs in Spinal Muscular Atrophy (SMA). Gems, or Gemini of coiled bodies, are compact structures that contain SMN protein and are found within cell nuclei. Gems are generally between 0.2 microns and 2 microns in diameter and, when viewed under an electron microscope, resemble a ball of tangled thread. Gems are thought to be involved in snRNP biogenesis. Mutant SOD1 alters SMN localization and prevent Gem formation, which is restored by SMN over-expression. In a mutant SOD1 mouse model of ALS, overexpression of SMN delayed the loss of Gems and disease onset. Thus, in some embodiments, induction of SMN expression provides a therapeutic benefit in ALS (e.g., in familial ALS due to mutant SOD1 (~10% of ALS)). TDP-43 and FUS/TLS interact with SMN in nuclear Gems, and all three proteins function in spliceosome maintenance by controlling levels of U snRNAs. FUS is involved in Gem formation, and the loss of Gems in FUS-deficient cells can be reversed in cells over-expressing exogenous SMN. Thus, a common process involved in the pathogenesis of ALS may be the neuronal loss of spliceosome integrity resulting in abnormal splicing and motor neuron death, which may be due to abnormalities in SMN-containing Gems.

Accordingly, methods and related single stranded oligonucleotides are provided herein that are useful for selectively inducing expression of SMN in cells of a subject having a motor neuron disease, such as ALS, Primary Lateral Sclerosis, Progressive Muscular Atrophy, Progressive Bulbar Palsy or Pseudobulbar Palsy. In some embodiments, methods are provided for inducing expression of particular splice variants of SMN1 or SMN2. Thus, in some embodiments, methods are provided that are useful for controlling the levels in a cell of particular SMN protein isoforms encoded by the splice variants. In some cases, the methods are useful for inducing expression of SMN proteins to levels sufficient to treat ALS. For example, according to some aspects of the invention methods are provided for increasing expression of full-length SMN protein in a cell for purposes of treating ALS. In some embodiments, the methods comprise delivering to the cell a first single stranded oligonucleotide complementary with a PRC2-associated region of SMN1 or SMN2 and a second single stranded oligonucleotide complementary with a splice control sequence of a precursor mRNA of SMN1 or SMN2, in amounts sufficient to increase expression of a mature mRNA of SMN1 or SMN2 that comprises (or includes) exon 7 in the cell. Further aspects of the invention are described in detailed herein.

Accordingly, in some embodiments, methods provided herein comprise a step of administering a single-stranded oligonucleotide as provided herein to a cell or a subject comprising a mutation in a gene selected from SOD1, FUS/TLS, or TDP-43. Mutations in SOD1, FUS/TLS, and TDP-43 have been associated with ALS in humans and animal models. Mutations in SOD1 associated with ALS include A4V, H46R, G37R, L38V, and G93A. Mutations in TDP-43 associated with ALS include D169G, K263E, N267S, G287S, G290A, S292N, G294A, G294V, G295S, G295R, G298S, M311V, A315T, A321G, A321V, Q331K, S332N, G335D, M337V, Q343R, N345K, G348C, G348V, N352S, N352T, R361S, P363A, Y374X, N378D, S379P, S379C, A382T, A382P, I383V, G384R, N390S, N390D, and S393L. Mutations in FUS/TLS associated with ALS include S57del, G156E, G191S, R216C, G225V, G230C, R234C, R234L, R224C, M254V, S402_P441delinsGGGG, S462F, G466VfsX14, R495X, G507D, K510E, S513P, R514G, R514S, G515C, H517Q, H517P, R518K, R518G, R521H, R521G, R521C, R522G, R524S, R524T, and P525L. As described above, mutations in these genes have been shown to affect SMN-containing Gem formation and/or activity.

Mutations in other genes and loci in addition to SOD1, FUS/TLS, and TDP-43 have also been associated with ALS. These genes are listed in the table below.

| Designation | OMIM ID | Gene | Chromosome Locus | NCBI Human Gene ID |
| --- | --- | --- | --- | --- |
| ALS1 | 105400 | SOD1 | 21q22.1 | 6647 |
| ALS2 | 205100 | ALS2 | 2q33.1 | 57679 |
| ALS3 | 606640 | Unknown | 18q21 | n/a |

-continued

Figure 4:
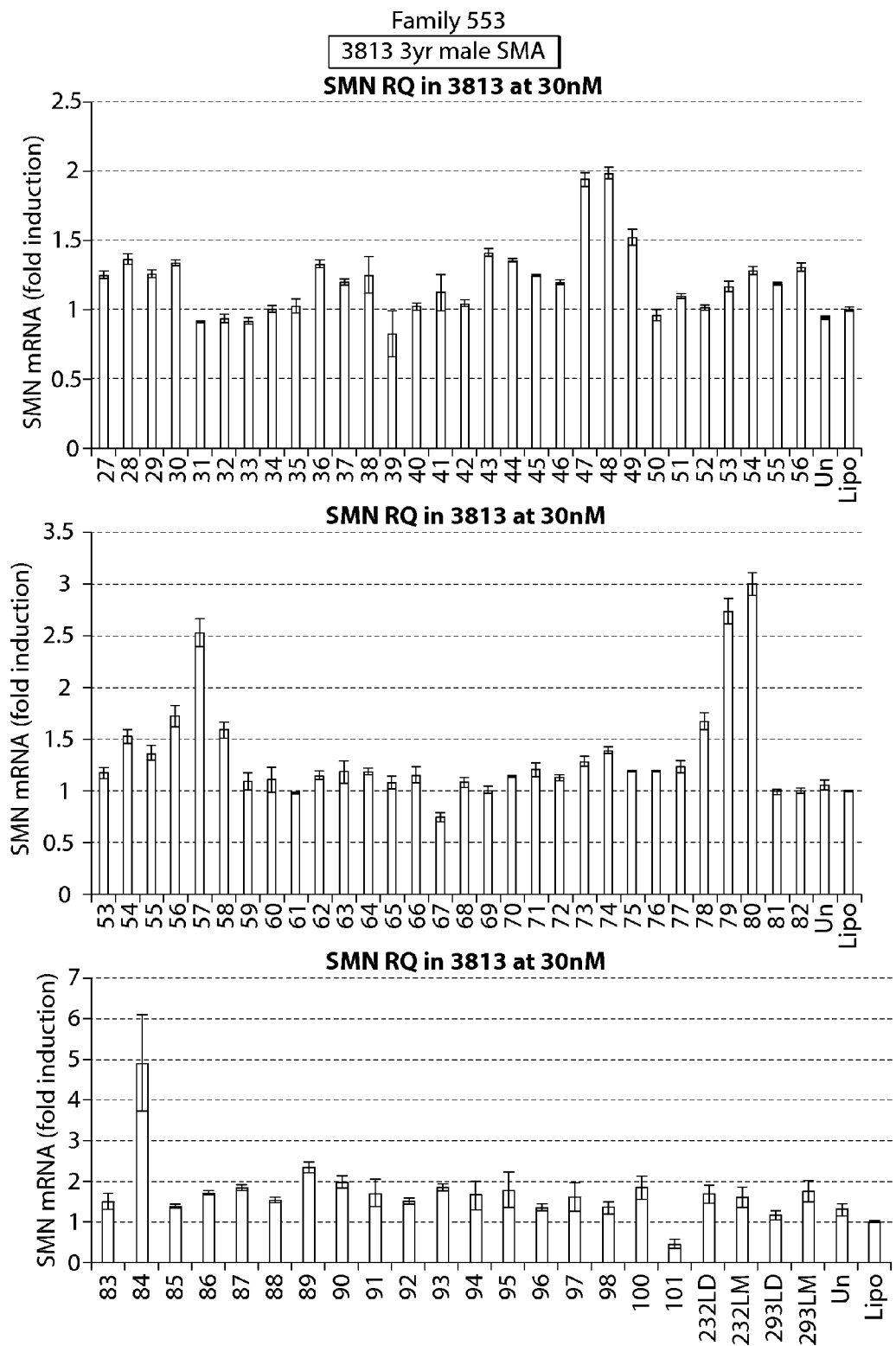
FIG. 4 depicts results of RT-PCR assays showing effects on SMN mRNA expression of oligonucleotides directed against a PRC2-associated region of SMN2 (oligos 1-52 and 59-101) and splice switching oligonucleotides (oligos 53-58) (PCR primers directed against exon 1 of SMN1/2.) in cell line 3813.

| Designation | OMIM ID | Gene | Chromosome Locus | NCBI Human Gene ID |
|---|---|---|---|---|
| ALS4 | 602433 | SETX | 9q34.13 | 23064 |
| ALS5 | 602099 | Unknown | 15q15.1-q21.1 | n/a |
| ALS6 | 608030 | FUS/TLS | 16p11.2 | 2521 |
| ALS7 | 608031 | Unknown | 20p13 | n/a |
| ALS8 | 608627 | VAPB | 20q13.3 | 9217 |
| ALS9 | 611895 | ANG | 14q11.2 | 283 |
| ALS10 | 612069 | TDP-43 | 1p36.2 | 23435 |
| ALS11 | 612577 | FIG4 | 6q21 | 9896 |
| ALS12 | 613435 | OPTN | 10p13 | 10133 |
| ALS13 | 183090 | ATXN2 | 12q24.12 | 6311 |
| ALS14 | 613954 | VCP | 9p13.3 | 7415 |
| ALS15 | 300857 | UBQLN2 | Xp11.23-p11.1 | 29978 |
| ALS16 | 614373 | SIGMAR1 | 9p13.3 | 10280 |
| ALS17 | 614696 | CHMP2B | 3p11 | 25978 |
| ALS18 | 614808 | PFN1 | 17p13.3 | 5216 |
| ALS-FTD | 105550 | C9orf72 | 9p21.2 | 203228 |

Accordingly, in some embodiments, methods provided herein comprise a step of administering a single-stranded oligonucleotide as provided herein to a cell or a subject comprising a mutation associated with ALS in a gene selected from SOD1, ALS2, SETX, FUS/TLS, VAPB, ANG, TDP-43, FIG4, OPTN, ATXN2, VCP, UBQLN2, SIGMAR1, CHMP2B, PFN1, or C9orf72 with an oligonucleotide as provided herein.

In some embodiments, the cell is a cell obtained from or present in a subject having ALS. In some embodiments, the cell is a motor neuron. Motor neurons are efferent nerves (also called effector neurons) that carry signals from the spinal cord to the muscles to produce movement. A motor neuron may directly or indirectly carry signals to the muscles.

Amyotrophic Lateral Sclerosis (ALS)

Aspects of the invention relate to subjects having ALS or cells or tissues obtained from subjects having ALS. ALS is a motor neuron disease characterized by degeneration of the upper and lower motor neurons, which eventually leads to muscle weakness and atrophy throughout the body.

In some embodiments, a subject treated with an oligonucleotide disclosed herein is a subject having one or more symptoms of ALS. ALS may be diagnosed based on symptoms (which may be identified through a physical examination by a medical professional) and/or a series of tests, some of which are designed to distinguish ALS from other diseases that have similar symptoms to ALS. Symptoms of ALS include difficulty breathing, difficulty swallowing (e.g., choking easily, drooling, or gagging), head drop due to weakness of the neck muscles, muscle cramps, muscle contractions called fasciculations, muscle weakness that slowly gets worse (commonly involves one part of the body first, such as the arm or hand, and may eventually lead to difficulty lifting, climbing stairs, and walking), paralysis, speech problems (e.g., slow or abnormal speech pattern), voice changes, hoarseness, and weight loss. A physical examination may be used to identify such symptoms in a patient by examining the patient for one or more of the following: weakness, muscle tremors, muscle spasms, muscle twitching, loss of muscle tissue, twitching of the tongue, abnormal reflexes, stiff or clumsy walk, increased reflexes at the joints, difficulty controlling crying or laughing (sometimes called emotional incontinence), or loss of gag reflex. Exemplary tests that may be used to diagnose or aid in diagnosis of ALS include, but are not limited to: blood and/or urine tests to distinguish ALS from other conditions; breathing test to see if lung muscles are affected; cervical spine CT or MRI to be identify disease or injury to the neck, which can mimic ALS; electromyography to see which nerves or muscles do not work properly; nerve conduction study; genetic testing; head CT or MRI to distinguish ALS from other conditions; swallowing studies; and spinal tap (lumbar puncture). Other conditions or diseases that cause ALS-like symptoms include infectious diseases (such as human immunodeficiency virus (HIV), human T-cell leukemia virus (HTLV), polio, West Nile virus, and Lyme disease), multiple sclerosis, post-polio syndrome, multifocal motor neuropathy, and spinal muscular atrophy.

In some embodiments, a subject diagnosed with ALS may be monitored for progression of the disease. In some embodiments, the subject is monitored using the ALS functional rating scale (ALSFRS, see, e.g., The Amyotrophic Lateral Sclerosis Functional Rating Scale: Assessment of Activities of Daily Living in Patients With Amyotrophic Lateral Sclerosis. Arch Neurol. 1996; 53(2):141-147) or the revised ALS functional rating scale (ALSFRS-R, see, e.g., Cedarbaum J M, Stambler N, Malta E, Fuller C, Hilt D, Thurmond B, Nakanishi A) or another appropriate scale. The ALSFRS-R: a revised ALS functional rating scale that incorporates assessments of respiratory function. BDNF ALS Study Group (Phase III). J Neurol Sci. 1999 Oct. 31; 169(1-2):13-21). The ALSFRS and ALSFRS-R measure the following categories of behavior: speech, salivation, swallowing, handwriting, cutting food and handling utensils (with or without gastrostomy), dressing and hygiene, turning in bed and adjusting bed clothes, walking, climbing stairs, and breathing. The ALSFRS-R further includes additional assessments of dyspnea, orthopnea, and the need for ventilatory support. An exemplary ALSFRS-R test is provided through the Center for Outcomes Research website under the ALS C.A.R.E project (see ALS Functional Rating Scale Scoring Tool Online). In some embodiments, a score may be calculated based on the characteristic of each of these categories (normal or slight disturbance giving a high score for each category, and marked or severe disturbance giving a low score for each category). In some embodiments, the score for each category is then added together to create a total score. In some embodiments, the test may be given multiple times, in order to track changes in the total score over time. In some embodiments, an increase may indicate progression of ALS; whereas decrease or unchanging score may indicate stabilization or regression of ALS.

Polycomb Repressive Complex 2 (PRC2)-Interacting RNAs

Aspects of the invention provided herein relate to the discovery of polycomb repressive complex 2 (PRC2)-interacting RNAs. Polycomb repressive complex 2 (PRC2) is a histone methyltransferase and a known epigenetic regulator involved in silencing of genomic regions through methylation of histone H3. Among other functions, PRC2 interacts with long noncoding RNAs (lncRNAs), such as RepA, Xist, and Tsix, to catalyze trimethylation of histone H3-lysine27. PRC2 contains four subunits, Eed, Suz12, RbAp48, and Ezh2. Aspects of the invention relate to the recognition that single stranded oligonucleotides that bind to PRC2-associated regions of RNAs (e.g., lncRNAs) that are expressed from within a genomic region that encompasses or that is in functional proximity to the SMN1 or SMN2 gene can induce or enhance expression of SMN1 or SMN2. In some embodiments, this upregulation is believed to result from inhibition of PRC2 mediated repression of SMN1 or SMN2.

As used herein, the term "PRC2-associated region" refers to a region of a nucleic acid that comprises or encodes a sequence of nucleotides that interact directly or indirectly with a component of PRC2. A PRC2-associated region may be present in a RNA (e.g., a long non-coding RNA (lncRNA)) that interacts with a PRC2. A PRC2-associated region may be present in a DNA that encodes an RNA that interacts with PRC2. In some cases, the PRC2-associated region is equivalently referred to as a PRC2-interacting region.

In some embodiments, a PRC2-associated region is a region of an RNA that crosslinks to a component of PRC2 in response to in situ ultraviolet irradiation of a cell that expresses the RNA, or a region of genomic DNA that encodes that RNA region. In some embodiments, a PRC2-associated region is a region of an RNA that immunoprecipitates with an antibody that targets a component of PRC2, or a region of genomic DNA that encodes that RNA region. In some embodiments, a PRC2-associated region is a region of an RNA that immunoprecipitates with an antibody that binds specifically to SUZ12, EED, EZH2 or RBBP4 (which as noted above are components of PRC2), or a region of genomic DNA that encodes that RNA region.

In some embodiments, a PRC2-associated region is a region of an RNA that is protected from nucleases (e.g., RNases) in an RNA-immunoprecipitation assay that employs an antibody that targets a component of PRC2, or a region of genomic DNA that encodes that protected RNA region. In some embodiments, a PRC2-associated region is a region of an RNA that is protected from nucleases (e.g., RNases) in an RNA-immunoprecipitation assay that employs an antibody that targets SUZ12, EED, EZH2 or RBBP4, or a region of genomic DNA that encodes that protected RNA region.

In some embodiments, a PRC2-associated region is a region of an RNA within which occur a relatively high frequency of sequence reads in a sequencing reaction of products of an RNA-immunoprecipitation assay that employs an antibody that targets a component of PRC2, or a region of genomic DNA that encodes that RNA region. In some embodiments, a PRC2-associated region is a region of an RNA within which occur a relatively high frequency of sequence reads in a sequencing reaction of products of an RNA-immunoprecipitation assay that employs an antibody that binds specifically to SUZ12, EED, EZH2 or RBBP4, or a region of genomic DNA that encodes that protected RNA region. In such embodiments, the PRC2-associated region may be referred to as a "peak."

In some embodiments, a PRC2-associated region comprises a sequence of 40 to 60 nucleotides that interact with PRC2 complex. In some embodiments, a PRC2-associated region comprises a sequence of 40 to 60 nucleotides that encode an RNA that interacts with PRC2. In some embodiments, a PRC2-associated region comprises a sequence of up to 5 kb in length that comprises a sequence (e.g., of 40 to 60 nucleotides) that interacts with PRC2. In some embodiments, a PRC2-associated region comprises a sequence of up to 5 kb in length within which an RNA is encoded that has a sequence (e.g., of 40 to 60 nucleotides) that is known to interact with PRC2. In some embodiments, a PRC2-associated region comprises a sequence of about 4 kb in length that comprise a sequence (e.g., of 40 to 60 nucleotides) that interacts with PRC2. In some embodiments, a PRC2-associated region comprises a sequence of about 4 kb in length within which an RNA is encoded that includes a sequence (e.g., of 40 to 60 nucleotides) that is known to interact with PRC2. In some embodiments, a PRC2-associated region has a sequence as set forth in any one of SEQ ID NOS: 9 to 29. In some embodiments, a PRC2-associated region has a sequence as set forth in any one of SEQ ID NOS: 24 to 29.

In some embodiments, single stranded oligonucleotides are provided that specifically bind to, or are complementary to, a PRC2-associated region in a genomic region that encompasses or that is in proximity to the SMN1 or SMN2 gene. In some embodiments, single stranded oligonucleotides are provided that specifically bind to, or are complementary to, a PRC2-associated region that has a sequence as set forth in any one of SEQ ID NOS: 9 to 29. In some embodiments, single stranded oligonucleotides are provided that specifically bind to, or are complementary to, a PRC2-associated region that has a sequence as set forth in any one of SEQ ID NOS: 9 to 29 combined with up to 2 kb, up to 5 kb, or up to 10 kb of flanking sequences from a corresponding genomic region to which these SEQ IDs map (e.g., in a human genome). In some embodiments, single stranded oligonucleotides have a sequence as set forth in any one of SEQ ID NOS: 30 to 13087 or 13108 to 13116. In some embodiments, single stranded oligonucleotides have a sequence as set forth in Table 2. In some embodiments, a PRC2 associated region of SMN1 or SMN2 against which a single stranded oligonucleotide is complementary is selected from SEQ ID NOS: 24-29. In some embodiments, a single stranded oligonucleotide that is complementary with a PRC2 associated region of SMN1 or SMN2 comprises a sequence selected from SEQ ID NOS: 1158-1159, 1171, 1482-1483, 1485-1486, 2465-2471, 2488-2490, 2542-2546, 2656-2657, 2833-2835, 3439-3440, 3916-3918, 4469-4472, 4821, 5429, 5537, 6061, 7327, 8330-13061, 13062-13087, and 13108-13116. In some embodiments, a single stranded oligonucleotide that is complementary with a PRC2 associated region of SMN1 or SMN2 comprises a sequence selected from 11395, 11394, 10169, and 10170.

Without being bound by a theory of invention, these oligonucleotides are able to interfere with the binding of and function of PRC2, by preventing recruitment of PRC2 to a specific chromosomal locus. For example, a single administration of single stranded oligonucleotides designed to specifically bind a PRC2-associated region lncRNA can stably displace not only the lncRNA, but also the PRC2 that binds to the lncRNA, from binding chromatin. After displacement, the full complement of PRC2 is not recovered for up to 24 hours. Further, lncRNA can recruit PRC2 in a cis fashion, repressing gene expression at or near the specific chromosomal locus from which the lncRNA was transcribed.

Methods of modulating gene expression are provided, in some embodiments, that may be carried out in vitro, ex vivo, or in vivo. It is understood that any reference to uses of compounds throughout the description contemplates use of the compound in preparation of a pharmaceutical composition or medicament for use in the treatment of condition (e.g., ALS) associated with decreased levels or activity of SMN1 or SMN2. Thus, as one nonlimiting example, this aspect of the invention includes use of such single stranded oligonucleotides in the preparation of a medicament for use in the treatment of disease, wherein the treatment involves upregulating expression of SMN1 or SMN2.

In further aspects of the invention, methods are provided for selecting a candidate oligonucleotide for activating expression of SMN1 or SMN2. The methods generally involve selecting as a candidate oligonucleotide, a single stranded oligonucleotide comprising a nucleotide sequence that is complementary to a PRC2-associated region (e.g., a nucleotide sequence as set forth in any one of SEQ ID NOS: 9 to 29). In some embodiments, sets of oligonucleotides may be selected that are enriched (e.g., compared with a random selection of oligonucleotides) in oligonucleotides that activate expression of SMN1 or SMN2.

Single Stranded Oligonucleotides for Modulating Expression of SMN1 or SMN2

In one aspect of the invention, single stranded oligonucleotides complementary to the PRC2-associated regions are provided for modulating expression of SMN1 or SMN2 in a cell. In some embodiments, expression of SMN1 or SMN2 is upregulated or increased. In some embodiments, single stranded oligonucleotides complementary to these PRC2-associated regions inhibit the interaction of PRC2 with long RNA transcripts such that gene expression is upregulated or increased. In some embodiments, single stranded oligonucleotides complementary to these PRC2-associated regions inhibit the interaction of PRC2 with long RNA transcripts, resulting in reduced methylation of histone H3 and reduced gene inactivation, such that gene expression is upregulated or increased. In some embodiments, this interaction may be disrupted or inhibited due to a change in the structure of the long RNA that prevents or reduces binding to PRC2. The oligonucleotide may be selected using any of the methods disclosed herein for selecting a candidate oligonucleotide for activating expression of SMN1 or SMN2.

The single stranded oligonucleotide may comprise a region of complementarity that is complementary with a PRC2-associated region of a nucleotide sequence set forth in any one of SEQ ID NOS: 1 to 8. The region of complementarity of the single stranded oligonucleotide may be complementary with at least 6, e.g., at least 7, at least 8, at least 9, at least 10, at least 15 or more consecutive nucleotides of the PRC2-associated region.

It should be appreciated that due the high homology between SMN1 and SMN2, single stranded oligonucleotides that are complementary with a PRC2-associated region of SMN1 are often also complementary with a corresponding PRC2-associated region of SMN2.

The PRC2-associated region may map to a position in a chromosome between 50 kilobases upstream of a 5'-end of the SMN1 or SMN2 gene and 50 kilobases downstream of a 3'-end of the SMN1 or SMN2 gene. The PRC2-associated region may map to a position in a chromosome between 25 kilobases upstream of a 5'-end of the SMN1 or SMN2 gene and 25 kilobases downstream of a 3'-end of the SMN1 or SMN2 gene. The PRC2-associated region may map to a position in a chromosome between 12 kilobases upstream of a 5'-end of the SMN1 or SMN2 gene and 12 kilobases downstream of a 3'-end of the SMN1 or SMN2 gene. The PRC2-associated region may map to a position in a chromosome between 5 kilobases upstream of a 5'-end of the SMN1 or SMN2 gene and 5 kilobases downstream of a 3'-end of the SMN1 or SMN2 gene.

The genomic position of the selected PRC2-associated region relative to the SMN1 or SMN2 gene may vary. For example, the PRC2-associated region may be upstream of the 5' end of the SMN1 or SMN2 gene. The PRC2-associated region may be downstream of the 3' end of the SMN1 or SMN2 gene. The PRC2-associated region may be within an intron of the SMN1 or SMN2 gene. The PRC2-associated region may be within an exon of the SMN1 or SMN2 gene. The PRC2-associated region may traverse an intron-exon junction, a 5'-UTR-exon junction or a 3'-UTR-exon junction of the SMN1 or SMN2 gene.

The single stranded oligonucleotide may comprise a sequence having the formula X-Y-Z, in which X is any nucleotide, Y is a nucleotide sequence of 6 nucleotides in length that is not a human seed sequence of a microRNA, and Z is a nucleotide sequence of varying length. In some embodiments X is the 5' nucleotide of the oligonucleotide. In some embodiments, when X is anchored at the 5' end of the oligonucleotide, the oligonucleotide does not have any nucleotides or nucleotide analogs linked 5' to X. In some embodiments, other compounds such as peptides or sterols may be linked at the 5' end in this embodiment as long as they are not nucleotides or nucleotide analogs. In some embodiments, the single stranded oligonucleotide has a sequence 5'X-Y-Z and is 8-50 nucleotides in length. Oligonucleotides that have these sequence characteristics are predicted to avoid the miRNA pathway. Therefore, in some embodiments, oligonucleotides having these sequence characteristics are unlikely to have an unintended consequence of functioning in a cell as a miRNA molecule. The Y sequence may be a nucleotide sequence of 6 nucleotides in length set forth in Table 1.

The single stranded oligonucleotide may have a sequence that does not contain guanosine nucleotide stretches (e.g., 3 or more, 4 or more, 5 or more, 6 or more consecutive guanosine nucleotides). In some embodiments, oligonucleotides having guanosine nucleotide stretches have increased non-specific binding and/or off-target effects, compared with oligonucleotides that do not have guanosine nucleotide stretches.

The single stranded oligonucleotide may have a sequence that has less than a threshold level of sequence identity with every sequence of nucleotides, of equivalent length, that map to a genomic position encompassing or in proximity to an off-target gene. For example, an oligonucleotide may be designed to ensure that it does not have a sequence that maps to genomic positions encompassing or in proximity with all known genes (e.g., all known protein coding genes) other than SMN1 or SMN2. In a similar embodiment, an oligonucleotide may be designed to ensure that it does not have a sequence that maps to any other known PRC2-associated region, particularly PRC2-associated regions that are functionally related to any other known gene (e.g., any other known protein coding gene). In either case, the oligonucleotide is expected to have a reduced likelihood of having off-target effects. The threshold level of sequence identity may be 50%, 60%, 70%, 80%, 85%, 90%, 95%, 99% or 100% sequence identity.

The single stranded oligonucleotide may have a sequence that is complementary to a PRC2-associated region that encodes an RNA that forms a secondary structure comprising at least two single stranded loops. In has been discovered that, in some embodiments, oligonucleotides that are complementary to a PRC2-associated region that encodes an RNA that forms a secondary structure comprising one or more single stranded loops (e.g., at least two single stranded loops) have a greater likelihood of being active (e.g., of being capable of activating or enhancing expression of a target gene) than a randomly selected oligonucleotide. In some cases, the secondary structure may comprise a double stranded stem between the at least two single stranded loops. Accordingly, the region of complementarity between the oligonucleotide and the PRC2-associated region may be at a location of the PRC2 associated region that encodes at least a portion of at least one of the loops. In some cases, the region of complementarity between the oligonucleotide and the PRC2-associated region may be at a location of the PRC2-associated region that encodes at least a portion of at least two of the loops. In some cases, the region of complementarity between the oligonucleotide and the PRC2-associated region may be at a location of the PRC2 associated region that encodes at least a portion of the double stranded stem. In some embodiments, a PRC2-associated region (e.g., of an lncRNA) is identified (e.g., using RIP-Seq methodology or information derived therefrom). In some embodiments, the predicted secondary structure RNA (e.g., lncRNA) containing the PRC2-associated region is determined using RNA secondary structure prediction algorithms, e.g., RNAfold, mfold. In some embodiments, oligonucleotides are designed to target a region of the RNA that forms a secondary structure comprising one or more single stranded loop (e.g., at least two single stranded loops) structures which may comprise a double stranded stem between the at least two single stranded loops.

The single stranded oligonucleotide may have a sequence that is has greater than 30% G-C content, greater than 40% G-C content, greater than 50% G-C content, greater than 60% G-C content, greater than 70% G-C content, or greater than 80% G-C content. The single stranded oligonucleotide may have a sequence that has up to 100% G-C content, up to 95% G-C content, up to 90% G-C content, or up to 80% G-C content. In some embodiments in which the oligonucleotide is 8 to 10 nucleotides in length, all but 1, 2, 3, 4, or 5 of the nucleotides of the complementary sequence of the PRC2-associated region are cytosine or guanosine nucleotides. In some embodiments, the sequence of the PRC2-associated region to which the single stranded oligonucleotide is complementary comprises no more than 3 nucleotides selected from adenine and uracil.

The single stranded oligonucleotide may be complementary to a chromosome of a different species (e.g., a mouse, rat, rabbit, goat, monkey, etc.) at a position that encompasses or that is in proximity to that species' homolog of SMN1 or SMN2. The single stranded oligonucleotide may be complementary to a human genomic region encompassing or in proximity to the SMN1 or SMN2 gene and also be complementary to a mouse genomic region encompassing or in proximity to the mouse homolog of SMN1 or SMN2. For example, the single stranded oligonucleotide may be complementary to a sequence as set forth in SEQ ID NO: 1, 2, 4, or 5, which is a human genomic region encompassing or in proximity to the SMN1 or SMN2 gene, and also be complementary to a sequence as set forth in SEQ ID NO:7 or 8, which is a mouse genomic region encompassing or in proximity to the mouse homolog of the SMN1 or SMN2 gene. Oligonucleotides having these characteristics may be tested in vivo or in vitro for efficacy in multiple species (e.g., human and mouse). This approach also facilitates development of clinical candidates for treating human disease by selecting a species in which an appropriate animal exists for the disease.

In some embodiments, the region of complementarity of the single stranded oligonucleotide is complementary with at least 8 to 15, 8 to 30, 8 to 40, or 10 to 50, or 5 to 50, or 5 to 40 bases, e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 consecutive nucleotides of a PRC2-associated region. In some embodiments, the region of complementarity is complementary with at least 8 consecutive nucleotides of a PRC2-associated region. In some embodiments the sequence of the single stranded oligonucleotide is based on an RNA sequence that binds to PRC2, or a portion thereof, said portion having a length of from 5 to 40 contiguous base pairs, or about 8 to 40 bases, or about 5 to 15, or about 5 to 30, or about 5 to 40 bases, or about 5 to 50 bases. Complementary, as the term is used in the art, refers to the capacity for precise pairing between two nucleotides. For example, if a nucleotide at a certain position of an oligonucleotide is capable of hydrogen bonding with a nucleotide at the same position of PRC2-associated region, then the single stranded nucleotide and PRC2-associated region are considered to be complementary to each other at that position. The single stranded nucleotide and PRC2-associated region are complementary to each other when a sufficient number of corresponding positions in each molecule are occupied by nucleotides that can hydrogen bond with each other through their bases. Thus, "complementary" is a term which is used to indicate a sufficient degree of complementarity or precise pairing such that stable and specific binding occurs between the single stranded nucleotide and PRC2-associated region. For example, if a base at one position of a single stranded nucleotide is capable of hydrogen bonding with a base at the corresponding position of a PRC2-associated region, then the bases are considered to be complementary to each other at that position. 100% complementarity is not required.

The single stranded oligonucleotide may be at least 80% complementary to (optionally one of at least 85%, 90%, 91%, 92%, 93%, 94%, 95%, 96%, 97%, 98%, 99% or 100% complementary to) the consecutive nucleotides of a PRC2-associated region. In some embodiments the single stranded oligonucleotide may contain 1, 2 or 3 base mismatches compared to the portion of the consecutive nucleotides of a PRC2-associated region. In some embodiments the single stranded oligonucleotide may have up to 3 mismatches over 15 bases, or up to 2 mismatches over 10 bases.

It is understood in the art that a complementary nucleotide sequence need not be 100% complementary to that of its target to be specifically hybridizable. In some embodiments, a complementary nucleic acid sequence for purposes of the present disclosure is specifically hybridizable when binding of the sequence to the target molecule (e.g., lncRNA) interferes with the normal function of the target (e.g., lncRNA) to cause a loss of activity (e.g., inhibiting PRC2-associated repression with consequent up-regulation of gene expression) and there is a sufficient degree of complementarity to avoid non-specific binding of the sequence to non-target sequences under conditions in which avoidance of non-specific binding is desired, e.g., under physiological conditions in the case of in vivo assays or therapeutic treatment, and in the case of in vitro assays, under conditions in which the assays are performed under suitable conditions of stringency.

In some embodiments, the single stranded oligonucleotide is 7, 8, 9, 10, 11, 12, 13, 14, 15, 16, 17, 18, 19, 20, 21, 22, 23, 24, 25, 26, 27, 28, 29, 30, 35, 40, 45, 50 or more nucleotides in length. In a preferred embodiment, the oligonucleotide is 8 to 30 nucleotides in length.

In some embodiments, the PRC2-associated region occurs on the same DNA strand as a gene sequence (sense). In some embodiments, the PRC2-associated region occurs on the opposite DNA strand as a gene sequence (anti-sense). Oligonucleotides complementary to a PRC2-associated region can bind either sense or anti-sense sequences. Base pairings may include both canonical Watson-Crick base pairing and non-Watson-Crick base pairing (e.g., Wobble base pairing and Hoogsteen base pairing). It is understood that for complementary base pairings, adenosine-type bases (A) are complementary to thymidine-type bases (T) or uracil-type bases (U), that cytosine-type bases (C) are complementary to guanosine-type bases (G), and that universal bases such as 3-nitropyrrole or 5-nitroindole can hybridize to and are considered complementary to any A, C, U, or T. Inosine (I) has also been considered in the art to be a universal base and is considered complementary to any A, C, U or T.

In some embodiments, any one or more thymidine (T) nucleotides (or modified nucleotide thereof) or uridine (U) nucleotides (or a modified nucleotide thereof) in a sequence provided herein, including a sequence provided in the sequence listing, may be replaced with any other nucleotide suitable for base pairing (e.g., via a Watson-Crick base pair) with an adenosine nucleotide. In some embodiments, any one or more thymidine (T) nucleotides (or modified nucleotide thereof) or uridine (U) nucleotides (or a modified nucleotide thereof) in a sequence provided herein, including a sequence provided in the sequence listing, may be suitably replaced with a different pyrimidine nucleotide or vice versa. In some embodiments, any one or more thymidine (T) nucleotides (or modified nucleotide thereof) in a sequence provided herein, including a sequence provided in the sequence listing, may be suitably replaced with a uridine (U) nucleotide (or a modified nucleotide thereof) or vice versa. In some embodiments, GC content of the single stranded oligonucleotide is preferably between about 30-60%. Contiguous runs of three or more Gs or Cs may not be preferable in some embodiments. Accordingly, in some embodiments, the oligonucleotide does not comprise a stretch of three or more guanosine nucleotides.

In some embodiments, the single stranded oligonucleotide specifically binds to, or is complementary to an RNA that is encoded in a genome (e.g., a human genome) as a single contiguous transcript (e.g., a non-spliced RNA). In some embodiments, the single stranded oligonucleotide specifically binds to, or is complementary to an RNA that is encoded in a genome (e.g., a human genome), in which the distance in the genome between the 5'end of the coding region of the RNA and the 3' end of the coding region of the RNA is less than 1 kb, less than 2 kb, less than 3 kb, less than 4 kb, less than 5 kb, less than 7 kb, less than 8 kb, less than 9 kb, less than 10 kb, or less than 20 kb.

It is to be understood that any oligonucleotide provided herein can be excluded.

In some embodiments, single stranded oligonucleotides disclosed herein may increase expression of mRNA corresponding to the gene by at least about 50% (i.e. 150% of normal or 1.5 fold), or by about 2 fold to about 5 fold. In some embodiments, expression may be increased by at least about 15 fold, 20 fold, 30 fold, 40 fold, 50 fold or 100 fold, or any range between any of the foregoing numbers. It has also been found that increased mRNA expression has been shown to correlate to increased protein expression.

In some or any of the embodiments of the oligonucleotides described herein, or processes for designing or synthesizing them, the oligonucleotides will upregulate gene expression and may specifically bind or specifically hybridize or be complementary to the PRC2 binding RNA that is transcribed from the same strand as a protein coding reference gene. The oligonucleotide may bind to a region of the PRC2 binding RNA that originates within or overlaps an intron, exon, intron exon junction, 5' UTR, 3' UTR, a translation initiation region, or a translation termination region of a protein coding sense strand of a reference gene (refGene).

In some or any of the embodiments of oligonucleotides described herein, or processes for designing or synthesizing them, the oligonucleotides will upregulate gene expression and may specifically bind or specifically hybridize or be complementary to a PRC2 binding RNA that transcribed from the opposite strand (the antisense strand) of a protein coding reference gene. The oligonucleotide may bind to a region of the PRC2 binding RNA that originates within or overlaps an intron, exon, intron exon junction, 5' UTR, 3' UTR, a translation initiation region, or a translation termination region of a protein coding antisense strand of a reference gene.

The oligonucleotides described herein may be modified, e.g., comprise a modified sugar moiety, a modified internucleoside linkage, a modified nucleotide and/or combinations thereof. In addition, the oligonucleotides can exhibit one or more of the following properties: do not induce substantial cleavage or degradation of the target RNA; do not cause substantially complete cleavage or degradation of the target RNA; do not activate the RNAse H pathway; do not activate RISC; do not recruit any Argonaute family protein; are not cleaved by Dicer; do not mediate alternative splicing; are not immune stimulatory; are nuclease resistant; have improved cell uptake compared to unmodified oligonucleotides; are not toxic to cells or mammals; may have improved endosomal exit; do interfere with interaction of lncRNA with PRC2, preferably the Ezh2 subunit but optionally the Suz12, Eed, RbAp46/48 subunits or accessory factors such as Jarid2; do decrease histone H3 lysine27 methylation and/or do upregulate gene expression.

Oligonucleotides that are designed to interact with RNA to modulate gene expression are a distinct subset of base sequences from those that are designed to bind a DNA target (e.g., are complementary to the underlying genomic DNA sequence from which the RNA is transcribed).

Splice Switching Oligonucleotides

Aspects of the invention provide strategies for targeting SMN1 or SMN2 precursor mRNA to affect splicing to minimize exon skipping. Accordingly, aspects of the invention provide therapeutic compounds useful for the treatment of ALS. In some embodiments, oligonucleotides, referred to herein as "splice switching oligonucleotides" are provided that modulate SMN2 splicing. Methods and related compositions, compounds, and kits are provided, in some embodiments, that are useful for increasing expression of full-length. SMN protein in a cell. The methods generally involve delivering to a cell a first single stranded oligonucleotide complementary with at least 8 consecutive nucleotides of a PRC2-associated region of SMN2 and a second single stranded oligonucleotide complementary with a splice control sequence of a precursor mRNA of SMN2, in amounts sufficient to increase expression of a mature mRNA of SMN2 that comprises (or includes) exon 7 in the cell. Any of the single stranded oligonucleotides that are complementary with at least 8 consecutive nucleotides of a PRC2-associated region of SMN1 or SMN2 may be used. It should be appreciated that single stranded oligonucleotides that are complementary with a splice control sequence may alternatively be referred herein, as splice switching oligonucleotides.

Splice switching oligonucleotides typically comprise a sequence complementary to a splice control sequence (e.g., a intronic splicing silencer sequence) of a precursor mRNA, and are capable of binding to and affecting processing of the precursor mRNA. Splice switching oligonucleotides may be complementary with a region of an exon, a region of an intron or an intron/exon junction. In some embodiments, the splice control sequence comprises the sequence: CAG-CAUUAUGAAAG (SEQ ID NO: 13100) or a portion thereof. In some embodiments, the splice control sequence comprises at least one hnRNAP binding sequence. In some embodiments, splice switching oligonucleotides that target SMN1 or SMN2 function based on the premise that there is a competition between the 3' splice sites of exons 7 and 8 for pairing with the 5' splice site of exon 6, so impairing the recognition of the 3' splice site of exon 8 favors exon 7 inclusion. In some embodiments, splice switching oligonucleotides are provided that promote SMN2 exon 7 inclusion and full-length SMN protein expression, in which the oligonucleotides are complementary to the intron 7/exon 8 junction. In some embodiments, splice switching oligonucleotide are composed of a segment complementary to an exon of SMN1 or SMN2 (e.g., exon 7). In some embodiments, splice switching oligonucleotides comprise a tail (e.g., a non-complementary tail) consisting of RNA sequences with binding motifs recognized by a serine/arginine-rich (SR) protein. In some embodiments, splice switching oligonucleotides are complementary (at least partially) with an intronic splicing silencer (ISS). In some embodiments, the ISS is in intron 6 or intron 7 of SMN1 or SMN2. In some embodiments, splice switching oligonucleotides comprise an antisense moiety complementary to a target exon or intron (e.g., of SMN1 or SMN2) and a minimal RS domain peptide similar to the splicing activation domain of SR proteins. In some embodiments, the splice switching oligonucleotide is 7, 8, 9, 10, 11, 12, 13, 14, 15, 16, 17, 18, 19, 20, 21, 22, 23, 24, 25, 26, 27, 28, 29, 30, 35, 40, 45, 50 or more nucleotides in length. In one embodiment, the oligonucleotide is 8 to 30 nucleotides in length.

Linkers

Any of the oligonucleotides disclosed herein may be linked to one or more other oligonucleotides disclosed herein by a linker, e.g., a cleavable linker. Accordingly, in some embodiments, compounds are provided that comprise a single stranded oligonucleotide complementary with a PRC2-associated region of a gene that is linked via a linker to a single stranded oligonucleotide complementary to a splice control sequence of a precursor mRNA of the gene. In some embodiments, compounds are provided that have the general formula A-B-C, in which A is a single stranded oligonucleotide complementary with a PRC2-associated region of a gene, B is a linker, and C is a single stranded oligonucleotide complementary to a splice control sequence of a precursor mRNA of the gene. In some embodiments, linker B comprises an oligonucleotide, peptide, low pH labile bond, or disulfide bond. In some embodiments, the compounds is orientated as 5'-A-B-C-3'. In some embodiments, the compound is orientated as 3'-A-B-C-5'. In some embodiments, where B is an oligonucleotide, the 3' end of A is linked to the 5' end of B, and the 3' end of B is linked to 5' end of C. In some embodiments, where B is an oligonucleotide, the 5' end of A is linked to the 3' end of B, and the 5' end of B is linked to 3' end of C. In some embodiments, where B is an oligonucleotide, the 5' end of A is linked to the 5' end of B, and/or the 3' end of B is linked to the 3' end of C. In some embodiments, where B is an oligonucleotide, the 3' end of A is linked to the 3' end of B, and/or the 5' end of B is linked to the 5' end of C.

The term "linker" generally refers to a chemical moiety that is capable of covalently linking two or more oligonucleotides. In some embodiments, at least one bond comprised or contained within the linker is capable of being cleaved (e.g., in a biological context, such as in a mammalian extract, such as an endosomal extract), such that at least two oligonucleotides are no longer covalently linked to one another after bond cleavage. It will be appreciated that, in some embodiments, a provided linker may include a region that is non-cleavable, as long as the linker also comprises at least one bond that is cleavable.

In some embodiments, the linker comprises a polypeptide that is more susceptible to cleavage by an endopeptidase in the mammalian extract than the oligonucleotides. The endopeptidase may be a trypsin, chymotrypsin, elastase, thermolysin, pepsin, or endopeptidase V8. The endopeptidase may be a cathepsin B, cathepsin D, cathepsin L, cathepsin C, papain, cathepsin S or endosomal acidic insulinase. For example, the linker comprise a peptide having an amino acid sequence selected from: ALAL, APISFFELG, FL, GFN, R/KXX, GRWHTVGLRWE, YL, GF, and FF, in which X is any amino acid.

In some embodiments, the linker comprises the formula $-(CH_2)_n S-S(CH_2)_m-$, wherein n and m are independently integers from 0 to 10.

In some embodiments, the linker may comprise an oligonucleotide that is more susceptible to cleavage by an endonuclease in the mammalian extract than the oligonucleotides. The linker may have a nucleotide sequence comprising from 1 to 10 thymidines or uridines. The linker may have a nucleotide sequence comprising deoxyribonucleotides linked through phosphodiester internucleotide linkages. The linker may have a nucleotide sequence comprising from 1 to 10 thymidines or uridines linked through phosphodiester internucleotide linkages. The linker may have a nucleotide sequence comprising from 1 to 10 thymidines or uridines linked through phosphorothioate internucleotide linkages.

In some embodiments, at least one linker is 2-fold, 3-fold, 4-fold, 5-fold, 10-fold or more sensitive to enzymatic cleavage in the presence of a mammalian extract than at least two oligonucleotides. It should be appreciated that different linkers can be designed to be cleaved at different rates and/or by different enzymes in compounds comprising two or more linkers. Similarly different linkers can be designed to be sensitive to cleavage in different tissues, cells or subcellular compartments in compounds comprising two or more linkers. This can advantageously permit compounds to have oligonucleotides that are released from compounds at different rates, by different enzymes, or in different tissues, cells or subcellular compartments thereby controlling release of the monomeric oligonucleotides to a desired in vivo location or at a desired time following administration.

In certain embodiments, linkers are stable (e.g., more stable than the oligonucleotides they link together) in plasma, blood or serum which are richer in exonucleases, and less stable in the intracellular environments which are relatively rich in endonucleases. In some embodiments, a linker is considered "non-cleavable" if the linker's half-life is at least 24, or 28, 32, 36, 48, 72, 96 hours or longer under the conditions described here, such as in liver homogenates. Conversely, in some embodiments, a linker is considered "cleavable" if the half-life of the linker is at most 10, or 8, 6, 5 hours or shorter.

In some embodiments, the linker is a nuclease-cleavable oligonucleotide linker. In some embodiments, the nuclease-cleavable linker contains one or more phosphodiester bonds in the oligonucleotide backbone. For example, the linker may contain a single phosphodiester bridge or 2, 3, 4, 5, 6, 7 or more phosphodiester linkages, for example as a string of 1-10 deoxynucleotides, e.g., dT, or ribonucleotides, e.g., rU, in the case of RNA linkers. In the case of dT or other DNA nucleotides dN in the linker, in certain embodiments the cleavable linker contains one or more phosphodiester linkages. In other embodiments, in the case of rU or other RNA nucleotides rN, the cleavable linker may consist of phosphorothioate linkages only. In contrast to phosphorothioate-linked deoxynucleotides, which in some embodiments are cleaved relatively slowly by nucleases (thus termed "noncleavable"), phosphorothioate-linked rU undergoes relatively rapid cleavage by ribonucleases and therefore is considered cleavable herein in some embodiments. It is also possible to combine dN and rN into the linker region, which are connected by phosphodiester or phosphorothioate linkages. In other embodiments, the linker can also contain chemically modified nucleotides, which are still cleavable by nucleases, such as, e.g., 2'-O-modified analogs. In particular, 2'-O-methyl or 2'-fluoro nucleotides can be combined with each other or with dN or rN nucleotides. Generally, in the case of nucleotide linkers, the linker is a part of the compound that is usually not complementary to a target, although it could be. This is because the linker is generally cleaved prior to action of the oligonucleotides on the target, and therefore, the linker identity with respect to a target is inconsequential. Accordingly, in some embodiments, a linker is an (oligo)nucleotide linker that is not complementary to any of the targets against which the oligonucleotides are designed.

In some embodiments, the cleavable linker is an oligonucleotide linker that contains a continuous stretch of deliberately introduced Rp phosphorothioate stereoisomers (e.g., 4, 5, 6, 7 or longer stretches). The Rp stereoisoform, unlike Sp isoform, is known to be susceptible to nuclease cleavage (Krieg et al., 2003, Oligonucleotides, 13:491-499). Such a linker would not include a racemic mix of PS linkaged oligonucleotides since the mixed linkages are relatively stable and are not likely to contain long stretches of the Rp stereoisomers, and therefore, considered "non-cleavable" herein. Thus, in some embodiments, a linker comprises a stretch of 4, 5, 6, 7 or more phosphorothioated nucleotides, wherein the stretch does not contain a substantial amount or any of the Sp stereoisoform. The amount could be considered substantial if it exceeds 10% on a per-mole basis.

In some embodiments, the linker is a non-nucleotide linker, for example, a single phosphodiester bridge. Another example of such cleavable linkers is a chemical group comprising a disulfide bond, for example, —$(CH_2)_n$—S—S—$(CH_2)_m$—, wherein n and m are integers from 0 to 10. In illustrative embodiments, n=m=6. Additional examples of non-nucleotide linkers are described below.

The linker can be designed so as to undergo a chemical or enzymatic cleavage reaction. Chemical reactions involve, for example, cleavage in acidic environments (e.g., endosomes), reductive cleavage (e.g., cytosolic cleavage) or oxidative cleavage (e.g., in liver microsomes). The cleavage reaction can also be initiated by a rearrangement reaction. Enzymatic reactions can include reactions mediated by nucleases, peptidases, proteases, phosphatases, oxidases, reductases, etc. For example, a linker can be pH-sensitive, cathepsin-sensitive, or predominantly cleaved in endosomes and/or cytosol.

In some embodiments, the linker comprises a peptide. In certain embodiments, the linker comprises a peptide which includes a sequence that is cleavable by an endopeptidase. In addition to the cleavable peptide sequence, the linker may comprise additional amino acid residues and/or non-peptide chemical moieties, such as an alkyl chain. In certain embodiments, the linker comprises Ala-Leu-Ala-Leu, which is a substrate for cathepsin B. See, for example, the maleimidocaproyl-Arg-Arg-Ala-Leu-Ala-Leu linkers described in Schmid et al, Bioconjugate Chem 2007, 18, 702-716. In certain embodiments, a cathepsin B-cleavable linker is cleaved in tumor cells. In certain embodiments, the linker comprises Ala-Pro-Ile-Ser-Phe-Phe-Glu-Leu-Gly, which is a substrate for cathepsins D, L, and B (see, for example, Fischer et al, Chembiochem 2006, 7, 1428-1434). In certain embodiments, a cathepsin-cleavable linker is cleaved in HeLA cells. In some embodiments, the linker comprises Phe-Lys, which is a substrate for cathepsin B. For example, in certain embodiments, the linker comprises Phe-Lys-p-aminobenzoic acid (PABA). See, e.g., the maleimidocaproyl-Phe-Lys-PABA linker described in Walker et al, Bioorg. Med. Chem. Lett. 2002, 12, 217-219. In certain embodiments, the linker comprises Gly-Phe-2-naphthylamide, which is a substrate for cathepsin C (see, for example, Berg et al. Biochem. J. 1994, 300, 229-235). In certain embodiments, a cathepsin C-cleavable linker is cleaved in hepatocytes. In some embodiments, the linker comprises a cathepsin S cleavage site. For example, in some embodiments, the linker comprises Gly-Arg-Trp-His-Thr-Val-Gly-Leu-Arg-Trp-Glu, Gly-Arg-Trp-Pro-Pro-Met-Gly-Leu-Pro-Trp-Glu, or Gly-Arg-Trp-His-Pro-Met-Gly-Ala-Pro-Trp-Glu, for example, as described in Lutzner et al, J. Biol. Chem. 2008, 283, 36185-36194. In certain embodiments, a cathepsin S-cleavable linker is cleaved in antigen presenting cells. In some embodiments, the linker comprises a papain cleavage site. Papain typically cleaves a peptide having the sequence —R/K—X—X (see Chapman et al, Annu. Rev. Physiol 1997, 59, 63-88). In certain embodiments, a papain-cleavable linker is cleaved in endosomes. In some embodiments, the linker comprises an endosomal acidic insulinase cleavage site. For example, in some embodiments, the linker comprises Tyr-Leu, Gly-Phe, or Phe-Phe (see, e.g., Authier et al, FEBS Lett. 1996, 389, 55-60). In certain embodiments, an endosomal acidic insulinase-cleavable linker is cleaved in hepatic cells.

In some embodiments, the linker is pH sensitive. In certain embodiments, the linker comprises a low pH-labile bond. As used herein, a low-pH labile bond is a bond that is selectively broken under acidic conditions (pH<7). Such bonds may also be termed endosomally labile bonds, because cell endosomes and lysosomes have a pH less than 7. For example, in certain embodiments, the linker comprises an amine, an imine, an ester, a benzoic imine, an amino ester, a diortho ester, a polyphosphoester, a polyphosphazene, an acetal, a vinyl ether, a hydrazone, an azidomethyl-methylmaleic anhydride, a thiopropionate, a masked endosomolytic agent or a citraconyl group.

In certain embodiments, the linker comprises a low pH-labile bond selected from the following: ketals that are labile in acidic environments (e.g., pH less than 7, greater than about 4) to form a diol and a ketone; acetals that are labile in acidic environments (e.g., pH less than 7, greater than about 4) to form a diol and an aldehyde; imines or iminiums that are labile in acidic environments (e.g., pH less than 7, greater than about 4) to form an amine and an aldehyde or a ketone; silicon-oxygen-carbon linkages that are labile under acidic condition; silicon-nitrogen (silazane) linkages; silicon-carbon linkages (e.g., arylsilanes, vinylsilanes, and allylsilanes); maleamates (amide bonds synthesized from maleic anhydride derivatives and amines); ortho esters; hydrazones; activated carboxylic acid derivatives (e.g., esters, amides) designed to undergo acid catalyzed hydrolysis); or vinyl ethers. Further examples may be found in International Patent Appln. Pub. No. WO 2008/022309, entitled POLYCONJUGATES FOR IN VIVO DELIVERY OF POLYNUCLEOTIDES, the contents of which are incorporated herein by reference.

In some embodiments, the linker comprises a masked endosomolytic agent. Endosomolytic polymers are polymers that, in response to a change in pH, are able to cause disruption or lysis of an endosome or provide for escape of a normally membrane-impermeable compound, such as a polynucleotide or protein, from a cellular internal membrane-enclosed vesicle, such as an endosome or lysosome. A subset of endosomolytic compounds is fusogenic compounds, including fusogenic peptides. Fusogenic peptides can facilitate endosomal release of agents such as oligomeric compounds to the cytoplasm. See, for example, US Patent Application Publication Nos. 20040198687, 20080281041, 20080152661, and 20090023890, which are incorporated herein by reference.

The linker can also be designed to undergo an organ/tissue-specific cleavage. For example, for certain targets, which are expressed in multiple tissues, only the knock-down in liver may be desirable, as knock-down in other organs may lead to undesired side effects. Thus, linkers susceptible to liver-specific enzymes, such as pyrrolase (TPO) and glucose-6-phosphatase (G-6-Pase), can be engineered, so as to limit the antisense effect to the liver mainly. Alternatively, linkers not susceptible to liver enzymes but susceptible to kidney-specific enzymes, such as gamma-glutamyltranspeptidase, can be engineered, so that the antisense effect is limited to the kidneys mainly. Analogously, intestine-specific peptidases cleaving Phe-Ala and Leu-Ala could be considered for orally administered multimeric oligonucleotides. Similarly, by placing an enzyme recognition site into the linker, which is recognized by an enzyme over-expressed in tumors, such as plasmin (e.g., PHEA-D-Val-Leu-Lys recognition site), tumor-specific knock-down should be feasible. By selecting the right enzyme recognition site in the linker, specific cleavage and knock-down should be achievable in many organs. In addition, the linker can also contain a targeting signal, such as N-acetyl galactosamine for liver targeting, or folate, vitamin A or RGD-peptide in the case of tumor or activated macrophage targeting. Accordingly, in some embodiments, the cleavable linker is organ- or tissue-specific, for example, liver-specific, kidney-specific, intestine-specific, etc.

The oligonucleotides can be linked through any part of the individual oligonucleotide, e.g., via the phosphate, the sugar (e.g., ribose, deoxyribose), or the nucleobase. In certain embodiments, when linking two oligonucleotides together, the linker can be attached e.g. to the 5'-end of the first oligonucleotide and the 3'-end of the second nucleotide, to the 5'-end of the first oligonucleotide and the 5'end of the second nucleotide, to the 3'-end of the first oligonucleotide and the 3'-end of the second nucleotide. In other embodiments, when linking two oligonucleotides together, the linker can attach internal residues of each oligonucleotide, e.g., via a modified nucleobase. One of ordinary skill in the art will understand that many such permutations are available for multimers. Further examples of appropriate linkers as well as methods for producing compounds having such linkers are disclosed in International Patent Application Number, PCT/US2012/055535, entitled MULTIMERIC OLIGONUCLEOTIDE COMPOUNDS, publication number WO2013040429 A1, the contents of which relating to linkers and related chemistries are incorporated herein by referenced in its entirety.

Methods for Selecting Candidate Oligonucleotides for Activating Expression of SMN1 or SMN2

Methods are provided herein for selecting a candidate oligonucleotide for activating or enhancing expression of SMN1 or SMN2. The target selection methods may generally involve steps for selecting single stranded oligonucleotides having any of the structural and functional characteristics disclosed herein. Typically, the methods involve one or more steps aimed at identifying oligonucleotides that target a PRC2-associated region that is functionally related to SMN1 or SMN2, for example a PRC2-associated region of a lncRNA that regulates expression of SMN1 or SMN2 by facilitating (e.g., in a cis-regulatory manner) the recruitment of PRC2 to the SMN1 or SMN2 gene. Such oligonucleotides are expected to be candidates for activating expression of SMN1 or SMN2 because of their ability to hybridize with the PRC2-associated region of a nucleic acid (e.g., a lncRNA). In some embodiments, this hybridization event is understood to disrupt interaction of PRC2 with the nucleic acid (e.g., a lncRNA) and as a result disrupt recruitment of PRC2 and its associated co-repressors (e.g., chromatin remodeling factors) to the SMN1 or SMN2 gene locus.

Methods of selecting a candidate oligonucleotide may involve selecting a PRC2-associated region (e.g., a nucleotide sequence as set forth in any one of SEQ ID NOS: 9 to 29) that maps to a chromosomal position encompassing or in proximity to the SMN1 or SMN2 gene (e.g., a chromosomal position having a sequence as set forth in any one of SEQ ID NOS: 1 to 8). The PRC2-associated region may map to the strand of the chromosome comprising the sense strand of the SMN1 or SMN2 gene, in which case the candidate oligonucleotide is complementary to the sense strand of the SMN1 or SMN2 gene (i.e., is antisense to the SMN1 or SMN2 gene). Alternatively, the PRC2-associated region may map to the strand of the first chromosome comprising the antisense strand of the SMN1 or SMN2 gene, in which case the oligonucleotide is complementary to the antisense strand (the template strand) of the SMN1 or SMN2 gene (i.e., is sense to the SMN1 or SMN2 gene).

Methods for selecting a set of candidate oligonucleotides that is enriched in oligonucleotides that activate expression of SMN1 or SMN2 may involve selecting one or more PRC2-associated regions that map to a chromosomal position that encompasses or that is in proximity to the SMN1 or SMN2 gene and selecting a set of oligonucleotides, in which each oligonucleotide in the set comprises a nucleotide sequence that is complementary with the one or more PRC2-associated regions. As used herein, the phrase, "a set of oligonucleotides that is enriched in oligonucleotides that activate expression of" refers to a set of oligonucleotides that has a greater number of oligonucleotides that activate expression of a target gene (e.g., SMN1 or SMN2) compared with a random selection of oligonucleotides of the same physicochemical properties (e.g., the same GC content, $T_m$, length etc.) as the enriched set.

Where the design and/or synthesis of a single stranded oligonucleotide involves design and/or synthesis of a sequence that is complementary to a nucleic acid or PRC2-associated region described by such sequence information, the skilled person is readily able to determine the complementary sequence, e.g., through understanding of Watson Crick base pairing rules which form part of the common general knowledge in the field.

In some embodiments design and/or synthesis of a single stranded oligonucleotide involves manufacture of an oligonucleotide from starting materials by techniques known to those of skill in the art, where the synthesis may be based on a sequence of a PRC2-associated region, or portion thereof.

Methods of design and/or synthesis of a single stranded oligonucleotide may involve one or more of the steps of:

Identifying and/or selecting PRC2-associated region;

Designing a nucleic acid sequence having a desired degree of sequence identity or complementarity to a PRC2-associated region or a portion thereof;

Synthesizing a single stranded oligonucleotide to the designed sequence;

Purifying the synthesized single stranded oligonucleotide; and

Optionally mixing the synthesized single stranded oligonucleotide with at least one pharmaceutically acceptable diluent, carrier or excipient to form a pharmaceutical composition or medicament.

Single stranded oligonucleotides so designed and/or synthesized may be useful in method of modulating gene expression as described herein.

Preferably, single stranded oligonucleotides of the invention are synthesized chemically. Oligonucleotides used to practice this invention can be synthesized in vitro by well-known chemical synthesis techniques.

Oligonucleotides of the invention can be stabilized against nucleolytic degradation such as by the incorporation of a modification, e.g., a nucleotide modification. For example, nucleic acid sequences of the invention include a phosphorothioate at least the first, second, or third internucleotide linkage at the 5' or 3' end of the nucleotide sequence. As another example, the nucleic acid sequence can include a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O—NMA). As another example, the nucleic acid sequence can include at least one 2'-O-methyl-modified nucleotide, and in some embodiments, all of the nucleotides include a 2'-O-methyl modification. In some embodiments, the nucleic acids are "locked," i.e., comprise nucleic acid analogues in which the ribose ring is "locked" by a methylene bridge connecting the 2'-O atom and the 4'-C atom.

It is understood that any of the modified chemistries or formats of single stranded oligonucleotides described herein can be combined with each other, and that one, two, three, four, five, or more different types of modifications can be included within the same molecule.

In some embodiments, the method may further comprise the steps of amplifying the synthesized single stranded oligonucleotide, and/or purifying the single stranded oligonucleotide (or amplified single stranded oligonucleotide), and/or sequencing the single stranded oligonucleotide so obtained.

As such, the process of preparing a single stranded oligonucleotide may be a process that is for use in the manufacture of a pharmaceutical composition or medicament for use in the treatment of disease, optionally wherein the treatment involves modulating expression of a gene associated with a PRC2-associated region.

In the methods described above a PRC2-associated region may be, or have been, identified, or obtained, by a method that involves identifying RNA that binds to PRC2.

Such methods may involve the following steps: providing a sample containing nuclear ribonucleic acids, contacting the sample with an agent that binds specifically to PRC2 or a subunit thereof, allowing complexes to form between the agent and protein in the sample, partitioning the complexes, synthesizing nucleic acid that is complementary to nucleic acid present in the complexes.

Where the single stranded oligonucleotide is based on a PRC2-associated region, or a portion of such a sequence, it may be based on information about that sequence, e.g., sequence information available in written or electronic form, which may include sequence information contained in publicly available scientific publications or sequence databases.

In some embodiments, candidate oligonucleotides may be tested in animal models and/or cell-based models of ALS. Animal and cell-based models of ALS are known in the art. Exemplary animal models of ALS include SOD1 mutant transgenic mice (e.g., SOD1$^{G93A}$ mice), SOD1 mutant transgenic zebrafish, ALS2 knock-out mice, ALS2 knock-down zebrafish, transgenic human WT FUS mice, known down and transgenic mutant FUS zebrafish, TDP-43 knock out mice, transgenic mutant TDP-43 mice, transgenic mutant TDP-43 zebrafish, transgenic mutant TDP-43 rats, Vps54$^{wr}$ mice, Tbce$^{pmn}$ mice, Neurofilament light chain overexpressing transgenic mice, Neurofilament heavy chain overexpressing transgenic mice, and Peripherin overexpressing transgenic mice (see, e.g., Jakob Maximilian Moser, Paolo Bigini, and Thomas Schmitt-John. The wobbler mouse, an ALS animal model. Mol Genet Genomics. 2013; 288(5-6): 207-229; and Bruijn L I, Miller T M, Cleveland D W. Unraveling the mechanisms involved in motor neuron degeneration in ALS. Annu Rev Neurosci. 2004; 27:723-749). Exemplary cell-based models include cells (primary or cell-lines) derived from ALS patients, such as NSC-34/hSOD1(G93A) cells and HeLa cells expressing FUS containing R495X ALS-causing mutation, or cells derived from an ALS animal model.

Nucleotide Analogues

In some embodiments, the oligonucleotide may comprise at least one ribonucleotide, at least one deoxyribonucleotide, and/or at least one bridged nucleotide. In some embodiments, the oligonucleotide may comprise a bridged nucleotide, such as a locked nucleic acid (LNA) nucleotide, a constrained ethyl (cEt) nucleotide, or an ethylene bridged nucleic acid (ENA) nucleotide. Examples of such nucleotides are disclosed herein and known in the art. In some embodiments, the oligonucleotide comprises a nucleotide analog disclosed in one of the following United States Patent or Patent Application Publications: U.S. Pat. No. 7,399,845, U.S. Pat. No. 7,741,457, U.S. Pat. No. 8,022,193, U.S. Pat. No. 7,569,686, U.S. Pat. No. 7,335,765, U.S. Pat. No. 7,314,923, U.S. Pat. No. 7,335,765, and U.S. Pat. No. 7,816,333, US 20110009471, the entire contents of each of which are incorporated herein by reference for all purposes. The oligonucleotide may have one or more 2' O-methyl nucleotides. The oligonucleotide may consist entirely of 2' O-methyl nucleotides.

Often the single stranded oligonucleotide has one or more nucleotide analogues. For example, the single stranded oligonucleotide may have at least one nucleotide analogue that results in an increase in $T_m$ of the oligonucleotide in a range of 1° C., 2° C., 3° C., 4° C., or 5° C. compared with an oligonucleotide that does not have the at least one nucleotide analogue. The single stranded oligonucleotide may have a plurality of nucleotide analogues that results in a total increase in $T_m$ of the oligonucleotide in a range of 2° C., 3° C., 4° C., 5° C., 6° C., 7° C., 8° C., 9° C., 10° C., 15° C., 20° C., 25° C., 30° C., 35° C., 40° C., 45° C. or more compared with an oligonucleotide that does not have the nucleotide analogue.

The oligonucleotide may be of up to 50 nucleotides in length in which 2 to 10, 2 to 15, 2 to 16, 2 to 17, 2 to 18, 2 to 19, 2 to 20, 2 to 25, 2 to 30, 2 to 40, 2 to 45, or more nucleotides of the oligonucleotide are nucleotide analogues. The oligonucleotide may be of 8 to 30 nucleotides in length in which 2 to 10, 2 to 15, 2 to 16, 2 to 17, 2 to 18, 2 to 19, 2 to 20, 2 to 25, 2 to 30 nucleotides of the oligonucleotide are nucleotide analogues.

The oligonucleotide may be of 8 to 15 nucleotides in length in which 2 to 4, 2 to 5, 2 to 6, 2 to 7, 2 to 8, 2 to 9, 2 to 10, 2 to 11, 2 to 12, 2 to 13, 2 to 14 nucleotides of the oligonucleotide are nucleotide analogues. Optionally, the oligonucleotides may have every nucleotide except 1, 2, 3, 4, 5, 6, 7, 8, 9, or 10 nucleotides modified.

The oligonucleotide may consist entirely of bridged nucleotides (e.g., LNA nucleotides, cEt nucleotides, ENA nucleotides). The oligonucleotide may comprise alternating deoxyribonucleotides and 2'-fluoro-deoxyribonucleotides. The oligonucleotide may comprise alternating deoxyribonucleotides and 2'-O-methyl nucleotides. The oligonucleotide may comprise alternating deoxyribonucleotides and ENA nucleotide analogues. The oligonucleotide may comprise alternating deoxyribonucleotides and LNA nucleotides. The oligonucleotide may comprise alternating LNA nucleotides and 2'-O-methyl nucleotides. The oligonucleotide may have a 5' nucleotide that is a bridged nucleotide (e.g., a LNA nucleotide, cEt nucleotide, ENA nucleotide). The oligonucleotide may have a 5' nucleotide that is a deoxyribonucleotide.

The oligonucleotide may comprise deoxyribonucleotides flanked by at least one bridged nucleotide (e.g., a LNA nucleotide, cEt nucleotide, ENA nucleotide) on each of the 5' and 3' ends of the deoxyribonucleotides. The oligonucleotide may comprise deoxyribonucleotides flanked by 1, 2, 3, 4, 5, 6, 7, 8 or more bridged nucleotides (e.g., LNA nucleotides, cEt nucleotides, ENA nucleotides) on each of the 5' and 3' ends of the deoxyribonucleotides. The 3' position of the oligonucleotide may have a 3' hydroxyl group. The 3' position of the oligonucleotide may have a 3' thiophosphate.

The oligonucleotide may be conjugated with a label. For example, the oligonucleotide may be conjugated with a biotin moiety, cholesterol, Vitamin A, folate, sigma receptor ligands, aptamers, peptides, such as CPP, hydrophobic molecules, such as lipids, ASGPR or dynamic polyconjugates and variants thereof at its 5' or 3' end.

Preferably the single stranded oligonucleotide comprises one or more modifications comprising: a modified sugar moiety, and/or a modified internucleoside linkage, and/or a modified nucleotide and/or combinations thereof. It is not necessary for all positions in a given oligonucleotide to be uniformly modified, and in fact more than one of the modifications described herein may be incorporated in a single oligonucleotide or even at within a single nucleoside within an oligonucleotide.

In some embodiments, the single stranded oligonucleotides are chimeric oligonucleotides that contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. Chimeric single stranded oligonucleotides of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures comprise, but are not limited to, U.S. Pat. Nos. 5,013,830; 5,149,797; 5, 220,007; 5,256,775; 5,366,878; 5,403,711; 5,491,133; 5,565,350; 5,623,065; 5,652,355; 5,652,356; and 5,700,922, each of which is herein incorporated by reference.

In some embodiments, the single stranded oligonucleotide comprises at least one nucleotide modified at the 2' position of the sugar, most preferably a 2'-O-alkyl, 2'-O-alkyl-O-alkyl or 2'-fluoro-modified nucleotide. In other preferred embodiments, RNA modifications include 2'-fluoro, 2'-amino and 2' O-methyl modifications on the ribose of pyrimidines, abasic residues or an inverted base at the 3' end of the RNA. Such modifications are routinely incorporated into oligonucleotides and these oligonucleotides have been shown to have a higher Tm (i.e., higher target binding affinity) than 2'-deoxyoligonucleotides against a given target.

A number of nucleotide and nucleoside modifications have been shown to make the oligonucleotide into which they are incorporated more resistant to nuclease digestion than the native oligodeoxynucleotide; these modified oligos survive intact for a longer time than unmodified oligonucleotides. Specific examples of modified oligonucleotides include those comprising modified backbones, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones, particularly $CH_2$—NH—O—$CH_2$, CH, ~N($CH_3$)~O~$CH_2$ (known as a methylene(methylimino) or MMI backbone, $CH_2$—O—N($CH_3$)—$CH_2$, $CH_2$—N($CH_3$)—N($CH_3$)—$CH_2$ and O—N($CH_3$)—$CH_2$—$CH_2$ backbones, wherein the native phosphodiester backbone is represented as O—P—O—$CH_2$,); amide backbones (see De Mesmaeker et al. Acc. Chem. Res. 1995, 28:366-374); morpholino backbone structures (see Summerton and Weller, U.S. Pat. No. 5,034,506); peptide nucleic acid (PNA) backbone (wherein the phosphodiester backbone of the oligonucleotide is replaced with a polyamide backbone, the nucleotides being bound directly or indirectly to the aza nitrogen atoms of the polyamide backbone, see Nielsen et al., Science 1991, 254, 1497). Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863; 4,476,301; 5,023,243; 5, 177,196; 5,188,897; 5,264,423; 5,276,019; 5,278,302; 5,286,717; 5,321,131; 5,399,676; 5,405,939; 5,453,496; 5,455, 233; 5,466,677; 5,476,925; 5,519,126; 5,536,821; 5,541,306; 5,550,111; 5,563, 253; 5,571,799; 5,587,361; and 5,625,050.

Morpholino-based oligomeric compounds are described in Dwaine A. Braasch and David R. Corey, Biochemistry, 2002, 41(14), 4503-4510); Genesis, volume 30, issue 3, 2001; Heasman, J., Dev. Biol., 2002, 243, 209-214; Nasevicius et al., Nat. Genet., 2000, 26, 216-220; Lacerra et al., Proc. Natl. Acad. Sci., 2000, 97, 9591-9596; and U.S. Pat. No. 5,034,506, issued Jul. 23, 1991. In some embodiments, the morpholino-based oligomeric compound is a phosphorodiamidate morpholino oligomer (PMO) (e.g., as described in Iverson, Curr. Opin. Mol. Ther., 3:235-238, 2001; and Wang et al., J. Gene Med., 12:354-364, 2010; the disclosures of which are incorporated herein by reference in their entireties).

Cyclohexenyl nucleic acid oligonucleotide mimetics are described in Wang et al., J. Am. Chem. Soc., 2000, 122, 8595-8602.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts; see U.S. Pat. Nos. 5,034,506; 5,166,315; 5,185,444; 5,214,134; 5,216,141; 5,235,033; 5,264, 562; 5, 264,564; 5,405,938; 5,434,257; 5,466,677; 5,470,967; 5,489,677; 5,541,307; 5,561,225; 5,596, 086; 5,602,240; 5,610,289; 5,602,240; 5,608,046; 5,610,289; 5,618,704; 5,623, 070; 5,663,312; 5,633,360; 5,677,437; and 5,677,439, each of which is herein incorporated by reference.

Modified oligonucleotides are also known that include oligonucleotides that are based on or constructed from arabinonucleotide or modified arabinonucleotide residues. Arabinonucleosides are stereoisomers of ribonucleosides, differing only in the configuration at the 2'-position of the sugar ring. In some embodiments, a 2'-arabino modification is 2'-F arabino. In some embodiments, the modified oligonucleotide is 2'-fluoro-D-arabinonucleic acid (FANA) (as described in, for example, Lon et al., Biochem., 41:3457-3467, 2002 and Min et al., Bioorg. Med. Chem. Lett., 12:2651-2654, 2002; the disclosures of which are incorporated herein by reference in their entireties). Similar modifications can also be made at other positions on the sugar, particularly the 3' position of the sugar on a 3' terminal nucleoside or in 2'-5' linked oligonucleotides and the 5' position of 5' terminal nucleotide.

PCT Publication No. WO 99/67378 discloses arabinonucleic acids (ANA) oligomers and their analogues for improved sequence specific inhibition of gene expression via association to complementary messenger RNA.

Other preferred modifications include ethylene-bridged nucleic acids (ENAs) (e.g., International Patent Publication No. WO 2005/042777, Morita et al., Nucleic Acid Res., Suppl 1:241-242, 2001; Surono et al., Hum. Gene Ther., 15:749-757, 2004; Koizumi, Curr. Opin. Mol. Ther., 8:144-149, 2006 and Horie et al., Nucleic Acids Symp. Ser (Oxf), 49:171-172, 2005; the disclosures of which are incorporated herein by reference in their entireties). Preferred ENAs include, but are not limited to, 2'-O,4'-C-ethylene-bridged nucleic acids.

Examples of LNAs are described in WO/2008/043753 and include compounds of the following general formula.

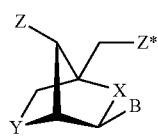

where X and Y are independently selected among the groups —O—, —S—, —N(H)—, N(R)—, —CH$_2$— or —CH— (if part of a double bond),
—CH$_2$—O—, —CH$_2$—S—, —CH$_2$—N(H)—, —CH$_2$—N(R)—, —CH$_2$—CH$_2$— or —CH$_2$—CH— (if part of a double bond),
—CH=CH—, where R is selected from hydrogen and C$_{1-4}$-alkyl; Z and Z* are independently selected among an internucleoside linkage, a terminal group or a protecting group; B constitutes a natural or non-natural nucleotide base moiety; and the asymmetric groups may be found in either orientation.

Preferably, the LNA used in the oligonucleotides described herein comprises at least one LNA unit according any of the formulas

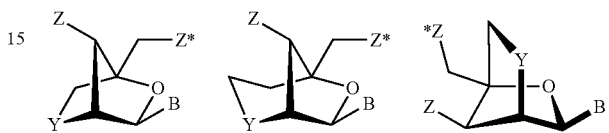

wherein Y is —O—, —S—, —NH—, or N(R$^H$); Z and Z* are independently selected among an internucleoside linkage, a terminal group or a protecting group; B constitutes a natural or non-natural nucleotide base moiety, and RH is selected from hydrogen and C$_{1-4}$-alkyl.

In some embodiments, the Locked Nucleic Acid (LNA) used in the oligonucleotides described herein comprises at least one Locked Nucleic Acid (LNA) unit according any of the formulas shown in Scheme 2 of PCT/DK2006/000512.

In some embodiments, the LNA used in the oligomer of the invention comprises internucleoside linkages selected from —O—P(O)$_2$—O—, —O—P(O,S)—O—, O—P(S)$_2$—O—, —S—P(O)$_2$—O—, —S—P(O,S)—O—, —S—P(S)$_2$—O—, —O—P(O)$_2$—S—, —O—P(O,S)—S—, —S—P(O)$_2$—S—, —O—PO(R$^H$)—O—, O—PO (OCH$_3$)—O—, —O—PO(NR$^H$)—O—, —O—PO (OCH$_2$CH$_2$S—R)—O—, —O—PO(BH$_3$)—O—, —O—PO (NHR$^H$)—O—, —O—P(O)$_2$—NR$^H$—, —NR$^H$—P(O)$_2$—O—, —NR$^H$—CO—O—, where R$^H$ is selected from hydrogen and C$_{1-4}$-alkyl.

Specifically preferred LNA units are shown in scheme 2:

Scheme 2

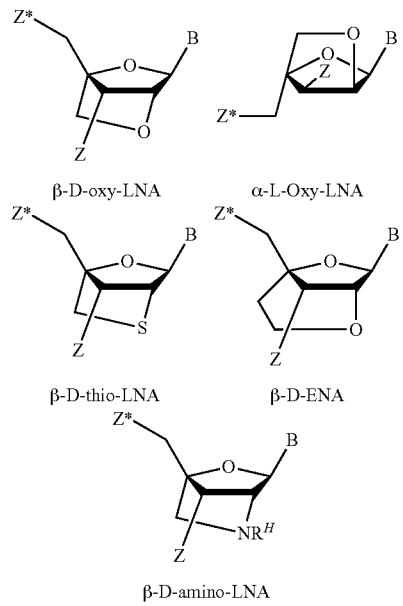

β-D-oxy-LNA

α-L-Oxy-LNA

β-D-thio-LNA

β-D-ENA

β-D-amino-LNA

The term "thio-LNA" comprises a locked nucleotide in which at least one of X or Y in the general formula above is selected from S or —CH$_2$—S—. Thio-LNA can be in both beta-D and alpha-L-configuration.

The term "amino-LNA" comprises a locked nucleotide in which at least one of X or Y in the general formula above is selected from —N(H)—, N(R)—, CH$_2$—N(H)—, and —CH$_2$—N(R)— where R is selected from hydrogen and C$_{1-4}$-alkyl. Amino-LNA can be in both beta-D and alpha-L-configuration.

The term "oxy-LNA" comprises a locked nucleotide in which at least one of X or Y in the general formula above represents —O— or —CH$_2$—O—. Oxy-LNA can be in both beta-D and alpha-L-configuration.

The term "ena-LNA" comprises a locked nucleotide in which Y in the general formula above is —CH$_2$—O— (where the oxygen atom of —CH$_2$—O— is attached to the 2'-position relative to the base B).

LNAs are described in additional detail herein.

One or more substituted sugar moieties can also be included, e.g., one of the following at the 2' position: OH, SH, SCH$_3$, F, OCN, OCH$_3$ OCH$_3$, OCH$_3$ O(CH$_2$)n CH$_3$, O(CH$_2$)n NH$_2$ or O(CH$_2$)n CH$_3$ where n is from 1 to about 10; C1 to C10 lower alkyl, alkoxyalkoxy, substituted lower alkyl, alkaryl or aralkyl; Cl; Br; CN; CF$_3$; OCF$_3$; O—, S—, or N-alkyl; O—, S—, or N-alkenyl; SOCH$_3$; SO$_2$ CH$_3$; ONO$_2$; NO$_2$; N$_3$; NH2; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy [2'-O—CH$_2$CH$_2$OCH$_3$, also known as 2'-O-(2-methoxyethyl)] (Martin et al, Helv. Chim. Acta, 1995, 78, 486). Other preferred modifications include 2'-methoxy (2'-O—CH$_3$), 2'-propoxy (2'-OCH$_2$ CH$_2$CH$_3$) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Single stranded oligonucleotides can also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, isocytosine, pseudoisocytosine, as well as synthetic nucleobases, e.g., 2-aminoadenine, 2-(methylamino)adenine, 2-(imidazolylalkyl)adenine, 2-(aminoalkylamino)adenine or other heterosubstituted alkyladenines, 2-thiouracil, 2-thiothymine, 5-bromouracil, 5-hydroxymethyluracil, 5-propynyluracil, 8-azaguanine, 7-deazaguanine, N6 (6-aminohexyl)adenine, 6-aminopurine, 2-aminopurine, 2-chloro-6-aminopurine and 2,6-diaminopurine or other diaminopurines. See, e.g., Kornberg, "DNA Replication," W. H. Freeman & Co., San Francisco 1980, pp 75-77; and Gebeyehu, G., et al. Nucl. Acids Res., 15:4513 (1987)). A "universal" base known in the art, e.g., inosine, can also be included. 5-Me-C substitutions have been shown to increase nucleic acid duplex stability by 0.6-1.2° C. (Sanghvi, in Crooke, and Lebleu, eds., Antisense Research and Applications, CRC Press, Boca Raton, 1993, pp. 276-278) and may be used as base substitutions.

It is not necessary for all positions in a given oligonucleotide to be uniformly modified, and in fact more than one of the modifications described herein may be incorporated in a single oligonucleotide or even at within a single nucleoside within an oligonucleotide.

In some embodiments, both a sugar and an internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, for example, an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al, Science, 1991, 254, 1497-1500.

Single stranded oligonucleotides can also include one or more nucleobase (often referred to in the art simply as "base") modifications or substitutions. As used herein, "unmodified" or "natural" nucleobases comprise the purine bases adenine (A) and guanine (G), and the pyrimidine bases thymine (T), cytosine (C) and uracil (U). Modified nucleobases comprise other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine.

Further, nucleobases comprise those disclosed in U.S. Pat. No. 3,687,808, those disclosed in "The Concise Encyclopedia of Polymer Science And Engineering", pages 858-859, Kroschwitz, ed. John Wiley & Sons, 1990; those disclosed by Englisch et al., Angewandle Chemie, International Edition, 1991, 30, page 613, and those disclosed by Sanghvi, Chapter 15, Antisense Research and Applications," pages 289-302, Crooke, and Lebleu, eds., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, comprising 2-aminopropyladenine, 5-propynyluracil and 5-propynylcytosine. 5-methylcytosine substitutions have been shown to increase nucleic acid duplex stability by 0.6-1.2<0>C (Sanghvi, et al., eds, "Antisense Research and Applications," CRC Press, Boca Raton, 1993, pp. 276-278) and are presently preferred base substitutions, even more particularly when combined with 2'-O-methoxyethyl sugar modifications. Modified nucleobases are described in U.S.

Pat. No. 3,687,808, as well as U.S. Pat. Nos. 4,845,205; 5,130,302; 5,134,066; 5,175, 273; 5, 367,066; 5,432,272; 5,457,187; 5,459,255; 5,484,908; 5,502,177; 5,525,711; 5,552,540; 5,587,469; 5,596,091; 5,614,617; 5,750,692, and 5,681,941, each of which is herein incorporated by reference.

In some embodiments, the single stranded oligonucleotides are chemically linked to one or more moieties or conjugates that enhance the activity, cellular distribution, or cellular uptake of the oligonucleotide. For example, one or more single stranded oligonucleotides, of the same or different types, can be conjugated to each other; or single stranded oligonucleotides can be conjugated to targeting moieties with enhanced specificity for a cell type or tissue type. Such moieties include, but are not limited to, lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al, Ann. N. Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Mancharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-t oxycholesterol moiety (Crooke et al., J. Pharmacol. Exp. Ther., 1996, 277, 923-937). See also U.S. Pat. Nos. 4,828,979; 4,948,882; 5,218,105; 5,525,465; 5,541,313; 5,545,730; 5,552, 538; 5,578,717, 5,580,731; 5,580,731; 5,591,584; 5,109,124; 5,118,802; 5,138,045; 5,414,077; 5,486, 603; 5,512,439; 5,578,718; 5,608,046; 4,587,044; 4,605,735; 4,667,025; 4,762, 779; 4,789,737; 4,824,941; 4,835,263; 4,876,335; 4,904,582; 4,958,013; 5,082, 830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391, 723; 5,416,203, 5,451,463; 5,510,475; 5,512,667; 5,514,785; 5, 565,552; 5,567,810; 5,574,142; 5,585,481; 5,587,371; 5,595,726; 5,597,696; 5,599,923; 5,599, 928 and 5,688,941, each of which is herein incorporated by reference.

These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention.

Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxy cholesterol moiety. See, e.g., U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

In some embodiments, single stranded oligonucleotide modification include modification of the 5' or 3' end of the oligonucleotide. In some embodiments, the 3' end of the oligonucleotide comprises a hydroxyl group or a thiophosphate. It should be appreciated that additional molecules (e.g. a biotin moiety or a fluorophor) can be conjugated to the 5' or 3' end of the single stranded oligonucleotide. In some embodiments, the single stranded oligonucleotide comprises a biotin moiety conjugated to the 5' nucleotide.

In some embodiments, the single stranded oligonucleotide comprises locked nucleic acids (LNA), ENA modified nucleotides, 2'-O-methyl nucleotides, or 2'-fluoro-deoxyribonucleotides. In some embodiments, the single stranded oligonucleotide comprises alternating deoxyribonucleotides and 2'-fluoro-deoxyribonucleotides. In some embodiments, the single stranded oligonucleotide comprises alternating deoxyribonucleotides and 2'-O-methyl nucleotides. In some embodiments, the single stranded oligonucleotide comprises alternating deoxyribonucleotides and ENA modified nucleotides. In some embodiments, the single stranded oligonucleotide comprises alternating deoxyribonucleotides and locked nucleic acid nucleotides. In some embodiments, the single stranded oligonucleotide comprises alternating locked nucleic acid nucleotides and 2'-O-methyl nucleotides.

In some embodiments, the 5' nucleotide of the oligonucleotide is a deoxyribonucleotide. In some embodiments, the 5' nucleotide of the oligonucleotide is a locked nucleic acid nucleotide. In some embodiments, the nucleotides of the oligonucleotide comprise deoxyribonucleotides flanked by at least one locked nucleic acid nucleotide on each of the 5' and 3' ends of the deoxyribonucleotides. In some embodiments, the nucleotide at the 3' position of the oligonucleotide has a 3' hydroxyl group or a 3' thiophosphate.

In some embodiments, the single stranded oligonucleotide comprises phosphorothioate internucleotide linkages. In some embodiments, the single stranded oligonucleotide comprises phosphorothioate internucleotide linkages between at least two nucleotides. In some embodiments, the single stranded oligonucleotide comprises phosphorothioate internucleotide linkages between all nucleotides.

It should be appreciated that the single stranded oligonucleotide can have any combination of modifications as described herein.

The oligonucleotide may comprise a nucleotide sequence having one or more of the following modification patterns.

(a) (X)Xxxxxx, (X)xXxxxx, (X)xxXxxx, (X)xxxXxx, (X)xxxxXx and (X)xxxxxX, (b) (X)XXxxxx, (X)XxXxxx, (X)XxxXxx, (X)XxxxXx, (X)XxxxxX, (X)xXXxxx, (X)xXxXxx, (X)xXxxXx, (X)xXxxxX, (X)xxXXxx, (X)xxXxXx, (X)xxXxxX, (X)xxxXXx, (X)xxxXxX and (X)xxxxXX, (c) (X)XXXxxx, (X)xXXXxx, (X)xxXXXx, (X)xxxXXX, (X)XXxXxx, (X)XXxxXx, (X)XXxxxX, (X)xXXxXx, (X)xXXxxX, (X)xxXXxX, (X)XxXXxx, (X)XxxXXx, (X)XxxxXX (X)XxxXXX, (X)xXxXXx, (X)xXxxXX, (X)xxXxXX, (X)xXxXxX and (X)XxXxXx, (d) (X)xxXXX, (X)xXxXXX, (X)xXXxXX, (X)xXXXxX, (X)xXXXXx, (X)XxxXXXX, (X)XxXxXX, (X)XxXXxX, (X)XxXXXx, (X)XXxxXX, (X)XXxXxX, (X)XXxXXx, (X)XXXxxX, (X)XXXxXx, (X)XXXXxx, and (X)XXXXxx, (e) (X)xXXXXX, (X)XxXXXX, (X)XXxXXX, (X)XXXxXX, (X)XXXXxX and (X)XXXXXx, and (f) XXXXXX, XxXXXXX, XXxXXXX, XXXxXXX, XXXXxXX, XXXXXxX and XXXXXXx, in which "X" denotes a nucleotide analogue, (X) denotes an optional nucleotide analogue, and "x" denotes a DNA or RNA nucleotide unit. Each of the above listed patterns may appear one or more times within an oligonucleotide, alone or in combination with any of the other disclosed modification patterns.

Methods for Modulating Gene Expression

In some embodiments, methods are provided for increasing expression of SMN protein in a cell. The methods, in some embodiments, involve delivering to the cell a first single stranded oligonucleotide complementary with a PRC2-associated region of SMN1 or SMN2 and a second single stranded oligonucleotide complementary with a splice control sequence of a precursor mRNA of SMN1 or SMN2, in amounts sufficient to increase expression of a mature mRNA of SMN1 or SMN2 that comprises (or includes) exon 7 in the cell. The first and second single stranded oligonucleotides may be delivered together or separately. The first and second single stranded oligonucleotides may be linked together, or unlinked, i.e., separate.

In some embodiments, methods are provided for treating ALS in a subject. The methods, in some embodiments, involve administering to a subject a first single stranded oligonucleotide complementary with a PRC2-associated region of SMN1 or SMN2 and a second single stranded oligonucleotide complementary with a splice control sequence of a precursor mRNA of SMN1 or SMN2, in amounts sufficient to increase expression of full length SMN protein in the subject to levels sufficient to improve one or more conditions associated with ALS. The first and second single stranded oligonucleotides may be administered together or separately. The first and second single stranded oligonucleotides may be linked together, or unlinked, i.e., separate. The first single stranded oligonucleotide may be administered within 1 hour, 2 hours, 3 hours, 4 hours, 8 hours, 12 hours, 24 hours, 48 hours or more of administration of the second single stranded oligonucleotide. The first single stranded oligonucleotide may be administered before or after the second single stranded oligonucleotide. The oligonucleotides may be administered once or on multiple occasions depending on the needs of the subject and/or judgment of the treating physician. In some cases, the oligonucleotides may be administered in cycles. The administration cycles may vary; for example, the administration cycle may be $2^{nd}$ oligo—$1^{st}$ oligo—$2^{nd}$ oligo—$1^{st}$ oligo and so on; or $1^{st}$ oligo-$2^{nd}$ oligo-$1^{st}$ oligo-$2^{nd}$ oligo, and so on; or $1^{st}$ oligo—$2^{nd}$ oligo—$2^{nd}$ oligo—$1^{st}$ oligo-$1^{st}$ oligo—$2^{nd}$ oligo—$2^{nd}$ oligo—$1^{st}$ oligo, and so on. The skilled artisan will be capable of selecting administration cycles and intervals between each administration that are appropriate for treating a particular subject.

In one aspect, the invention relates to methods for modulating gene expression in a cell (e.g., a cell for which SMN1 or SMN2 levels are reduced) for research purposes (e.g., to study the function of the gene in the cell). In another aspect, the invention relates to methods for modulating gene expression in a cell (e.g., a cell for which SMN1 or SMN2 levels are reduced) for gene or epigenetic therapy. The cells can be in vitro, ex vivo, or in vivo (e.g., in a subject who has a disease resulting from reduced expression or activity of SMN1 or SMN2. In some embodiments, methods for modulating gene expression in a cell comprise delivering a single stranded oligonucleotide as described herein. In some embodiments, delivery of the single stranded oligonucleotide to the cell results in a level of expression of gene that is at least 5%, 10%, 20%, 30%, 40%, 50%, 60%, 70%, 80%, 90%, 100%, 200% or more greater than a level of expression of gene in a control cell to which the single stranded oligonucleotide has not been delivered. In certain embodiments, delivery of the single stranded oligonucleotide to the cell results in a level of expression of gene that is at least 50% greater than a level of expression of gene in a control cell to which the single stranded oligonucleotide has not been delivered.

In another aspect of the invention, methods comprise administering to a subject (e.g. a human) a composition comprising a single stranded oligonucleotide as described herein to increase protein levels in the subject. In some embodiments, the increase in protein levels is at least 5%, 10%, 20%, 30%, 40%, 50%, 60%, 70%, 80%, 90%, 100%, 200%, or more, higher than the amount of a protein in the subject before administering.

As another example, to increase expression of SMN1 or SMN2 in a cell, the methods include introducing into the cell a single stranded oligonucleotide that is sufficiently complementary to a PRC2-associated region (e.g., of a long non-coding RNA) that maps to a genomic position encompassing or in proximity to the SMN1 or SMN2 gene.

In another aspect of the invention provides methods of treating a condition (e.g., ALS) associated with decreased levels of expression or activity of SMN1 or SMN2 in a subject, the method comprising administering a single stranded oligonucleotide as described herein.

A subject can include a non-human mammal, e.g. mouse, rat, guinea pig, rabbit, cat, dog, goat, cow, or horse. In preferred embodiments, a subject is a human. Single stranded oligonucleotides have been employed as therapeutic moieties in the treatment of disease states in animals, including humans. Single stranded oligonucleotides can be useful therapeutic modalities that can be configured to be useful in treatment regimes for the treatment of cells, tissues and animals, especially humans.

For therapeutics, an animal, preferably a human, suspected of having ALS is treated by administering single stranded oligonucleotide in accordance with this invention. For example, in one non-limiting embodiment, the methods comprise the step of administering to the animal in need of treatment, a therapeutically effective amount of a single stranded oligonucleotide as described herein.

Formulation, Delivery, and Dosing

The oligonucleotides described herein can be formulated for administration to a subject for treating a condition (e.g., ALS) associated with decreased levels or activity of SMN protein. It should be understood that the formulations, compositions and methods can be practiced with any of the oligonucleotides disclosed herein. In some embodiments, formulations are provided that comprise a first single stranded oligonucleotide complementary with a PRC2-associated region of a gene and a second single stranded oligonucleotide complementary to a splice control sequence of a precursor mRNA of the gene. In some embodiments, formulations are provided that comprise a first single stranded oligonucleotide complementary with a PRC2-associated region of a gene that is linked via a linker with a second single stranded oligonucleotide complementary to a splice control sequence of a precursor mRNA of the gene. Thus, it should be appreciated that in some embodiments, a first single stranded oligonucleotide complementary with a PRC2-associated region of a gene is linked with a second single stranded oligonucleotide complementary to a splice control sequence of a precursor mRNA of the gene, and in other embodiments, the single stranded oligonucleotides are not linked. Single stranded oligonucleotides that are not linked may be administered to a subject or delivered to a cell simultaneously (e.g., within the same composition) or separately.

The formulations may conveniently be presented in unit dosage form and may be prepared by any methods well known in the art of pharmacy. The amount of active ingredient (e.g., an oligonucleotide or compound of the invention) which can be combined with a carrier material to produce a single dosage form will vary depending upon the host being treated, the particular mode of administration, e.g., intradermal or inhalation. The amount of active ingredient which can be combined with a carrier material to produce a single dosage form will generally be that amount of the compound which produces a therapeutic effect, e.g. tumor regression.

Pharmaceutical formulations of this invention can be prepared according to any method known to the art for the manufacture of pharmaceuticals. Such formulations can contain sweetening agents, flavoring agents, coloring agents and preserving agents. A formulation can be admixtured with nontoxic pharmaceutically acceptable excipients which are suitable for manufacture. Formulations may comprise one or more diluents, emulsifiers, preservatives, buffers, excipients, etc. and may be provided in such forms as liquids, powders, emulsions, lyophilized powders, sprays, creams, lotions, controlled release formulations, tablets, pills, gels, on patches, in implants, etc.

A formulated single stranded oligonucleotide composition can assume a variety of states. In some examples, the composition is at least partially crystalline, uniformly crystalline, and/or anhydrous (e.g., less than 80, 50, 30, 20, or 10% water). In another example, the single stranded oligonucleotide is in an aqueous phase, e.g., in a solution that includes water. The aqueous phase or the crystalline compositions can, e.g., be incorporated into a delivery vehicle, e.g., a liposome (particularly for the aqueous phase) or a particle (e.g., a microparticle as can be appropriate for a crystalline composition). Generally, the single stranded oligonucleotide composition is formulated in a manner that is compatible with the intended method of administration.

In some embodiments, the composition is prepared by at least one of the following methods: spray drying, lyophilization, vacuum drying, evaporation, fluid bed drying, or a combination of these techniques; or sonication with a lipid, freeze-drying, condensation and other self-assembly.

A single stranded oligonucleotide preparation can be formulated or administered (together or separately) in combination with another agent, e.g., another therapeutic agent or an agent that stabilizes a single stranded oligonucleotide, e.g., a protein that complexes with single stranded oligonucleotide. Still other agents include chelators, e.g., EDTA (e.g., to remove divalent cations such as $Mg^{2+}$), salts, RNAse inhibitors (e.g., a broad specificity RNAse inhibitor such as RNAsin) and so forth. In some embodiments, the other agent used in combination with the single stranded oligonucleotide is an agent that also regulates SMN expression. In some embodiments, the other agent is a growth hormone, a histone deacetylase inhibitor, a hydroxycarbamide (hydroxyurea), a natural polyphenol compound (e.g., resveratrol, curcumin), prolactin, or salbutamol. Examples of histone deacetylase inhibitors that may be used include aliphatic compounds (e.g., butyrates (e.g., sodium butyrate and sodium phenylbutyrate) and valproic acid), benzamides (e.g., M344), and hydroxamic acids (e.g., CBHA, SBHA, Entinostat (MS-275)) Panobinostat (LBH-589), Trichostatin A, Vorinostat (SAHA)), In one embodiment, the single stranded oligonucleotide preparation includes another single stranded oligonucleotide, e.g., a second single stranded oligonucleotide that modulates expression and/or mRNA processing of a second gene or a second single stranded oligonucleotide that modulates expression of the first gene. Still other preparation can include at least 3, 5, ten, twenty, fifty, or a hundred or more different single stranded oligonucleotide species. Such single stranded oligonucleotides can mediated gene expression with respect to a similar number of different genes. In one embodiment, the single stranded oligonucleotide preparation includes at least a second therapeutic agent (e.g., an agent other than an oligonucleotide).

Route of Delivery

A composition that includes a single stranded oligonucleotide can be delivered to a subject by a variety of routes. Exemplary routes include: intravenous, intradermal, topical, rectal, parenteral, anal, intravaginal, intranasal, pulmonary, ocular. The term "therapeutically effective amount" is the amount of oligonucleotide present in the composition that is needed to provide the desired level of SMN1 or SMN2 expression in the subject to be treated to give the anticipated physiological response. The term "physiologically effective amount" is that amount delivered to a subject to give the desired palliative or curative effect. The term "pharmaceutically acceptable carrier" means that the carrier can be administered to a subject with no significant adverse toxicological effects to the subject.

The single stranded oligonucleotide molecules of the invention can be incorporated into pharmaceutical compositions suitable for administration. Such compositions typically include one or more species of single stranded oligonucleotide and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The pharmaceutical compositions of the present invention may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip, subcutaneous, intraperitoneal or intramuscular injection, or intrathecal or intraventricular administration.

The route and site of administration may be chosen to enhance targeting. For example, to target muscle cells, intramuscular injection into the muscles of interest would be a logical choice. Lung cells might be targeted by administering the single stranded oligonucleotide in aerosol form. The vascular endothelial cells could be targeted by coating a balloon catheter with the single stranded oligonucleotide and mechanically introducing the oligonucleotide.

Topical administration refers to the delivery to a subject by contacting the formulation directly to a surface of the subject. The most common form of topical delivery is to the skin, but a composition disclosed herein can also be directly applied to other surfaces of the body, e.g., to the eye, a mucous membrane, to surfaces of a body cavity or to an internal surface. As mentioned above, the most common topical delivery is to the skin. The term encompasses several routes of administration including, but not limited to, topical and transdermal. These modes of administration typically include penetration of the skin's permeability barrier and efficient delivery to the target tissue or stratum. Topical administration can be used as a means to penetrate the epidermis and dermis and ultimately achieve systemic delivery of the composition. Topical administration can also be used as a means to selectively deliver oligonucleotides to the epidermis or dermis of a subject, or to specific strata thereof, or to an underlying tissue.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Transdermal delivery is a valuable route for the administration of lipid soluble therapeutics. The dermis is more permeable than the epidermis and therefore absorption is much more rapid through abraded, burned or denuded skin. Inflammation and other physiologic conditions that increase blood flow to the skin also enhance transdermal adsorption. Absorption via this route may be enhanced by the use of an oily vehicle (inunction) or through the use of one or more penetration enhancers. Other effective ways to deliver a composition disclosed herein via the transdermal route include hydration of the skin and the use of controlled release topical patches. The transdermal route provides a potentially effective means to deliver a composition disclosed herein for systemic and/or local therapy. In addition, iontophoresis (transfer of ionic solutes through biological membranes under the influence of an electric field), phonophoresis or sonophoresis (use of ultrasound to enhance the absorption of various therapeutic agents across biological membranes, notably the skin and the cornea), and optimization of vehicle characteristics relative to dose position and retention at the site of administration may be useful methods for enhancing the transport of topically applied compositions across skin and mucosal sites.

Both the oral and nasal membranes offer advantages over other routes of administration. For example, oligonucleotides administered through these membranes may have a rapid onset of action, provide therapeutic plasma levels, avoid first pass effect of hepatic metabolism, and avoid exposure of the oligonucleotides to the hostile gastrointestinal (GI) environment. Additional advantages include easy access to the membrane sites so that the oligonucleotide can be applied, localized and removed easily.

In oral delivery, compositions can be targeted to a surface of the oral cavity, e.g., to sublingual mucosa which includes the membrane of ventral surface of the tongue and the floor of the mouth or the buccal mucosa which constitutes the lining of the cheek. The sublingual mucosa is relatively permeable thus giving rapid absorption and acceptable bioavailability of many agents. Further, the sublingual mucosa is convenient, acceptable and easily accessible.

A pharmaceutical composition of single stranded oligonucleotide may also be administered to the buccal cavity of a human being by spraying into the cavity, without inhalation, from a metered dose spray dispenser, a mixed micellar pharmaceutical formulation as described above and a propellant. In one embodiment, the dispenser is first shaken prior to spraying the pharmaceutical formulation and propellant into the buccal cavity.

Compositions for oral administration include powders or granules, suspensions or solutions in water, syrups, slurries, emulsions, elixirs or non-aqueous media, tablets, capsules, lozenges, or troches. In the case of tablets, carriers that can be used include lactose, sodium citrate and salts of phosphoric acid. Various disintegrants such as starch, and lubricating agents such as magnesium stearate, sodium lauryl sulfate and talc, are commonly used in tablets. For oral administration in capsule form, useful diluents are lactose and high molecular weight polyethylene glycols. When aqueous suspensions are required for oral use, the nucleic acid compositions can be combined with emulsifying and suspending agents. If desired, certain sweetening and/or flavoring agents can be added.

Parenteral administration includes intravenous drip, subcutaneous, intraperitoneal or intramuscular injection, intrathecal or intraventricular administration. In some embodiments, parental administration involves administration directly to the site of disease (e.g. injection into a tumor).

Formulations for parenteral administration may include sterile aqueous solutions which may also contain buffers, diluents and other suitable additives. Intraventricular injection may be facilitated by an intraventricular catheter, for example, attached to a reservoir. For intravenous use, the total concentration of solutes should be controlled to render the preparation isotonic.

Any of the single stranded oligonucleotides described herein can be administered to ocular tissue. For example, the compositions can be applied to the surface of the eye or nearby tissue, e.g., the inside of the eyelid. For ocular administration, ointments or droppable liquids may be delivered by ocular delivery systems known to the art such as applicators or eye droppers. Such compositions can include mucomimetics such as hyaluronic acid, chondroitin sulfate, hydroxypropyl methylcellulose or poly(vinyl alcohol), preservatives such as sorbic acid, EDTA or benzylchronium chloride, and the usual quantities of diluents and/or carriers. The single stranded oligonucleotide can also be administered to the interior of the eye, and can be introduced by a needle or other delivery device which can introduce it to a selected area or structure.

Pulmonary delivery compositions can be delivered by inhalation by the patient of a dispersion so that the composition, preferably single stranded oligonucleotides, within the dispersion can reach the lung where it can be readily absorbed through the alveolar region directly into blood circulation. Pulmonary delivery can be effective both for systemic delivery and for localized delivery to treat diseases of the lungs.

Pulmonary delivery can be achieved by different approaches, including the use of nebulized, aerosolized, micellular and dry powder-based formulations. Delivery can be achieved with liquid nebulizers, aerosol-based inhalers, and dry powder dispersion devices. Metered-dose devices are preferred. One of the benefits of using an atomizer or inhaler is that the potential for contamination is minimized because the devices are self-contained. Dry powder dispersion devices, for example, deliver agents that may be readily formulated as dry powders. A single stranded oligonucleotide composition may be stably stored as lyophilized or spray-dried powders by itself or in combination with suitable powder carriers. The delivery of a composition for inhalation can be mediated by a dosing timing element which can include a timer, a dose counter, time measuring device, or a time indicator which when incorporated into the device enables dose tracking, compliance monitoring, and/or dose triggering to a patient during administration of the aerosol medicament.

The term "powder" means a composition that consists of finely dispersed solid particles that are free flowing and capable of being readily dispersed in an inhalation device and subsequently inhaled by a subject so that the particles reach the lungs to permit penetration into the alveoli. Thus, the powder is said to be "respirable." Preferably the average particle size is less than about 10 μm in diameter preferably with a relatively uniform spheroidal shape distribution. More preferably the diameter is less than about 7.5 μm and most preferably less than about 5.0 μm. Usually the particle size distribution is between about 0.1 μm and about 5 μm in diameter, particularly about 0.3 μm to about 5 μm.

The term "dry" means that the composition has a moisture content below about 10% by weight (% w) water, usually below about 5% w and preferably less it than about 3% w. A dry composition can be such that the particles are readily dispersible in an inhalation device to form an aerosol.

The types of pharmaceutical excipients that are useful as carrier include stabilizers such as human serum albumin (HSA), bulking agents such as carbohydrates, amino acids and polypeptides; pH adjusters or buffers; salts such as sodium chloride; and the like. These carriers may be in a crystalline or amorphous form or may be a mixture of the two.

Suitable pH adjusters or buffers include organic salts prepared from organic acids and bases, such as sodium citrate, sodium ascorbate, and the like; sodium citrate is preferred. Pulmonary administration of a micellar single stranded oligonucleotide formulation may be achieved through metered dose spray devices with propellants such as tetrafluoroethane, heptafluoroethane, dimethylfluoropropane, tetrafluoropropane, butane, isobutane, dimethyl ether and other non-CFC and CFC propellants.

Exemplary devices include devices which are introduced into the vasculature, e.g., devices inserted into the lumen of a vascular tissue, or which devices themselves form a part of the vasculature, including stents, catheters, heart valves, and other vascular devices. These devices, e.g., catheters or stents, can be placed in the vasculature of the lung, heart, or leg.

Other devices include non-vascular devices, e.g., devices implanted in the peritoneum, or in organ or glandular tissue, e.g., artificial organs. The device can release a therapeutic substance in addition to a single stranded oligonucleotide, e.g., a device can release insulin.

In one embodiment, unit doses or measured doses of a composition that includes single stranded oligonucleotide are dispensed by an implanted device. The device can include a sensor that monitors a parameter within a subject. For example, the device can include pump, e.g., and, optionally, associated electronics.

Tissue, e.g., cells or organs can be treated with a single stranded oligonucleotide, ex vivo and then administered or implanted in a subject. The tissue can be autologous, allogeneic, or xenogeneic tissue. E.g., tissue can be treated to reduce graft v. host disease. In other embodiments, the tissue is allogeneic and the tissue is treated to treat a disorder characterized by unwanted gene expression in that tissue. E.g., tissue, e.g., hematopoietic cells, e.g., bone marrow hematopoietic cells, can be treated to inhibit unwanted cell proliferation. Introduction of treated tissue, whether autologous or transplant, can be combined with other therapies. In some implementations, the single stranded oligonucleotide treated cells are insulated from other cells, e.g., by a semipermeable porous barrier that prevents the cells from leaving the implant, but enables molecules from the body to reach the cells and molecules produced by the cells to enter the body. In one embodiment, the porous barrier is formed from alginate.

In one embodiment, a contraceptive device is coated with or contains a single stranded oligonucleotide. Exemplary devices include condoms, diaphragms, IUD (implantable uterine devices, sponges, vaginal sheaths, and birth control devices.

Dosage

In one aspect, the invention features a method of administering a single stranded oligonucleotide (e.g., as a compound or as a component of a composition) to a subject (e.g., a human subject). In some embodiments, the methods involve administering a compound (e.g., a compound of the general formula A-B-C, as disclosed herein, or an single stranded oligonucleotide,) in a unit dose to a subject. In one embodiment, the unit dose is between about 10 mg and 25 mg per kg of bodyweight. In one embodiment, the unit dose is between about 1 mg and 100 mg per kg of bodyweight. In one embodiment, the unit dose is between about 0.1 mg and 500 mg per kg of bodyweight. In some embodiments, the unit dose is more than 0.001, 0.005, 0.01, 0.05, 0.1, 0.5, 1, 2, 5, 10, 25, 50 or 100 mg per kg of bodyweight.

The defined amount can be an amount effective to treat or prevent a disease or disorder, e.g., a disease or disorder associated with the SMN1 or SMN2. The unit dose, for example, can be administered by injection (e.g., intravenous or intramuscular), an inhaled dose, or a topical application.

In some embodiments, the unit dose is administered daily. In some embodiments, less frequently than once a day, e.g., less than every 2, 4, 8 or 30 days. In another embodiment, the unit dose is not administered with a frequency (e.g., not a regular frequency). For example, the unit dose may be administered a single time. In some embodiments, the unit dose is administered more than once a day, e.g., once an hour, two hours, four hours, eight hours, twelve hours, etc.

In one embodiment, a subject is administered an initial dose and one or more maintenance doses of a single stranded oligonucleotide. The maintenance dose or doses are generally lower than the initial dose, e.g., one-half less of the initial dose. A maintenance regimen can include treating the subject with a dose or doses ranging from 0.0001 to 100 mg/kg of body weight per day, e.g., 100, 10, 1, 0.1, 0.01, 0.001, or 0.0001 mg per kg of bodyweight per day. The maintenance doses may be administered no more than once every 1, 5, 10, or 30 days. Further, the treatment regimen may last for a period of time which will vary depending upon the nature of the particular disease, its severity and the overall condition of the patient. In some embodiments the dosage may be delivered no more than once per day, e.g., no more than once per 24, 36, 48, or more hours, e.g., no more than once for every 5 or 8 days. Following treatment, the patient can be monitored for changes in his condition and for alleviation of the symptoms of the disease state. The dosage of the oligonucleotide may either be increased in the event the patient does not respond significantly to current dosage levels, or the dose may be decreased if an alleviation of the symptoms of the disease state is observed, if the disease state has been ablated, or if undesired side-effects are observed.

The effective dose can be administered in a single dose or in two or more doses, as desired or considered appropriate under the specific circumstances. If desired to facilitate repeated or frequent infusions, implantation of a delivery device, e.g., a pump, semi-permanent stent (e.g., intravenous, intraperitoneal, intracisternal or intracapsular), or reservoir may be advisable.

In some embodiments, the pharmaceutical composition includes a plurality of single stranded oligonucleotide species. In some embodiments, the pharmaceutical composition comprises a first single stranded oligonucleotide complementary with a PRC2-associated region of a gene (e.g., SMN1 or SMN2), and a second single stranded oligonucleotide complementary to a splice control sequence of a precursor mRNA of a gene (e.g., SMN1 or SMN2). In some embodiments, the pharmaceutical composition includes a compound comprising the general formula A-B-C, in which A is a single stranded oligonucleotide complementary with a PRC2-associated region of a gene, B is a linker, and C is a single stranded oligonucleotide complementary to a splice control sequence of a precursor mRNA of the gene.

In another embodiment, the single stranded oligonucleotide species has sequences that are non-overlapping and non-adjacent to another species with respect to a naturally occurring target sequence (e.g., a PRC2-associated region). In another embodiment, the plurality of single stranded oligonucleotide species is specific for different PRC2-associated regions. In another embodiment, the single stranded oligonucleotide is allele specific. In some cases, a patient is treated with a single stranded oligonucleotide in conjunction with other therapeutic modalities.

Following successful treatment, it may be desirable to have the patient undergo maintenance therapy to prevent the recurrence of the disease state, wherein the compound of the invention is administered in maintenance doses, ranging from 0.0001 mg to 100 mg per kg of body weight.

The concentration of the single stranded oligonucleotide composition is an amount sufficient to be effective in treating or preventing a disorder or to regulate a physiological condition in humans. The concentration or amount of single stranded oligonucleotide administered will depend on the parameters determined for the agent and the method of administration, e.g. nasal, buccal, pulmonary. For example, nasal formulations may tend to require much lower concentrations of some ingredients in order to avoid irritation or burning of the nasal passages. It is sometimes desirable to dilute an oral formulation up to 10-100 times in order to provide a suitable nasal formulation.

Certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a single stranded oligonucleotide can include a single treatment or, preferably, can include a series of treatments. It will also be appreciated that the effective dosage of a single stranded oligonucleotide used for treatment may increase or decrease over the course of a particular treatment. For example, the subject can be monitored after administering a single stranded oligonucleotide composition. Based on information from the monitoring, an additional amount of the single stranded oligonucleotide composition can be administered.

Dosing is dependent on severity and responsiveness of the disease condition to be treated, with the course of treatment lasting from several days to several months, or until a cure is effected or a diminution of disease state is achieved. Optimal dosing schedules can be calculated from measurements of SMN1 or SMN2 expression levels in the body of the patient. Persons of ordinary skill can easily determine optimum dosages, dosing methodologies and repetition rates. Optimum dosages may vary depending on the relative potency of individual compounds, and can generally be estimated based on EC50s found to be effective in in vitro and in vivo animal models. In some embodiments, the animal models include transgenic animals that express a human SMN1 or SMN2. In another embodiment, the composition for testing includes a single stranded oligonucleotide that is complementary, at least in an internal region, to a sequence that is conserved between SMN1 or SMN2 in the animal model and the SMN1 or SMN2 in a human.

In one embodiment, the administration of the single stranded oligonucleotide composition is parenteral, e.g. intravenous (e.g., as a bolus or as a diffusible infusion), intradermal, intraperitoneal, intramuscular, intrathecal, intraventricular, intracranial, subcutaneous, transmucosal, buccal, sublingual, endoscopic, rectal, oral, vaginal, topical, pulmonary, intranasal, urethral or ocular. Administration can be provided by the subject or by another person, e.g., a health care provider. The composition can be provided in measured doses or in a dispenser which delivers a metered dose. Selected modes of delivery are discussed in more detail below.

Kits

In certain aspects of the invention, kits are provided, comprising a container housing a composition comprising a single stranded oligonucleotide. In some embodiments, the kits comprise a container housing a single stranded oligonucleotide complementary with of a PRC2-associated region of a gene; and a second container housing a single stranded oligonucleotide complementary to a splice control sequence of a precursor mRNA of the gene. In some embodiments, the kits comprise a container housing a single stranded oligonucleotide complementary with of a PRC2-associated region of a gene and a single stranded oligonucleotide complementary to a splice control sequence of a precursor mRNA of the gene. In some embodiments, the composition is a pharmaceutical composition comprising a single stranded oligonucleotide and a pharmaceutically acceptable carrier. In some embodiments, the individual components of the pharmaceutical composition may be provided in one container. Alternatively, it may be desirable to provide the components of the pharmaceutical composition separately in two or more containers, e.g., one container for single stranded oligonucleotides, and at least another for a carrier compound. The kit may be packaged in a number of different configurations such as one or more containers in a single box. The different components can be combined, e.g., according to instructions provided with the kit. The components can be combined according to a method described herein, e.g., to prepare and administer a pharmaceutical composition. The kit can also include a delivery device.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

The invention is further described in the following examples, which do not limit the scope of the invention described in the claims.

Example 1: Oligonucleotides Targeting PRC2-Associated Regions that Upregulate SMN1

Materials and Methods:
Real Time PCR

RNA was harvested from the cells using Promega SV 96 Total RNA Isolation system or Trizol omitting the DNAse step. In separate pilot experiments, 50 ng of RNA was determined to be sufficient template for the reverse transcriptase reaction. RNA harvested from cells was normalized so that 50 ng of RNA was input to each reverse transcription reaction. For the few samples that were too dilute to reach this limit, the maximum input volume was added. Reverse transcriptase reaction was performed using the Superscript II kit and real time PCR performed on cDNA samples using icycler SYBR green chemistry (Biorad). A baseline level of mRNA expression for each target gene was determined through quantitative PCR as outlined above. Baseline levels were also determined for mRNA of various housekeeping genes which are constitutively expressed. A "control" housekeeping gene with approximately the same level of baseline expression as the target gene was chosen for comparison purposes.

Protein Expression (ELISA)

ELISA to determine SMN protein was carried out per manufacturer's instructions (SMN ELISA kit #ADI-900-209, Enzo Life Sciences). Data was normalized to total protein as measured by bicinchoninic acid (BCA) assay (Pierce cat #: 23225).

Cell Culture

Human hepatocyte Hep3B, human hepatocyte HepG2 cells, mouse hepatoma Hepa1-6 cells, and human renal proximal tubule epithelial cells (RPTEC) were cultured using conditions known in the art (see, e.g. Current Protocols in Cell Biology). Other cell lines tested were neuronal cell lines (SK-N-AS, U-87) and SMN patient fibroblasts. Details of the cell lines used in the experiments described herein are provided in Table 5.

TABLE 5

Cell lines

| Cell line | Source | Species | Gender | Cell Type | Tissue | Status | Culture Conditions |
|---|---|---|---|---|---|---|---|
| RPTEC | Lonza | human | N/A | proximal tubule epithelial cells | kidney | primary | Clonetics™ REGM™ BulletKit™ (CC-3190) |
| Hep3B | ATCC | human | M | hepatocytes | liver | immortalized | Eagle's MEM + 10% FBS |
| SK-N-AS | ATCC | human | F | neuroblast | brain | immortalized | DMEM + 10% FBS |
| U-87 | ATCC | human | M | gliobastoma | brain | immortalized | Eagle's MEM + 10% FBS |
| GM03813 | Coriell Institute | human | F | fibroblast | skin | immortalized | MEM + 10% FBS |
| GM03814 | Coriell Institute | human | M | fibroblast | skin | immortalized | MEM + 10% FBS |
| GM09677 | Coriell Institute | human | M | fibroblast | skin | immortalized | MEM + 10% FBS |
| GM00232 | Coriell Institute | human | M | fibroblast | skin | immortalized | MEM + 10% FBS |
| GM03815 | Coriell Institute | human | M | fibroblast | skin | immortalized | MEM + 10% FBS |
| GM22592 | Coriell Institute | human | M | fibroblast | skin | immortalized | MEM + 10% FBS |
| GM10684 | Coriell Institute | human | F | B-lymphocyte | blood | immortalized | MEM + 10% FBS |
| GM00321 (normal) | Coriell Institute | human | F | fibroblast | skin | immortalized | MEM + 10% FBS |

Oligonucleotide Design

Oligonucleotides were designed within PRC2-interacting regions in order to upregulate SMN1. The sequence and structure of each oligonucleotide is shown in Table 2. The following table provides a description of the nucleotide analogs, modifications and intranucleotide linkages used for certain oligonucleotides tested and described in Table 2.

In Vitro Transfection of Cells with Oligonucleotides

Cells were seeded into each well of 24-well plates at a density of 25,000 cells per 500 uL and transfections were performed with Lipofectamine and the single stranded oligonucleotides. Control wells contained Lipofectamine alone. At 48 hours post-transfection, approximately 200 uL of cell culture supernatants were stored at −80 C for ELISA. At 48 hours post-transfection, RNA was harvested from the cells and quantitative PCR was carried out as outlined above. The percent induction of target mRNA expression by each oligonucleotide was determined by normalizing mRNA levels in the presence of the oligonucleotide to the mRNA levels in the presence of control (Lipofectamine alone). This was compared side-by-side with the increase in mRNA expression of the "control" housekeeping gene.

Results:

In Vitro Delivery of Single Stranded Oligonucleotides Upregulated SMN1 Expression Oligonucleotides were designed as candidates for upregulating SMN1 expression. A total of 52 single stranded oligonucleotides were designed to be complementary to a PRC2-interacting region within a sequence as set forth in SEQ ID NO: 1, 2, 4, or 5. Oligonucleotides were tested in at least duplicate. The sequence and structural features of the oligonucleotides are set forth in Table 2. Briefly, cells were transfected in vitro with the oligonucleotides as described above. SMN1 expression in cells following treatment was evaluated by qRT-PCR. Oligonucleotides that upregulated SMN1 expression were identified. Further details are outlined in Table 2.

Table 7 shows further results from experiments in which oligonucleotides were transfected into cells at a particular concentration [oligo] and 48 or 72 h later RNA was prepared and qRTPCR assays carried out to determine mRNA levels of full length (FL) or delta7 SMN. In other cases, oligos were administered gymnotically to cells at 10 μM and RNA harvested 9 days post treatment. The cell lines tested were neuronal cell lines (SK-N-AS, U-87) and SMN patient fibroblasts.

Table 8 shows results from experiments in which oligonucleotides were transfected into cells in combination with either one or two more oligos or small molecule compounds at a particular concentration ([oligo], [2nd], [3rd]) and 48 or 72 h later RNA was prepared and qRTPCR assays carried out to determine mRNA levels of full length (FL) or delta7 SMN. The cell lines tested were SMN patient fibroblasts.

Table 9 shows results from experiments in which oligonucleotides were transfected into cells in combination with either one or two more oligos or as dimers or by gymnotic treatment at a particular concentration ([oligo], [2nd], [3rd]) and 24, 48, 72 or 216 h later cell lysates were prepared and ELISA assays carried out to determine SMN protein levels. The cell lines tested were SMN patient fibroblasts.

Tables

TABLE 1

| Non-Seed hexamer sequences. |
| --- |
| AAAAAA, AAAAAG, AAAACA, AAAAGA, AAAAGC, AAAAGG, AAAAUA, AAACAA, AAACAC, AAACAG, |
| AAACAU, AAACCC, AAACCU, AAACGA, AAACGC, AAACGU, AAACUA, AAACUC, AAACUU, AAAGAU, |
| AAAGCC, AAAGGA, AAAGGG, AAAGUC, AAAUAC, AAAUAU, AAAUCG, AAAUCU, AAAUGC, AAAUGU, |
| AAAUUA, AAAUUG, AACAAC, AACAAG, AACAAU, AACACA, AACACG, AACAGA, AACAGC, AACAGG, |
| AACAUC, AACAUG, AACCAA, AACCAC, AACCAG, AACCAU, AACCCC, AACCCG, AACCGA, AACCGC, |
| AACCGG, AACCUA, AACCUU, AACGAA, AACGAC, AACGAG, AACGAU, AACGCU, AACGGG, AACGGU, |
| AACGUA, AACGUC, AACGUG, AACGUU, AACUAU, AACUCA, AACUCC, AACUCG, AACUGA, AACUGC, |
| AACUGU, AACUUA, AACUUC, AACUUG, AACUUU, AAGAAA, AAGAAG, AAGAAU, AAGACG, AAGAGA, |
| AAGAGC, AAGAGG, AAGAGU, AAGAUU, AAGCAA, AAGCAC, AAGCAG, AAGCAU, AAGCCA, AAGCCC, |
| AAGCCG, AAGCCU, AAGCGA, AAGCGG, AAGCGU, AAGCUA, AAGGAA, AAGGAC, AAGGCU, AAGGGC, |
| AAGGGU, AAGGUU, AAGUAA, AAGUAC, AAGUAU, AAGUCC, AAGUCG, AAGUGA, AAGUGG, AAGUUA, |
| AAGUUU, AAUAAA, AAUAAC, AAUAAG, AAUAAU, AAUACA, AAUACC, AAUACG, AAUAGA, AAUAGC, |
| AAUAGG, AAUAGU, AAUAUC, AAUAUU, AAUCAA, AAUCAU, AAUCCA, AAUCCC, AAUCCG, AAUCGA, |
| AAUCGC, AAUCGU, AAUCUA, AAUCUG, AAUCUU, AAUGAA, AAUGAC, AAUGAG, AAUGAU, AAUGCG, |
| AAUGCU, AAUGGA, AAUGGU, AAUGUA, AAUGUC, AAUGUG, AAUUAA, AAUUAC, AAUUAG, AAUUCC, |
| AAUUCG, AAUUGA, AAUUGG, AAUUGU, AAUUUC, AAUUUG, ACAAAA, ACAAAC, ACAAAG, ACAAAU, |
| ACAACC, ACAACG, ACAACU, ACAAGA, ACAAGC, ACAAGU, ACAAUC, ACAAUG, ACAAUU, ACACAG, |
| ACACCA, ACACCC, ACACCG, ACACCU, ACACGA, ACACGC, ACACGU, ACACUC, ACACUG, ACACUU, |
| ACAGAA, ACAGAC, ACAGCC, ACAGCG, ACAGCU, ACAGGG, ACAGUC, ACAGUG, ACAGUU, ACAUAA, |
| ACAUAC, ACAUCC, ACAUCG, ACAUCU, ACAUGA, ACAUGC, ACAUGU, ACAUUG, ACAUUU, ACCAAA, |
| ACCAAC, ACCAAG, ACCAAU, ACCACC, ACCACG, ACCAGA, ACCAGU, ACCAUA, ACCAUG, ACCAUU, |
| ACCCAA, ACCCAC, ACCCCA, ACCCCG, ACCCGA, ACCCGC, ACCCUA, ACCCUC, ACCCUU, ACCGAA, |
| ACCGAC, ACCGAU, ACCGCA, ACCGCC, ACCGCG, ACCGCU, ACCGGA, ACCGGC, ACCGGU, ACCGUA, |

TABLE 1-continued

Non-Seed hexamer sequences.

ACCGUC, ACCGUG, ACCGUU, ACCUAA, ACCUAC, ACCUAG, ACCUAU, ACCUCA, ACCUCC, ACCUCG,
ACCUCU, ACCUGA, ACCUGC, ACCUGU, ACCUUA, ACCUUC, ACCUUU, ACGAAA, ACGAAC, ACGAAG,
ACGAAU, ACGACA, ACGACC, ACGACG, ACGACU, ACGAGA, ACGAGC, ACGAGG, ACGAGU, ACGAUA,
ACGAUC, ACGAUG, ACGAUU, ACGCAA, ACGCAG, ACGCAU, ACGCCC, ACGCCG, ACGCCU, ACGCGA,
ACGCGG, ACGCGU, ACGCUA, ACGCUG, ACGCUU, ACGGAA, ACGGAC, ACGGAG, ACGGAU, ACGGCC,
ACGGCG, ACGGCU, ACGGGC, ACGGGG, ACGGGU, ACGGUA, ACGGUC, ACGGUG, ACGGUU, ACGUAA,
ACGUAC, ACGUAU, ACGUCC, ACGUCG, ACGUCU, ACGUGA, ACGUGC, ACGUGG, ACGUGU, ACGUUA,
ACGUUC, ACGUUG, ACGUUU, ACUAAA, ACUAAG, ACUAAU, ACUACA, ACUACC, ACUACG, ACUACU,
ACUAGG, ACUAUC, ACUAUG, ACUAUU, ACUCAU, ACUCCC, ACUCCG, ACUCCU, ACUCGA, ACUCGC,
ACUCGG, ACUCUC, ACUCUU, ACUGAG, ACUGAU, ACUGCC, ACUGCG, ACUGCU, ACUGGG, ACUGGU,
ACUGUC, ACUUAA, ACUUAC, ACUUAU, ACUUCA, ACUUCC, ACUUCG, ACUUCU, ACUUGA, ACUUGC,
ACUUGU, ACUUUA, ACUUUC, ACUUUG, AGAAAA, AGAAAC, AGAAAG, AGAACC, AGAACG, AGAACU,
AGAAGC, AGAAGU, AGAAUA, AGAAUC, AGAAUG, AGAAUU, AGACAA, AGACAC, AGACAU, AGACCA,
AGACCC, AGACCG, AGACCU, AGACGA, AGACGC, AGACGU, AGACUA, AGACUC, AGACUU, AGAGAC,
AGAGAG, AGAGAU, AGAGCC, AGAGCG, AGAGCU, AGAGGC, AGAGGG, AGAGGU, AGAGUA, AGAGUU,
AGAUAC, AGAUAG, AGAUAU, AGAUCC, AGAUCG, AGAUCU, AGAUGA, AGAUGC, AGAUGG, AGAUUA,
AGAUUC, AGAUUG, AGAUUU, AGCAAC, AGCACA, AGCACG, AGCACU, AGCAGA, AGCAUA, AGCAUC,
AGCAUG, AGCCAA, AGCCAU, AGCCCA, AGCCGA, AGCCGC, AGCCGG, AGCCGU, AGCCUA, AGCCUC,
AGCGAA, AGCGAG, AGCGAU, AGCGCA, AGCGCC, AGCGCG, AGCGCU, AGCGGA, AGCGGC, AGCGGU,
AGCGUA, AGCGUC, AGCGUG, AGCGUU, AGCUAA, AGCUAC, AGCUAG, AGCUAU, AGCUCA, AGCUCC,
AGCUCG, AGCUCU, AGCUGA, AGCUGG, AGCUGU, AGCUUC, AGCUUU, AGGAAU, AGGACC, AGGACG,
AGGAGA, AGGAGU, AGGAUA, AGGCAA, AGGCAU, AGGCCG, AGGCGA, AGGCGC, AGGCGG, AGGCUA,
AGGCUC, AGGCUU, AGGGAC, AGGGAU, AGGGGA, AGGGGU, AGGGUA, AGGGUG, AGGUAA,
AGGUAC, AGGUCA, AGGUCC, AGGUCU, AGGUGA, AGGUGC, AGGUGG, AGGUGU, AGGUUC,
AGGUUG, AGUAAA, AGUAAG, AGUAAU, AGUACA, AGUACG, AGUAGC, AGUAGG, AGUAUA, AGUAUC,
AGUAUG, AGUAUU, AGUCAA, AGUCAC, AGUCAG, AGUCAU, AGUCCA, AGUCCG, AGUCCU, AGUCGA,
AGUCGC, AGUCGG, AGUCGU, AGUCUA, AGUCUC, AGUCUG, AGUCUU, AGUGAA, AGUGAC, AGUGCG,
AGUGGG, AGUGUC, AGUUAA, AGUUAC, AGUUAG, AGUUCC, AGUUCG, AGUUGA, AGUUGC,
AGUUGU, AGUUUA, AGUUUC, AGUUUG, AGUUUU, AUAAAC, AUAAAU, AUAACA, AUAACC, AUAACG,
AUAACU, AUAAGA, AUAAGC, AUAAGG, AUAAGU, AUAAUC, AUAAUG, AUAAUU, AUACAC, AUACAG,
AUACAU, AUACCA, AUACCC, AUACCG, AUACGA, AUACGC, AUACGG, AUACGU, AUACUA, AUACUC,
AUACUG, AUACUU, AUAGAA, AUAGAC, AUAGAU, AUAGCA, AUAGCG, AUAGCU, AUAGGA, AUAGGU,
AUAGUA, AUAGUC, AUAGUG, AUAGUU, AUAUAC, AUAUAG, AUAUCC, AUAUCG, AUAUCU, AUAUGA,
AUAUGC, AUAUGG, AUAUGU, AUAUUC, AUAUUG, AUAUUU, AUCAAA, AUCAAC, AUCAAG, AUCAAU,
AUCACA, AUCACC, AUCACG, AUCAGC, AUCAGG, AUCCAA, AUCCAU, AUCCCC, AUCCCG, AUCCGA,
AUCCGC, AUCCGG, AUCCUA, AUCCUC, AUCCUG, AUCGAA, AUCGAC, AUCGAG, AUCGAU, AUCGCA,
AUCGCC, AUCGCG, AUCGCU, AUCGGC, AUCGGG, AUCGGU, AUCGUC, AUCGUG, AUCGUU, AUCUAA,
AUCUAC, AUCUAG, AUCUAU, AUCUCC, AUCUCG, AUCUGU, AUCUUG, AUCUUU, AUGAAA, AUGAAC,
AUGAAG, AUGAAU, AUGACC, AUGACU, AUGAGG, AUGAGU, AUGAUA, AUGAUC, AUGAUU, AUGCAA,

TABLE 1-continued

Non-Seed hexamer sequences.

AUGCAG, AUGCCA, AUGCCC, AUGCCG, AUGCGA, AUGCGG, AUGCGU, AUGCUC, AUGCUU, AUGGAC, AUGGCC, AUGGGA, AUGGGC, AUGGGU, AUGGUC, AUGGUG, AUGUAC, AUGUAU, AUGUCA, AUGUCC, AUGUCG, AUGUGU, AUGUUA, AUGUUC, AUUAAA, AUUAAC, AUUAAG, AUUAAU, AUUACA, AUUACC, AUUACG, AUUACU, AUUAGA, AUUAGC, AUUAGG, AUUAGU, AUUAUA, AUUAUC, AUUAUG, AUUCAC, AUUCCA, AUUCCG, AUUCCU, AUUCGA, AUUCGC, AUUCGG, AUUCGU, AUUCUA, AUUCUC, AUUCUU, AUUGAA, AUUGAC, AUUGAU, AUUGCC, AUUGCG, AUUGCU, AUUGGA, AUUGGC, AUUGGG, AUUGGU, AUUGUA, AUUGUC, AUUGUG, AUUGUU, AUUUAA, AUUUAG, AUUUAU, AUUUCC, AUUUCG, AUUUCU, AUUUGA, AUUUGC, AUUUGU, AUUUUA, AUUUUC, AUUUUG, AUUUUU, CAAAAG, CAAACA, CAAACC, CAAACG, CAAACU, CAAAGA, CAAAGG, CAAAUA, CAAAUU, CAACAC, CAACAU, CAACCA, CAACCC, CAACCG, CAACGA, CAACGC, CAACGG, CAACGU, CAACUA, CAACUC, CAACUG, CAACUU, CAAGAA, CAAGAC, CAAGAU, CAAGCA, CAAGCC, CAAGCG, CAAGCU, CAAGGA, CAAGGG, CAAGUC, CAAGUG, CAAGUU, CAAUAA, CAAUAC, CAAUAG, CAAUCC, CAAUCG, CAAUCU, CAAUGA, CAAUGC, CAAUGG, CAAUGU, CAAUUC, CAAUUG, CAAUUU, CACAAU, CACACA, CACACG, CACACU, CACAGA, CACAGC, CACAGG, CACAUA, CACAUC, CACAUU, CACCAA, CACCAC, CACCAU, CACCCA, CACCCC, CACCCG, CACCGA, CACCGC, CACCGG, CACCGU, CACCUA, CACCUU, CACGAA, CACGAC, CACGAG, CACGAU, CACGCA, CACGCC, CACGCU, CACGGA, CACGGC, CACGGG, CACGGU, CACGUA, CACGUC, CACGUG, CACGUU, CACUAA, CACUAG, CACUAU, CACUCA, CACUCG, CACUGA, CACUGC, CACUGG, CACUUA, CACUUC, CACUUU, CAGAAA, CAGAAG, CAGAAU, CAGACC, CAGACG, CAGAGC, CAGAUA, CAGAUC, CAGCCG, CAGCCU, CAGCGA, CAGCGC, CAGCGG, CAGCGU, CAGCUC, CAGCUU, CAGGAU, CAGGGG, CAGGGU, CAGGUA, CAGGUC, CAGGUU, CAGUAC, CAGUCG, CAGUUG, CAUAAA, CAUAAC, CAUAAG, CAUAAU, CAUACA, CAUACC, CAUACG, CAUACU, CAUAGA, CAUAGG, CAUAGU, CAUAUA, CAUAUC, CAUAUG, CAUCAA, CAUCAC, CAUCAG, CAUCAU, CAUCCA, CAUCCC, CAUCCG, CAUCGA, CAUCGC, CAUCGG, CAUCGU, CAUCUA, CAUCUC, CAUCUG, CAUCUU, CAUGAA, CAUGAC, CAUGAG, CAUGAU, CAUGCA, CAUGCC, CAUGCG, CAUGCU, CAUGGC, CAUGGG, CAUGGU, CAUGUA, CAUGUC, CAUGUU, CAUUAA, CAUUAC, CAUUAG, CAUUCA, CAUUCC, CAUUCG, CAUUCU, CAUUGA, CAUUGG, CAUUUC, CAUUUG, CAUUUU, CCAAAA, CCAAAC, CCAAAG, CCAAAU, CCAACA, CCAACC, CCAACG, CCAACU, CCAAGA, CCAAGC, CCAAGG, CCAAUC, CCAAUG, CCAAUU, CCACAA, CCACAC, CCACAG, CCACAU, CCACCA, CCACCC, CCACCG, CCACCU, CCACGA, CCACGC, CCACGG, CCACGU, CCACUA, CCACUC, CCACUU, CCAGAA, CCAGAC, CCAGAG, CCAGCC, CCAGGU, CCAGUC, CCAGUU, CCAUAA, CCAUAC, CCAUAG, CCAUAU, CCAUCA, CCAUCC, CCAUCU, CCAUGA, CCAUGC, CCAUGG, CCAUUC, CCAUUG, CCAUUU, CCCAAC, CCCAAG, CCCAAU, CCCACA, CCCAGA, CCCAGC, CCCAGU, CCCAUA, CCCAUC, CCCAUG, CCCAUU, CCCCAA, CCCCAG, CCCCAU, CCCCCC, CCCCCG, CCCCCU, CCCCGA, CCCCGC, CCCCGU, CCCCUA, CCCCUC, CCCGAA, CCCGAC, CCCGAU, CCCGCA, CCCGCU, CCCGGA, CCCGGC, CCCGUA, CCCGUG, CCCGUU, CCCUAA, CCCUAG, CCCUCA, CCCUCU, CCCUGC, CCCUUA, CCCUUC, CCCUUU, CCGAAA, CCGAAC, CCGAAU, CCGACA, CCGACC, CCGACG, CCGACU, CCGAGA, CCGAGG, CCGAGU, CCGAUA, CCGAUC, CCGAUG, CCGAUU, CCGCAA, CCGCAC, CCGCAG, CCGCAU, CCGCCA, CCGCCC, CCGCCG, CCGCCU, CCGCGA, CCGCGC, CCGCGG, CCGCGU, CCGCUA, CCGCUC, CCGCUG, CCGCUU, CCGGAA, CCGGAU, CCGGCA, CCGGCC, CCGGCG, CCGGCU, CCGGGA, CCGGGC, CCGGGG, CCGGGU, CCGGUA, CCGGUC, CCGGUG, CCGUAA, CCGUAG,

TABLE 1-continued

Non-Seed hexamer sequences.

CCGUAU, CCGUCA, CCGUCC, CCGUCG, CCGUGA, CCGUGU, CCGUUA, CCGUUC, CCGUUG, CCGUUU,
CCUAAC, CCUAAG, CCUAAU, CCUACA, CCUACC, CCUACG, CCUACU, CCUAGA, CCUAGC, CCUAGG,
CCUAGU, CCUAUA, CCUAUC, CCUAUG, CCUAUU, CCUCAA, CCUCAC, CCUCAG, CCUCAU, CCUCCA,
CCUCCC, CCUCCG, CCUCGA, CCUCGC, CCUCGG, CCUCGU, CCUCUA, CCUCUG, CCUGAC, CCUGAU,
CCUGCA, CCUGGG, CCUGGU, CCUGUU, CCUUAA, CCUUAC, CCUUAG, CCUUAU, CCUUCG, CCUUGA,
CCUUGU, CCUUUA, CCUUUC, CCUUUU, CGAAAA, CGAAAC, CGAAAG, CGAAAU, CGAACA, CGAACC,
CGAACG, CGAACU, CGAAGA, CGAAGC, CGAAGG, CGAAGU, CGAAUA, CGAAUC, CGAAUG, CGAAUU,
CGACAA, CGACAC, CGACAU, CGACCA, CGACCU, CGACGA, CGACGC, CGACGG, CGACGU, CGACUA,
CGACUG, CGACUU, CGAGAA, CGAGAC, CGAGAG, CGAGAU, CGAGCA, CGAGCC, CGAGCG, CGAGCU,
CGAGGC, CGAGGG, CGAGGU, CGAGUA, CGAGUC, CGAGUG, CGAGUU, CGAUAA, CGAUAC, CGAUAG,
CGAUAU, CGAUCA, CGAUCC, CGAUCG, CGAUCU, CGAUGA, CGAUGC, CGAUGG, CGAUGU, CGAUUA,
CGAUUC, CGAUUG, CGAUUU, CGCAAA, CGCAAC, CGCAAG, CGCAAU, CGCACA, CGCACC, CGCACG,
CGCAGA, CGCAGC, CGCAGG, CGCAGU, CGCAUA, CGCAUC, CGCAUG, CGCAUU, CGCCAA, CGCCAC,
CGCCAG, CGCCAU, CGCCCA, CGCCCC, CGCCCG, CGCCGA, CGCCGC, CGCCGG, CGCCGU, CGCCUA,
CGCCUG, CGCCUU, CGCGAA, CGCGAC, CGCGAG, CGCGAU, CGCGCA, CGCGCC, CGCGCG, CGCGCU,
CGCGGA, CGCGGC, CGCGGG, CGCGGU, CGCGUA, CGCGUC, CGCGUG, CGCGUU, CGCUAA, CGCUAC,
CGCUAG, CGCUAU, CGCUCA, CGCUCC, CGCUCG, CGCUCU, CGCUGA, CGCUGC, CGCUGG, CGCUGU,
CGCUUA, CGCUUC, CGCUUG, CGGAAA, CGGAAC, CGGAAG, CGGACA, CGGACC, CGGACG, CGGACU,
CGGAGC, CGGAGG, CGGAGU, CGGAUA, CGGAUU, CGGCAA, CGGCAC, CGGCAG, CGGCCA, CGGCCC,
CGGCCG, CGGCGC, CGGCGG, CGGCGU, CGGCUA, CGGCUC, CGGCUG, CGGCUU, CGGGAA, CGGGAC,
CGGGAG, CGGGAU, CGGGCA, CGGGCC, CGGGCG, CGGGCU, CGGGGU, CGGGUA, CGGGUC, CGGGUG,
CGGUAA, CGGUAC, CGGUAG, CGGUAU, CGGUCA, CGGUCG, CGGUCU, CGGUGA, CGGUGG, CGGUGU,
CGGUUA, CGGUUC, CGGUUG, CGGUUU, CGUAAA, CGUAAC, CGUAAG, CGUAAU, CGUACA, CGUACG,
CGUACU, CGUAGA, CGUAGC, CGUAGG, CGUAGU, CGUAUA, CGUAUC, CGUAUG, CGUAUU, CGUCAA,
CGUCAC, CGUCAG, CGUCAU, CGUCCA, CGUCCC, CGUCCG, CGUCCU, CGUCGA, CGUCGG, CGUCGU,
CGUCUA, CGUCUC, CGUCUG, CGUCUU, CGUGAA, CGUGAC, CGUGAG, CGUGAU, CGUGCC, CGUGCG,
CGUGCU, CGUGGA, CGUGGG, CGUGGU, CGUGUA, CGUGUG, CGUUAA, CGUUAC, CGUUAG,
CGUUAU, CGUUCA, CGUUCC, CGUUCG, CGUUCU, CGUUGA, CGUUGC, CGUUGU, CGUUUA, CGUUUC,
CGUUUU, CUAAAA, CUAAAC, CUAAAU, CUAACA, CUAACC, CUAACG, CUAACU, CUAAGA, CUAAGC,
CUAAGU, CUAAUA, CUAAUC, CUAAUG, CUACAC, CUACAU, CUACCA, CUACCC, CUACCG, CUACCU,
CUACGA, CUACGC, CUACGG, CUACGU, CUACUA, CUACUC, CUACUG, CUAGAA, CUAGAG, CUAGAU,
CUAGCA, CUAGCC, CUAGCG, CUAGCU, CUAGGA, CUAGGG, CUAGGU, CUAGUG, CUAGUU, CUAUAA,
CUAUAG, CUAUAU, CUAUCA, CUAUCC, CUAUCG, CUAUCU, CUAUGA, CUAUGC, CUAUGG, CUAUGU,
CUAUUA, CUAUUG, CUCAAC, CUCAAG, CUCAAU, CUCACC, CUCACG, CUCAGC, CUCAUA, CUCAUC,
CUCAUG, CUCAUU, CUCCAC, CUCCCC, CUCCCG, CUCCGA, CUCCGC, CUCCGG, CUCCUA, CUCCUC,
CUCCUU, CUCGAA, CUCGAC, CUCGAG, CUCGAU, CUCGCA, CUCGCC, CUCGCG, CUCGGG, CUCGGU,
CUCGUA, CUCGUC, CUCGUG, CUCGUU, CUCUAA, CUCUAC, CUCUAU, CUCUCA, CUCUCC, CUCUCU,
CUCUGC, CUCUGU, CUCUUA, CUCUUG, CUGAAG, CUGACC, CUGACG, CUGAGC, CUGAUA, CUGAUC,
CUGCCG, CUGCCU, CUGCGA, CUGCUA, CUGCUU, CUGGAG, CUGGAU, CUGGCG, CUGGGU, CUGUAC,

TABLE 1-continued

Non-Seed hexamer sequences.

CUGUCA, CUGUCC, CUGUCG, CUGUGG, CUGUGU, CUGUUA, CUGUUU, CUUAAC, CUUAAG, CUUAAU,
CUUACC, CUUACG, CUUAGA, CUUAGC, CUUAGG, CUUAGU, CUUAUA, CUUAUC, CUUAUG, CUUAUU,
CUUCAG, CUUCAU, CUUCCA, CUUCCC, CUUCCG, CUUCCU, CUUCGA, CUUCGC, CUUCGG, CUUCGU,
CUUCUA, CUUGAC, CUUGAG, CUUGAU, CUUGCA, CUUGCC, CUUGCG, CUUGCU, CUUGGC, CUUGGU,
CUUGUU, CUUUAC, CUUUAG, CUUUAU, CUUUCA, CUUUCG, CUUUCU, CUUUGA, CUUUGC, CUUUGU,
CUUUUA, CUUUUC, CUUUUG, CUUUUU, GAAAAA, GAAAAG, GAAAAU, GAAACC, GAAACG, GAAAGA,
GAAAGC, GAAAGU, GAAAUA, GAAAUC, GAAAUG, GAAAUU, GAACAA, GAACAC, GAACAG, GAACAU,
GAACCA, GAACCC, GAACCG, GAACCU, GAACGA, GAACGC, GAACGG, GAACGU, GAACUA, GAACUG,
GAACUU, GAAGAC, GAAGAG, GAAGCA, GAAGCG, GAAGCU, GAAGUC, GAAUAA, GAAUAC, GAAUAG,
GAAUAU, GAAUCC, GAAUCG, GAAUCU, GAAUGA, GAAUGC, GAAUGU, GAAUUA, GAAUUC, GAAUUU,
GACAAA, GACAAG, GACAAU, GACACC, GACAGA, GACAGG, GACAUA, GACAUG, GACAUU, GACCAA,
GACCAC, GACCAG, GACCCA, GACCCC, GACCCG, GACCGC, GACCGG, GACCGU, GACCUA, GACCUC,
GACCUU, GACGAA, GACGAC, GACGAG, GACGAU, GACGCA, GACGCC, GACGCG, GACGCU, GACGGA,
GACGGC, GACGGG, GACGGU, GACGUA, GACGUC, GACGUG, GACGUU, GACUAA, GACUAC, GACUAG,
GACUAU, GACUCA, GACUCC, GACUCG, GACUGG, GACUGU, GACUUA, GACUUG, GACUUU, GAGAAU,
GAGAGA, GAGAGC, GAGAGG, GAGAUA, GAGAUC, GAGCAA, GAGCAU, GAGCCA, GAGCGA, GAGCGG,
GAGCGU, GAGGGU, GAGGUC, GAGGUG, GAGUAA, GAGUAG, GAGUCC, GAGUUC, GAGUUU,
GAUAAA, GAUAAC, GAUAAG, GAUAAU, GAUACA, GAUACC, GAUACG, GAUACU, GAUAGA, GAUAGC,
GAUAGG, GAUAGU, GAUAUA, GAUCAA, GAUCAC, GAUCAU, GAUCCA, GAUCCC, GAUCCU, GAUCGC,
GAUCGG, GAUCGU, GAUCUA, GAUCUG, GAUCUU, GAUGAA, GAUGAC, GAUGAG, GAUGCA, GAUGCC,
GAUGCG, GAUGCU, GAUGGC, GAUGGG, GAUGGU, GAUGUG, GAUGUU, GAUUAA, GAUUAC,
GAUUAG, GAUUAU, GAUUCA, GAUUCG, GAUUCU, GAUUGA, GAUUGC, GAUUUA, GAUUUC,
GAUUUG, GAUUUU, GCAAAC, GCAAAG, GCAAAU, GCAACA, GCAACC, GCAAGC, GCAAGU, GCAAUA,
GCAAUC, GCAAUG, GCAAUU, GCACAA, GCACAC, GCACAG, GCACCC, GCACCG, GCACCU, GCACGA,
GCACGC, GCACGU, GCACUA, GCACUC, GCACUG, GCACUU, GCAGAU, GCAGCC, GCAGCG, GCAGGC,
GCAGUA, GCAGUC, GCAGUG, GCAGUU, GCAUAA, GCAUAG, GCAUAU, GCAUCG, GCAUCU, GCAUGA,
GCAUGC, GCAUGG, GCAUGU, GCAUUA, GCAUUC, GCAUUG, GCAUUU, GCCAAA, GCCAAC, GCCAAU,
GCCACA, GCCACC, GCCACG, GCCAGA, GCCAGU, GCCAUA, GCCAUC, GCCAUG, GCCAUU, GCCCAA,
GCCCAC, GCCCAG, GCCCCG, GCCCGA, GCCCGG, GCCCGU, GCCGAA, GCCGAC, GCCGAG, GCCGAU,
GCCGCA, GCCGCU, GCCGGA, GCCGGC, GCCGGG, GCCGGU, GCCGUA, GCCGUC, GCCGUG, GCCGUU,
GCCUAA, GCCUAU, GCCUCA, GCCUCC, GCCUCG, GCCUGA, GCCUUA, GCCUUU, GCGAAA, GCGAAC,
GCGAAG, GCGAAU, GCGACC, GCGACG, GCGACU, GCGAGA, GCGAGC, GCGAGG, GCGAGU, GCGAUA,
GCGAUC, GCGAUG, GCGAUU, GCGCAA, GCGCAC, GCGCAG, GCGCAU, GCGCCA, GCGCCC, GCGCCU,
GCGCGA, GCGCGU, GCGCUA, GCGCUC, GCGCUG, GCGCUU, GCGGAA, GCGGAC, GCGGAU, GCGGCA,
GCGGCC, GCGGCU, GCGGGA, GCGGUA, GCGGUC, GCGGUU, GCGUAA, GCGUAC, GCGUAG, GCGUAU,
GCGUCA, GCGUCC, GCGUCG, GCGUCU, GCGUGA, GCGUGC, GCGUGG, GCGUGU, GCGUUA, GCGUUC,
GCGUUG, GCGUUU, GCUAAA, GCUAAC, GCUAAG, GCUAAU, GCUACC, GCUACG, GCUACU, GCUAGA,
GCUAGG, GCUAGU, GCUAUA, GCUAUC, GCUAUU, GCUCAA, GCUCAC, GCUCAG, GCUCAU, GCUCCA,
GCUCCC, GCUCCG, GCUCGA, GCUCGC, GCUCGU, GCUCUA, GCUCUC, GCUCUU, GCUGAA, GCUGAC,

TABLE 1-continued

Non-Seed hexamer sequences.

GCUGAU, GCUGCA, GCUGCC, GCUGCG, GCUGCU, GCUGUG, GCUGUU, GCUUAC, GCUUAG, GCUUAU,

GCUUCA, GCUUCG, GCUUGA, GCUUGG, GCUUGU, GCUUUA, GCUUUG, GGAAAG, GGAACA, GGAACC,

GGAACG, GGAACU, GGAAGU, GGAAUA, GGAAUC, GGAAUU, GGACAA, GGACAC, GGACAG, GGACAU,

GGACCG, GGACGA, GGACGC, GGACGU, GGACUA, GGACUC, GGACUU, GGAGAC, GGAGCA, GGAGCG,

GGAGGG, GGAGUA, GGAUAA, GGAUAC, GGAUCA, GGAUCC, GGAUCG, GGAUCU, GGAUGC, GGAUUA,

GGAUUG, GGCAAU, GGCACA, GGCACU, GGCAGA, GGCAUA, GGCAUC, GGCCAC, GGCCAG, GGCCCC,

GGCCGA, GGCCGC, GGCCGU, GGCCUA, GGCCUG, GGCCUU, GGCGAA, GGCGAG, GGCGAU, GGCGCA,

GGCGCU, GGCGGU, GGCGUA, GGCGUC, GGCGUG, GGCGUU, GGCUAA, GGCUAC, GGCUAG, GGCUAU,

GGCUCC, GGCUCG, GGCUGA, GGCUUA, GGCUUC, GGCUUG, GGGAAU, GGGACA, GGGAGA, GGGAGU,

GGGAUA, GGGAUU, GGGCAA, GGGCAC, GGGCAG, GGGCCG, GGGCGG, GGGGCC, GGGGGG,

GGGGGU, GGGGUA, GGGUAC, GGGUAU, GGGUCA, GGGUCC, GGGUCG, GGGUGA, GGGUGC,

GGGUUA, GGGUUG, GGUAAA, GGUAAC, GGUAAG, GGUAAU, GGUACA, GGUACC, GGUACG,

GGUACU, GGUAGC, GGUAGG, GGUAGU, GGUAUA, GGUAUC, GGUAUG, GGUCAA, GGUCAC,

GGUCAG, GGUCAU, GGUCCA, GGUCCG, GGUCCU, GGUCGA, GGUCGC, GGUCGG, GGUCGU, GGUCUC,

GGUCUU, GGUGAA, GGUGAC, GGUGAU, GGUGCA, GGUGCC, GGUGGC, GGUGUA, GGUGUC,

GGUUAA, GGUUAG, GGUUAU, GGUUCA, GGUUCC, GGUUCG, GGUUGC, GGUUUC, GGUUUU,

GUAAAA, GUAAAG, GUAAAU, GUAACC, GUAACG, GUAACU, GUAAGA, GUAAGC, GUAAGG, GUAAGU,

GUAAUA, GUAAUC, GUAAUG, GUAAUU, GUACAA, GUACAC, GUACAG, GUACAU, GUACCA, GUACCC,

GUACCG, GUACCU, GUACGA, GUACGC, GUACGG, GUACGU, GUACUA, GUACUC, GUACUG, GUACUU,

GUAGAA, GUAGAC, GUAGCA, GUAGCC, GUAGCG, GUAGCU, GUAGGA, GUAGGC, GUAGGG,

GUAGGU, GUAGUA, GUAGUC, GUAUAA, GUAUAC, GUAUAG, GUAUAU, GUAUCA, GUAUCG,

GUAUCU, GUAUGA, GUAUGC, GUAUGG, GUAUUA, GUAUUG, GUAUUU, GUCAAA, GUCAAG,

GUCAAU, GUCACA, GUCACC, GUCACG, GUCAGA, GUCAGC, GUCAGG, GUCAUA, GUCAUC, GUCAUG,

GUCCAA, GUCCAC, GUCCAU, GUCCCC, GUCCCU, GUCCGA, GUCCGC, GUCCGG, GUCCGU, GUCCUA,

GUCCUG, GUCCUU, GUCGAA, GUCGAC, GUCGAG, GUCGAU, GUCGCA, GUCGCC, GUCGCG, GUCGCU,

GUCGGA, GUCGGC, GUCGGG, GUCGGU, GUCGUA, GUCGUC, GUCGUU, GUCUAA, GUCUAG, GUCUCA,

GUCUCC, GUCUCG, GUCUGA, GUCUGG, GUCUGU, GUCUUC, GUCUUU, GUGAAA, GUGAAC, GUGAAG,

GUGACC, GUGACG, GUGAGA, GUGAGC, GUGAGU, GUGAUC, GUGAUG, GUGAUU, GUGCAC,

GUGCAU, GUGCCC, GUGCCG, GUGCGA, GUGCGG, GUGCGU, GUGCUA, GUGCUC, GUGCUG,

GUGGAG, GUGGCG, GUGGCU, GUGGGU, GUGGUC, GUGGUG, GUGUAA, GUGUAG, GUGUCG,

GUGUGA, GUGUGC, GUGUGU, GUGUUG, GUGUUU, GUUAAA, GUUAAC, GUUAAG, GUUACA,

GUUACC, GUUACG, GUUACU, GUUAGA, GUUAGC, GUUAGU, GUUAUA, GUUAUC, GUUAUG,

GUUAUU, GUUCAA, GUUCAC, GUUCAG, GUUCCA, GUUCCG, GUUCGA, GUUCGC, GUUCGG, GUUCGU,

GUUCUA, GUUCUG, GUUGAA, GUUGAC, GUUGAG, GUUGAU, GUUGCG, GUUGCU, GUUGGA,

GUUGGC, GUUGGU, GUUGUC, GUUGUG, GUUGUU, GUUUAA, GUUUAC, GUUUAG, GUUUAU,

GUUUCA, GUUUCC, GUUUCU, GUUUGA, GUUUGC, GUUUGG, GUUUGU, GUUUUA, GUUUUC,

GUUUUU, UAAAAA, UAAAAC, UAAAAG, UAAAAU, UAAACA, UAAACC, UAAACG, UAAACU, UAAAGA,

UAAAGG, UAAAGU, UAAAUA, UAAAUC, UAAAUG, UAAAUU, UAACAA, UAACAC, UAACAG, UAACCA,

UAACCC, UAACCG, UAACCU, UAACGA, UAACGC, UAACGG, UAACGU, UAACUA, UAACUG, UAACUU,

TABLE 1-continued

Non-Seed hexamer sequences.

UAAGAG, UAAGAU, UAAGCA, UAAGCC, UAAGCG, UAAGCU, UAAGGA, UAAGGC, UAAGGG, UAAGGU,

UAAGUA, UAAGUC, UAAGUG, UAAGUU, UAAUAA, UAAUCA, UAAUCC, UAAUCG, UAAUCU, UAAUGA,

UAAUGG, UAAUGU, UAAUUA, UAAUUC, UAAUUG, UACAAC, UACAAG, UACAAU, UACACC, UACACG,

UACACU, UACAGA, UACAGC, UACAUA, UACAUC, UACAUU, UACCAA, UACCAC, UACCAG, UACCAU,

UACCCC, UACCCG, UACCCU, UACCGA, UACCGC, UACCGG, UACCGU, UACCUA, UACCUG, UACGAA,

UACGAC, UACGAG, UACGAU, UACGCA, UACGCC, UACGCG, UACGCU, UACGGC, UACGGG, UACGGU,

UACGUA, UACGUC, UACGUG, UACGUU, UACUAA, UACUAC, UACUAG, UACUAU, UACUCA, UACUCC,

UACUCG, UACUCU, UACUGA, UACUGC, UACUGG, UACUUA, UACUUG, UACUUU, UAGAAA, UAGAAG,

UAGAAU, UAGACA, UAGACG, UAGAGA, UAGAGC, UAGAGU, UAGAUA, UAGAUC, UAGAUG, UAGCAU,

UAGCCC, UAGCCG, UAGCCU, UAGCGA, UAGCGC, UAGCGU, UAGCUA, UAGCUC, UAGCUG, UAGGAA,

UAGGAU, UAGGCG, UAGGCU, UAGGGU, UAGGUC, UAGGUG, UAGGUU, UAGUAA, UAGUAC,

UAGUAG, UAGUAU, UAGUCA, UAGUCG, UAGUGU, UAGUUA, UAGUUC, UAGUUG, UAGUUU,

UAUAAC, UAUAAG, UAUACU, UAUAGA, UAUAGC, UAUAGG, UAUAGU, UAUAUA, UAUAUC, UAUAUG,

UAUAUU, UAUCAA, UAUCAC, UAUCAU, UAUCCA, UAUCCC, UAUCCG, UAUCCU, UAUCGA, UAUCGC,

UAUCGG, UAUCGU, UAUCUA, UAUCUC, UAUCUG, UAUCUU, UAUGAA, UAUGAC, UAUGAG,

UAUGAU, UAUGCA, UAUGCG, UAUGCU, UAUGGA, UAUGGC, UAUGUC, UAUGUG, UAUGUU,

UAUUAG, UAUUCA, UAUUCC, UAUUCG, UAUUCU, UAUUGA, UAUUGG, UAUUUA, UAUUUC,

UAUUUG, UAUUUU, UCAAAA, UCAAAC, UCAAAG, UCAACC, UCAACU, UCAAGA, UCAAGC, UCAAUA,

UCAAUC, UCAAUG, UCAAUU, UCACCC, UCACCG, UCACCU, UCACGA, UCACGC, UCACGG, UCACGU,

UCACUA, UCACUC, UCACUU, UCAGAA, UCAGAC, UCAGAG, UCAGCG, UCAGCU, UCAGGA, UCAGGC,

UCAGGU, UCAGUC, UCAGUU, UCAUAA, UCAUCA, UCAUCC, UCAUCG, UCAUGC, UCAUGG, UCAUGU,

UCAUUA, UCAUUG, UCCAAA, UCCAAC, UCCAAG, UCCAAU, UCCACA, UCCACC, UCCACG, UCCAGC,

UCCAGG, UCCAUA, UCCAUC, UCCAUU, UCCCAA, UCCCAG, UCCCAU, UCCCCC, UCCCCG, UCCCCU,

UCCCGA, UCCCGC, UCCCGG, UCCCGU, UCCCUA, UCCCUC, UCCGAA, UCCGAC, UCCGAG, UCCGAU,

UCCGCA, UCCGCC, UCCGGA, UCCGGC, UCCGGU, UCCGUA, UCCGUC, UCCGUG, UCCUAA, UCCUCA,

UCCUCG, UCCUCU, UCCUGC, UCCUGU, UCCUUA, UCCUUC, UCCUUU, UCGAAA, UCGAAC, UCGAAG,

UCGAAU, UCGACA, UCGACC, UCGACG, UCGACU, UCGAGA, UCGAGC, UCGAGG, UCGAUA, UCGAUC,

UCGAUG, UCGAUU, UCGCAA, UCGCAC, UCGCAG, UCGCAU, UCGCCA, UCGCCC, UCGCCG, UCGCCU,

UCGCGA, UCGCGC, UCGCGU, UCGCUA, UCGCUC, UCGGAA, UCGGAC, UCGGAG, UCGGAU, UCGGCA,

UCGGCU, UCGGGG, UCGGGU, UCGGUC, UCGGUG, UCGGUU, UCGUAA, UCGUAC, UCGUAG,

UCGUAU, UCGUCA, UCGUCC, UCGUCG, UCGUCU, UCGUGA, UCGUGU, UCGUUA, UCGUUC, UCGUUG,

UCGUUU, UCUAAC, UCUAAG, UCUAAU, UCUACA, UCUACC, UCUACG, UCUACU, UCUAGC, UCUAGG,

UCUAGU, UCUAUA, UCUAUC, UCUAUG, UCUAUU, UCUCAG, UCUCAU, UCUCCG, UCUCGC, UCUCGG,

UCUCGU, UCUCUC, UCUGAA, UCUGAU, UCUGCA, UCUGCG, UCUGCU, UCUGGC, UCUGGU, UCUGUC,

UCUGUG, UCUGUU, UCUUAA, UCUUAC, UCUUAG, UCUUAU, UCUUCA, UCUUCC, UCUUCG, UCUUCU,

UCUUGC, UCUUGG, UCUUGU, UCUUUA, UCUUUC, UCUUUG, UCUUUU, UGAAAA, UGAAAC,

UGAACA, UGAACC, UGAAGG, UGAAUC, UGAAUG, UGACAA, UGACAC, UGACAG, UGACCA, UGACCC,

UGACCG, UGACGA, UGACGC, UGACGG, UGACGU, UGACUA, UGACUC, UGACUU, UGAGAG, UGAGAU,

UGAGCA, UGAGCC, UGAGCU, UGAGGC, UGAGGU, UGAGUA, UGAGUU, UGAUAC, UGAUAG,

TABLE 1-continued

Non-Seed hexamer sequences.

UGAUAU, UGAUCA, UGAUCG, UGAUCU, UGAUGA, UGAUGC, UGAUGG, UGAUGU, UGAUUA,
UGAUUC, UGAUUG, UGAUUU, UGCAAC, UGCAAG, UGCACA, UGCACG, UGCAGG, UGCAGU, UGCAUC,
UGCCCA, UGCCCC, UGCCCG, UGCCGA, UGCCGC, UGCCGG, UGCCGU, UGCCUA, UGCCUC, UGCCUG,
UGCCUU, UGCGAA, UGCGAC, UGCGAU, UGCGCC, UGCGCG, UGCGCU, UGCGGC, UGCGGG, UGCGGU,
UGCGUA, UGCGUC, UGCGUG, UGCGUU, UGCUAC, UGCUAU, UGCUCC, UGCUCG, UGCUGC, UGCUGG,
UGCUGU, UGCUUA, UGCUUU, UGGAAC, UGGAAG, UGGAGC, UGGAUC, UGGAUU, UGGCAA,
UGGCAC, UGGCAG, UGGCCG, UGGCCU, UGGCGA, UGGCGC, UGGCGU, UGGCUA, UGGCUC, UGGCUU,
UGGGAA, UGGGCA, UGGGCC, UGGGGC, UGGGUC, UGGUAA, UGGUAG, UGGUAU, UGGUCC,
UGGUCG, UGGUCU, UGGUGA, UGGUGC, UGGUGG, UGGUGU, UGGUUA, UGGUUG, UGUAAA,
UGUAAC, UGUAAG, UGUACC, UGUACG, UGUACU, UGUAGA, UGUAGC, UGUAGU, UGUAUC,
UGUAUU, UGUCAA, UGUCAC, UGUCAG, UGUCAU, UGUCCA, UGUCCC, UGUCCG, UGUCGA, UGUCGC,
UGUCGG, UGUCGU, UGUCUA, UGUCUC, UGUGAC, UGUGAG, UGUGAU, UGUGCA, UGUGGU,
UGUGUA, UGUGUU, UGUUAC, UGUUAG, UGUUAU, UGUUCA, UGUUCC, UGUUCG, UGUUGG,
UGUUGU, UGUUUA, UGUUUC, UGUUUG, UGUUUU, UUAAAA, UUAAAC, UUAAAG, UUAAAU,
UUAACC, UUAACG, UUAACU, UUAAGU, UUAAUA, UUAAUC, UUAAUG, UUAAUU, UUACAA, UUACAC,
UUACAG, UUACAU, UUACCA, UUACCC, UUACCG, UUACCU, UUACGA, UUACGC, UUACGG, UUACGU,
UUACUA, UUACUC, UUACUG, UUACUU, UUAGAA, UUAGAC, UUAGCC, UUAGCG, UUAGCU, UUAGGC,
UUAGGU, UUAGUA, UUAGUC, UUAGUU, UUAUAA, UUAUAC, UUAUAG, UUAUAU, UUAUCC,
UUAUCG, UUAUCU, UUAUGA, UUAUGG, UUAUGU, UUAUUA, UUAUUC, UUAUUG, UUAUUU,
UUCAAC, UUCAAU, UUCACA, UUCACC, UUCACG, UUCACU, UUCAGC, UUCAGG, UUCAGU, UUCAUA,
UUCAUC, UUCAUG, UUCAUU, UUCCAA, UUCCCA, UUCCCG, UUCCGA, UUCCGU, UUCCUU, UUCGAA,
UUCGAC, UUCGAG, UUCGAU, UUCGCA, UUCGCC, UUCGCG, UUCGCU, UUCGGA, UUCGGC, UUCGGG,
UUCGGU, UUCGUA, UUCGUC, UUCGUG, UUCGUU, UUCUAC, UUCUAG, UUCUCA, UUCUCG,
UUCUGG, UUCUUA, UUCUUU, UUGAAA, UUGAAC, UUGAAG, UUGAAU, UUGACC, UUGACG,
UUGACU, UUGAGA, UUGAGC, UUGAGU, UUGAUA, UUGAUC, UUGAUG, UUGAUU, UUGCAA,
UUGCAC, UUGCAG, UUGCAU, UUGCCC, UUGCCG, UUGCGA, UUGCGC, UUGCGG, UUGCGU, UUGCUA,
UUGCUC, UUGCUG, UUGCUU, UUGGAA, UUGGAG, UUGGCC, UUGGCG, UUGGCU, UUGGGC,
UUGGGU, UUGGUA, UUGGUG, UUGUAA, UUGUAC, UUGUCA, UUGUCG, UUGUCU, UUGUGC,
UUGUGG, UUGUUA, UUGUUG, UUGUUU, UUUAAA, UUUAAC, UUUAAG, UUUAAU, UUUACA,
UUUACC, UUUACG, UUUACU, UUUAGA, UUUAGC, UUUAGG, UUUAGU, UUUAUA, UUUAUC,
UUUAUG, UUUAUU, UUUCAU, UUUCCA, UUUCCG, UUUCCU, UUUCGA, UUUCGC, UUUCGG,
UUUCGU, UUUCUA, UUUCUC, UUUCUG, UUUCUU, UUUGAA, UUUGAC, UUUGAG, UUUGAU,
UUUGCC, UUUGCU, UUUGGA, UUUGGC, UUUGGG, UUUGGU, UUUGUA, UUUGUC, UUUGUU,
UUUUAA, UUUUAG, UUUUAU, UUUUCC, UUUUCG, UUUUCU, UUUUGA, UUUUGC, UUUUGG,
UUUUGU, UUUUUA, UUUUUC, UUUUUU

TABLE 2

Oligonucleotide sequences made for testing

| Oligo Name | RQ | RQ SE | Gene Name | Expt Type | Cell Line/Tissue | [Oligo] | Assay Type | Coordinates_g |
|---|---|---|---|---|---|---|---|---|
| SMN1-01 | 0.812671952 | 0.135251351 | SMN1 | in vitro | RPTEC | 100 | qRTPCR | SMN1: 21157U20 |
| SMN1-01 | 0.857032101 | 0.027318737 | SMN1 | in vitro | RPTEC | 50 | qRTPCR | SMN1: 21157U20 |
| SMN1-01 | 0.167998915 | 0.167998672 | SMN1 | in vitro | Hep3B | 50 | qRTPCR | SMN1: 21157U20 |
| SMN1-01 | 1.048125302 | 0.039302784 | SMN1 | in vitro | Hep3B | 100 | qRTPCR | SMN1: 21157U20 |
| SMN1-01 | 1.381704207 | 0.053290565 | SMN1 | in vitro | Hep3B | 10 | qRTPCR | SMN1: 21157U20 |
| SMN1-01 | 0.979869247 | 0.020515227 | SMN1 | in vitro | Hep3B | 30 | qRTPCR | SMN1: 21157U20 |
| SMN1-02 | 0.760000318 | 0.042993212 | SMN1 | in vitro | RPTEC | 100 | qRTPCR | SMN1: 21158U20 |
| SMN1-02 | 0.987138447 | 0.068187998 | SMN1 | in vitro | RPTEC | 50 | qRTPCR | SMN1: 21158U20 |
| SMN1-02 | 2.252494526 | 1.803190669 | SMN1 | in vitro | Hep3B | 50 | qRTPCR | SMN1: 21158U20 |
| SMN1-02 | 1.114387973 | 0.026733251 | SMN1 | in vitro | Hep3B | 100 | qRTPCR | SMN1: 21158U20 |
| SMN1-02 | 1.34641929 | 0.027641281 | SMN1 | in vitro | Hep3B | 10 | qRTPCR | SMN1: 21158U20 |
| SMN1-02 | 1.153697083 | 0.024999991 | SMN1 | in vitro | Hep3B | 30 | qRTPCR | SMN1: 21158U20 |
| SMN1-03 | 1.90722975 | 0.525939296 | SMN1 | in vitro | RPTEC | 100 | qRTPCR | SMN1: 21159U20 |
| SMN1-03 | 1.132758264 | 0.094640177 | SMN1 | in vitro | RPTEC | 50 | qRTPCR | SMN1: 21159U20 |
| SMN1-03 | 0.29619174 | 0.173282309 | SMN1 | in vitro | Hep3B | 50 | qRTPCR | SMN1: 21159U20 |
| SMN1-03 | 1.48817935 | 0.172719507 | SMN1 | in vitro | Hep3B | 100 | qRTPCR | SMN1: 21159U20 |
| SMN1-03 | 1.29932826 | 0.059825228 | SMN1 | in vitro | Hep3B | 10 | qRTPCR | SMN1: 21159U20 |
| SMN1-03 | 1.511567814 | 0.054178175 | SMN1 | in vitro | Hep3B | 30 | qRTPCR | SMN1: 21159U20 |
| SMN1-04 | 1.048306517 | 0.243934543 | SMN1 | in vitro | RPTEC | 100 | qRTPCR | SMN1: 21160U20 |
| SMN1-04 | 1.322407267 | 0.100022392 | SMN1 | in vitro | RPTEC | 50 | qRTPCR | SMN1: 21160U20 |
| SMN1-04 | 0.133170013 | 0.032824391 | SMN1 | in vitro | Hep3B | 50 | qRTPCR | SMN1: 21160U20 |
| SMN1-04 | 1.289550163 | 0.330195987 | SMN1 | in vitro | Hep3B | 100 | qRTPCR | SMN1: 21160U20 |
| SMN1-04 | 1.280225492 | 0.062577972 | SMN1 | in vitro | Hep3B | 10 | qRTPCR | SMN1: 21160U20 |
| SMN1-04 | 1.488482795 | 0.044641287 | SMN1 | in vitro | Hep3B | 30 | qRTPCR | SMN1: 21160U20 |
| SMN1-05 | 0.876747527 | 0.087392504 | SMN1 | in vitro | RPTEC | 100 | qRTPCR | SMN1: 21161U20 |
| SMN1-05 | 1.167120345 | 0.069814091 | SMN1 | in vitro | RPTEC | 50 | qRTPCR | SMN1: 21161U20 |
| SMN1-05 | 0.088317863 | 0.039887014 | SMN1 | in vitro | Hep3B | 50 | qRTPCR | SMN1: 21161U20 |
| SMN1-05 | 1.310053256 | 0.234231348 | SMN1 | in vitro | Hep3B | 100 | qRTPCR | SMN1: 21161U20 |
| SMN1-05 | 1.038699643 | 0.056421362 | SMN1 | in vitro | Hep3B | 10 | qRTPCR | SMN1: 21161U20 |
| SMN1-05 | 0.859144751 | 0.039970015 | SMN1 | in vitro | Hep3B | 30 | qRTPCR | SMN1: 21161U20 |
| SMN1-06 | 0.704659891 | 0.087244119 | SMN1 | in vitro | RPTEC | 100 | qRTPCR | SMN1: 21162U20 |
| SMN1-06 | 1.11194006 | 0.088571377 | SMN1 | in vitro | RPTEC | 50 | qRTPCR | SMN1: 21162U20 |
| SMN1-06 | 0.57685962 | 0.246186541 | SMN1 | in vitro | Hep3B | 50 | qRTPCR | SMN1: 21162U20 |
| SMN1-06 | 1.419418884 | 0.432447122 | SMN1 | in vitro | Hep3B | 100 | qRTPCR | SMN1: 21162U20 |
| SMN1-06 | 1.146251704 | 0.051891541 | SMN1 | in vitro | Hep3B | 10 | qRTPCR | SMN1: 21162U20 |
| SMN1-06 | 1.030682317 | 0.013070835 | SMN1 | in vitro | Hep3B | 30 | qRTPCR | SMN1: 21162U20 |
| SMN1-07 | 0.682085732 | 0.084885351 | SMN1 | in vitro | RPTEC | 100 | qRTPCR | SMN1: 21163U20 |
| SMN1-07 | 0.975853552 | 0.034178542 | SMN1 | in vitro | RPTEC | 50 | qRTPCR | SMN1: 21163U20 |
| SMN1-07 | 1.013252314 | 0.118540759 | SMN1 | in vitro | Hep3B | 50 | qRTPCR | SMN1: 21163U20 |
| SMN1-07 | 1.039381902 | 0.059815387 | SMN1 | in vitro | Hep3B | 100 | qRTPCR | SMN1: 21163U20 |
| SMN1-07 | 1.156949605 | 0.107385405 | SMN1 | in vitro | Hep3B | 10 | qRTPCR | SMN1: 21163U20 |
| SMN1-07 | 1.239503954 | 0.134603844 | SMN1 | in vitro | Hep3B | 30 | qRTPCR | SMN1: 21163U20 |
| SMN1-08 | 0.948714888 | 0.142708231 | SMN1 | in vitro | RPTEC | 100 | qRTPCR | SMN1: 21164U20 |
| SMN1-08 | 1.312080445 | 0.058464993 | SMN1 | in vitro | RPTEC | 50 | qRTPCR | SMN1: 21164U20 |
| SMN1-08 | 0.216530007 | 0.177400555 | SMN1 | in vitro | Hep3B | 50 | qRTPCR | SMN1: 21164U20 |
| SMN1-08 | 2.082151781 | 0.815184252 | SMN1 | in vitro | Hep3B | 100 | qRTPCR | SMN1: 21164U20 |
| SMN1-08 | 1.010090604 | 0.200588791 | SMN1 | in vitro | Hep3B | 10 | qRTPCR | SMN1: 21164U20 |
| SMN1-08 | 1.223947667 | 0.295307243 | SMN1 | in vitro | Hep3B | 30 | qRTPCR | SMN1: 21164U20 |
| SMN1-09 | 0.77519063 | 0.098695118 | SMN1 | in vitro | RPTEC | 100 | qRTPCR | SMN1: 21165U20 |
| SMN1-09 | 1.685731616 | 0.014884028 | SMN1 | in vitro | RPTEC | 50 | qRTPCR | SMN1: 21165U20 |
| SMN1-09 | 0.621406781 | 0.227211261 | SMN1 | in vitro | Hep3B | 50 | qRTPCR | SMN1: 21165U20 |
| SMN1-09 | 0.85593922 | 0.256108337 | SMN1 | in vitro | Hep3B | 100 | qRTPCR | SMN1: 21165U20 |
| SMN1-09 | 0.940186097 | 0.197008464 | SMN1 | in vitro | Hep3B | 10 | qRTPCR | SMN1: 21165U20 |
| SMN1-09 | 0.864481145 | 0.162739271 | SMN1 | in vitro | Hep3B | 30 | qRTPCR | SMN1: 21165U20 |
| SMN1-10 | 0.945730986 | 0.08072952 | SMN1 | in vitro | RPTEC | 100 | qRTPCR | SMN1: 21166U20 |
| SMN1-10 | 1.574526902 | 0.123062684 | SMN1 | in vitro | RPTEC | 50 | qRTPCR | SMN1: 21166U20 |
| SMN1-10 | 0.482822242 | 0.131557474 | SMN1 | in vitro | Hep3B | 50 | qRTPCR | SMN1: 21166U20 |
| SMN1-10 | 1.280629128 | 0.17088425 | SMN1 | in vitro | Hep3B | 100 | qRTPCR | SMN1: 21166U20 |
| SMN1-10 | 1.127254654 | 0.152486374 | SMN1 | in vitro | Hep3B | 10 | qRTPCR | SMN1: 21166U20 |
| SMN1-10 | 1.069571458 | 0.122106758 | SMN1 | in vitro | Hep3B | 30 | qRTPCR | SMN1: 21166U20 |
| SMN1-11 | 0.774436979 | 0.038076182 | SMN1 | in vitro | RPTEC | 100 | qRTPCR | SMN1: 21167U20 |
| SMN1-11 | 1.562714254 | 0.158043098 | SMN1 | in vitro | RPTEC | 50 | qRTPCR | SMN1: 21167U20 |
| SMN1-11 | 0.463655938 | 0.295513886 | SMN1 | in vitro | Hep3B | 50 | qRTPCR | SMN1: 21167U20 |
| SMN1-11 | 0.957611652 | 0.334137541 | SMN1 | in vitro | Hep3B | 100 | qRTPCR | SMN1: 21167U20 |
| SMN1-11 | 1.225973818 | 0.223472758 | SMN1 | in vitro | Hep3B | 10 | qRTPCR | SMN1: 21167U20 |
| SMN1-11 | 1.089302259 | 0.126414268 | SMN1 | in vitro | Hep3B | 30 | qRTPCR | SMN1: 21167U20 |
| SMN1-12 | 0.981429476 | 0.07937384 | SMN1 | in vitro | RPTEC | 100 | qRTPCR | SMN1: 21168U20 |
| SMN1-12 | 1.585088128 | 0.05291912 | SMN1 | in vitro | RPTEC | 50 | qRTPCR | SMN1: 21168U20 |
| SMN1-12 | 0.208586047 | 0.187017655 | SMN1 | in vitro | Hep3B | 50 | qRTPCR | SMN1: 21168U20 |
| SMN1-12 | 3.266965896 | 2.002074369 | SMN1 | in vitro | Hep3B | 100 | qRTPCR | SMN1: 21168U20 |
| SMN1-12 | 1.03381379 | 0.204376291 | SMN1 | in vitro | Hep3B | 10 | qRTPCR | SMN1: 21168U20 |
| SMN1-12 | 1.137471671 | 0.246791954 | SMN1 | in vitro | Hep3B | 30 | qRTPCR | SMN1: 21168U20 |
| SMN1-13 | 0.749636437 | 0.103277003 | SMN1 | in vitro | RPTEC | 100 | qRTPCR | SMN1: 21169U20 |
| SMN1-13 | 1.175989263 | 0.122355585 | SMN1 | in vitro | RPTEC | 50 | qRTPCR | SMN1: 21169U20 |
| SMN1-13 | 0.161499159 | 0.079356287 | SMN1 | in vitro | Hep3B | 50 | qRTPCR | SMN1: 21169U20 |

TABLE 2-continued

Oligonucleotide sequences made for testing

| Oligo Name | RQ | RQ SE | Gene Name | Expt Type | Cell Line/Tissue | [Oligo] | Assay Type | Coordinates_g |
|---|---|---|---|---|---|---|---|---|
| SMN1-13 | 1.287763591 | 0.090306717 | SMN1 | in vitro | Hep3B | 100 | qRTPCR | SMN1: 21169U20 |
| SMN1-13 | 1.3368516 | 0.177814975 | SMN1 | in vitro | Hep3B | 10 | qRTPCR | SMN1: 21169U20 |
| SMN1-13 | 1.037772291 | 0.039404507 | SMN1 | in vitro | Hep3B | 30 | qRTPCR | SMN1: 21169U20 |
| SMN1-14 | 0.771635177 | 0.086041959 | SMN1 | in vitro | RPTEC | 100 | qRTPCR | SMN1: 21170U20 |
| SMN1-14 | 1.467048548 | 0.073113884 | SMN1 | in vitro | RPTEC | 50 | qRTPCR | SMN1: 21170U20 |
| SMN1-14 | 1.978254154 | 1.352951156 | SMN1 | in vitro | Hep3B | 50 | qRTPCR | SMN1: 21170U20 |
| SMN1-14 | 1.311990937 | 0.073121634 | SMN1 | in vitro | Hep3B | 100 | qRTPCR | SMN1: 21170U20 |
| SMN1-14 | 1.12892777 | 0.147162701 | SMN1 | in vitro | Hep3B | 10 | qRTPCR | SMN1: 21170U20 |
| SMN1-14 | 0.855795121 | 0.017797181 | SMN1 | in vitro | Hep3B | 30 | qRTPCR | SMN1: 21170U20 |
| SMN1-15 | 0.891491964 | 0.039822032 | SMN1 | in vitro | RPTEC | 100 | qRTPCR | SMN1: 21171U20 |
| SMN1-15 | 1.573440342 | 0.117453017 | SMN1 | in vitro | RPTEC | 50 | qRTPCR | SMN1: 21171U20 |
| SMN1-15 | 0.366043104 | 0.117162019 | SMN1 | in vitro | Hep3B | 50 | qRTPCR | SMN1: 21171U20 |
| SMN1-15 | 1.738217394 | 0.520148155 | SMN1 | in vitro | Hep3B | 100 | qRTPCR | SMN1: 21171U20 |
| SMN1-15 | 1.383201337 | 0.101830776 | SMN1 | in vitro | Hep3B | 10 | qRTPCR | SMN1: 21171U20 |
| SMN1-15 | 1.619495052 | 0.038364989 | SMN1 | in vitro | Hep3B | 30 | qRTPCR | SMN1: 21171U20 |
| SMN1-16 | 0.73721881 | 0.038067583 | SMN1 | in vitro | RPTEC | 100 | qRTPCR | SMN1: 21172U20 |
| SMN1-16 | 1.441616196 | 0.059823944 | SMN1 | in vitro | RPTEC | 50 | qRTPCR | SMN1: 21172U20 |
| SMN1-16 | 0.510056605 | 0.286522659 | SMN1 | in vitro | Hep3B | 50 | qRTPCR | SMN1: 21172U20 |
| SMN1-16 | 1.381914214 | 0.247880229 | SMN1 | in vitro | Hep3B | 100 | qRTPCR | SMN1: 21172U20 |
| SMN1-16 | 1.310073573 | 0.026347093 | SMN1 | in vitro | Hep3B | 10 | qRTPCR | SMN1: 21172U20 |
| SMN1-16 | 1.418132646 | 0.082371708 | SMN1 | in vitro | Hep3B | 30 | qRTPCR | SMN1: 21172U20 |
| SMN1-17 | 1.219065651 | 0.281987674 | SMN1 | in vitro | RPTEC | 100 | qRTPCR | SMN1: 21173U20 |
| SMN1-17 | 1.274819195 | 0.179527293 | SMN1 | in vitro | RPTEC | 50 | qRTPCR | SMN1: 21173U20 |
| SMN1-17 | 0.416739222 | 0.066066242 | SMN1 | in vitro | Hep3B | 50 | qRTPCR | SMN1: 21173U20 |
| SMN1-17 | 3.331843017 | 0.970174873 | SMN1 | in vitro | Hep3B | 100 | qRTPCR | SMN1: 21173U20 |
| SMN1-17 | 1.260856522 | 0.038565799 | SMN1 | in vitro | Hep3B | 10 | qRTPCR | SMN1: 21173U20 |
| SMN1-17 | 1.609045311 | 0.10487434 | SMN1 | in vitro | Hep3B | 30 | qRTPCR | SMN1: 21173U20 |
| SMN1-18 | 0.868441941 | 0.088184698 | SMN1 | in vitro | RPTEC | 100 | qRTPCR | SMN1: 21174U20 |
| SMN1-18 | 1.221663574 | 0.064445539 | SMN1 | in vitro | RPTEC | 50 | qRTPCR | SMN1: 21174U20 |
| SMN1-18 | 10.28455167 | 3.929310832 | SMN1 | in vitro | Hep3B | 50 | qRTPCR | SMN1: 21174U20 |
| SMN1-18 | 1.800920764 | 0.42559045 | SMN1 | in vitro | Hep3B | 100 | qRTPCR | SMN1: 21174U20 |
| SMN1-18 | 1.261752602 | 0.069817143 | SMN1 | in vitro | Hep3B | 10 | qRTPCR | SMN1: 21174U20 |
| SMN1-18 | 1.592700796 | 0.199280916 | SMN1 | in vitro | Hep3B | 30 | qRTPCR | SMN1: 21174U20 |
| SMN1-19 | 0.705512452 | 0.06496675 | SMN1 | in vitro | RPTEC | 100 | qRTPCR | SMN1: 21175U20 |
| SMN1-19 | 1.43433309 | 0.075936965 | SMN1 | in vitro | RPTEC | 50 | qRTPCR | SMN1: 21175U20 |
| SMN1-19 | 0.538932156 | 0.309273594 | SMN1 | in vitro | Hep3B | 50 | qRTPCR | SMN1: 21175U20 |
| SMN1-19 | 1.17374637 | 0.179415746 | SMN1 | in vitro | Hep3B | 100 | qRTPCR | SMN1: 21175U20 |
| SMN1-19 | 1.186141471 | 0.036729063 | SMN1 | in vitro | Hep3B | 10 | qRTPCR | SMN1: 21175U20 |
| SMN1-19 | 1.834775368 | 0.155761723 | SMN1 | in vitro | Hep3B | 30 | qRTPCR | SMN1: 21175U20 |
| SMN1-20 | 0.826303453 | 0.062998254 | SMN1 | in vitro | RPTEC | 100 | qRTPCR | SMN1: 21176U20 |
| SMN1-20 | 1.505786689 | 0.170697984 | SMN1 | in vitro | RPTEC | 50 | qRTPCR | SMN1: 21176U20 |
| SMN1-20 | 0.06244992 | 0.049069571 | SMN1 | in vitro | Hep3B | 50 | qRTPCR | SMN1: 21176U20 |
| SMN1-20 | 1.541480855 | 0.461158669 | SMN1 | in vitro | Hep3B | 100 | qRTPCR | SMN1: 21176U20 |
| SMN1-20 | 1.089985692 | 0.043750568 | SMN1 | in vitro | Hep3B | 10 | qRTPCR | SMN1: 21176U20 |
| SMN1-20 | 1.41531375 | 0.146502726 | SMN1 | in vitro | Hep3B | 30 | qRTPCR | SMN1: 21176U20 |
| SMN1-21 | 0.865566453 | 0.209455026 | SMN1 | in vitro | RPTEC | 100 | qRTPCR | SMN1: 21177U20 |
| SMN1-21 | 1.466688787 | 0.116267764 | SMN1 | in vitro | RPTEC | 50 | qRTPCR | SMN1: 21177U20 |
| SMN1-21 | 0.388233514 | 0.139680869 | SMN1 | in vitro | Hep3B | 50 | qRTPCR | SMN1: 21177U20 |
| SMN1-21 | 1.366269447 | 0.239420557 | SMN1 | in vitro | Hep3B | 100 | qRTPCR | SMN1: 21177U20 |
| SMN1-21 | 1.354554841 | 0.013175463 | SMN1 | in vitro | Hep3B | 10 | qRTPCR | SMN1: 21177U20 |
| SMN1-21 | 2.026968382 | 0.27827902 | SMN1 | in vitro | Hep3B | 30 | qRTPCR | SMN1: 21177U20 |
| SMN1-22 | 0.639934851 | 0.011679891 | SMN1 | in vitro | RPTEC | 100 | qRTPCR | SMN1: 21178U20 |
| SMN1-22 | 1.242593923 | 0.02840519 | SMN1 | in vitro | RPTEC | 50 | qRTPCR | SMN1: 21178U20 |
| SMN1-22 | 0.229857922 | 0.128101282 | SMN1 | in vitro | Hep3B | 50 | qRTPCR | SMN1: 21178U20 |
| SMN1-22 | 1.499722255 | 0.568788539 | SMN1 | in vitro | Hep3B | 100 | qRTPCR | SMN1: 21178U20 |
| SMN1-22 | 1.234783764 | 0.017119432 | SMN1 | in vitro | Hep3B | 10 | qRTPCR | SMN1: 21178U20 |
| SMN1-22 | 1.509695591 | 0.175764156 | SMN1 | in vitro | Hep3B | 30 | qRTPCR | SMN1: 21178U20 |
| SMN1-23 | 0.748031845 | 0.083732479 | SMN1 | in vitro | RPTEC | 100 | qRTPCR | SMN1: 21179U20 |
| SMN1-23 | 1.33910973 | 0.070877143 | SMN1 | in vitro | RPTEC | 50 | qRTPCR | SMN1: 21179U20 |
| SMN1-23 | 0.384143384 | 0.14723735 | SMN1 | in vitro | Hep3B | 50 | qRTPCR | SMN1: 21179U20 |
| SMN1-23 | 2.620195611 | 0.342101826 | SMN1 | in vitro | Hep3B | 100 | qRTPCR | SMN1: 21179U20 |
| SMN1-23 | 1.473663866 | 0.053762605 | SMN1 | in vitro | Hep3B | 10 | qRTPCR | SMN1: 21179U20 |
| SMN1-23 | 1.920800418 | 0.127336842 | SMN1 | in vitro | Hep3B | 30 | qRTPCR | SMN1: 21179U20 |
| SMN1-24 | 0.907436601 | 0.24201681 | SMN1 | in vitro | RPTEC | 100 | qRTPCR | SMN1: 21180U20 |
| SMN1-24 | 1.28379369 | 0.158661709 | SMN1 | in vitro | RPTEC | 50 | qRTPCR | SMN1: 21180U20 |
| SMN1-24 | 0.963100208 | 0.117802422 | SMN1 | in vitro | Hep3B | 50 | qRTPCR | SMN1: 21180U20 |
| SMN1-24 | 0.994753299 | 0.268415648 | SMN1 | in vitro | Hep3B | 100 | qRTPCR | SMN1: 21180U20 |
| SMN1-24 | 0.965440348 | 0.032646295 | SMN1 | in vitro | Hep3B | 10 | qRTPCR | SMN1: 21180U20 |
| SMN1-24 | 1.140566171 | 0.10163121 | SMN1 | in vitro | Hep3B | 30 | qRTPCR | SMN1: 21180U20 |
| SMN1-25 | 0.908854808 | 0.076026035 | SMN1 | in vitro | RPTEC | 100 | qRTPCR | SMN1: 21181U20 |
| SMN1-25 | 1.226185041 | 0.044422705 | SMN1 | in vitro | RPTEC | 50 | qRTPCR | SMN1: 21181U20 |
| SMN1-25 | 1.055082301 | 0.326768036 | SMN1 | in vitro | Hep3B | 50 | qRTPCR | SMN1: 21181U20 |
| SMN1-25 | 0.969185038 | 0.226484866 | SMN1 | in vitro | Hep3B | 100 | qRTPCR | SMN1: 21181U20 |
| SMN1-25 | 1.00974636 | 0.122120737 | SMN1 | in vitro | Hep3B | 10 | qRTPCR | SMN1: 21181U20 |
| SMN1-25 | 1.081303639 | 0.101827303 | SMN1 | in vitro | Hep3B | 30 | qRTPCR | SMN1: 21181U20 |

TABLE 2-continued

Oligonucleotide sequences made for testing

| Oligo Name | RQ | RQ SE | Gene Name | Expt Type | Cell Line/Tissue | [Oligo] | Assay Type | Coordinates_g |
|---|---|---|---|---|---|---|---|---|
| SMN1-26 | 0.876444072 | 0.070457909 | SMN1 | in vitro | RPTEC | 100 | qRTPCR | SMN1: 21182U20 |
| SMN1-26 | 1.632434888 | 0.061512357 | SMN1 | in vitro | RPTEC | 50 | qRTPCR | SMN1: 21182U20 |
| SMN1-26 | 0.071593319 | 0.071592884 | SMN1 | in vitro | Hep3B | 50 | qRTPCR | SMN1: 21182U20 |
| SMN1-26 | 1.999202516 | 0.420387669 | SMN1 | in vitro | Hep3B | 100 | qRTPCR | SMN1: 21182U20 |
| SMN1-26 | 0.974107584 | 0.066863661 | SMN1 | in vitro | Hep3B | 10 | qRTPCR | SMN1: 21182U20 |
| SMN1-26 | 1.030227891 | 0.096105098 | SMN1 | in vitro | Hep3B | 30 | qRTPCR | SMN1: 21182U20 |
| SMN1-27 | 0.834365703 | 0.108102871 | SMN1 | in vitro | RPTEC | 100 | qRTPCR | SMN1: 21157U15 |
| SMN1-27 | 1.589954219 | 0.093101653 | SMN1 | in vitro | RPTEC | 50 | qRTPCR | SMN1: 21157U15 |
| SMN1-27 | 0.747186714 | 0.007807701 | SMN1 | in vitro | Hep3B | 30 | qRTPCR | SMN1: 21157U15 |
| SMN1-27 | 1.049068744 | 0.092645193 | SMN1 | in vitro | Hep3B | 10 | qRTPCR | SMN1: 21157U15 |
| SMN1-28 | 1.058343694 | 0.208931576 | SMN1 | in vitro | RPTEC | 100 | qRTPCR | SMN1: 21158U15 |
| SMN1-28 | 1.402348414 | 0.101950771 | SMN1 | in vitro | RPTEC | 50 | qRTPCR | SMN1: 21158U15 |
| SMN1-28 | 1.150224316 | 0.080077707 | SMN1 | in vitro | Hep3B | 30 | qRTPCR | SMN1: 21158U15 |
| SMN1-28 | 1.219828396 | 0.031782762 | SMN1 | in vitro | Hep3B | 10 | qRTPCR | SMN1: 21158U15 |
| SMN1-29 | 0.712268587 | 0.077572838 | SMN1 | in vitro | RPTEC | 100 | qRTPCR | SMN1: 21159U15 |
| SMN1-29 | 1.145305552 | 0.044575389 | SMN1 | in vitro | RPTEC | 50 | qRTPCR | SMN1: 21159U15 |
| SMN1-29 | 0.937393865 | 0.015700783 | SMN1 | in vitro | Hep3B | 30 | qRTPCR | SMN1: 21159U15 |
| SMN1-29 | 1.208521962 | 0.084021899 | SMN1 | in vitro | Hep3B | 10 | qRTPCR | SMN1: 21159U15 |
| SMN1-30 | 0.869504109 | 0.147682779 | SMN1 | in vitro | RPTEC | 100 | qRTPCR | SMN1: 21160U15 |
| SMN1-30 | 1.166995709 | 0.128900531 | SMN1 | in vitro | RPTEC | 50 | qRTPCR | SMN1: 21160U15 |
| SMN1-30 | 1.069533423 | 0.042258392 | SMN1 | in vitro | Hep3B | 30 | qRTPCR | SMN1: 21160U15 |
| SMN1-30 | 1.004618999 | 0.068245537 | SMN1 | in vitro | Hep3B | 10 | qRTPCR | SMN1: 21160U15 |
| SMN1-31 | 1.223685297 | 0.155258366 | SMN1 | in vitro | Hep3B | 30 | qRTPCR | SMN1: 21161U15 |
| SMN1-31 | 0.936569575 | 0.083367899 | SMN1 | in vitro | Hep3B | 10 | qRTPCR | SMN1: 21161U15 |
| SMN1-32 | 1.032978469 | 0.02312057 | SMN1 | in vitro | Hep3B | 30 | qRTPCR | SMN1: 21162U15 |
| SMN1-32 | 1.053045821 | 0.030158389 | SMN1 | in vitro | Hep3B | 10 | qRTPCR | SMN1: 21162U15 |
| SMN1-33 | 1.046361407 | 0.038971809 | SMN1 | in vitro | Hep3B | 30 | qRTPCR | SMN1: 21163U15 |
| SMN1-33 | 1.233302232 | 0.063255341 | SMN1 | in vitro | Hep3B | 10 | qRTPCR | SMN1: 21163U15 |
| SMN1-34 | 1.079876751 | 0.09859402 | SMN1 | in vitro | Hep3B | 30 | qRTPCR | SMN1: 21164U15 |
| SMN1-34 | 1.271026183 | 0.067019476 | SMN1 | in vitro | Hep3B | 10 | qRTPCR | SMN1: 21164U15 |
| SMN1-35 | 0.861464008 | 0.024095912 | SMN1 | in vitro | Hep3B | 30 | qRTPCR | SMN1: 21165U15 |
| SMN1-35 | 0.836966392 | 0.054159619 | SMN1 | in vitro | Hep3B | 10 | qRTPCR | SMN1: 21165U15 |
| SMN1-36 | 1.26636324 | 0.046963681 | SMN1 | in vitro | Hep3B | 30 | qRTPCR | SMN1: 21166U15 |
| SMN1-36 | 1.326257117 | 0.039674649 | SMN1 | in vitro | Hep3B | 10 | qRTPCR | SMN1: 21166U15 |
| SMN1-37 | 1.232690086 | 0.043476252 | SMN1 | in vitro | Hep3B | 30 | qRTPCR | SMN1: 21167U15 |
| SMN1-37 | 1.144632987 | 0.058433353 | SMN1 | in vitro | Hep3B | 10 | qRTPCR | SMN1: 21167U15 |
| SMN1-38 | 0.843241863 | 0.033808043 | SMN1 | in vitro | Hep3B | 30 | qRTPCR | SMN1: 21168U15 |
| SMN1-38 | 0.93818033 | 0.011376217 | SMN1 | in vitro | Hep3B | 10 | qRTPCR | SMN1: 21168U15 |
| SMN1-39 | 0.663746249 | 0.045527014 | SMN1 | in vitro | Hep3B | 30 | qRTPCR | SMN1: 21169U15 |
| SMN1-39 | 0.891764551 | 0.019395327 | SMN1 | in vitro | Hep3B | 10 | qRTPCR | SMN1: 21169U15 |
| SMN1-40 | 0.888138653 | 0.081401804 | SMN1 | in vitro | Hep3B | 30 | qRTPCR | SMN1: 21170U15 |
| SMN1-40 | 0.871602899 | 0.065372936 | SMN1 | in vitro | Hep3B | 10 | qRTPCR | SMN1: 21170U15 |
| SMN1-41 | 0.882466148 | 0.031016749 | SMN1 | in vitro | Hep3B | 30 | qRTPCR | SMN1: 21171U15 |
| SMN1-41 | 1.093694765 | 0.025996502 | SMN1 | in vitro | Hep3B | 10 | qRTPCR | SMN1: 21171U15 |
| SMN1-42 | 0.956860836 | 0.043558382 | SMN1 | in vitro | Hep3B | 30 | qRTPCR | SMN1: 21172U15 |
| SMN1-42 | 1.151755999 | 0.067662107 | SMN1 | in vitro | Hep3B | 10 | qRTPCR | SMN1: 21172U15 |
| SMN1-43 | 1.341919782 | 0.08080776 | SMN1 | in vitro | Hep3B | 30 | qRTPCR | SMN1: 21173U15 |
| SMN1-43 | 1.692919815 | 0.084669198 | SMN1 | in vitro | Hep3B | 10 | qRTPCR | SMN1: 21173U15 |
| SMN1-44 | 0 | 0 | SMN1 | NA | NA | 0 | NA | SMN1: 21174U15 |
| SMN1-45 | 1.807236897 | 0.11410948 | SMN1 | in vitro | Hep3B | 30 | qRTPCR | SMN1: 21175U15 |
| SMN1-45 | 1.377773703 | 0.108540058 | SMN1 | in vitro | Hep3B | 10 | qRTPCR | SMN1: 21175U15 |
| SMN1-46 | 1.545649538 | 0.064006814 | SMN1 | in vitro | Hep3B | 30 | qRTPCR | SMN1: 21176U15 |
| SMN1-46 | 1.354291504 | 0.038498944 | SMN1 | in vitro | Hep3B | 10 | qRTPCR | SMN1: 21176U15 |
| SMN1-47 | 2.711598361 | 0.260043446 | SMN1 | in vitro | Hep3B | 30 | qRTPCR | SMN1: 21177U15 |
| SMN1-47 | 1.986674786 | 0.119436675 | SMN1 | in vitro | Hep3B | 10 | qRTPCR | SMN1: 21177U15 |
| SMN1-48 | 1.482342195 | 0.063036343 | SMN1 | in vitro | Hep3B | 30 | qRTPCR | SMN1: 21178U15 |
| SMN1-48 | 2.597350628 | 0.145439801 | SMN1 | in vitro | Hep3B | 10 | qRTPCR | SMN1: 21178U15 |
| SMN1-49 | 1.534493905 | 0.110688365 | SMN1 | in vitro | Hep3B | 30 | qRTPCR | SMN1: 21179U15 |
| SMN1-49 | 2.223340784 | 0.148702992 | SMN1 | in vitro | Hep3B | 10 | qRTPCR | SMN1: 21179U15 |
| SMN1-50 | 0.897421396 | 0.034254931 | SMN1 | in vitro | Hep3B | 30 | qRTPCR | SMN1: 21180U15 |
| SMN1-50 | 1.132362781 | 0.078523003 | SMN1 | in vitro | Hep3B | 10 | qRTPCR | SMN1: 21180U15 |
| SMN1-51 | 1.157921368 | 0.044256319 | SMN1 | in vitro | Hep3B | 30 | qRTPCR | SMN1: 21181U15 |
| SMN1-51 | 1.177604665 | 0.038060353 | SMN1 | in vitro | Hep3B | 10 | qRTPCR | SMN1: 21181U15 |
| SMN1-52 | 0.973548353 | 0.051461583 | SMN1 | in vitro | Hep3B | 30 | qRTPCR | SMN1: 21182U15 |
| SMN1-52 | 1.068355642 | 0.060851146 | SMN1 | in vitro | Hep3B | 10 | qRTPCR | SMN1: 21182U15 |

TABLE 3

Oligonucleotide Modifications

| Symbol | Feature Description |
|---|---|
| bio | 5' biotin |
| dAs | DNA w/3' thiophosphate |
| dCs | DNA w/3' thiophosphate |
| dGs | DNA w/3' thiophosphate |
| dTs | DNA w/3' thiophosphate |
| dG | DNA |
| enaAs | ENA w/3' thiophosphate |
| enaCs | ENA w/3' thiophosphate |
| enaGs | ENA w/3' thiophosphate |
| enaTs | ENA w/3' thiophosphate |
| fluAs | 2'-fluoro w/3' thiophosphate |
| fluCs | 2'-fluoro w/3' thiophosphate |
| fluGs | 2'-fluoro w/3' thiophosphate |
| fluUs | 2'-fluoro w/3' thiophosphate |
| lnaAs | LNA w/3' thiophosphate |
| lnaCs | LNA w/3' thiophosphate |
| lnaGs | LNA w/3' thiophosphate |
| lnaTs | LNA w/3' thiophosphate |
| omeAs | 2'-OMe w/3' thiophosphate |
| omeCs | 2'-OMe w/3' thiophosphate |
| omeGs | 2'-OMe w/3' thiophosphate |
| omeTs | 2'-OMe w/3' thiophosphate |
| lnaAs-Sup | LNA w/3' thiophosphate at 3' terminus |
| lnaCs-Sup | LNA w/3' thiophosphate at 3' terminus |
| lnaGs-Sup | LNA w/3' thiophosphate at 3' terminus |
| lnaTs-Sup | LNA w/3' thiophosphate at 3' terminus |
| lnaA-Sup | LNA w/3' OH at 3' terminus |
| lnaC-Sup | LNA w/3' OH at 3' terminus |
| lnaG-Sup | LNA w/3' OH at 3' terminus |
| lnaT-Sup | LNA w/3' OH at 3' terminus |
| omeA-Sup | 2'-OMe w/3' OH at 3' terminus |
| omeC-Sup | 2'-OMe w/3' OH at 3' terminus |
| omeG-Sup | 2'-OMe w/3' OH at 3' terminus |
| omeU-Sup | 2'-OMe w/3' OH at 3' terminus |
| moeAs | 2'-O-MOE w/3' thiophosphate |
| moeCs | 2'-O-MOE w/3' thiophosphate |
| moeGs | 2'-O-MOE w/3' thiophosphate |
| moeTs | 2'-O-MOE w/3' thiophosphate |
| dAs-Sup | DNA w/3' thiophosphate at 3' terminus |
| dCs-Sup | DNA w/3' thiophosphate at 3' terminus |
| dGs-Sup | DNA w/3' thiophosphate at 3' terminus |
| dTs-Sup | DNA w/3' thiophosphate at 3' terminus |
| dA-Sup | DNA w/3' OH at 3' terminus |
| dC-Sup | DNA w/3' OH at 3' terminus |
| dG-Sup | DNA w/3' OH at 3' terminus |
| dT-Sup | DNA w/3' OH at 3' terminus |

BRIEF DESCRIPTION OF SEQUENCE LISTING

| SeqID | Chrom | Gene | Chrom Start | Chrom End | Strand | Name |
|---|---|---|---|---|---|---|
| 1 | chr5 | SMN1 | 70208768 | 70260838 | + | human SMN1 |
| 2 | chr5 | SMN2 | 69333350 | 69385422 | + | human SMN2 |
| 3 | chr9 | SMNP | 20319406 | 20344375 | + | human SMNP |
| 4 | chr5 | SMN1 | 70208768 | 70260838 | − | human SMN1_revComp |
| 5 | chr5 | SMN2 | 69333350 | 69385422 | − | human SMN2_revComp |
| 6 | chr9 | SMNP | 20319406 | 20344375 | − | human SMNP_revComp |
| 7 | chr13 | Smn1 | 100881160 | 100919653 | + | mouse Smn1 |
| 8 | chr13 | Smn1 | 100881160 | 100919653 | − | mouse Smn1_revComp |
| 9 | chr5 | SMN1 | 70240095 | 70240127 | + | S48-193240 |
| 9 | chr5 | SMN2 | 69364672 | 69364704 | + | S48-193240 |
| 10 | chr5 | SMN1 | 70214393 | 70214822 | + | S48-441814 |
| 10 | chr5 | SMN2 | 69338976 | 69339405 | + | S48-441814 |
| 11 | chr5 | SMN1 | 70214064 | 70214108 | + | S48-441815 |
| 11 | chr5 | SMN2 | 69338647 | 69338691 | + | S48-441815 |
| 12 | chr5 | SMN1 | 70214276 | 70214317 | + | S48-473289 |
| 12 | chr5 | SMN2 | 69338859 | 69338900 | + | S48-473289 |
| 13 | chr5 | SMN1 | 70214445 | 70214472 | + | S48-473290 |
| 13 | chr5 | SMN2 | 69339028 | 69339055 | + | S48-473290 |
| 14 | chr5 | SMN1 | 70238095 | 70242127 | + | S48-193240 + 2K |
| 15 | chr5 | SMN2 | 69362672 | 69366704 | + | S48-193240 + 2K |
| 16 | chr5 | SMN1 | 70212393 | 70216822 | + | S48-441814 + 2K |
| 17 | chr5 | SMN2 | 69336976 | 69341405 | + | S48-441814 + 2K |
| 18 | chr5 | SMN1 | 70212064 | 70216108 | + | S48-441815 + 2K |
| 19 | chr5 | SMN2 | 69336647 | 69340691 | + | S48-441815 + 2K |
| 20 | chr5 | SMN1 | 70212276 | 70216317 | + | S48-473289 + 2K |
| 21 | chr5 | SMN2 | 69336859 | 69340900 | + | S48-473289 + 2K |
| 22 | chr5 | SMN1 | 70212445 | 70216472 | + | S48-473290 + 2K |
| 23 | chr5 | SMN2 | 69337028 | 69341055 | + | S48-473290 + 2K |
| 24 | chr5 | SMN1 | 70240510 | 70240551 | − | S48-193241 |
| 24 | chr5 | SMN2 | 69365087 | 69365128 | − | S48-193241 |
| 25 | chr5 | SMN1 | 70241924 | 70241968 | − | S48-193242 |
| 25 | chr5 | SMN2 | 69366499 | 69366543 | − | S48-193242 |
| 26 | chr5 | SMN1 | 70238510 | 70242551 | − | S48-193241 + 2K |
| 27 | chr5 | SMN2 | 69363087 | 69367128 | − | S48-193241 + 2K |
| 28 | chr5 | SMN1 | 70239924 | 70243968 | − | S48-193242 + 2K |
| 29 | chr5 | SMN2 | 69364499 | 69368543 | − | S48-193242 + 2K |
| 13100 | chr5 | SMN1 | 70247831 | 70247845 | + | Splice control sequence |
| 13100 | chr5 | SMN2 | 69372411 | 69372425 | + | Splice control sequence |
| 13101 | chr5 | SMN2 | 69372402 | 69372845 | + | Intron 7 |

Single Strand Oligonucleotides (Antisense Strand of Target Gene)

SeqID range: 30 to 8329, 13088-13094

Example SeqIDs w/o G Runs:

30-142, 156-560, 575-780, 794-912, 926-1013, 1027-1078, 1092-1286, 1300-1335, 1349-1385, 1399-1453, 1460-1527, 1548-1555, 1571-1653, 1675-1691, 1706-1802, 1816-1883, 1897-2009, 2023-2141, 2165-2289, 2303-2320, 2334-2447, 2461-2494, 2508-2526, 2540-2545, 2571-2635, 2651-2670, 2689-2763, 2772-2814, 2828-2854, 2868-3030, 3044-3256, 3270-3360, 3374-3400, 3414-3722, 3737, 3759-3783, 3797-3970, 3986-4059, 4073-4153, 4175-4240, 4255-4415, 4438-4441, 4456-4472, 4484-4505, 4513-4516, 4531-4546, 4560-4650, 4664-4751, 4766-4918, 4932-5035, 5049-5064, 5091-5189, 5203-5448, 5459-5503, 5508-5520, 5535-5654, 5668-5863, 5877-6016, 6025-6029, 6054-6063, 6078-6215, 6229-6701, 6715-6729, 6744-6869, 6883-6945, 6959-6968, 6982-7085, 7099-7173, 7195-7247, 7255-7268, 7273-7309, 7320-7335, 7349-7442, 7456-7465, 7479-7727, 7740-7951, 7977-8208, 8223-8255, 8257-8296, 8304-8312, 8319-8329, 13093-13094

Example SeqIDs w/o miR Seeds:

30-32, 34-39, 45-62, 64-72, 77-142, 145-151, 153, 157-184, 186-202, 205-246, 249, 251-260, 263, 266-320, 322, 326-328, 331, 333-341, 343-344, 346-394, 396-445, 447-541, 543-562, 564-596, 599-605, 607-646, 648-673, 677-701, 703-735, 737-772, 774-781, 785, 787-793, 795-809, 812, 814-815, 819-820, 822-827, 833-834, 836, 838-850, 852-876, 879, 883-886, 889-890, 892, 894, 897, 899, 901-906, 909, 911, 919, 921-935, 940, 942-1012, 1016-1063, 1065-1067, 1069-1095, 1097-1147, 1149-1166, 1168-1190, 1193-1214, 1217, 1227-1237, 1240, 1244, 1246-1251, 1258-1281, 1283-1312, 1314-1333, 1335, 1337-1356, 1358-1364, 1367, 1369-1381, 1384, 1388-1389, 1392-1404, 1406-1417, 1421-1441, 1443, 1445, 1447-1460, 1462-1492, 1494-1500, 1502, 1506-1512, 1514-1531, 1533, 1535-1539, 1543-1558, 1561-1562, 1564-1601, 1603-1614, 1616-1633, 1635-1646, 1648-1656, 1658, 1661-1675, 1678-1716, 1718-1740, 1742-1750, 1752-1785, 1788-1795, 1798, 1804-1871, 1873-1884, 1892-1973, 1976-1992, 1998-2032, 2034-2053, 2055-2077, 2079-2116, 2118-2135, 2138, 2142, 2149, 2151-2153, 2155-2162, 2165-2174, 2178, 2181-2254, 2256-2268, 2271-2293, 2296-2298, 2301-2312, 2314-2323, 2325-2427, 2429-2438, 2441, 2445, 2450-2476, 2478-2489, 2492-2494, 2497-2513, 2515, 2521-2526, 2529-2545, 2547-2571, 2573-2610, 2613-2620, 2622-2639, 2641, 2644, 2651-2743, 2745, 2747-2755, 2760-2775, 2777-2825, 2828-2841, 2844-2861, 2864-2888, 2894-2954, 2956-2988, 2991-3006, 3008-3043, 3046, 3048-3239, 3241-3253, 3256-3268, 3270-3273, 3276-3320, 3322-3355, 3357-3404, 3406-3428, 3430-3488, 3490-3491, 3493-3522, 3524-3552, 3554-3569, 3571-3650, 3653-3670, 3672-3688, 3690-3717, 3719-3724, 3727-3736, 3743, 3746, 3749, 3751-3821, 3823-3842, 3844, 3846, 3848, 3851, 3855, 3858, 3861-3863, 3866-3881, 3883, 3887-3907, 3909-3917, 3919-3924, 3926-3942, 3944-3952, 3956-3970, 3976-3988, 3991-3998, 4001-4008, 4010-4022, 4026, 4028-4039, 4041-4048, 4051-4059, 4063-4070, 4072-4073, 4075, 4078, 4080-4104, 4106-4124, 4126, 4129-4140, 4143-4153, 4156-4162, 4166-4171, 4174-4196, 4201-4241, 4244-4252, 4254-4285, 4289-4318, 4320-4324, 4327, 4330-4331, 4333-4335, 4337-4351, 4353-4414, 4417, 4419-4425, 4427-4433, 4435, 4438-4446, 4449-4450, 4452-4462, 4470-4472, 4474-4510, 4512-4517, 4520-4546, 4548, 4551-4590, 4592-4619, 4623-4696, 4699, 4701, 4703-4752, 4755-4877, 4879-4949, 4951-5007, 5010, 5013-5046, 5049-5059, 5061-5063, 5066, 5069-5078, 5080-5119, 5121-5131, 5134-5168, 5171-5189, 5191-5228, 5230-5341, 5343-5405, 5407-5426, 5429-5437, 5439-5476, 5478-5491, 5494-5516, 5518-5556, 5558-5572, 5574-5647, 5649, 5652-5653, 5657-5729, 5731-5742, 5744-5769, 5771-5780, 5782-5866, 5868, 5870-5876, 5879-5881, 5884-5899, 5902-5951, 5954-5993, 6000-6006, 6009-6016, 6019-6033, 6035-6065, 6067-6073, 6080-6165, 6168-6249, 6252-6257, 6261-6282, 6284-6289, 6291-6301, 6305-6367, 6369-6378, 6380-6398, 6401-6412, 6415, 6417-6447, 6449-6456, 6458-6500, 6502-6563, 6565-6589, 6591-6612, 6616-6660, 6663-6702, 6704-6748, 6753, 6758-6763, 6765, 6768-6807, 6810, 6812-6872, 6874-6877, 6879-6913, 6915-6916, 6919, 6922, 6924-6926, 6928, 6930-6936, 6940-6959, 6962, 6964-6990, 6992, 6996, 6998-6999, 7004-7038, 7042-7085, 7087, 7089, 7092-7134, 7136-7140, 7142-7143, 7146-7150, 7152-7157, 7159-7171, 7175, 7177-7178, 7180-7196, 7198-7220, 7223, 7231-7237, 7239, 7242-7246, 7250-7273, 7275-7308, 7310-7312, 7314-7317, 7319-7330, 7332-7400, 7402-7437, 7439, 7441-7466, 7470-7491, 7493, 7495, 7497, 7499, 7502-7614, 7622-7628, 7631-7646, 7649-7651, 7655-7657, 7661-7672, 7676, 7679-7721, 7723-7800, 7802-7803, 7805-7906, 7908, 7910-7939, 7943-7953, 7956-7964, 7966-7981, 7983, 7985-7999, 8002, 8004-8034, 8036-8046, 8048-8080, 8084-8094, 8096-8112, 8114-8115, 8117-8139, 8141-8143, 8146-8148, 8150-8187, 8190-8216, 8218-8229, 8232-8238, 8240-8250, 8253-8255, 8257-8275, 8278-8296, 8299-8304, 8306-8329, 13093-13094

Single Strand Oligonucleotides (Sense Strand of Target Gene)

SeqID range: 1158-1159, 1171, 1482-1483, 1485-1486, 2465-2471, 2488-2490, 2542-2546, 2656-2657, 2833-2835, 3439-3440, 3916-3918, 4469-4472, 4821, 5429, 5537, 6061, 7327, 8330-13061, 13062-13087, 13108-13116

Example SeqIDs w/o G Runs:

1158-1159, 1171, 1482-1483, 1485-1486, 2465-2471, 2488-2490, 2542-2545, 2656-2657, 2833-2835, 3439-3440, 3916-3918, 4469-4472, 4821, 5429, 5537, 6061, 7327, 8330-8495, 8520-8560, 8574-8837, 8857-8882, 8907-8964, 8978-9298, 9312-9382, 9394-9640, 9656-9753, 9767-9974, 9988-10261, 10275-10276, 10290-10301, 10315-10434, 10448-10613, 10623-10641, 10644-10676, 10678-10704, 10714-10802, 10822-11161, 11175-11192, 11207-11386, 11400-11730, 11744-11745, 11759-11852, 11857-11900, 11914-11984, 11999-12011, 12026-12153, 12163-12175, 12178-12195, 12198-12212, 12216-12536, 12547-12564, 12575-12664, 12674-12758, 12772-12797, 12800-12840, 12854-13061, 13062-13069

Example SeqIDs w/o miR Seeds:

1158-1159, 1171, 1482-1483, 1485-1486, 2465-2471, 2488-2489, 2542-2545, 2656-2657, 2833-2835, 3439-3440, 3916-3917, 4470-4472, 4821, 5429, 5537, 6061, 7327, 8330-8334, 8336-8345, 8347, 8351-8373, 8375-8390, 8392-8399, 8401-8413, 8415-8455, 8457-8493, 8495, 8497-8502, 8510-8517, 8520, 8525, 8527-8634, 8637-8653, 8655-8671, 8673-8718, 8721-8822, 8824-8825, 8827-8842, 8849-8879, 8881-8892, 8894-8902, 8905-8906, 8914-8927, 8929, 8931, 8935, 8937-8975, 8980-8992, 8994, 8996-8997, 8999-9001, 9003, 9005-9086, 9089-9124, 9126-9286, 9288-9307, 9310-9359, 9362-9420, 9425-9427, 9429-9432, 9434, 9436-9437, 9439-9461, 9464-9483, 9486, 9488-9498, 9500-9511, 9513, 9515-9650, 9653-9667, 9669, 9671-9723, 9725-9869, 9871-9872, 9874-9879, 9881-9889, 9891-9973, 9975-10077, 10080-10097, 10099, 10101-10127, 10129-10166, 10168-10170, 10172-10184, 10186-10230, 10232-10237, 10239-10260, 10262-10272, 10274-10342, 10344-10400, 10402-10423, 10426-10441, 10445-10556, 10560, 10562-10580, 10582-10606, 10609-10647, 10650, 10652-10704, 10706, 10710-10713, 10716-10731, 10733-10824, 10826-10842, 10844-10903, 10906-10907, 10909-11101, 11104, 11106-

11134, 11137-11138, 11145-11161, 11164-11173, 11175-11181, 11184, 11186-11203, 11207-11212, 11214-11229, 11243-11259, 11261-11347, 11351-11397, 11399-11740, 11742-11747, 11749-11790, 11792-11817, 11821-11852, 11854-11904, 11908-11944, 11946-11959, 11961, 11964-11984, 11986-12007, 12009-12022, 12024-12092, 12095-12119, 12121-12133, 12135-12144, 12146-12157, 12159-12225, 12227-12231, 12233-12300, 12302-12329, 12332-12333, 12335-12382, 12385-12411, 12414-12416, 12418-12444, 12446-12455, 12457-12461, 12465, 12468-12474, 12476-12499, 12501-12536, 12538-12544, 12547-12553, 12559-12610, 12612-12626, 12628-12631, 12633-12637, 12640-12645, 12648-12657, 12659-12671, 12673-12679, 12683-12710, 12712, 12714-12747, 12750, 12752-12766, 12769, 12771-12806, 12808-12826, 12828-12829, 12831, 12833-12846, 12848-12849, 12854-12931, 12933-12946, 12948-13061, 13064, 13066-13068, 13071-13072, 13075, 13077-13081, 13083, 13085, 13087

Figure 1:
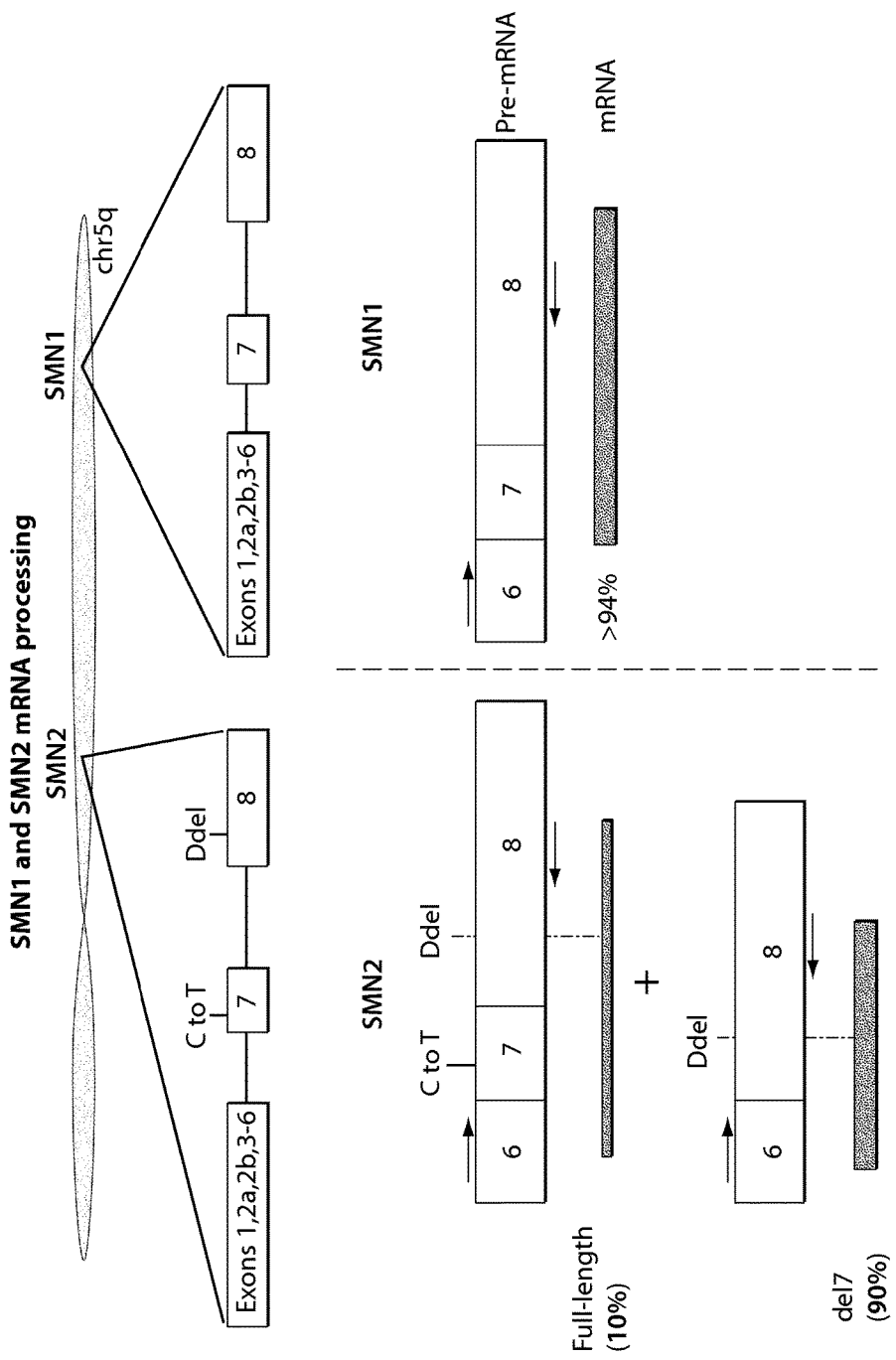
FIG. 1 provides a schematic of SMN1 and SMN2 mRNA processing
Figure 2:
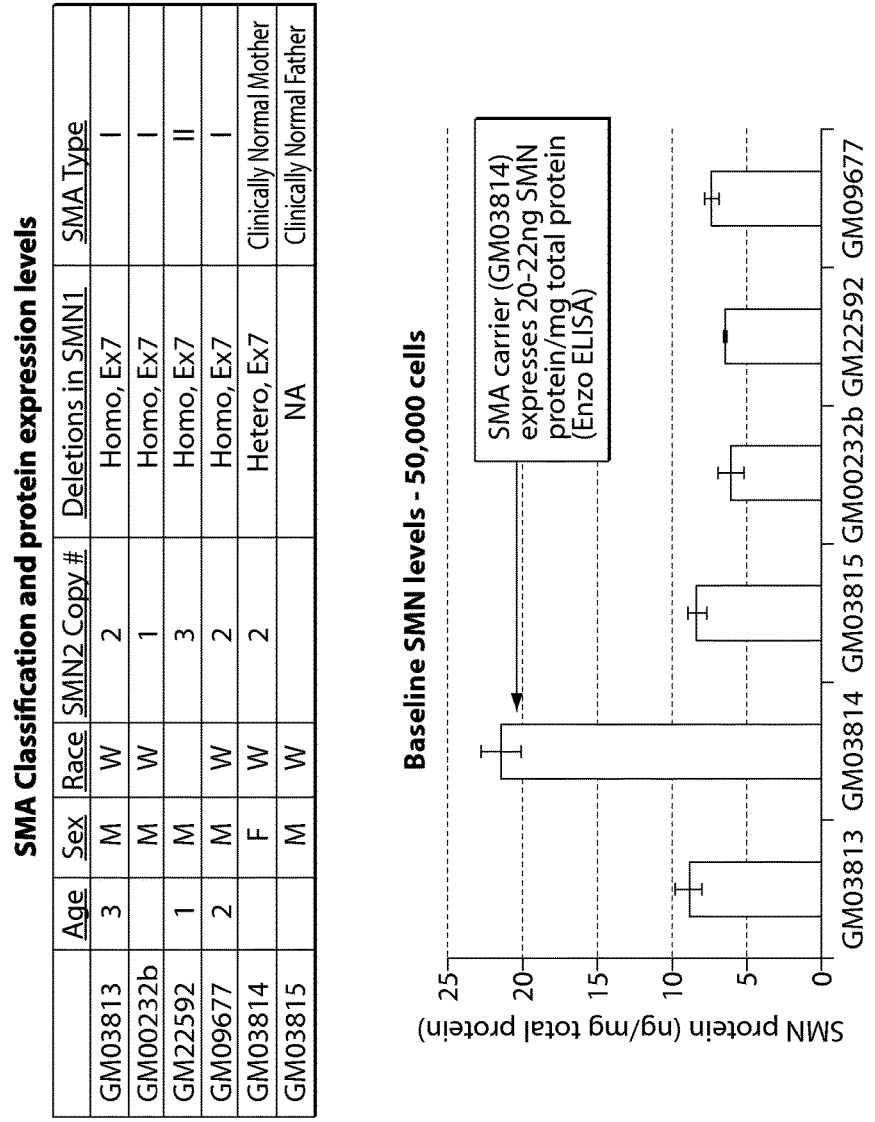
FIG. 2 provides a table outlining genotypes and patent information of cell lines tested in Example 2. Baseline SMN protein levels in the cell lines are also depicted.
Figure 3:
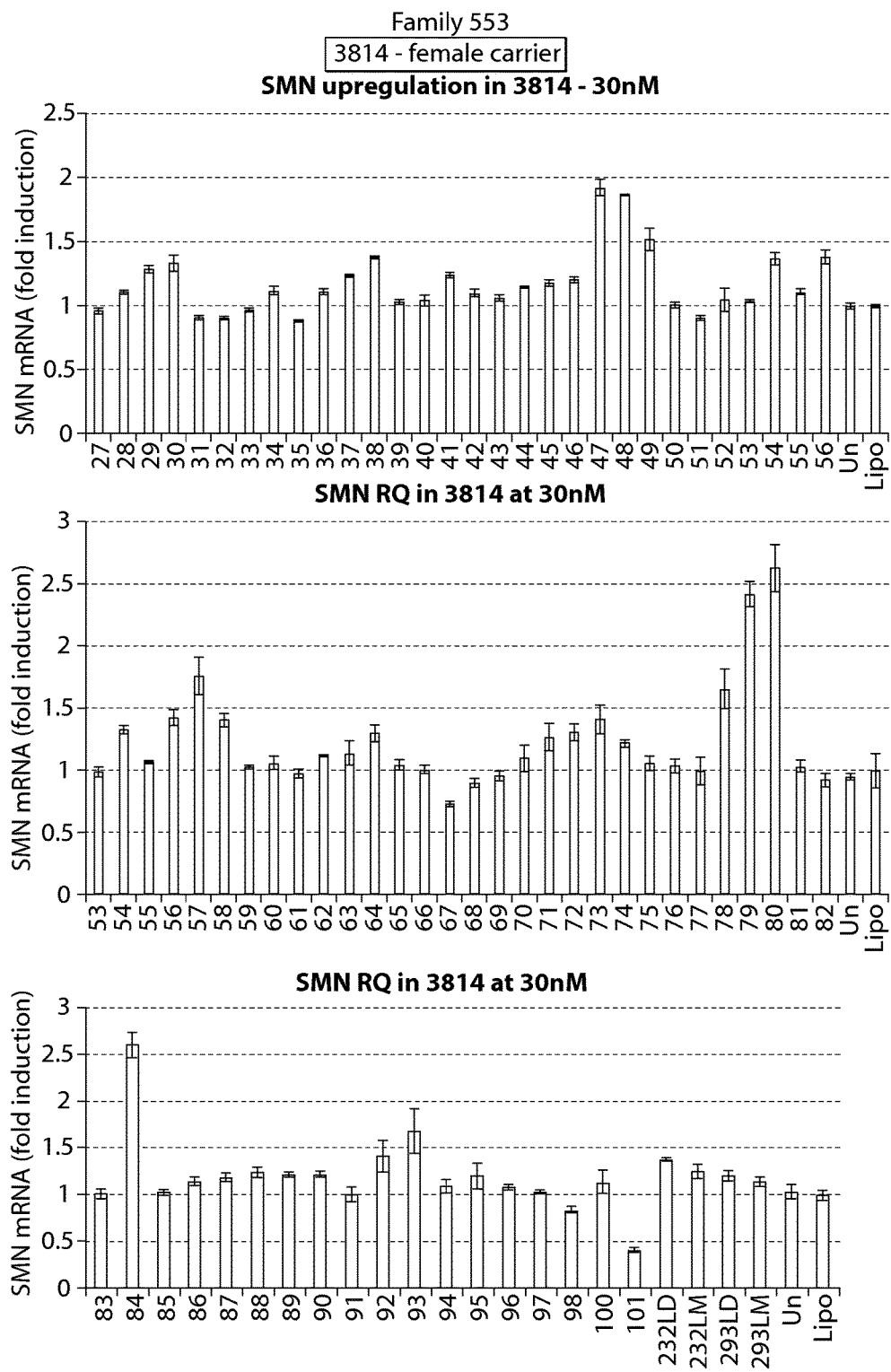
FIG. 3 depicts results of RT-PCR assays showing effects on SMN mRNA expression of oligonucleotides directed against a PRC2-associated region of SMN2 (oligos 1-52 and 59-101) and splice switching oligonucleotides (oligos 53-58) (PCR primers directed against exon 1 of SMN1/2.) in cell line 3814.
Figure 5:
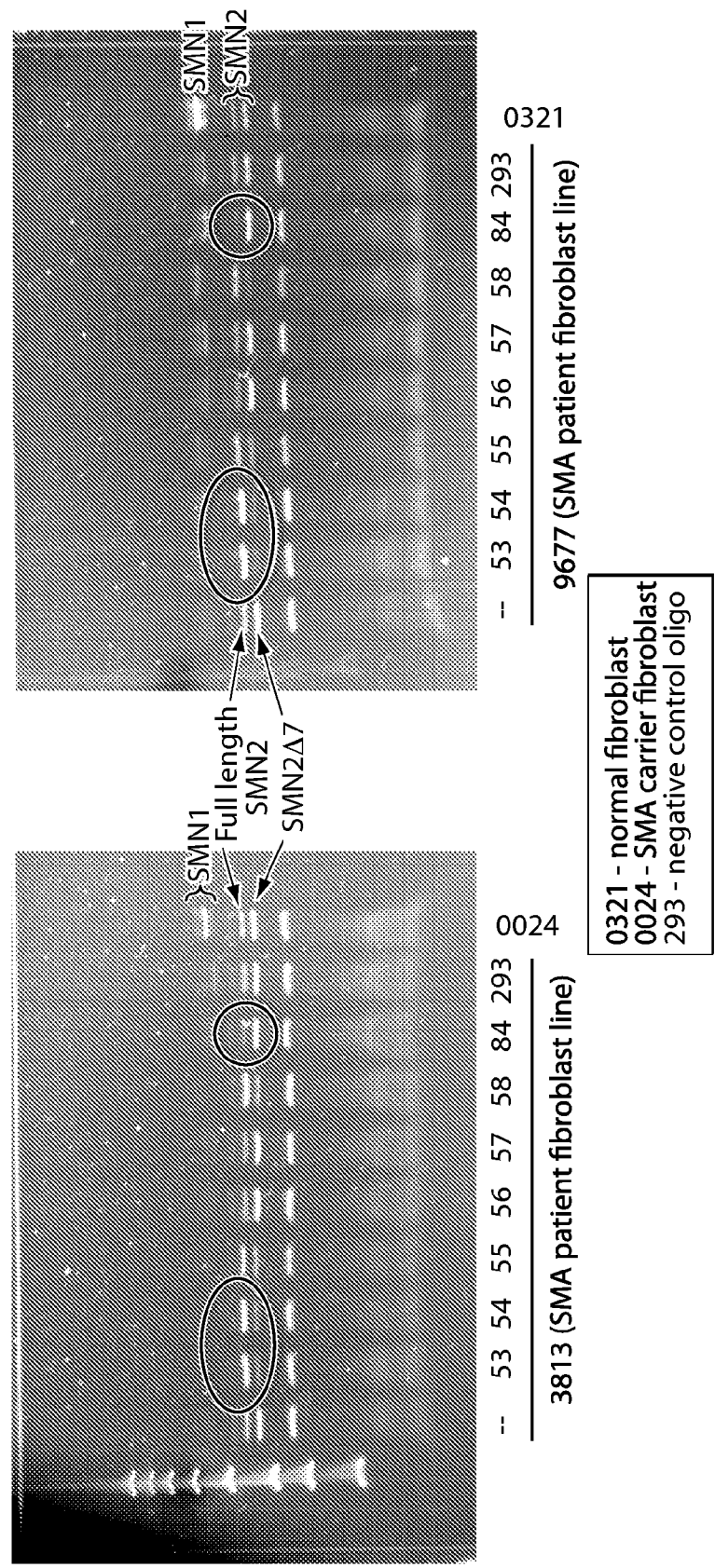
FIG. 5 shows that splice switching oligonucleotides (oligoes 53-58) increase expression of full length SMN2. Results are based on a gel separation analysis of PCR products obtained following a DdeI restriction digest. Two cell lines were tested, 3813 and 9677. Oligo 84, which targets a PRC2-associated region of SMN2, did not exhibit an increase in full length SMN2 expression when delivered alone to cells.
Figures 1, 6:
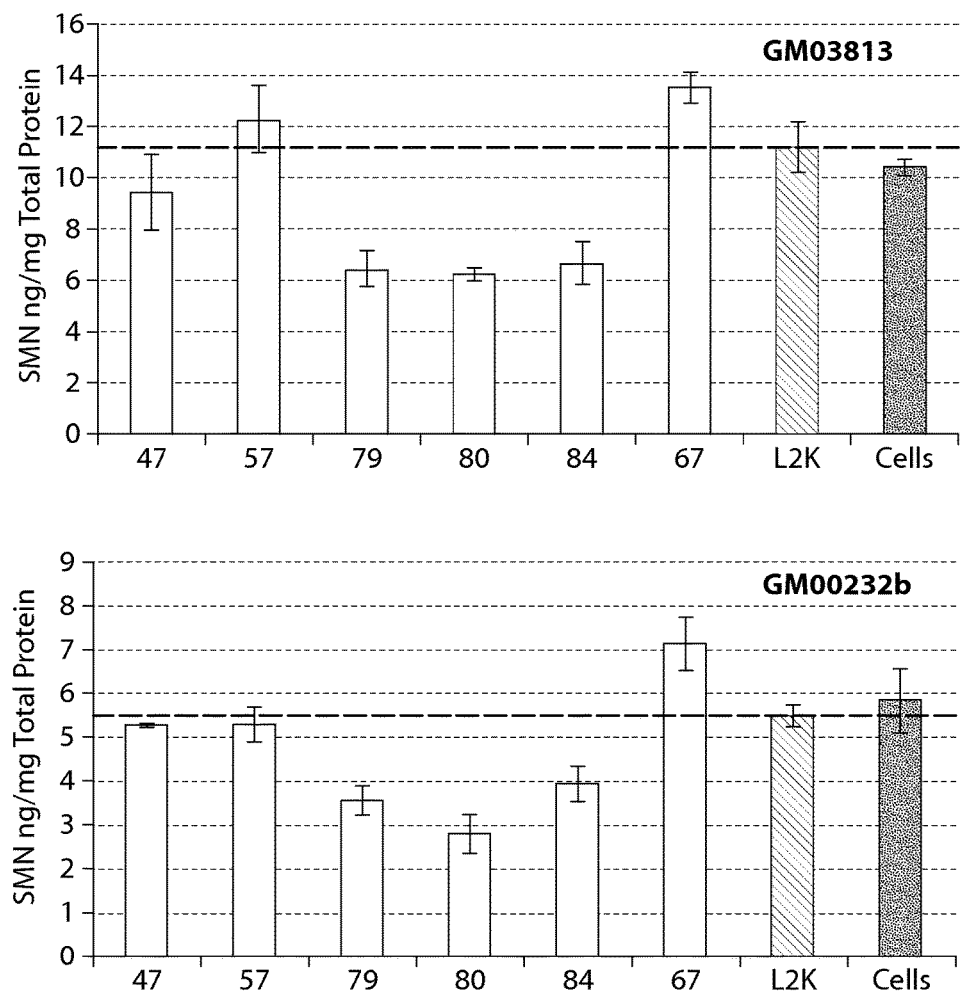
FIG. 6 provides results of an SMN ELISA (Enzo) showing that certain oligonucleotides directed against a PRC2-associated region of SMN2 alone do not significantly increase SMN2 protein 24 h post-transfection in certain patient fibroblasts with reduced SMN expression (compared to Lipofectamine treated cells—dashed line).
Figures 2, 6:
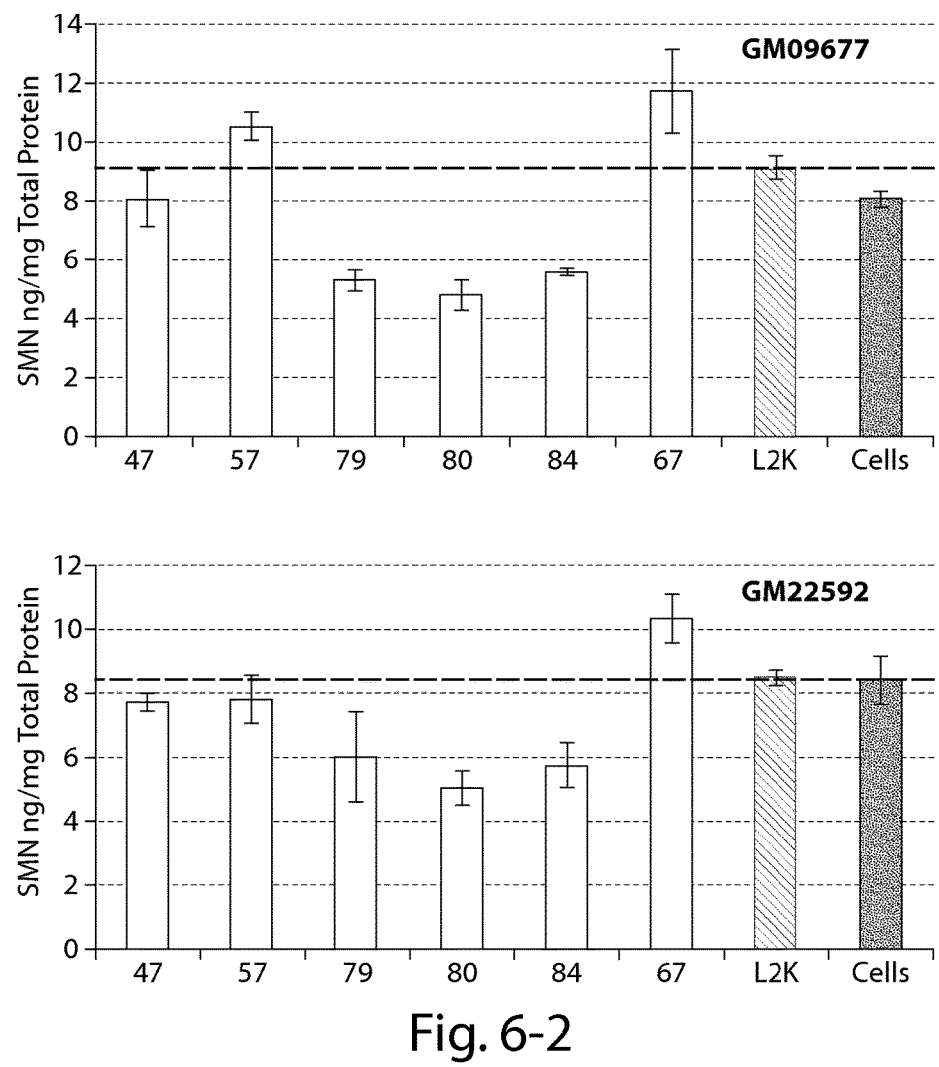
Figures 1, 7:
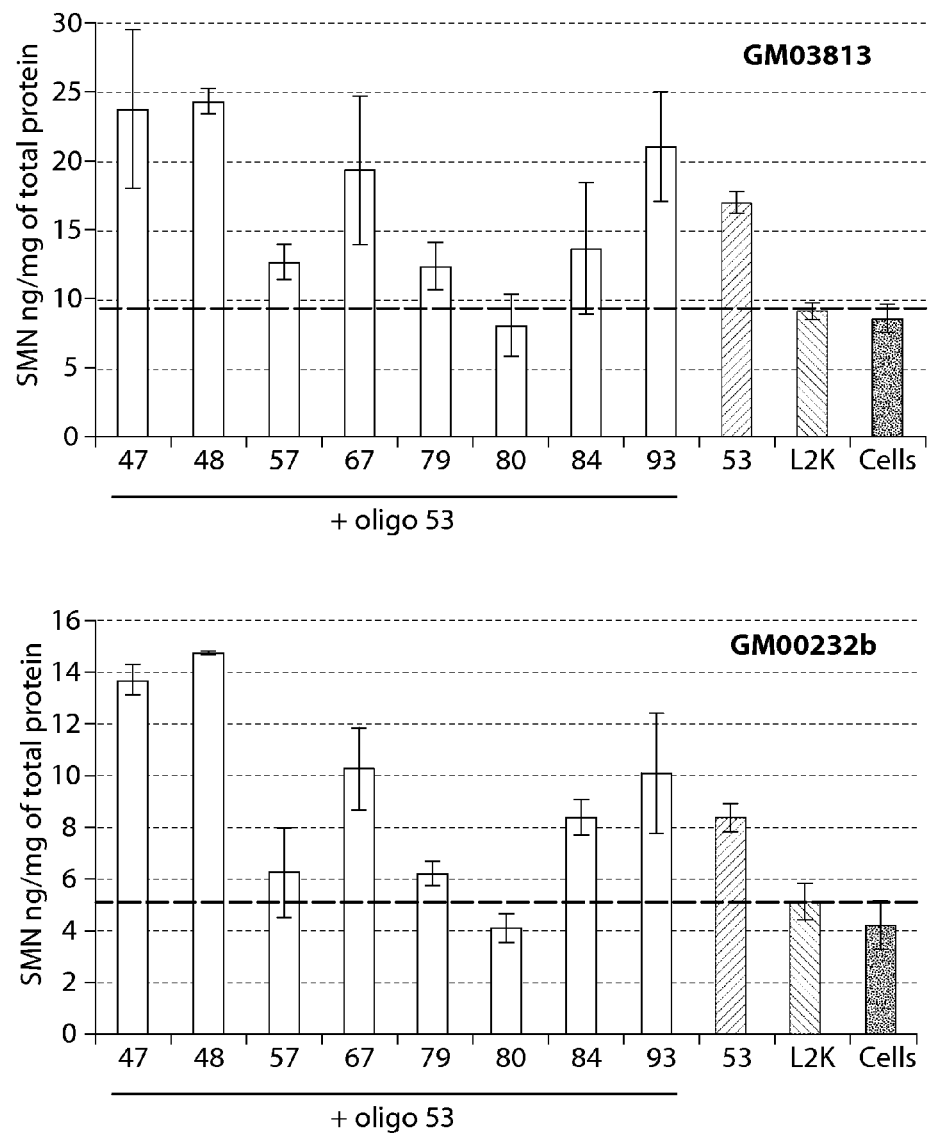
FIG. 7 provides results of an SMN ELISA showing that oligonucleotides directed against a PRC2-associated region of SMN2 in combination with a splice switching oligonucleotide (oligo 53) significantly increase SMN2 protein 24 h post-transfection in patient fibroblasts with reduced SMN expression (compared to Lipofectamine treated cells— dashed line).
Figures 2, 7:
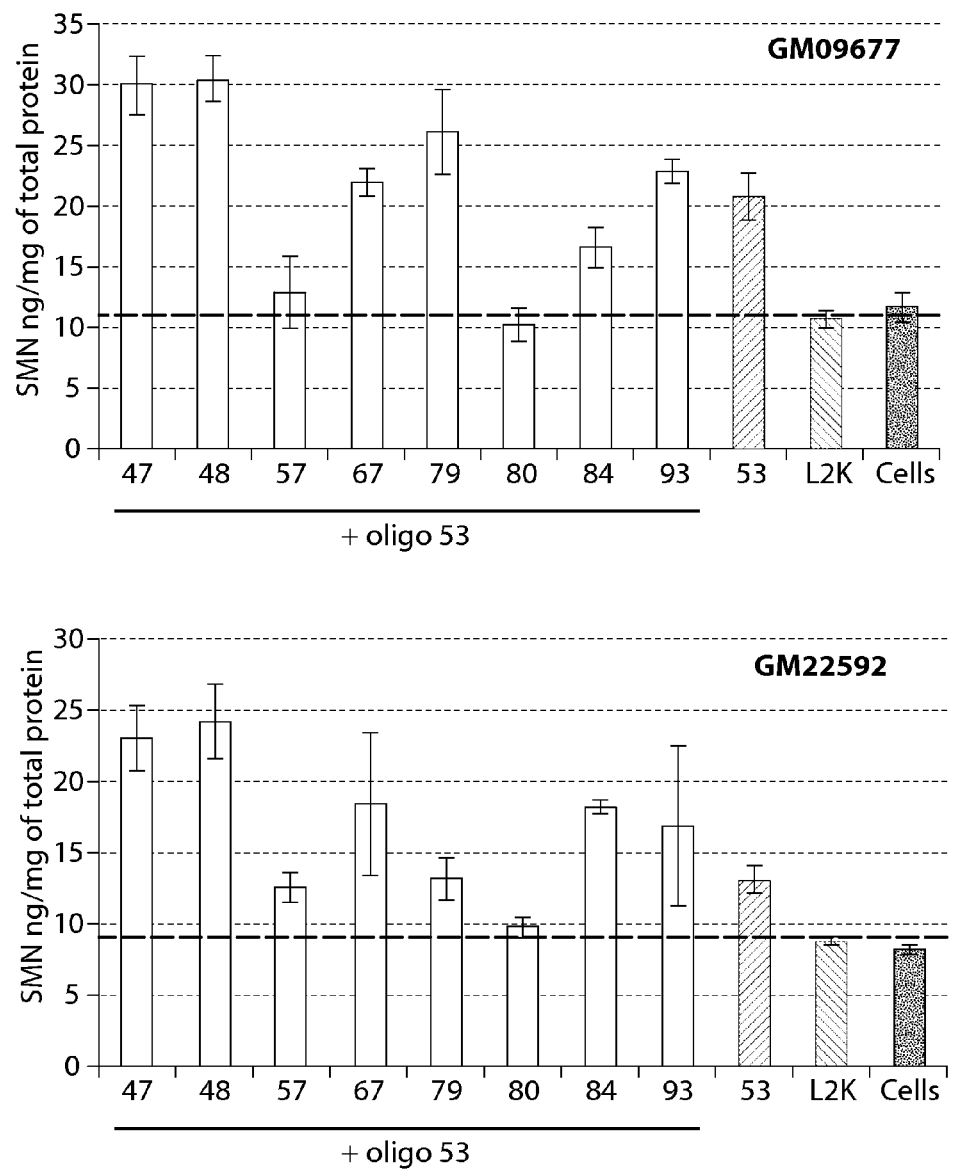
Figures 1, 8:
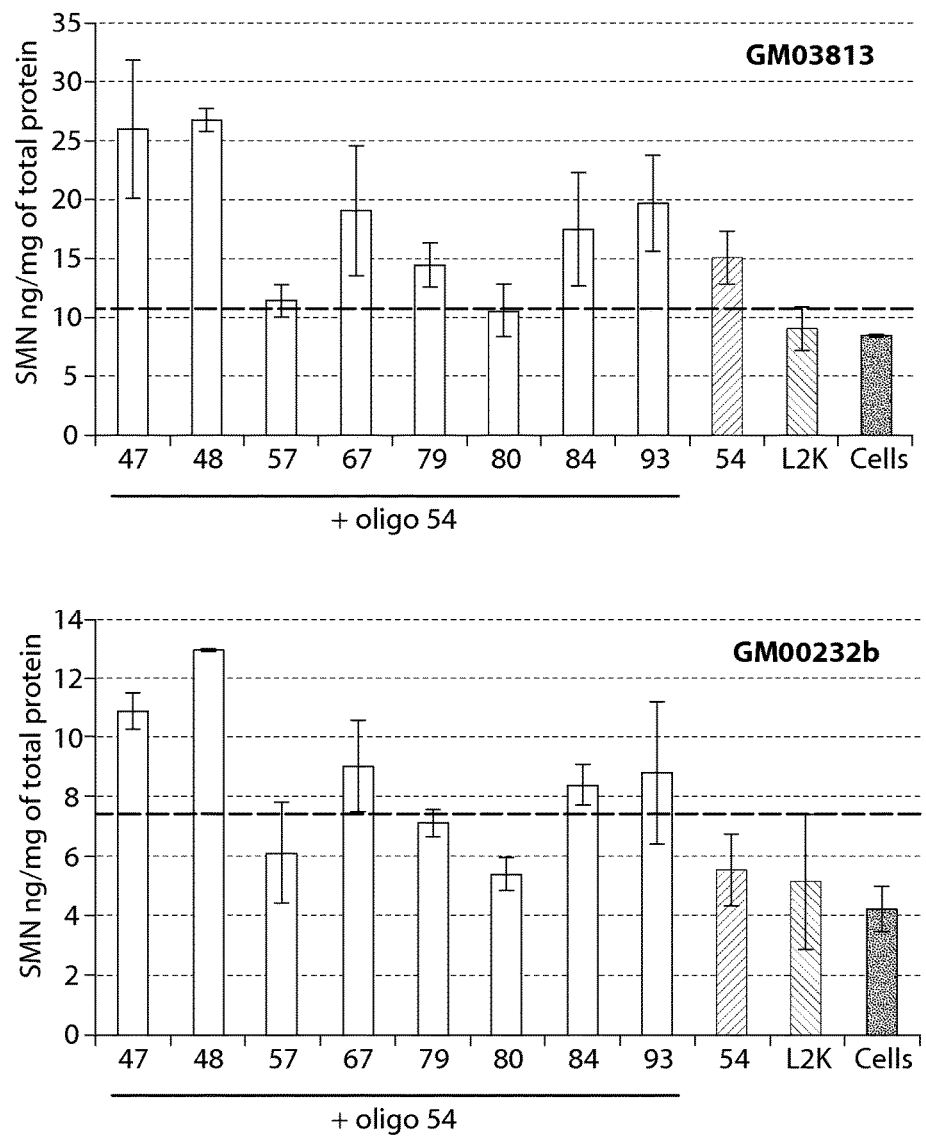
FIG. 8 provides results of an SMN ELISA showing that oligonucleotides directed against a PRC2-associated region of SMN2 in combination with a splice switching oligonucleotide (oligo 54) significantly increase SMN2 protein 24 h post-transfection in patient fibroblasts with reduced SMN expression (compared to Lipofectamine treated cells— dashed line).
Figures 2, 8:
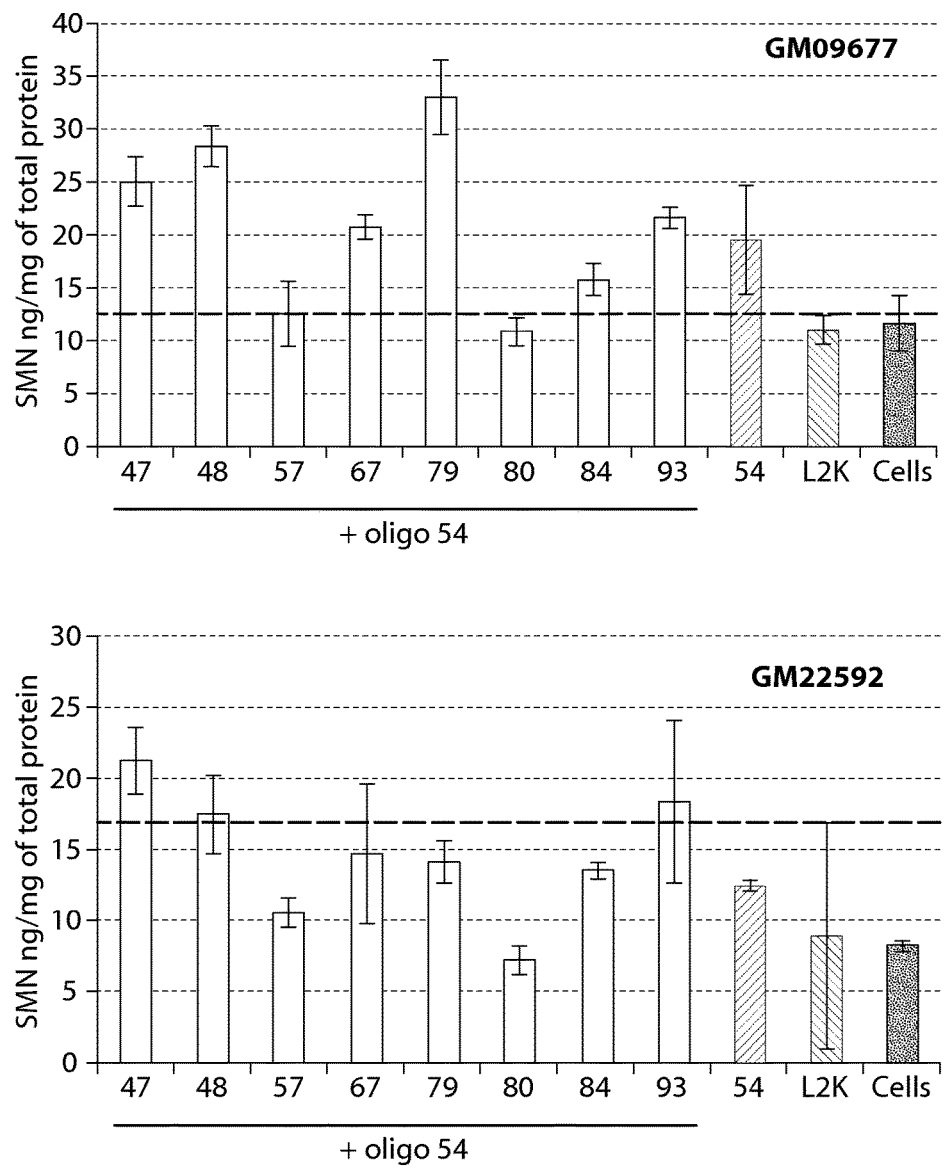
Figure 9:
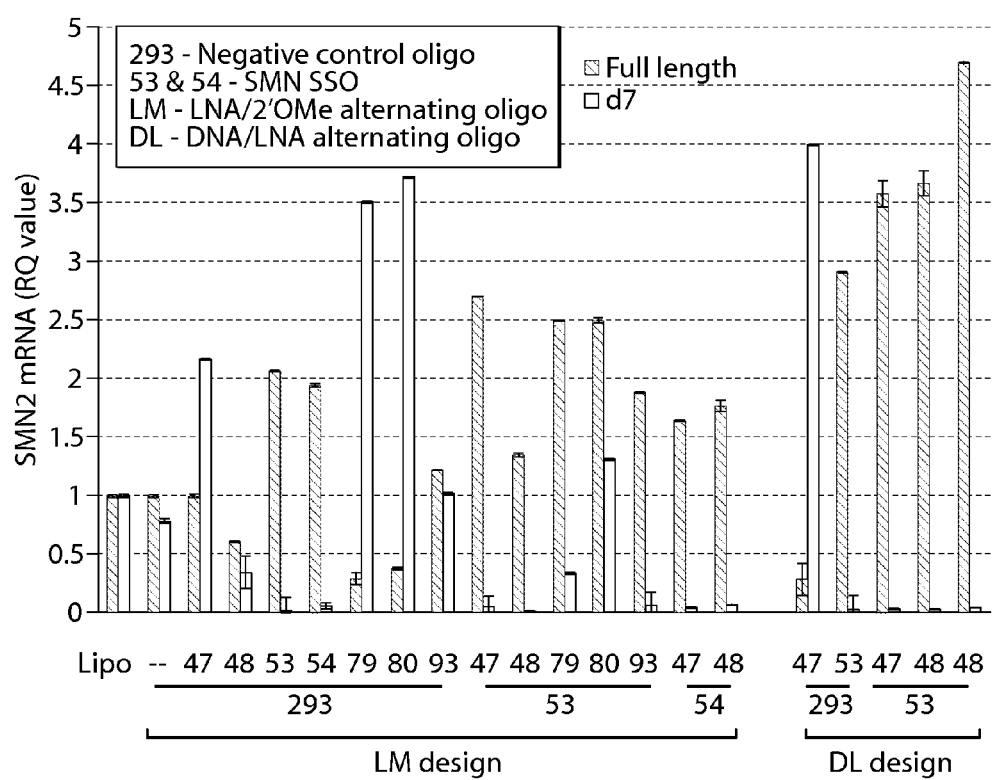
FIG. 9 provides results of an RT-PCR assay showing that oligonucleotides directed against a PRC2-associated region of SMN2 in combination with a splice switching oligonucleotide (oligo 53 or 54) significantly increase SMN2 protein 24 h post-transfection in SMA patient fibroblasts (compared to negative control oligo and Lipofectamine treated cells).

Example 2: Selective Upregulation of Exon 7 Containing SMN2 Transcripts Using Oligonucleotides Targeting PRC2-Interacting Regions that Upregulate SMN2 and Splice-Switching Oligonucleotides Oligo Design:
Oligonucleotides targeting PRC2-interacting regions (lncRNA peaks) in the SMN1/2 gene loci were designed. These oligos were synthesized with various DNA base modifications, modification placements, inter-nucleoside bonds and inter-oligo linkers (oligos 1-52 and 59-101) as outlined in Table 4.
Splice switching oligos (SSO) were designed based on sequences of SMN2. Various modifications of such SSOs in length and chemistry were prepared (oligos 53-58).
Universal negative control oligos (oligo 232 and 293) were also designed using on bioinformatic analysis.
Methods:
Cell Culture:
Six fibroblast cell lines and one lymphoblast cell line were obtained from the Coriell Institute (FIG. 2). The cells were either transfected with the oligos using Lipofectamine 2000 (Fibroblasts) or by electroporation or unassisted delivery (lymphoblast) to ascertain effects of the oligonucleotides on SMN1/2 mRNA and protein expression. All experiments were carried out as biological triplicates.
mRNA and Protein Expression:
mRNA Expression
1. On day 1, patient fibroblasts with reduced SMN expression were seeded into each well of 96-well plates at a density of 5,000 cells per 100 uL.
2. On day 2, transfections were performed using Lipofectamie2000 per manufacturer's instructions with oligos at either 10 nM or 30 nM.
3. 48 hours post-transfection, Ambion Cells-to-CT kit was used to directly obtain qRT-PCR results from the cells per manufacturer's instructions.
4. Quantitative PCR evaluation was completed using Taqman FAST qPCR on StepOne Plus, and change in mRNA expression was quantified using the delta delta Ct method by normalizing SMN expression to a housekeeper gene (B2M).
Protein Expression (ELISA)—
ELISA to determine SMN protein was carried out per manufacturer's instructions (SMN ELISA kit #ADI-900-209, Enzo Life Sciences). Briefly, SMN fibroblasts were cultures at 40,000 cells/well of a 24-well tissue culture coated plate on day 1. Cells were transfected with the oligos using Lipofectamine2000 on day 2 and cell lysates prepared at 24 and 48 hours post-treatment. ELISA was carried out per manufacturer's instructions. Subsequently fold induction of SMN protein was determined by normalizing SMN protein levels induced by oligonucleotides to the SMN protein levels induced by Lipofectamine treatment alone.
Splice Switching Assay (DdeI Assay)—
SMN2-derived transcripts contain a unique DdeI restriction element introduced because of a nucleotide polymorphism not present in SMN1 and are differentiated from SMN1-derived transcripts because of the faster migration of the SMN2 products. Briefly, patient fibroblasts with reduced SMN expression were treated with oligonucleotides targeting PRC2-interacting regions with or without SSO at 30 nM each as described before. RT-PCR was carried out with an SMN exon 5 forward primer and an exon 8 reverse primer to generate cDNAs that were then digested with DdeI. The SMN1 transcript, if present, migrates at a slower rate than the DdeI-digested SMN2 transcript and is seen as the first band from the top of the gel. The second band from the top indicates full length SMN2 (accurately spliced form) and the third band indicates the incorrectly spliced SMN2delta7. (FIG. 5)
Results
Amyotrophic lateral sclerosis (ALS) and spinal muscular atrophy (SMA) are both neurodegenerative diseases in which motor neurons degenerate and die, leading to muscle weakness and ultimately paralysis. In both cases, motor neurons exhibit defects in spliceosome integrity as indicated by disruption of Gems (Gemini of coiled bodies).
In some embodiments, the SMN1 gene is mutated in such a way that it is unable to correctly code the SMN protein— due to either a deletion encompassing at least a portion of exon 7 or to other mutations. SMA patients, however, generally retain at least one copy of the SMN2 gene (with many having 2 or more copies) that still expresses small amounts of SMN protein. The SMN2 gene has a C to T mutation (compared with SMN1) in exon 7 that alters splicing of its precursor mRNA such that exon 7 is spliced out at a high frequency. Consequently, only about 10% of the normal levels of full length SMN protein are produced from SMN2. (See FIG. 1)
Six SMA fibroblast cell lines and one lymphoblast cell line were obtained from the Coriell Institute (FIG. 2). Cells were transfected with oligonucleotides (oligos 1-52 and 59-101) directed against a PRC2-associated region of SMN2 and RT-PCR assays were conducted to evaluate effects on SMN mRNA expression. (See FIGS. 3 and 4 for results in cell lines 3814 and 3813). It is expected that oligos directed againsted a PRC2-associated region of SMN may further enhance SMN protein expression when wild-type SMN1 is present, e.g., in cells from subjects with ALS. In separate experiments, cells were transfected with oligonucleotides (oligos 53-58) directed at a splice control sequence in intron 7 of SMN2 and RT-PCR assays were conducted to evaluate effects on SMN mRNA expression (See FIGS. 3 and 4 for results in cell lines 3814 and 3813). Splice switching oligonucleotides (oligos 53-58) were found to increase expression of full length SMN2 based on a gel separation analysis of PCR products obtained following a DdeI restriction digest; whereas certain oligonucleotides directed against a PRC2-associated region of SMN2 did not. (FIG. 5)
SMN ELISA (Enzo) assays were conducted and revealed that certain oligonucleotides directed against a PRC2-associated region of SMN2 alone did not significantly increase full length SMN protein 24 h post-transfection in certain SMA patient fibroblasts. (FIG. 6) However, the same SMN ELISA assays showed that oligonucleotides directed against a PRC2-associated region of SMN2 in combination with a splice switching oligonucleotide (oligo 53 or 54) significantly increase full length SMN protein 24 h post-transfection in SMA patient fibroblasts above that observed with splice switching oligonucleotides alone. (FIGS. 7 and 8). RT-PCR assays were conducted and showed that oligonucleotides directed against a PRC2-associated region of SMN2 in combination with a splice switching oligonucleotide (oligo 53 or 54) significantly increased SMN2 protein 24 h post-transfection in SMA patient fibroblasts. (FIG. 9.) These experiments were conducted modified oligonucleotides with either alternating LNA and 2'OMe nucleotides or alternating DNA and LNA nucleotides.

In summary, the results of Example 2 show that certain oligos targeting PRC2 associated regions of SMN2 induce SMN RNA expression (e.g., of the SMNΔ7 transcript) SMA patient-derived fibroblasts. The results also show that, in some embodiments, splice-switching oligos may not induce SMN RNA expression, but rather shift SMN RNA splicing to the full-length transcript. Finally, the results show that combination of splice switching oligos with PRC2-associated region targeting oligos substantially increases full length SMN protein in cells from SMA patients.

TABLE 4

Oligonucleotide sequences made for testing human cells obtained from subjects with Spinal Muscular Atrophy (See Table 3 for structural features of formatted sequence).

| Oligo Name | Base Sequence | Formatted Sequence | SeqID |
|---|---|---|---|
| SMN1-01 m03 | ATTCTCTTGA TGATGCTGAT | omeAs; omeUs; omeUs; omeCs; omeUs; omeCs; omeUs; omeUs; omeGs; omeAs; omeUs; omeGs; omeAs; omeUs; omeGs; omeCs; omeUs; omeGs; omeAs; omeU-Sup | 13062 |
| SMN1-02 m03 | TTCTCTTGAT GATGCTGAT G | omeUs; omeUs; omeCs; omeUs; omeCs; omeUs; omeUs; omeGs; omeAs; omeUs; omeGs; omeAs; omeUs; omeGs; omeCs; omeUs; omeGs; omeAs; omeUs; omeG-Sup | 13063 |
| SMN1-03 m03 | TCTCTTGATG ATGCTGATGC | omeUs; omeCs; omeUs; omeCs; omeUs; omeUs; omeGs; omeAs; omeUs; omeGs; omeAs; omeUs; omeGs; omeCs; omeUs; omeGs; omeAs; omeUs; omeGs; omeC-Sup | 13064 |
| SMN1-04 m03 | CTCTTGATGA TGCTGATGCT | omeCs; omeUs; omeCs; omeUs; omeUs; omeGs; omeAs; omeUs; omeGs; omeAs; omeUs; omeGs; omeCs; omeUs; omeGs; omeAs; omeUs; omeGs; omeCs; omeU-Sup | 13065 |
| SMN1-05 m03 | TCTTGATGAT GCTGATGCTT | omeUs; omeCs; omeUs; omeUs; omeGs; omeAs; omeUs; omeGs; omeAs; omeUs; omeGs; omeCs; omeUs; omeGs; omeAs; omeUs; omeGs; omeCs; omeUs; omeU-Sup | 13066 |
| SMN1-06 m03 | CTTGATGATG CTGATGCTTT | omeCs; omeUs; omeUs; omeGs; omeAs; omeUs; omeGs; omeAs; omeUs; omeCs; omeUs; omeGs; omeAs; omeUs; omeGs; omeCs; omeUs; omeUs; omeU-Sup | 13067 |
| SMN1-07 m03 | TTGATGATGC TGATGCTTTG | omeUs; omeUs; omeGs; omeAs; omeUs; omeGs; omeAs; omeUs; omeGs; omeCs; omeUs; omeGs; omeAs; omeUs; omeGs; omeCs; omeUs; omeUs; omeUs; omeG-Sup | 13068 |
| SMN1-08 m03 | TGATGATGCT GATGCTTTGG | omeUs; omeGs; omeAs; omeUs; omeGs; omeAs; omeUs; omeGs; omeCs; omeUs; omeGs; omeAs; omeUs; omeGs; omeCs; omeUs; omeUs; omeUs; omeGs; omeG-Sup | 13069 |
| SMN1-09 m03 | GATGATGCT GATGCTTTGG G | omeGs; omeAs; omeUs; omeGs; omeAs; omeUs; omeGs; omeCs; omeUs; omeGs; omeAs; omeUs; omeGs; omeCs; omeUs; omeUs; omeUs; omeGs; omeGs; omeG-Sup | 13070 |
| SMN1-10 m03 | ATGATGCTGA TGCTTTGGGA | omeAs; omeUs; omeGs; omeAs; omeUs; omeGs; omeCs; omeUs; omeGs; omeAs; omeUs; omeGs; omeCs; omeUs; omeUs; omeUs; omeGs; omeGs; omeGs; omeA-Sup | 13071 |
| SMN1-11 m03 | TGATGCTGAT GCTTTGGGA A | omeUs; omeGs; omeAs; omeUs; omeGs; omeCs; omeUs; omeGs; omeAs; omeUs; omeGs; omeCs; omeUs; omeUs; omeUs; omeGs; omeGs; omeGs; omeAs; omeA-Sup | 13072 |
| SMN1-12 m03 | GATGCTGAT GCTTTGGGA AG | omeGs; omeAs; omeUs; omeGs; omeCs; omeUs; omeGs; omeAs; omeUs; omeGs; omeCs; omeUs; omeUs; omeUs; omeGs; omeGs; omeGs; omeAs; omeAs; omeG-Sup | 13073 |
| SMN1-13 m03 | ATGCTGATGC TTTGGGAAGT | omeAs; omeUs; omeGs; omeCs; omeUs; omeGs; omeAs; omeUs; omeGs; omeCs; omeUs; omeUs; omeUs; omeGs; omeGs; omeGs; omeAs; omeAs; omeGs; omeU-Sup | 13074 |
| SMN1-14 m03 | TGCTGATGCT TTGGGAAGT A | omeUs; omeGs; omeCs; omeUs; omeGs; omeAs; omeUs; omeGs; omeCs; omeUs; omeUs; omeUs; omeGs; omeGs; omeGs; omeAs; omeAs; omeGs; omeUs; omeA-Sup | 13075 |

TABLE 4-continued

Oligonucleotide sequences made for testing human cells obtained from subjects with Spinal Muscular Atrophy (See Table 3 for structural features of formatted sequence).

| Oligo Name | Base Sequence | Formatted Sequence | SeqID |
|---|---|---|---|
| SMN1-15 m03 | GCTGATGCTT TGGGAAGTA T | omeGs; omeCs; omeUs; omeGs; omeAs; omeUs; omeGs; omeCs; omeUs; omeUs; omeUs; omeUs; omeGs; omeGs; omeAs; omeAs; omeGs; omeUs; omeAs; omeU-Sup | 13076 |
| SMN1-16 m03 | CTGATGCTTT GGGAAGTAT G | omeCs; omeUs; omeGs; omeAs; omeUs; omeGs; omeCs; omeUs; omeUs; omeUs; omeGs; omeGs; omeGs; omeAs; omeAs; omeGs; omeUs; omeAs; omeUs; omeG-Sup | 13077 |
| SMN1-17 m03 | TGATGCTTTG GGAAGTATG T | omeUs; omeGs; omeAs; omeUs; omeGs; omeCs; omeUs; omeUs; omeUs; omeGs; omeGs; omeGs; omeAs; omeAs; omeGs; omeUs; omeAs; omeUs; omeGs; omeU-Sup | 13078 |
| SMN1-18 m03 | GATGCTTTGG GAAGTATGTT | omeGs; omeAs; omeUs; omeGs; omeCs; omeUs; omeUs; omeUs; omeGs; omeGs; omeGs; omeAs; omeAs; omeGs; omeUs; omeAs; omeUs; omeGs; omeUs; omeU-Sup | 13079 |
| SMN1-19 m03 | ATGCTTTGGG AAGTATGTTA | omeAs; omeUs; omeGs; omeCs; omeUs; omeUs; omeUs; omeGs; omeGs; omeGs; omeAs; omeAs; omeGs; omeUs; omeAs; omeUs; omeGs; omeUs; omeUs; omeA-Sup | 13080 |
| SMN1-20 m03 | TGCTTTGGGA AGTATGTTAA | omeUs; omeGs; omeCs; omeUs; omeUs; omeUs; omeGs; omeGs; omeGs; omeAs; omeAs; omeGs; omeUs; omeAs; omeUs; omeGs; omeUs; omeUs; omeAs; omeA-Sup | 13081 |
| SMN1-21 m03 | GCTTTGGGA AGTATGTTAA T | omeGs; omeCs; omeUs; omeUs; omeUs; omeGs; omeGs; omeGs; omeAs; omeAs; omeGs; omeUs; omeAs; omeUs; omeGs; omeUs; omeUs; omeAs; omeAs; omeU-Sup | 13082 |
| SMN1-22 m03 | CTTTGGGAA GTATGTTAAT T | omeCs; omeUs; omeUs; omeUs; omeGs; omeGs; omeGs; omeAs; omeAs; omeGs; omeUs; omeAs; omeUs; omeGs; omeUs; omeUs; omeAs; omeAs; omeUs; omeU-Sup | 13083 |
| SMN1-23 m03 | TTTGGGAAGT ATGTTAATTT | omeUs; omeUs; omeUs; omeGs; omeGs; omeGs; omeAs; omeAs; omeGs; omeUs; omeAs; omeUs; omeGs; omeUs; omeUs; omeAs; omeAs; omeUs; omeUs; omeU-Sup | 13084 |
| SMN1-24 m03 | TTGGGAAGT ATGTTAATTT C | omeUs; omeUs; omeGs; omeGs; omeGs; omeAs; omeAs; omeGs; omeUs; omeAs; omeUs; omeGs; omeUs; omeUs; omeAs; omeAs; omeUs; omeUs; omeUs; omeC-Sup | 13085 |
| SMN1-25 m03 | TGGGAAGTA TGTTAATTTC A | omeUs; omeGs; omeGs; omeGs; omeAs; omeAs; omeGs; omeUs; omeAs; omeUs; omeGs; omeUs; omeUs; omeAs; omeAs; omeUs; omeUs; omeUs; omeCs; omeA-Sup | 13086 |
| SMN1-26 m03 | GGGAAGTAT GTTAATTTCA T | omeGs; omeGs; omeGs; omeAs; omeAs; omeGs; omeUs; omeAs; omeUs; omeGs; omeUs; omeUs; omeAs; omeAs; omeUs; omeUs; omeUs; omeCs; omeAs; omeU-Sup | 13087 |
| SMN1-27 m01 | ATTCTCTTGA TGATG | InaAs; omeUs; InaTs; omeCs; InaTs; omeCs; InaTs; omeUs; InaGs; omeAs; InaTs; omeGs; InaAs; omeUs; InaG-Sup | 11374 |
| SMN1-28 m01 | TTCTCTTGAT GATGC | InaTs; omeUs; InaCs; omeUs; InaCs; omeUs; InaTs; omeGs; InaAs; omeUs; InaGs; omeAs; InaTs; omeGs; InaC-Sup | 11375 |
| SMN1-29 m01 | TCTCTTGATG ATGCT | InaTs; omeCs; InaTs; omeCs; InaTs; omeUs; InaGs; omeAs; InaTs; omeGs; InaAs; omeUs; InaGs; omeCs; InaT-Sup | 11376 |
| SMN1-30 m01 | CTCTTGATGA TGCTG | InaCs; omeUs; InaCs; omeUs; InaTs; omeGs; InaAs; omeUs; InaGs; omeAs; InaTs; omeGs; InaCs; omeUs; InaG-Sup | 11377 |
| SMN1-31 m01 | TCTTGATGAT GCTGA | InaTs; omeCs; InaTs; omeUs; InaGs; omeAs; InaTs; omeGs; InaAs; omeUs; InaGs; omeCs; InaTs; omeGs; InaA-Sup | 11378 |
| SMN1-32 m01 | CTTGATGATG CTGAT | InaCs; omeUs; InaTs; omeGs; InaAs; omeUs; InaGs; omeAs; InaTs; omeGs; InaCs; omeUs; InaGs; omeAs; InaT-Sup | 11379 |
| SMN1-33 m01 | TTGATGATGC TGATG | InaTs; omeUs; InaGs; omeAs; InaTs; omeGs; InaAs; omeUs; InaGs; omeCs; InaTs; omeGs; InaAs; omeUs; InaG-Sup | 11380 |
| SMN1-34 m01 | TGATGATGCT GATGC | InaTs; omeGs; InaAs; omeUs; InaGs; omeAs; InaTs; omeGs; InaCs; omeUs; InaGs; omeAs; InaTs; omeGs; InaC-Sup | 11381 |

TABLE 4-continued

Oligonucleotide sequences made for testing human cells obtained from subjects with Spinal Muscular Atrophy (See Table 3 for structural features of formatted sequence).

| Oligo Name | Base Sequence | Formatted Sequence | SeqID |
|---|---|---|---|
| SMN1-35 m01 | GATGATGCT GATGCT | InaGs; omeAs; InaTs; omeGs; InaAs; omeUs; InaGs; omeCs; InaTs; omeGs; InaAs; omeUs; InaGs; omeCs; InaT-Sup | 11382 |
| SMN1-36 m01 | ATGATGCTGA TGCTT | InaAs; omeUs; InaGs; omeAs; InaTs; omeGs; InaCs; omeUs; InaGs; omeAs; InaTs; omeGs; InaCs; omeUs; InaT-Sup | 11383 |
| SMN1-37 m01 | TGATGCTGAT GCTTT | InaTs; omeGs; InaAs; omeUs; InaGs; omeCs; InaTs; omeGs; InaAs; omeUs; InaGs; omeCs; InaTs; omeUs; InaT-Sup | 11384 |
| SMN1-38 m01 | GATGCTGAT GCTTTG | InaGs; omeAs; InaTs; omeGs; InaCs; omeUs; InaGs; omeAs; InaTs; omeGs; InaCs; omeUs; InaTs; omeUs; InaG-Sup | 11385 |
| SMN1-39 m01 | ATGCTGATGC TTTGG | InaAs; omeUs; InaGs; omeCs; InaTs; omeGs; InaAs; omeUs; InaGs; omeCs; InaTs; omeUs; InaTs; omeGs; InaG-Sup | 11386 |
| SMN1-40 m01 | TGCTGATGCT TTGGG | InaTs; omeGs; InaCs; omeUs; InaGs; omeAs; InaTs; omeGs; InaCs; omeUs; InaTs; omeUs; InaGs; omeGs; InaG-Sup | 11387 |
| SMN1-41 m01 | GCTGATGCTT TGGGA | InaGs; omeCs; InaTs; omeGs; InaAs; omeUs; InaGs; omeCs; InaTs; omeUs; InaTs; omeGs; InaGs; omeGs; InaA-Sup | 11388 |
| SMN1-42 m01 | CTGATGCTTT GGGAA | InaCs; omeUs; InaGs; omeAs; InaTs; omeGs; InaCs; omeUs; InaTs; omeUs; InaGs; omeGs; InaGs; omeAs; InaA-Sup | 11389 |
| SMN1-43 m01 | TGATGCTTTG GGAAG | InaTs; omeGs; InaAs; omeUs; InaGs; omeCs; InaTs; omeUs; InaTs; omeGs; InaGs; omeGs; InaAs; omeAs; InaG-Sup | 11390 |
| SMN1-44 m01 | GATGCTTTGG GAAGT | InaGs; omeAs; InaTs; omeGs; InaCs; omeUs; InaTs; omeUs; InaTs; omeGs; InaGs; omeGs; InaAs; omeAs; InaG-Sup omeGs; InaAs; omeAs; InaGs; omeGs; InaT-Sup | 11391 |
| SMN1-45 m01 | ATGCTTTGGG AAGTA | InaAs; omeUs; InaGs; omeCs; InaTs; omeUs; InaTs; omeUs; InaGs; omeGs; InaGs; omeAs; InaAs; omeGs; InaA-Sup | 11392 |
| SMN1-46 m01 | TGCTTTGGGA AGTAT | InaTs; omeGs; InaCs; omeUs; InaTs; omeUs; InaTs; omeGs; InaGs; omeGs; InaAs; omeAs; InaGs; omeAs; InaT-Sup | 11393 |
| SMN1-47 m02 | GCTTTGGGA AGTATG | dGs; InaCs; dTs; InaTs; dTs; InaGs; dGs; InaGs; dAs; InaAs; dGs; InaTs; dAs; InaTs; dG-Sup | 11394 |
| SMN1-47 m01 | GCTTTGGGA AGTATG | InaGs; omeCs; InaTs; omeUs; InaTs; omeGs; InaGs; omeGs; InaAs; omeAs; InaGs; omeUs; InaAs; omeUs; InaG-Sup | 11394 |
| SMN1-48 m05 | CTTTGGGAA GTATGT | dCs; InaTs; dTs; InaTs; dGs; InaGs; dGs; InaAs; dAs; InaGs; dTs; InaAs; dTs; InaGs; dT-Sup | 11395 |
| SMN1-48 m01 | CTTTGGGAA GTATGT | InaCs; omeUs; InaTs; omeUs; InaTs; omeGs; InaGs; omeAs; InaAs; omeGs; InaTs; omeAs; InaTs; omeGs; InaT-Sup | 11395 |
| SMN1-49 m01 | TTTGGGAAGT ATGTT | InaTs; omeUs; InaTs; omeGs; InaGs; omeAs; InaAs; omeGs; InaTs; omeAs; InaTs; omeGs; InaTs; omeUs; InaT-Sup | 11396 |
| SMN1-50 m01 | TTGGGAAGT ATGTTA | InaTs; omeUs; InaGs; omeGs; InaGs; omeAs; InaAs; omeGs; InaTs; omeAs; InaTs; omeGs; InaTs; omeUs; InaA-Sup | 11397 |
| SMN1-51 m01 | TGGGAAGTA TGTTAA | InaTs; omeGs; InaGs; omeGs; InaAs; omeAs; InaGs; omeUs; InaAs; omeUs; InaGs; omeUs; InaTs; omeAs; InaA-Sup | 11398 |
| SMN1-52 m01 | GGGAAGTAT GTTAAT | InaGs; omeGs; InaGs; omeAs; InaAs; omeGs; InaTs; omeAs; InaTs; omeGs; InaTs; omeUs; InaAs; omeAs; InaT-Sup | 11399 |
| SMN1-53 m02 | TCACTTTCAT AATGCTGG | dTs; InaCs; dAs; InaCs; dTs; InaTs; dTs; InaCs; dAs; InaTs; dAs; InaAs; dTs; InaGs; dCs; InaTs; dGs; InaG-Sup | 13088 |
| SMN1-53 m12 | TCACTTTCAT AATGCTGG | InaTs; dCs; InaAs; dCs; InaTs; dTs; InaTs; dCs; InaAs; dTs; InaAs; dAs; InaTs; dGs; InaCs; dTs; InaGs; dG-Sup | 13088 |
| SMN1-54 m01 | TCACTTTCAT AATGCTGG | InaTs; omeCs; InaAs; omeCs; InaTs; omeUs; InaTs; omeCs; InaAs; omeUs; InaAs; omeAs; InaTs; omeGs; InaCs; omeUs; InaGs; omeG-Sup | 13088 |
| SMN1-53 m03 | TCACTTTCAT AATGCTGG | omeUs; omeCs; omeAs; omeCs; omeUs; omeUs; omeUs; omeCs; omeAs; omeUs; omeAs; omeAs; omeUs; omeGs; omeCs; omeUs; omeGs; omeG-Sup | 13088 |

TABLE 4-continued

Oligonucleotide sequences made for testing human cells obtained from subjects with Spinal Muscular Atrophy (See Table 3 for structural features of formatted sequence).

| Oligo Name | Base Sequence | Formatted Sequence | SeqID |
|---|---|---|---|
| SMN1-55 m01 | TCACTTTCATAATGC | InaTs; omeCs; InaAs; omeCs; InaTs; omeUs; InaTs; omeCs; InaAs; omeUs; InaAs; omeAs; InaTs; omeGs; InaC-Sup | 13089 |
| SMN1-56 m01 | CACTTTCATAATGCT | InaCs; omeAs; InaCs; omeUs; InaTs; omeUs; InaCs; omeAs; InaTs; omeAs; InaAs; omeUs; InaGs; omeCs; InaT-Sup | 13090 |
| SMN1-57 m02 | ACTTTCATAATGCTG | dAs; InaCs; dTs; InaTs; dTs; InaCs; dAs; InaTs; dAs; InaAs; dTs; InaGs; dCs; InaTs; dG-Sup | 13091 |
| SMN1-57 m01 | ACTTTCATAATGCTG | InaAs; omeCs; InaTs; omeUs; InaTs; omeCs; InaAs; omeUs; InaAs; omeAs; InaTs; omeGs; InaCs; omeUs; InaG-Sup | 13091 |
| SMN1-58 m01 | CTTTCATAATGCTGG | InaCs; omeUs; InaTs; omeUs; InaCs; omeAs; InaTs; omeAs; InaAs; omeUs; InaGs; omeCs; InaTs; omeGs; InaG-Sup | 13092 |
| SMN1-59 m01 | AGACCAGTTTTACCT | InaAs; omeGs; InaAs; omeCs; InaCs; omeAs; InaGs; omeUs; InaTs; omeUs; InaTs; omeAs; InaCs; omeCs; InaT-Sup | 3650 |
| SMN1-60 m01 | CCTAGCTACTTTGAA | InaCs; omeCs; InaTs; omeAs; InaGs; omeCs; InaTs; omeAs; InaCs; omeUs; InaTs; omeUs; InaGs; omeAs; InaA-Sup | 13093 |
| SMN1-61 m01 | TCCTAGCTACTTTGA | InaTs; omeCs; InaCs; omeUs; InaAs; omeGs; InaCs; omeUs; InaAs; omeCs; InaTs; omeUs; InaTs; omeGs; InaA-Sup | 13094 |
| SMN1-62 m01 | GAAATATTCCTTATA | InaGs; omeAs; InaAs; omeAs; InaTs; omeAs; InaTs; omeUs; InaCs; omeCs; InaTs; omeUs; InaAs; omeUs; InaA-Sup | 10065 |
| SMN1-63 m01 | AAATATTCCTTATAG | InaAs; omeAs; InaAs; omeUs; InaAs; omeUs; InaTs; omeCs; InaCs; omeUs; InaTs; omeAs; InaTs; omeAs; InaG-Sup | 10066 |
| SMN1-64 m01 | AATATTCCTTATAGC | InaAs; omeAs; InaTs; omeAs; InaTs; omeUs; InaCs; omeCs; InaTs; omeUs; InaAs; omeUs; InaAs; omeGs; InaC-Sup | 10067 |
| SMN1-65 m01 | ATATTCCTTATAGCC | InaAs; omeUs; InaAs; omeUs; InaTs; omeCs; InaCs; omeUs; InaTs; omeAs; InaTs; omeAs; InaGs; omeCs; InaC-Sup | 10068 |
| SMN1-66 m01 | TATTCCTTATAGCCA | InaTs; omeAs; InaTs; omeUs; InaCs; omeCs; InaTs; omeUs; InaAs; omeUs; InaAs; omeGs; InaCs; omeCs; InaA-Sup | 10069 |
| SMN1-67 m01 | ATTCCTTATAGCCAG | InaAs; omeUs; InaTs; omeCs; InaCs; omeUs; InaTs; omeAs; InaTs; omeAs; InaGs; omeCs; InaCs; omeAs; InaG-Sup | 10070 |
| SMN1-68 m01 | TTCCTTATAGCCAGG | InaTs; omeUs; InaCs; omeCs; InaTs; omeUs; InaAs; omeUs; InaAs; omeGs; InaCs; omeCs; InaAs; omeGs; InaG-Sup | 10071 |
| SMN1-69 m01 | TCCTTATAGCCAGGT | InaTs; omeCs; InaCs; omeUs; InaTs; omeUs; InaAs; omeUs; InaAs; omeGs; InaCs; omeCs; InaAs; omeGs; InaG-Sup | 10072 |
| SMN1-70 m01 | CCTTATAGCCAGGTC | InaCs; omeCs; InaTs; omeUs; InaAs; omeUs; InaAs; omeGs; InaCs; omeCs; InaAs; omeGs; InaGs; omeUs; InaC-Sup | 10073 |
| SMN1-71 m01 | CTTATAGCCAGGTCT | InaCs; omeUs; InaTs; omeAs; InaTs; omeAs; InaGs; omeCs; InaCs; omeAs; InaGs; omeGs; InaTs; omeCs; InaT-Sup | 10074 |
| SMN1-72 m01 | TTATAGCCAGGTCTA | InaTs; omeUs; InaAs; omeUs; InaAs; omeGs; InaCs; omeCs; InaAs; omeGs; InaGs; omeUs; InaCs; omeUs; InaA-Sup | 10075 |
| SMN1-73 m01 | GCCAGGTCTAAAATT | InaGs; omeCs; InaCs; omeAs; InaGs; omeGs; InaTs; omeCs; InaTs; omeAs; InaAs; omeAs; InaAs; omeUs; InaT-Sup | 10080 |
| SMN1-74 m01 | CCAGGTCTAAAATTC | InaCs; omeCs; InaAs; omeGs; InaGs; omeUs; InaCs; omeUs; InaAs; omeAs; InaAs; omeAs; InaTs; omeUs; InaC-Sup | 10081 |
| SMN1-75 m01 | CAGGTCTAAAATTCA | InaCs; omeAs; InaGs; omeGs; InaTs; omeCs; InaTs; omeAs; InaAs; omeAs; InaAs; omeUs; InaTs; omeCs; InaA-Sup | 10082 |
| SMN1-76 m01 | GGTCTAAAATTCAAT | InaGs; omeGs; InaTs; omeCs; InaTs; omeAs; InaAs; omeAs; InaAs; omeUs; InaTs; omeCs; InaAs; omeAs; InaT-Sup | 10084 |
| SMN1-77 m01 | CTAAAATTCAATGGC | InaCs; omeUs; InaAs; omeAs; InaAs; omeAs; InaTs; omeUs; InaCs; omeAs; InaAs; omeUs; InaGs; omeGs; InaC-Sup | 10087 |

TABLE 4-continued

Oligonucleotide sequences made for testing human cells obtained from
subjects with Spinal Muscular Atrophy (See Table 3 for structural features of formatted
sequence).

| Oligo Name | Base Sequence | Formatted Sequence | SeqID |
|---|---|---|---|
| SMN1-77 m03 | CTAAAATTCAATGGC | omeCs; omeUs; omeAs; omeAs; omeAs; omeAs; omeUs; omeUs; omeCs; omeAs; omeAs; omeUs; omeGs; omeGs; omeC-Sup | 10087 |
| SMN1-78 m01 | GGACCACCAGTAAGT | InaGs; omeGs; InaAs; omeCs; InaCs; omeAs; InaCs; omeCs; InaAs; omeGs; InaTs; omeAs; InaAs; omeGs; InaT-Sup | 10168 |
| SMN1-79 m02 | GACCACCAGTAAGTA | dGs; InaAs; dCs; InaCs; dAs; InaCs; dCs; InaAs; dGs; InaTs; dAs; InaAs; dGs; InaTs; dA-Sup | 10169 |
| SMN1-79 m01 | GACCACCAGTAAGTA | InaGs; omeAs; InaCs; omeCs; InaAs; omeCs; InaCs; omeAs; InaGs; omeUs; InaAs; omeAs; InaGs; omeUs; InaA-Sup | 10169 |
| SMN1-80 m02 | ACCACCAGTAAGTAA | dAs; InaCs; dCs; InaAs; dCs; lnaCs; dAs; InaGs; dTs; InaAs; dAs; InaGs; dTs; InaAs; dA-Sup | 10170 |
| SMN1-80 m01 | ACCACCAGTAAGTAA | InaAs; omeCs; InaCs; omeAs; InaCs; omeCs; InaAs; omeGs; InaTs; omeAs; InaAs; omeGs; InaTs; omeAs; InaA-Sup | 10170 |
| SMN1-81 m01 | TTCTGTTACCCAGAT | InaTs; omeUs; InaCs; omeUs; InaGs; omeUs; InaTs; omeAs; InaCs; omeCs; InaCs; omeAs; InaGs; omeAs; InaT-Sup | 10337 |
| SMN1-82 m01 | TCTGTTACCCAGATG | InaTs; omeCs; InaTs; omeGs; InaTs; omeUs; InaAs; omeCs; InaCs; omeCs; InaAs; omeGs; InaAs; omeUs; InaG-Sup | 10338 |
| SMN1-83 m01 | CTGTTACCCAGATGC | InaCs; omeUs; InaGs; omeUs; InaTs; omeAs; InaCs; omeCs; InaCs; omeAs; InaGs; omeAs; InaTs; omeGs; InaC-Sup | 10339 |
| SMN1-84 m02 | TTTTTAGGTATTAAC | dTs; InaTs; dTs; InaTs; dTs; InaAs; dGs; InaGs; dTs; InaAs; dTs; InaTs; dAs; InaAs; dC-Sup | 10763 |
| SMN1-84 m01 | TTTTTAGGTATTAAC | InaTs; omeUs; InaTs; omeUs; InaTs; omeAs; InaGs; omeGs; InaTs; omeAs; InaTs; omeUs; InaAs; omeAs; InaC-Sup | 10763 |
| SMN1-85 m01 | TTTTAGGTATTAACA | InaTs; omeUs; InaTs; omeUs; InaGs; omeGs; InaAs; omeUs; InaAs; omeUs; InaTs; omeAs; InaAs; omeCs; InaA-Sup | 10764 |
| SMN1-86 m01 | CATAGCTTCATAGTG | InaCs; omeAs; InaTs; omeAs; InaGs; omeCs; InaTs; omeUs; InaCs; omeAs; InaTs; omeAs; InaGs; omeUs; InaG-Sup | 10949 |
| SMN1-87 m01 | TAGCTTCATAGTGGA | InaTs; omeAs; InaGs; omeCs; InaTs; omeUs; InaCs; omeAs; InaTs; omeAs; InaGs; omeUs; InaGs; omeGs; InaA-Sup | 10951 |
| SMN1-88 m01 | AGCTTCATAGTGGAA | InaAs; omeGs; InaCs; omeUs; InaTs; omeCs; InaAs; omeUs; InaAs; omeGs; InaTs; omeGs; InaGs; omeAs; InaA-Sup | 10952 |
| SMN1-89 m01 | GCTTCATAGTGGGAAC | InaGs; omeCs; InaTs; omeUs; InaCs; omeAs; InaTs; omeAs; InaGs; omeUs; InaGs; omeGs; InaAs; omeAs; InaC-Sup | 10953 |
| SMN1-90 m01 | CTTCATAGTGGAACA | InaCs; omeUs; InaTs; omeCs; InaUs; omeAs; InaTs; omeAs; InaGs; omeUs; InaGs; omeGs; InaAs; omeAs; InaA-Sup | 10954 |
| SMN1-91 m01 | TCATGGTACATGAGT | InaTs; omeCs; InaAs; omeUs; InaGs; omeGs; InaTs; omeAs; InaCs; omeAs; InaTs; omeGs; InaAs; omeGs; InaT-Sup | 11415 |
| SMN1-92 m01 | TGGTACATGAGTGGC | InaTs; omeGs; InaGs; omeUs; InaAs; omeCs; InaAs; omeUs; InaGs; omeAs; InaGs; omeUs; InaGs; omeGs; InaC-Sup | 11418 |
| SMN1-93 m02 | GGTACATGAGTGGCT | dGs; InaGs; dTs; InaAs; dCs; InaAs; dTs; InaGs; dAs; InaGs; dTs; InaGs; dGs; InaCs; dT-Sup | 11419 |
| SMN1-93 m01 | GGTACATGAGTGGCT | InaGs; omeGs; InaTs; omeAs; InaCs; omeAs; InaTs; omeGs; InaAs; omeGs; InaTs; omeGs; InaGs; omeCs; InaT-Sup | 11419 |
| SMN1-94 m01 | TACATGAGTGGCTAT | InaTs; omeAs; InaCs; omeAs; InaTs; omeGs; InaAs; omeGs; InaTs; omeGs; InaGs; omeCs; InaTs; omeAs; InaT-Sup | 11421 |
| SMN1-95 m01 | ACATGAGTGGCTATC | InaAs; omeCs; InaAs; omeUs; InaGs; omeAs; InaGs; omeUs; InaGs; omeGs; InaCs; omeUs; InaAs; omeUs; InaC-Sup | 11422 |
| SMN1-96 m01 | CATGAGTGGCTATCA | InaCs; omeAs; InaTs; omeGs; InaAs; omeGs; InaTs; omeGs; InaGs; omeCs; InaTs; omeAs; InaTs; omeCs; InaA-Sup | 11423 |

TABLE 4-continued

Oligonucleotide sequences made for testing human cells obtained from subjects with Spinal Muscular Atrophy (See Table 3 for structural features of formatted sequence).

| Oligo Name | Base Sequence | Formatted Sequence | SeqID |
|---|---|---|---|
| SMN1-97 m01 | CTGGCTATTATATGG | InaCs; omeUs; InaGs; omeGs; InaCs; omeUs; InaAs; omeUs; InaTs; omeAs; InaTs; omeAs; InaTs; omeGs; InaG-Sup | 11440 |
| SMN1-98 m01 | TGGCTATTATATGGT | InaTs; omeGs; InaGs; omeCs; InaTs; omeAs; InaTs; omeUs; InaAs; omeUs; InaAs; omeUs; InaGs; omeGs; InaT-Sup | 11441 |
| SMN1-99 m01 | GGCTATTATATGGTA | InaGs; omeGs; InaCs; omeUs; InaAs; omeUs; InaTs; omeAs; InaTs; omeAs; InaTs; omeGs; InaGs; omeUs; InaA-Sup | 11442 |
| SMN1-100 m01 | GCTATTATATGGTAA | InaGs; omeCs; InaTs; omeAs; InaTs; omeAs; InaTs; omeAs; InaTs; omeGs; InaGs; omeUs; InaAs; omeAs; InaA-Sup | 11443 |
| SMN1-101 m01 | GTATCATCTGTGTGT | InaGs; omeUs; InaAs; omeUs; InaCs; omeAs; InaTs; omeCs; InaTs; omeGs; InaTs; omeGs; InaT-Sup | 12369 |
| SMN1-102 m01 | GCTTTGGGAAGTATGTTTTTCACTTTCATAATGCTGG | InaGs; omeCs; InaTs; omeUs; InaTs; omeGs; InaGs; omeGs; InaAs; omeAs; InaGs; omeUs; InaAs; omeUs; InaG; dT; dT; dT; dT; InaTs; omeCs; InaAs; omeCs; InaTs; omeUs; InaTs; omeCs; InaAs; omeUs; InaAs; omeAs; InaTs; omeGs; InaCs; omeUs; InaGs; omeG-Sup | 13097 |
| SMN1-103 m01 | CTTTGGGAAGTATGTTTTTCACTTTCATAATGCTGG | InaCs; omeUs; InaTs; omeUs; InaGs; omeGs; InaGs; omeAs; InaAs; omeGs; InaTs; omeAs; InaTs; omeGs; InaT; dT; dT; dT; dT; InaTs; omeCs; InaAs; omeCs; InaTs; omeUs; InaTs; omeCs; InaAs; omeUs; InaAs; omeAs; InaTs; omeGs; InaCs; omeUs; InaGs; omeG-Sup | 13102 |
| SMN1-104 m01 | GGTACATGAGTGGCTTTTTCACTTTCATAATGCTGG | InaGs; omeGs; InaTs; omeAs; InaCs; omeAs; InaTs; omeGs; InaAs; omeGs; InaTs; omeGs; InaGs; omeCs; InaT; dT; dT; dT; dT; InaTs; omeCs; InaAs; omeCs; InaTs; omeUs; InaTs; omeCs; InaAs; omeUs; InaAs; omeAs; InaTs; omeGs; InaCs; omeUs; InaGs; omeG-Sup | 13099 |
| SMN1-105 m01 | TGATGCTGATGCTTTTTTTCTAAAATTCAATGGC | InaTs; omeGs; InaAs; omeUs; InaGs; omeCs; InaTs; omeGs; InaAs; omeUs; InaGs; omeCs; InaTs; omeUs; InaT; dT; dT; dT; dT; InaCs; omeUs; InaAs; omeAs; InaAs; omeAs; InaTs; omeUs; InaCs; omeAs; InaAs; omeUs; InaGs; omeGs; InaC-Sup | 13103 |
| SMN1-106 m01 | CTAAAATTCAATGGCTTTTCTAAAATTCAATGGC | InaCs; omeUs; InaAs; omeAs; InaAs; omeAs; InaTs; omeUs; InaCs; omeAs; InaAs; omeUs; InaGs; omeGs; InaC; dT; dT; dT; dT; InaCs; omeUs; InaAs; omeAs; InaAs; omeAs; InaTs; omeUs; InaCs; omeAs; InaAs; omeUs; InaGs; omeGs; InaC-Sup | 13104 |
| SMN1-107 m01 | CTGTTACCCAGATGCTTTTCTAAAATTCAATGGC | InaCs; omeUs; InaGs; omeUs; InaTs; omeAs; InaCs; omeCs; InaCs; omeAs; InaGs; omeAs; InaTs; omeGs; InaC; dT; dT; dT; dT; InaCs; omeUs; InaAs; omeAs; InaAs; omeAs; InaTs; omeUs; InaCs; omeAs; InaAs; omeUs; InaGs; omeGs; InaC-Sup | 13105 |
| SMN1-108 m01 | CTTCATAGTGGAACATTTCTAAAATTCAATGGC | InaCs; omeUs; InaTs; omeCs; InaAs; omeUs; InaAs; omeGs; InaTs; omeGs; InaGs; omeAs; InaAs; omeCs; InaA; dT; dT; dT; dT; InaCs; omeUs; InaAs; omeAs; InaAs; omeAs; InaTs; omeUs; InaCs; omeAs; InaAs; omeUs; InaGs; omeGs; InaC-Sup | 13106 |
| SMN1-109 m01 | TCACTTTCATAATGCTGGTTTTTCACTTTCATAATGCTGG | InaTs; omeCs; InaAs; omeCs; InaTs; omeUs; InaTs; omeCs; InaAs; omeUs; InaAs; omeAs; InaTs; omeGs; InaCs; omeUs; InaGs; omeG; dT; dT; dT; dT; InaTs; omeCs; InaAs; omeCs; InaTs; omeUs; InaTs; omeCs; InaAs; omeUs; InaAs; omeAs; InaTs; omeGs; InaCs; omeUs; InaGs; omeG-Sup | 13107 |
| SMN1-110 m01 | AAATTCAATGGCCCA | InaAs; omeAs; InaAs; omeUs; InaTs; omeCs; InaAs; omeAs; InaTs; omeGs; InaGs; omeCs; InaCs; omeCs; InaA-Sup | 10090 |
| SMN1-111 m01 | AATTCAATGGCCCAC | InaAs; omeAs; InaTs; omeUs; InaCs; omeAs; InaAs; omeUs; InaGs; omeGs; InaCs; omeCs; InaCs; omeAs; InaC-Sup | 10091 |
| SMN1-112 m01 | ATTCAATGGCCCACC | InaAs; omeUs; InaTs; omeCs; InaAs; omeAs; InaTs; omeGs; InaGs; omeCs; InaCs; omeCs; InaAs; omeCs; InaC-Sup | 10092 |
| SMN1-113 m01 | TTCAATGGCCCACCA | InaTs; omeUs; InaCs; omeAs; InaAs; omeUs; InaGs; omeGs; InaCs; omeCs; InaCs; omeAs; InaCs; omeCs; InaA-Sup | 10093 |

TABLE 4-continued

Oligonucleotide sequences made for testing human cells obtained from subjects with Spinal Muscular Atrophy (See Table 3 for structural features of formatted sequence).

| Oligo Name | Base Sequence | Formatted Sequence | SeqID |
|---|---|---|---|
| SMN1-114 m01 | TCAATGGCCCACCAC | InaTs; omeCs; InaAs; omeAs; InaTs; omeGs; InaGs; omeCs; InaCs; omeCs; InaAs; omeCs; InaCs; omeAs; InaC-Sup | 10094 |
| SMN1-115 m01 | CAATGGCCCACCACC | InaCs; omeAs; InaAs; omeUs; InaGs; omeGs; InaCs; omeCs; InaCs; omeAs; InaCs; omeCs; InaAs; omeCs; InaC-Sup | 10095 |
| SMN1-116 m01 | AATGGCCCACCACCG | InaAs; omeAs; InaTs; omeGs; InaGs; omeCs; InaCs; omeCs; InaAs; omeCs; InaCs; omeAs; InaCs; omeCs; InaG-Sup | 10096 |
| SMN1-117 m01 | ATGGCCCACCACCGC | InaAs; omeUs; InaGs; omeGs; InaCs; omeCs; InaCs; omeAs; InaCs; omeCs; InaAs; omeCs; InaCs; omeGs; InaC-Sup | 10097 |
| SMN1-118 m01 | AATGCCTTTCTGTTA | InaAs; omeAs; InaTs; omeGs; InaCs; omeCs; InaTs; omeUs; InaTs; omeCs; InaTs; omeGs; InaTs; omeUs; InaA-Sup | 10330 |
| SMN1-119 m01 | ATGCCTTTCTGTTAC | InaAs; omeUs; InaGs; omeCs; InaCs; omeUs; InaTs; omeUs; InaCs; omeUs; InaGs; omeUs; InaTs; omeAs; InaC-Sup | 10331 |
| SMN1-120 m01 | TGCCTTTCTGTTACC | InaTs; omeGs; InaCs; omeCs; InaTs; omeUs; InaTs; omeCs; InaTs; omeGs; InaTs; omeUs; InaAs; omeCs; InaC-Sup | 10332 |
| SMN1-121 m01 | GCCTTTCTGTTACCC | InaGs; omeCs; InaCs; omeUs; InaUs; omeUs; InaCs; omeUs; InaGs; omeUs; InaTs; omeAs; InaCs; omeCs; InaC-Sup | 10333 |
| SMN1-122 m01 | CCTTTCTGTTACCCA | InaCs; omeCs; InaTs; omeUs; InaCs; omeUs; InaGs; omeUs; InaTs; omeUs; InaAs; omeCs; InaCs; omeCs; InaA-Sup | 10334 |
| SMN1-123 m01 | CTTTCTGTTACCCAG | InaCs; omeUs; InaTs; omeUs; InaCs; omeUs; InaGs; omeUs; InaTs; omeAs; InaCs; omeCs; InaCs; omeAs; InaG-Sup | 10335 |
| SMN1-124 m01 | TTTCTGTTACCCAGA | InaTs; omeUs; InaTs; omeCs; InaTs; omeGs; InaTs; omeUs; InaAs; omeCs; InaCs; omeCs; InaAs; omeGs; InaA-Sup | 10336 |
| SMN1-125 m01 | TGTTACCCAGATGCA | InaTs; omeGs; InaTs; omeUs; InaAs; omeCs; InaCs; omeCs; InaAs; omeGs; InaAs; omeUs; InaGs; omeCs; InaA-Sup | 10340 |
| SMN1-126 m01 | GTTACCCAGATGCAG | InaGs; omeUs; InaTs; omeAs; InaCs; omeCs; InaCs; omeAs; InaGs; omeAs; InaTs; omeGs; InaCs; omeAs; InaG-Sup | 10341 |
| SMN1-127 m01 | TTACCCAGATGCAGT | InaTs; omeUs; InaAs; omeCs; InaCs; omeCs; InaAs; omeGs; InaAs; omeUs; InaGs; omeCs; InaAs; omeGs; InaT-Sup | 10342 |
| SMN1-128 m01 | ACCCAGATGCAGTGC | InaAs; omeCs; InaCs; omeCs; InaAs; omeGs; InaAs; omeUs; InaGs; omeCs; InaAs; omeGs; InaTs; omeGs; InaC-Sup | 10344 |
| SMN1-129 m01 | CCCAGATGCAGTGCT | InaCs; omeCs; InaCs; omeAs; InaGs; omeAs; InaTs; omeGs; InaCs; omeAs; InaGs; omeUs; InaGs; omeCs; InaT-Sup | 10345 |
| SMN1-130 m01 | CCAGATGCAGTGCTC | InaCs; omeCs; InaAs; omeGs; InaAs; omeUs; InaGs; omeCs; InaAs; omeGs; InaTs; omeGs; InaCs; omeUs; InaC-Sup | 10346 |
| SMN1-131 m01 | CAGATGCAGTGCTCT | InaCs; omeAs; InaGs; omeAs; InaTs; omeGs; InaCs; omeAs; InaGs; omeUs; InaGs; omeCs; InaTs; omeCs; InaT-Sup | 10347 |

TABLE 4-continued

Oligonucleotide sequences made for testing human cells obtained from subjects with Spinal Muscular Atrophy (See Table 3 for structural features of formatted sequence).

| Oligo Name | Base Sequence | Formatted Sequence | SeqID |
|---|---|---|---|
| SMN1-132 m01 | AGATGCAGTGCTCTT | InaAs; omeGs; InaAs; omeUs; InaGs; omeCs; InaAs; omeGs; InaTs; omeGs; InaCs; omeUs; InaCs; omeUs; InaT-Sup | 10348 |
| SMN1-133 m01 | TTTTACTCATAGCTT | InaTs; omeUs; InaTs; omeUs; InaAs; omeCs; InaTs; omeCs; InaAs; omeUs; InaAs; omeGs; InaCs; omeUs; InaT-Sup | 10942 |
| SMN1-134 m01 | TTTACTCATAGCTTC | InaTs; omeUs; InaTs; omeAs; InaCs; omeUs; InaCs; omeAs; InaTs; omeAs; InaGs; omeCs; InaTs; omeUs; InaC-Sup | 10943 |
| SMN1-135 m01 | TTACTCATAGCTTCA | InaTs; omeUs; InaAs; omeCs; InaTs; omeCs; InaAs; omeUs; InaGs; omeCs; InaCs; omeUs; InaTs; omeCs; InaA-Sup | 10944 |
| SMN1-136 m01 | TACTCATAGCTTCAT | InaTs; omeAs; InaCs; omeUs; InaCs; omeAs; InaTs; omeAs; InaGs; omeCs; InaTs; omeUs; InaCs; omeAs; InaT-Sup | 10945 |
| SMN1-137 m01 | ACTCATAGCTTCATA | InaAs; omeCs; InaTs; omeCs; InaAs; omeUs; InaAs; omeGs; InaCs; omeUs; InaTs; omeCs; InaAs; omeUs; InaA-Sup | 10946 |
| SMN1-138 m01 | CTCATAGCTTCATAG | InaCs; omeUs; InaCs; omeAs; InaTs; omeAs; InaGs; omeCs; InaTs; omeUs; InaCs; omeAs; InaTs; omeAs; InaG-Sup | 10947 |
| SMN1-139 m01 | TCATAGCTTCATAGT | InaTs; omeCs; InaAs; omeUs; InaAs; omeGs; InaCs; omeUs; InaTs; omeCs; InaAs; omeUs; InaAs; omeGs; InaT-Sup | 10948 |
| SMN1-140 m01 | ATAGCTTCATAGTGG | InaAs; omeUs; InaAs; omeGs; InaCs; omeUs; InaTs; omeCs; InaAs; omeUs; InaAs; omeGs; InaTs; omeGs; InaG-Sup | 10950 |
| SMN1-141 m01 | TTCATAGTGGAACAG | InaTs; omeUs; InaCs; omeAs; InaTs; omeAs; InaGs; omeUs; InaGs; omeGs; InaAs; omeAs; InaCs; omeAs; InaG-Sup | 10955 |
| SMN1-142 m01 | TCATAGTGGAACAGA | InaTs; omeCs; InaAs; omeUs; InaAs; omeGs; InaTs; omeGs; InaGs; omeAs; InaAs; omeCs; InaAs; omeGs; InaA-Sup | 10956 |
| SMN1-143 m01 | CATAGTGGAACAGAT | InaCs; omeAs; InaTs; omeAs; InaGs; omeUs; InaGs; omeGs; InaAs; omeAs; InaCs; omeAs; InaGs; omeAs; InaT-Sup | 10957 |
| SMN1-144 m01 | ATAGTGGAACAGATA | InaAs; omeUs; InaAs; omeGs; InaTs; omeGs; InaGs; omeAs; InaAs; omeCs; InaAs; omeGs; InaAs; omeUs; InaA-Sup | 10958 |
| SMN1-145 m01 | TAGTGGAACAGATAC | InaTs; omeAs; InaGs; omeUs; InaGs; omeGs; InaAs; omeAs; InaCs; omeAs; InaGs; omeAs; InaTs; omeAs; InaC-Sup | 10959 |
| SMN1-146 m01 | AGTGGAACAGATACA | InaAs; omeGs; InaTs; omeGs; InaGs; omeAs; InaAs; omeCs; InaAs; omeGs; InaAs; omeUs; InaAs; omeCs; InaA-Sup | 10960 |
| SMN1-147 m01 | GTGGAACAGATACAT | InaGs; omeUs; InaGs; omeGs; InaAs; omeAs; InaCs; omeAs; InaGs; omeAs; InaTs; omeAs; InaCs; omeAs; InaT-Sup | 10961 |
| SMN1-148 m01 | TGGAACAGATACATA | InaTs; omeGs; InaGs; omeAs; InaAs; omeCs; InaAs; omeGs; InaAs; omeUs; InaAs; omeCs; InaAs; omeUs; InaA-Sup | 10962 |
| SMN1-149 m01 | TGTCCAGATTCTCTT | InaTs; omeGs; InaTs; omeCs; InaCs; omeAs; InaGs; omeAs; InaTs; omeUs; InaCs; omeUs; InaCs; omeUs; InaT-Sup | 11367 |

TABLE 4-continued

Oligonucleotide sequences made for testing human cells obtained from subjects with Spinal Muscular Atrophy (See Table 3 for structural features of formatted sequence).

| Oligo Name | Base Sequence | Formatted Sequence | SeqID |
|---|---|---|---|
| SMN1-150 m01 | GTCCAGATTC TCTTG | InaGs; omeUs; InaCs; omeCs; InaAs; omeGs; InaAs; omeUs; InaTs; omeCs; InaTs; omeCs; InaTs; omeUs; InaG-Sup | 11368 |
| SMN1-151 m01 | TCCAGATTCT CTTGA | InaTs; omeCs; InaCs; omeAs; InaGs; omeAs; InaTs; omeUs; InaCs; omeUs; InaCs; omeUs; InaTs; omeGs; InaA-Sup | 11369 |
| SMN1-152 m01 | CCAGATTCTC TTGAT | InaCs; omeCs; InaAs; omeGs; InaAs; omeUs; InaTs; omeCs; InaTs; omeCs; InaTs; omeUs; InaGs; omeAs; InaT-Sup | 11370 |
| SMN1-153 m01 | CAGATTCTCT TGATG | InaCs; omeAs; InaGs; omeAs; InaTs; omeUs; InaCs; omeUs; InaCs; omeUs; InaTs; omeGs; InaAs; omeUs; InaG-Sup | 11371 |
| SMN1-154 m01 | AGATTCTCTT GATGA | InaAs; omeGs; InaAs; omeUs; InaTs; omeCs; InaTs; omeCs; InaTs; omeUs; InaGs; omeAs; InaTs; omeGs; InaA-Sup | 11372 |
| SMN1-155 m01 | GATTCTCTTG ATGAT | InaGs; omeAs; InaTs; omeUs; InaCs; omeUs; InaCs; omeUs; InaTs; omeGs; InaAs; omeUs; InaGs; omeAs; InaT-Sup | 11373 |
| SMN1-156 m01 | GGAAGTATG TTAATT | InaGs; omeGs; InaAs; omeAs; InaGs; omeUs; InaAs; omeUs; InaGs; omeUs; InaUs; omeAs; InaAs; omeUs; InaT-Sup | 11400 |
| SMN1-157 m01 | GAAGTATGTT AATTT | InaGs; omeAs; InaAs; omeGs; InaUs; omeAs; InaUs; omeGs; InaUs; omeUs; InaAs; omeAs; InaUs; omeUs; InaT-Sup | 11401 |
| SMN1-158 m01 | AAGTATGTTA ATTTC | InaAs; omeAs; InaGs; omeUs; InaAs; omeUs; InaGs; omeUs; InaUs; omeAs; InaAs; omeUs; InaUs; omeUs; InaC-Sup | 11402 |
| SMN1-159 m01 | AGTATGTTAA TTTCA | InaAs; omeGs; InaTs; omeAs; InaGs; omeUs; InaAs; omeAs; InaTs; omeUs; InaTs; omeCs; InaA-Sup | 11403 |
| SMN1-160 m01 | GTATGTTAAT TTCAT | InaGs; omeUs; InaAs; omeUs; InaGs; omeUs; InaAs; omeAs; InaUs; omeUs; InaCs; omeAs; InaT-Sup | 11404 |
| SMN1-161 m01 | TATGTTAATT TCATG | InaTs; omeAs; InaTs; omeGs; InaTs; omeUs; InaAs; omeAs; InaTs; omeUs; InaTs; omeCs; InaAs; omeUs; InaG-Sup | 11405 |
| SMN1-162 m01 | ATGTTAATTT CATGG | InaAs; omeUs; InaGs; omeUs; InaUs; omeAs; InaAs; omeUs; InaUs; omeUs; InaCs; omeAs; InaTs; omeGs; InaG-Sup | 11406 |
| SMN1-163 m01 | TGAAATATTC CTTAT | InaTs; omeGs; InaAs; omeAs; InaAs; omeUs; InaAs; omeUs; InaTs; omeCs; InaCs; omeUs; InaTs; omeAs; InaT-Sup | 10064 |
| SMN1-164 m01 | TATAGCCAGG TCTAA | InaTs; omeAs; InaTs; omeAs; InaGs; omeCs; InaCs; omeAs; InaGs; omeGs; InaTs; omeCs; InaTs; omeAs; InaA-Sup | 10076 |
| SMN1-165 m01 | ATAGCCAGGT CTAAA | InaAs; omeUs; InaAs; omeGs; InaCs; omeCs; InaAs; omeGs; InaGs; omeUs; InaCs; omeUs; InaAs; omeAs; InaA-Sup | 10077 |
| SMN1-166 m01 | AGGTCTAAAA TTCAA | InaAs; omeGs; InaGs; omeUs; InaCs; omeUs; InaAs; omeAs; InaAs; omeAs; InaTs; omeUs; InaCs; omeAs; InaA-Sup | 10083 |
| SMN1-167 m01 | GTCTAAAATT CAATG | InaGs; omeUs; InaCs; omeUs; InaAs; omeAs; InaAs; omeAs; InaTs; omeUs; InaCs; omeAs; InaAs; omeUs; InaG-Sup | 10085 |

TABLE 4-continued

Oligonucleotide sequences made for testing human cells obtained from subjects with Spinal Muscular Atrophy (See Table 3 for structural features of formatted sequence).

| Oligo Name | Base Sequence | Formatted Sequence | SeqID |
|---|---|---|---|
| SMN1-168 m01 | TCTAAAATTCAATGG | InaTs; omeCs; InaTs; omeAs; InaAs; omeAs; InaAs; omeUs; InaTs; omeCs; InaAs; omeAs; InaTs; omeGs; InaG-Sup | 10086 |
| SMN1-169 m01 | TAAAATTCAATGGCC | InaTs; omeAs; InaAs; InaAs; omeUs; InaTs; omeCs; InaAs; omeAs; InaTs; omeGs; InaGs; omeCs; InaC-Sup | 10088 |
| SMN1-170 m01 | AAAATTCAATGGCCC | InaAs; omeAs; InaAs; InaTs; omeUs; InaCs; omeAs; InaAs; omeUs; InaGs; omeGs; InaCs; omeCs; InaC-Sup | 10089 |
| unc-232 m12 | CTACGCGTCGACGGT | InaCs; dTs; InaAs; dCs; InaGs; dCs; InaGs; dTs; InaCs; dGs; InaAs; dCs; InaGs; dGs; InaT-Sup | 13095 |
| unc-232 m01 | CTACGCGTCGACGGT | InaCs; omeUs; InaAs; omeCs; InaGs; omeCs; InaGs; omeUs; InaCs; omeGs; InaAs; omeCs; InaGs; omeGs; InaT-Sup | 13095 |
| unc-293 m12 | CCGATTCGCGCGTAA | InaCs; dCs; InaGs; dAs; InaTs; dTs; InaCs; dGs; InaCs; dGs; InaCs; dGs; InaTs; dAs; InaA-Sup | 13096 |
| unc-293 m01 | CCGATTCGCGCGTAA | InaCs; omeCs; InaGs; omeAs; InaTs; omeUs; InaCs; omeGs; InaCs; omeGs; InaCs; omeGs; InaTs; omeAs; InaA-Sup | 13096 |
| SMN1-246 m01 | TGATGCTGATGCT | InaTs; omeGs; InaAs; omeUs; InaGs; omeCs; InaTs; omeGs; InaAs; omeUs; InaGs; omeCs; InaTs; | 13108 |
| SMN1-246 m16 | TGATGCTGATGCT | omeUs; InaGs; omeAs; InaTs; omeGs; InaCs; omeUs; InaGs; omeAs; InaTs; omeGs; InaCs; omeU | 13108 |
| SMN1-37 m19 | TGATGCTGATGCTTT | InaTs; omeGs; omeAs; InaTs; omeGs; omeCs; InaTs; omeGs; omeAs; InaTs; omeGs; omeCs; InaTs; omeUs; omeU | 13109 |
| SMN1-37 m20 | TGATGCTGATGCTTT | InaTs; InaGs; omeAs; omeUs; InaGs; omeCs; InaTs; omeGs; omeAs; InaTs; omeGs; omeCs; InaTs; InaTs; omeU | 13109 |
| SMN1-435 m01 | CTTCATAGTGG | InaCs; omeUs; InaTs; omeCs; InaAs; omeUs; InaAs; omeGs; InaTs; omeGs; InaG | 13110 |
| SMN1-438 m01 | TCATAGTGGAACA | InaTs; omeCs; InaAs; omeUs; InaAs; omeGs; InaTs; omeGs; InaGs; omeAs; InaAs; omeCs; InaAs; | 13111 |
| SMN1-439 m01 | TCATAGTGGAA | InaTs; omeCs; InaAs; omeUs; InaAs; omeGs; InaTs; omeGs; InaGs; omeAs; InaA | 13112 |
| SMN1-90 m18 | CTTCATAGTGGAACA | InaCs; InaTs; omeUs; InaCs; InaAs; omeUs; InaAs; InaGs; omeUs; InaGs; InaGs; omeAs; InaAs; InaCs; omeA | 10954 |
| SMN1-90 m19 | CTTCATAGTGGAACA | InaCs; omeUs; omeUs; omeCs; omeAs; omeUs; InaAs; omeGs; omeUs; InaGs; omeGs; omeAs; InaAs; omeCs; omeA | 10954 |
| SMN1-90 m20 | CTTCATAGTGGAACA | InaCs; InaTs; omeUs; omeCs; InaAs; omeUs; InaAs; InaTs; omeAs; omeGs; InaTs; InaGs; omeGs; omeAs; InaAs; InaCs; omeA | 10954 |
| SMN1-457 m01 | GTGGAACAGATAC | InaGs; omeUs; InaGs; omeGs; InaAs; omeAs; InaCs; omeAs; omeAs; InaTs; omeAs; InaCs; | 13113 |
| SMN1-458 m01 | GTGGAACAGAT | InaGs; omeUs; InaGs; omeGs; InaAs; omeAs; InaCs; omeAs; InaGs; omeAs; InaT | 13114 |

TABLE 4-continued

Oligonucleotide sequences made for testing human cells obtained from subjects with Spinal Muscular Atrophy (See Table 3 for structural features of formatted sequence).

| Oligo Name | Base Sequence | Formatted Sequence | SeqID |
|---|---|---|---|
| SMN1-459 m01 | GTGGAACAG | InaGs; omeUs; InaGs; omeGs; InaAs; omeAs; InaCs; omeAs; InaG | 13115 |

Example 3: Confirmation of PRC2 Mechanism of Action

Materials And Methods:
Oligonucleotides

The oligos used in Example 3 are shown in Table 6 below and/or in Table 4 (See Table 3 for structural features of formatted sequence).

TABLE 6

| Oligo Name | Base Sequence | Formatted Sequence | SeqID |
|---|---|---|---|
| SMN1-77 m01 | CTAAAATTCA ATGGC | InaCs; omeUs; InaAs; omeAs; InaAs; omeAs; InaTs; omeUs; InaCs; omeAs; InaAs; omeUs; InaGs; omeGs; InaC-Sup | 10087 |
| SMN1-83 m01 | CTGTTACCCA GATGC | InaCs; omeUs; InaGs; omeUs; InaTs; omeAs; InaCs; omeCs; InaCs; omeAs; InaGs; omeAs; InaTs; omeGs; InaC-Sup | 10339 |
| SMN1-90 m01 | CTTCATAGTG GAACA | InaCs; omeUs; InaTs; omeCs; InaAs; omeUs; InaAs; omeGs; InaTs; omeGs; InaGs; omeAs; InaAs; omeCs; InaA-Sup | 10954 |
| SMN1-37 m01 | TGATGCTGAT GCTTT | InaTs; omeGs; InaAs; omeUs; InaGs; omeCs; InaTs; omeGs; InaAs; omeUs; InaGs; omeCs; InaTs; omeUs; InaT-Sup | 11384 |
| SMN1-143 m01 | CATAGTGGA ACAGAT | InaCs; omeAs; InaTs; omeAs; InaGs; omeUs; InaGs; omeGs; InaAs; omeAs; InaCs; omeAs; InaGs; omeAs; InaT-Sup | 10957 |
| SMN1-144 m01 | ATAGTGGAA CAGATA | InaAs; omeUs; InaAs; omeGs; InaTs; omeGs; InaGs; omeAs; InaAs; omeCs; InaAs; omeGs; InaAs; omeUs; InaA-Sup | 10958 |
| SMN-243 m01 | GATGATGCT GATGCTTT | InaGs; omeAs; InaTs; omeGs; InaAs; omeUs; InaGs; omeCs; InaTs; omeGs; InaAs; omeUs; InaGs; omeCs; InaTs; omeUs; InaT-Sup | 13116 |
| SMN1-54 m01 | TCACTTTCAT AATGCTGG | InaTs; omeCs; InaAs; omeCs; InaTs; omeUs; InaTs; omeCs; InaAs; omeUs; InaAs; omeAs; InaTs; omeGs; InaCs; omeUs; InaGs; omeG-Sup | 13088 |
| SMN1-54 m15 | TCACTTTCAT AATGCTGG | moeTs; moeCs; moeAs; moeCs; moeTs; moeTs; moeTs; moeCs; moeAs; moeTs; moeAs; moeAs; moeTs; moeGs; moeCs; moeTs; moeGs; moeG-Sup | 13088 |

Non Human Primate (NHP) Dose Response Curves

Non-human primate Cynomolgous monkey fibroblasts (NHP) was purchased from the Coriell Institute (Coriell cat #: AG21329) and cultured in MEM (Eagle) Alpha modification with nucleosides and 2 mM L-Glutamine and 15% FBS. Cells were plated at $1 \times 10^4$ cells per well of 96 well plate. 24 hours later oligonucleotides were transfected into cells with Lipofectamine 2000 (LifeTechnology cat #11668-019) generating a dose response curve spanning 200-1.5 nM final concentrations. Oligos combined with cells without media change for 48 hours prior to mRNA expression analysis.

qPCR

For SMN full length (FL) qPCR, cDNA was prepared using Cells to Ct (LifeTechnology cat #4391851C and 4391852C) according to manufacturer's instructions. qPCR was performed using TaqMan probes (IDT) designed previously (Hua et al 2010 Genes and Dev 24:1634-1644) and housekeeping GAPDH TaqMan assay (LifeTechnology cat #Hs02758991_g1) Analysis was conducted by ΔΔCt method.

Full Length SMN probes:

```
                               (SEQ ID NO: 13117)
Fwd primer:    5'-GCTGATGCTTTGGGAAGTATGTTA-3'

(SEQ ID NO: 13118)
Rev primer:    5'-CACCTTCCTTCTTTTTGATTTTGTC-3'

(SEQ ID NO: 13119)
Probe          5'-TACATGAGTGGCTATCATACT-3'
```

For SMN full length (FL) and Δ7 (del7) SMN qPCR, cDNA was prepared using Cells to Ct (LifeTechnology cat #4391851C and 4391852C) according to manufacturer's instructions. qPCR was performed using TaqMan probes (IDT) designed previously (Hua et al 2010 Genes and Dev 24:1634-1644) and housekeeping GAPDH TaqMan assay (LifeTechnology cat #Hs02758991_g1). Analysis was conducted by AACt method.

```
Full Length SMN probes:
                                    (SEQ ID NO: 13117)
Fwd primer:      5'-GCTGATGCTTTGGGAAGTATGTTA-3'

(SEQ ID NO: 13118)
Rev primer:      5'-CACCTTCCTTCTTTTTGATTTTGTC-3'

(SEQ ID NO: 13119)
Probe            5'-TACATGAGTGGCTATCATACT-3'

Δ7 SMN probe:
                                    (SEQ ID NO: 13120)
Fwd Primer:      5'-TGGACCACCAATAATTCCCC-3'

(SEQ ID NO: 13121)
Rev Primer:      5'-ATGCCAGCATTTCCATATAATAGCC-3'

(SEQ ID NO: 13122)
Probe            5'-TCCAGATTCTCTTGATGATG-3'
```

PRC2-Associated SMN Oligos in Combination with Splice-Switching Oligo Experiments To assess effects of PRC2-associated SMN oligos with a splice-switching oligo a matrixed approach consisting of two different methods was taken. (i) While maintaining the concentration of PRC2 SMN oligo at 30 nM, the splice-switching oligo was combined at the following concentrations of 192, 96, 48, 24, 12, 6, 3 and 1.5 pM. (ii) While maintaining the concentration of splice-switching oligo at 300 pM, the PRC2 SMN oligo was combined at the following concentrations of 100, 50, 25, 12.5, 6.25, 3.125, 1.56 nM.

For each set of experiments these combinations were transfected into SMA derived fibroblasts cells obtained from Coriell Institute (Coriell cat #: GM9677) using Lipofectamine 2000 according to the manufacturer's instructions. Cells were plated at $1 \times 10^4$ cells per well of a 96 well plate. The following day the cells were transfected with their respective combination of oligo. Oligos were left on cells without media change for 48 hours prior to mRNA expression analysis.

Chromatin Immunoprecipitation (ChIP)

Cells were crosslinked with 1% formaldehyde for 10 minutes at room temperature and then quenched with glycine. Chromatin was prepared and sonicated (Covaris S200) to a size range of 300-500 bp. Antibodies for H3, H3K27me3, H3K36me3, EZH2, and RNA Polymerase II Serine 2 (Abcam) and H3K4me3 (Millipore) were coupled to Protein G magnetic beads (NEB), washed, and then resuspended in IP blocking buffer. Chromatin lysates were added to the beads and immunoprecipitated overnight at 4° C. Immunoprecipitations were washed, RNase A (Roche) treated, Proteinase K (Roche) treated, and the crosslinks were reversed by incubation overnight at 65° C. DNA was purified, precipitated, and resuspended in nuclease-free water. Custom Taqman probe sets were used to determine the enrichment of DNA.

Results:

Experiments were performed to confirm that SMN expression was regulated by PRC2 and that SMN oligos designed to target PRC2-associated regions could upregulate SMN expression. Firstly, EED, a component of the PRC2 complex, was knocked down in GM09677 cells using 3 siRNAs specific for EED. EED siRNA were purchased from Qiagen (EED #3: catalog number SI00376299; EED #6: catalog number SI03037335). RNA was extracted from the treated cells using standard protocols. EED and SMN2 mRNA levels were measured after siRNA treatment with 50 nM concentration of siRNA for 3 days. It was found that full-length SMN2 mRNA levels were upregulated after EED siRNA treatment, confirming PRC2 involvement in SMN expression regulation (FIG. 10). Cells were then treated with SMN Oligos 77 and 83, which were designed to target PRC2-associated regions in SMN, described in Table 4 or Table 6 at 30 nM concentration for 3 days. RNA was then extracted and SMN2 levels were measured. It was found that both SMN oligos 77 and 83 upregulated SMN2 levels compared to controls (FIG. 10), confirming that oligos that target PRC2-associated regions can upregulate SMN levels.

Next, chromatin immunoprecipitation (ChIP) was used to determine the chromatin status at the SMN locus (FIG. 11A). It was found that knockdown of PRC2 components EED and EZH2 reduced the presence of EZH2 in SMN chromatin (FIG. 11B). Histone 3 is trimethylated at Lysine 27 (the H3K27m3 modification) by the action of EZH2, the histone methyltransferase enzyme in the PRC2 complex. This H3K27m3 modification is understood to repress transcription. EED and EZH1/2 knockdown also slightly decreased the H3K27m3 mark (FIG. 11C). The decrease in H3K27m3 was not as great as the decrease in EZH2 because it typically requires longer periods of time to observe the loss of the H3K27m3 mark. These data show that knockdown of PRC2 components leads to decreases in the presence of EZH2 and H3K27m3 in the SMN gene chromatin, indicating that PRC2 normally acts at the SMN gene. It was also found that knockdown of PRC2 components led to an increase in marks of transcriptional activity, e.g., an increase in RNA Pol II S2 and H3K36m3 within regions of the SMN locus (FIG. 12). The H3K36m3 modification is a mark of transcriptional elongation. The increase in the presence of RNA polymerase II and the H3K36m3 modification indicate that knockdown of PRC2 leads to increased SMN transcription. Therefore, PRC2 does normally repress the transcription of the SMN gene. The HOXC13 gene was used as a positive control for the EED and EZH1/2 knockdown as it is known to be repressed by PRC2. Therefore, it was found that EED knockdown decreased EZH2, decreased the repressive H3K27 methylation mark, increased the H3K36 methylation mark of transcriptional elongation, and increased the presence of RNA polymerase II at this genomic location (FIG. 11D).

Subsequently, chromatin status was measured after treatment with SMN oligos. GM09677 cells were treated with 30 nM concentration of SMN oligos 77 and 83 for 3 days. It was found that oligos 77 and 83 reduced EZH2 association in the SMN gene locus (FIG. 13A). The loss of EZH2 association was not observed with splice-switching oligos. H3K27me3 was decreased with SMN oligo 83 treatment, consistent with oligo treatment blocking the recruitment of EZH2, the histone methyltransferase that applies the H3K27me3 repressive chromatin modification (FIG. 13B). Oligo treatment did not affect the HOXC13 promoter chromatin content (FIG. 13C). This latter result indicates selectivity of the action of the oligos as they only block recruitment of PRC2 to the SMN gene, but do not affect PRC2 activity at HOXC13, another PRC2-regulated gene. SMN oligo treatment also increased marks of transcriptional elongation, e.g., H3K36m3 and RNA pol II S2, similar to the knockdown of PRC2 components (FIG. 14). An exemplary splice-switching oligo, on the other hand, did not increase marks of transcriptional elongation (FIG. 15). These results indicate that SMN upregulating oligo treatment increases transcription in a manner that is consistent with the inhibition of the recruitment of PRC2 to the SMN gene.

SMN oligos then were tested in non-human primate (NHP) cells to assess levels of SMN1 expression. It was found that many SMN oligos upregulated levels of SMN1 in NHP cells in a dose-dependent manner (FIG. 16A). Exon 7 exclusion is a human-specific phenomenon occurring in SMA patients, and is not observed in NHPs (Rochette C F et al. Hum Genet. 2001 March; 108(3):255-66. PMID: 11354640). As a result, exemplary splice switching oligos were not able to upregulate SMN expression in NHP cells (FIG. 16B).

These results confirm that oligonucleotides targeting PRC2-associated RNAs (which may be referred herein to as PRC2-targeting oligos) are capable of upregulating expression wild-type SMN1. These results are particularly relevant with respect to treatment of ALS patient through SMN upregulation, because ALS patients typically possess wild-type SMN1 gene and thus would be responsive to upregulation via PRC2-targeting oligos.

Next, SMN oligos designed to target PRC2-associated regions and SMN splice-switching oligo treatments were combined to determine if having oligos with multiple mechanisms of action would have an synergistic effect. It was found that combining SMN PRC2-targeting oligos with splice-switching oligos to treat cells resulted in increased upregulation of SMN2 compared to single oligo treatment (FIG. 17).

Lastly, several SMN oligos designed to target PRC2-associated regions were tested in GM09677 cells for their ability to upregulate SMN2 mRNA and protein levels. GM09677 cells were treated with a 30 nM concentration of SMN oligos for 3 days. It was found that all oligos tested upregulated full-length SMN mRNA to some degree, with some oligos upregulating SMN mRNA over 2-fold above control levels (FIG. 18). It was also found that the oligos tested upregulated SMN protein by at least 2-fold over control levels (FIG. 19). Several splice-switching oligos were also tested in GM09677 cells for their ability to upregulate SMN2 mRNA and protein levels. GM09677 cells were treated with a 30 nM concentration of splicing oligos for 3 days. It was found that all splice-switching oligos tested upregulated full-length SMN mRNA to some degree, with some oligos upregulating SMN mRNA over 2-fold above control levels (FIG. 20). It was also found that the splice-switching oligos tested upregulated SMN protein by at least 3-fold over control levels (FIG. 21).

In summary, it was found that PRC2 knockdown increased SMN expression, RNA polymerase occupancy and activating chromatin marks (indicating transcriptional activation), and decreased EZH2 association with the SMN gene. Similarly, SMN oligos designed to target PRC2-associated regions also increased SMN1 and 2 expression, RNA polymerase occupancy and activating chromatin marks (indicating transcriptional activation), and decreased EZH2 association with a SMN gene. Further, combining oligos that involved different mechanisms of action may result in increased SMN expression compared to use of single oligos.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10174328B2). An electronic copy of the "Sequence Listing" will also be available from the USPTO upon request and payment of the fee set forth in 37 CFR 1.19(b)(3).

What is claimed is:

1. A method of increasing expression of SMN in a cell of a subject having ALS, the method comprising delivering to the cell a first single stranded oligonucleotide comprising a region of complementarity that is complementary with at least 8 consecutive nucleotides of a PRC2-associated region of an SMN gene, wherein the first single stranded oligonucleotide is up to 21 nucleotides in length, wherein the cell comprises a genetic alteration associated with the ALS in SOD1, ALS2, SETX, FUS/TLS, VAPB, ANG, TDP-43, FIG4, OPTN, ATXN2, VCP, UBQLN2, SIGMAR1, CHMP2B, PFN1 or C9orf72.

2. The method of claim 1, wherein the cell is a motor neuron.

3. The method of claim 1, wherein the first single stranded oligonucleotides comprises a sequence that is 5'X—Y—Z, wherein X is any nucleotide and wherein X is anchored at the 5' end of the oligonucleotide, Y is a nucleotide sequence of 6 nucleotides in length that is not a human seed sequence of a microRNA, and Z is a nucleotide sequence of 1 to 14 nucleotides in length.

4. The method of claim 1, wherein the method further comprises administering a second single stranded oligonucleotide complementary with a splice control sequence of a precursor mRNA of SMN2.

5. The method of claim 4, wherein the splice control sequence resides in an exon of SMN2.

6. The method of claim 5, wherein the exon is exon 7 or exon 8.

7. The method of claim 4, wherein the splice control sequence traverses an intron-exon junction of SMN2.

8. The method of claim 7, wherein the intron-exon junction is the intron 6/exon 7 junction or the intron 7/exon 8 junction.

9. The method of claim 4, wherein the splice control sequence resides in an intron of SMN2.

10. The method of claim 9, wherein the intron is intron 6 or intron 7.

11. The method of claim 4, wherein the first single stranded oligonucleotide and the second single stranded oligonucleotide are administered simultaneously.

12. The method of claim 4, wherein the first single stranded oligonucleotide is covalently linked to the second single stranded oligonucleotide through a linker.

13. The method of claim 12, wherein the linker comprises an oligonucleotide, a peptide, a low pH-labile bond, or a disulfide bond.

14. The method of claim 4, wherein at least one nucleotide of the first or second single stranded oligonucleotide is a nucleotide analogue.

15. The method of claim 4, wherein the first single stranded oligonucleotide or second single stranded oligonucleotide comprises at least one ribonucleotide, at least one deoxyribonucleotide, or at least one bridged nucleotide.

16. The method of claim 4, wherein the second single stranded oligonucleotide is 8 to 30 nucleotides in length.

17. The method of claim 16, wherein the cell comprises an SMN1 gene that does not have a mutation associated with Spinal Muscular Atrophy (SMA).

18. A method increasing levels of SMN in a subject having ALS, the method comprising administering a first single stranded oligonucleotide comprising a region of complementarity that is complementary with at least 8 consecutive nucleotides of a PRC2-associated region of an SMN gene to the subject, wherein the first single stranded oligonucleotide is up to 21 nucleotides in length, and wherein the subject has a mutation in a gene selected from SOD1, FUS/TLS, or TDP-43.

19. A method of treating ALS in a subject, the method comprising administering a first single stranded oligonucleotide comprising a region of complementarity that is complementary with at least 8 consecutive nucleotides of a PRC2-associated region of an SMN gene to the subject, wherein the first single stranded oligonucleotide is up to 21 nucleotides in length, and wherein the subject has a mutation in a gene selected from SOD1, FUS/TLS, or TDP-43.

20. The method of claim 18, wherein the single stranded oligonucleotide is administered intrathecally.

21. The method of claim 18, wherein the first single stranded oligonucleotides comprises a sequence that is 5'X—Y—Z, wherein X is any nucleotide and wherein X is anchored at the 5' end of the oligonucleotide, Y is a nucleotide sequence of 6 nucleotides in length that is not a human seed sequence of a microRNA, and Z is a nucleotide sequence of 1 to 14 nucleotides in length.

22. The method of claim 18, wherein at least one nucleotide of the first single stranded oligonucleotide is a nucleotide analogue.

23. The method of claim 18, wherein the method further comprises administering a second single stranded oligonucleotide complementary with a splice control sequence of a precursor mRNA of SMN2.

24. The method of claim 23, wherein the splice control sequence resides in an exon of SMN2.

25. The method of claim 24, wherein the exon is exon 7 or exon 8.

26. The method of claim 23, wherein the splice control sequence traverses an intron-exon junction of SMN2.

27. The method of claim 26, wherein the intron-exon junction is the intron 6/exon 7 junction or the intron 7/exon 8 junction.

28. The method of claim 23, wherein the splice control sequence resides in an intron of SMN2.

29. The method of claim 28, wherein the intron is intron 6 or intron 7.

30. The method of claim 23, wherein the first single stranded oligonucleotide and the second single stranded oligonucleotide are administered simultaneously.

31. The method of claim 23, wherein the first single stranded oligonucleotide is covalently linked to the second single stranded oligonucleotide through a linker.

32. The method of claim 31, wherein the linker comprises an oligonucleotide, a peptide, a low pH-labile bond, or a disulfide bond.

33. The method of claim 23, wherein at least one nucleotide of the second single stranded oligonucleotide is a nucleotide analogue.

34. The method of claim 23, wherein the first single stranded oligonucleotide or second single stranded oligonucleotide comprises at least one ribonucleotide, at least one deoxyribonucleotide, or at least one bridged nucleotide.

35. The method of claim 33, wherein the second single stranded oligonucleotide is 8 to 30 nucleotides in length.

36. A method for promoting Gem formation in cells having a spliceosome defect, the method comprising:
delivering to the cells a single stranded oligonucleotide comprising a region of complementarity that is complementary with at least 8 consecutive nucleotides of a PRC2-associated region of an SMN gene, wherein the first single stranded oligonucleotide is up to 21 nucleotides in length; and
evaluating spliceosome integrity in the cells prior to and/or following delivery of the single stranded oligonucleotide to the cells.

37. The method of claim 36, wherein the cell is a motor neuron of a patient having a motor neuron disease.

38. The method of claim 37, wherein the motor neuron disease is ALS or SMA.

39. The method of claim 36, wherein evaluating spliceosome intergrity comprises determining the localization of FUS, TDP-43, SMN, Gemin3, Gemin4 or another Gem marker in the nuclei of the cells.

40. The method of claim 36, wherein the cells comprise an SMN1 gene that does not have a mutation associated with Spinal Muscular Atrophy (SMA).

41. A method of increasing expression of SMN in a cell of a subject having ALS, the method comprising delivering to the cell a first single stranded oligonucleotide comprising a region of complementarity that is complementary with at least 8 consecutive nucleotides of a PRC2-associated region of an SMN gene, wherein the first single stranded oligonucleotide is up to 21 nucleotides in length, wherein the cell comprises an SMN1 gene that does not have a mutation associated with Spinal Muscular Atrophy (SMA).

42. The method of claim 41, wherein the cell comprises a genetic alteration associated with the ALS in SOD1, ALS2, SETX, FUS/TLS, VAPB, ANG, TDP-43, FIG. 4, OPTN, ATXN2, VCP, UBQLN2, SIGMAR1, CHMP2B, PFN1, or C9orf72.

43. The method of claim 41, wherein the first single stranded oligonucleotides comprises a sequence that is 5'X—Y—Z, wherein X is any nucleotide and wherein X is anchored at the 5' end of the oligonucleotide, Y is a nucleotide sequence of 6 nucleotides in length that is not a human seed sequence of a microRNA, and Z is a nucleotide sequence of 1 to 14 nucleotides in length.

44. The method of claim 41, wherein the method further comprises administering a second single stranded oligonucleotide complementary with a splice control sequence of a precursor mRNA of SMN2.

45. A method for promoting Gem formation in cells having a spliceosome defect, the method comprising delivering to the cells a single stranded oligonucleotide comprising a region of complementarity that is complementary with at least 8 consecutive nucleotides of a PRC2-associated region of an SMN gene, wherein the first single stranded oligonucleotide is up to 21 nucleotides in length, wherein the cells comprise an SMN1 gene that does not have a mutation associated with Spinal Muscular Atrophy (SMA).

* * * * *

UNITED STATES PATENT AND TRADEMARK OFFICE
CERTIFICATE OF CORRECTION

PATENT NO. : 10,174,328 B2
APPLICATION NO. : 15/026774
DATED : January 8, 2019
INVENTOR(S) : Arthur M. Krieg et al.

It is certified that error appears in the above-identified patent and that said Letters Patent is hereby corrected as shown below:

In the Claims

Column 109, Claim 17, Line 21, "The method of claim 16" should read --The method of claim 1--.

Signed and Sealed this
Twenty-sixth Day of March, 2019

Andrei Iancu
*Director of the United States Patent and Trademark Office*